United States Patent
Ishibuchi et al.

(10) Patent No.: US 8,354,401 B2
(45) Date of Patent: Jan. 15, 2013

(54) OXAZOLIDINONE AMIDE AROMATIC COMPOUNDS FOR SUPRESSING MMP-9 PRODUCTION

(75) Inventors: Seigo Ishibuchi, Osaka (JP); Hidemasa Hikawa, Funabashi (JP); Akiko Tarao, Osaka (JP); Jun-ichi Endoh, Osaka (JP); Kunitomo Adachi, Osaka (JP); Kazuhiro Maeda, Osaka (JP); Kaoru Tashiro, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 0 days.

(21) Appl. No.: 13/126,119

(22) PCT Filed: Oct. 27, 2009

(86) PCT No.: PCT/JP2009/068386
§ 371 (c)(1),
(2), (4) Date: Jul. 8, 2011

(87) PCT Pub. No.: WO2010/050461
PCT Pub. Date: May 6, 2010

(65) Prior Publication Data
US 2011/0263571 A1    Oct. 27, 2011

(30) Foreign Application Priority Data

Oct. 27, 2008    (JP) .................................. 2008-276147

(51) Int. Cl.
*A01N 43/62* (2006.01)
*A61K 31/55* (2006.01)

(52) U.S. Cl. ............... 514/218; 514/253.1; 514/254.02; 514/252.11; 514/326; 514/318; 544/369; 544/357; 544/365; 546/194; 546/209

(58) Field of Classification Search ............... 514/218, 514/253.1, 254.02, 252.11, 326, 318; 544/369, 544/357, 364; 546/194, 209
See application file for complete search history.

(56) References Cited

U.S. PATENT DOCUMENTS

2007/0155714 A1 *  7/2007  Hubschwerlen et al.  514/210.21

FOREIGN PATENT DOCUMENTS

| JP | 2003-321368 A | 11/2003 |
|----|---------------|---------|
| JP | 2004-359657 A | 12/2004 |
| JP | 2008-069088 A | 3/2008 |
| WO | WO 98/39315 A1 | 9/1998 |
| WO | WO 2004/096221 A | 11/2004 |
| WO | WO 2005/058888 A2 | 6/2005 |
| WO | WO 2006/088919 A2 | 8/2006 |

OTHER PUBLICATIONS

Ainiala et al., *Arthritis & Rheumatism*, 50(3): 858-865 (Mar. 2004).
Gordeev et al., *Bioorganic & Medicinal Chemistry Letters*, 13(23): 4213-4216 (2003).
Huang et al., *J. Natl. Cancer Inst.*, 94: 1134-1142 (2002).
Ito et al., *Japan Matrix Club Taikai*, 48: 82-83 (2001).
Itoh et al., *The Journal of Immunology*, 169: 2643-2647 (2002).
Konttinen et al., *Ann. Rheum. Dis.*, 58: 691-697 (1999).
Masuhara et al., *Arthritis & Rheumatism*, 46(10): 2625-2631 (Oct. 2002).
McQuibban et al., *Science*, 289: 1202-1206 (2000).
Medina et al., *Journal of Leukocyte Biology*, 79: 954-962 (2006).
Mohtai et al., *J. Clin. Invest.*, 92: 179-185 (1993).
Opdenakker et al., *Lancet Neurol.*, 2: 747-756 (2003).
Japanese Patent Office, International Search Report in International Application No. PCT/JP2009/068386 (Dec. 22, 2009).
Ledour et al., *Bioorganic & Medicinal Chem.*, 16(18): 8745-8759 (2008).
Tamura et al., *J. Med. Chem.*, 41(4): 640-649 (1998).
European Patent Office, Supplementary European Search Report in European Patent Application No. 09823571 (Mar. 28, 2012).

* cited by examiner

*Primary Examiner* — Yong Chu
*Assistant Examiner* — Valerie Rodriguez-Garcia
(74) *Attorney, Agent, or Firm* — Leydig, Voit & Mayer, Ltd.

(57) ABSTRACT

Provided are a novel low-molecular-weight compound that suppresses production of induction type MMPs, particularly MMP-9, rather than production of hemostatic type MMP-2, as well as a prophylactic/therapeutic drug for autoimmune diseases or osteoarthritis. An amide derivative represented by the following formula (I)

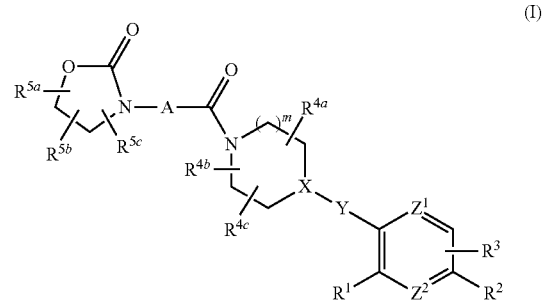

wherein each symbol is as defined in the specification, a pharmacologically acceptable salt thereof, or a hydrate or solvate thereof.

14 Claims, No Drawings

OXAZOLIDINONE AMIDE AROMATIC COMPOUNDS FOR SUPRESSING MMP-9 PRODUCTION

TECHNICAL FIELD

The present invention relates to a novel amide derivative showing a selective MMP-9 production suppressive action and pharmaceutical use thereof.

BACKGROUND ART

Matrix metalloprotease (MMPs) is an enzyme group playing a key role in the binding tissue degradation in living organisms. The activity of MMPs is controlled by each step of 1) production of latent enzyme (proMMP) by gene expression, 2) activation of proMMP, 3) activity inhibition by TIMP which is an inhibitor of active enzymes. MMPs includes two types of hemostatic type and induction type, the former includes MMP-2 and MMP-14, and the latter includes many MMPs such as MMP-1, 3, 9, 13 etc. Particularly, promoted production or expression in rheumatoid arthritis, osteoarthritis, multiple sclerosis, systemic lupus erythematosus and inflammatory bowel diseases (ulcerative colitis, Crohn's disease) by MMP-9 has been acknowledged, and the involvement of MMP-9 in these pathologies has been suggested [Ann. Rheum. Dis., vol. 58, page 691-697 (1999) (non-patent document 1), J. Clin. Invest., vol. 92, page 179-185 (1993) (non-patent document 2), Arthritis Rheum., vol. 46, page 2625-2631 (2002) (non-patent document 3), Lancet Neurol., vol. 2, page 747-756 (2003) (non-patent document 4), Arthritis Rheum., vol. 50, page 858-865 (2004) (non-patent document 5), Journal of Leukocyte Biology, vol. 79, page 954-962 (2006) (non-patent document 9)].

In addition, it has been suggest from the studies of MMP knockout mouse that MMP-9 is involved in the formation and progression of cancer, MMP-9 plays an important role in the progression of arthritis and articular destruction [J. Natl. Cancer Inst., vol. 94, 1134-1142 (2002) (non-patent document 6), J. Immunol., vol. 169, 2643-2647 (2002) (non-patent document 7)]. On the other hand, MMP-2 shows an anti-inflammatory action and the action mechanism thereof is considered to be degradation of MCP-3 and the like [Science, vol. 289, page 1202-1206 (2000) (non-patent document 8)]. Therefore, a medicament that does not influence MMP-2 production and selectively suppresses MMP-9 production can be expected as a novel therapeutic drug.

JP-A-2004-359657 (patent document 1) discloses leptomycin B, which is a medicament that inhibits MMP-9 production, and a derivative thereof.

DOCUMENT LIST

Patent Document patent document 1: JP-A-2004-359657

Non-Patent Documents non-patent document 1: Ann. Rheum. Dis., vol. 58, page 691-697 (1999)
non-patent document 2: J. Clin. Invest., vol. 92, page 179-185 (1993)
non-patent document 3: Arthritis Rheum., vol. 46, page 2625-2631 (2002)
non-patent document 4: Lancet Neurol., vol. 2, page 747-756 (2003)
non-patent document 5: Arthritis Rheum., vol. 50, page 858-865 (2004)
non-patent document 6: J. Natl. Cancer Inst., vol. 94, page 1134-1142 (2002)
non-patent document 7: J. Immunol., vol. 169, page 2643-2647 (2002)
non-patent document 8: Science, vol. 289, page 1202-1206 (2000)
non-patent document 9: Journal of Leukocyte Biology, vol. 79, page 954-962 (2006)

SUMMARY OF THE INVENTION

Problems to be Solved by the Invention

The problem of the present invention is to provide a novel low-molecular-weight compound that suppresses production of induction type MMPs, particularly MMP-9, rather than production of hemostatic type MMP-2.

Means of Solving the Problems

In view of the above-mentioned problems, the present inventors have conducted intensive studies in an attempt to find a low-molecular-weight compound showing an MMP-9 production suppressive action. As a result, they have found that the amide derivative of the present invention suppresses production of induction type MMPs, particularly MMP-9, rather than production of hemostatic type MMP-2, which resulted in the completion of the present invention.

Accordingly, the present invention is as described below.

1. An amide derivative represented by the following formula (I)

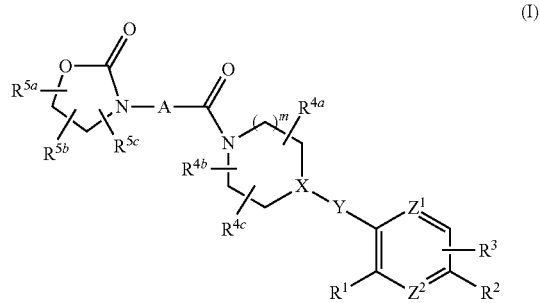

wherein A is a group represented by the following formula

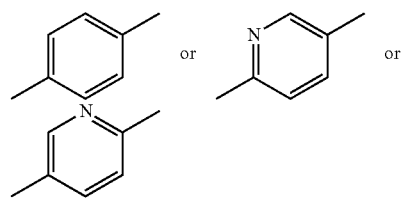

wherein benzene and pyridine optionally have one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6, and cyclic aminosulfonyl, the right bond is bonded to carbonyl, and the left bond is bonded to a nitrogen atom, $R^1$ and $R^2$ are the same or different and each is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), alkoxycarbonyl having a total carbon number of 2-7 and optionally having substituent(s), carbamoyl, acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6 or cyclic aminosulfonyl, and $R^1$ and $R^2$ do not simultaneously show a hydrogen atom, $R^3$ is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), alkoxycarbonyl having a total carbon number of 2-7 and optionally having substituent(s), carboxy, carbamoyl, acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6 or cyclic aminosulfonyl, $R^{4a}$, $R^{4b}$ and $R^{4c}$ are each independently a hydrogen atom, alkyl having a carbon number of 1-6 and optionally having substituent(s), oxo or alkoxy having a carbon number of 1-6 and optionally having substituent(s), $R^{5a}$, $R^{5b}$ and $R^{5c}$ are the same or different and each is a hydrogen atom, alkyl having a carbon number of 1-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxycarbonyl having a total carbon number of 2-7 and optionally having substituent(s) or oxo, X is a carbon atom (any of $R^{4a}$, $R^{4b}$ and $R^{4c}$ may be bonded to the carbon atom, but the carbon atom is not substituted by oxo) or a nitrogen atom (when Y is a single bond, the nitrogen atom may be oxidized to form N-oxide), Y is a single bond, carbonyl or an oxygen atom, $Z^1$ and $Z^2$ are each independently a carbon atom (substituent $R^3$ is optionally bonded to the carbon atom) or a nitrogen atom, and m is 1 or 2, a pharmacologically acceptable salt thereof, or a hydrate or solvate thereof.

2. The amide derivative of the above-mentioned 1 wherein A is a group represented by the following formula

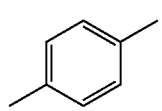

wherein benzene optionally has one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6 and cyclic aminosulfonyl, the right bond is bonded to carbonyl, and the left bond is bonded to a nitrogen atom, a pharmacologically acceptable salt thereof, or a hydrate or solvate thereof.

3. The amide derivative of the above-mentioned 1 wherein A is a group represented by the following formula

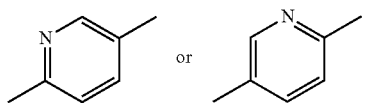

wherein pyridine optionally has one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6 and cyclic aminosulfonyl, the right bond is bonded to carbonyl, and the left bond is bonded to a nitrogen atom, a pharmacologically acceptable salt thereof, or a hydrate or solvate thereof.

4. The amide derivative of any of the above-mentioned 1. to 3., wherein benzene and pyridine for A optionally have one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, hydroxyl group, nitro, cyano, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylsulfonylamino having a carbon number of 1-6 and cycloalkylsulfonylamino having a carbon number of 3-6, a pharmacologically acceptable salt thereof, or a hydrate or solvate thereof.

5. The amide derivative of any of the above-mentioned 1. to 4., wherein X is a carbon atom (any of $R^{4a}$, $R^{4b}$ and $R^{4c}$ may be bonded to the carbon atom, but the carbon atom is not substituted by oxo), a pharmacologically acceptable salt thereof, or a hydrate or solvate thereof.

6. The amide derivative of any of the above-mentioned 1. to 4., wherein $R^1$ and $R^2$ are the same or different and each is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, cyano, alkylthio having a carbon number of 1-6 and optionally having substituent(s), alkylsulfinyl having a carbon number of 1-6 and optionally having substituent(s) or alkylsulfonyl having a carbon number of 1-6 and optionally having substituent(s), wherein $R^1$ and $R^2$ are not simultaneously hydrogen atoms, $R^3$ is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, cyano, alkylthio having a carbon number of 1-6 and optionally having substituent(s), alkylsulfinyl having a carbon number of 1-6 and optionally having substituent(s) or alkylsulfonyl having a carbon number of 1-6 and optionally having substituent(s), $R^{4a}$, $R^{4b}$ and $R^{4c}$ are each independently a hydrogen atom or alkyl having a carbon number of 1-6 and optionally having substituent(s), $R^{5a}$, $R^{5b}$ and $R^{5c}$ are the same or different hydrogen atom, alkyl having a carbon number of 1-6 and optionally having substituent(s) or aryl having a carbon number of 6-10 and optionally having substituent(s), X is a carbon atom (any of $R^{4a}$, $R^{4b}$ and $R^{4c}$ may be bonded to the carbon atom, but the carbon atom is not substituted by oxo), Y is carbonyl or an oxygen atom, $Z^1$ and $Z^2$ are each a carbon atom (substituent $R^3$ is optionally bonded to the carbon atom), and m is 1, a pharmacologically acceptable salt thereof, or a hydrate or solvate thereof.

7. The amide derivative of any of the above-mentioned 1. to 4., wherein X is a nitrogen atom (nitrogen atom may be oxidized to form N-oxide), a pharmacologically acceptable salt thereof, or a hydrate or solvate thereof.

8. The amide derivative of any of the above-mentioned 1. to 4., wherein $R^1$ and $R^2$ are the same or different and each is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, cyano, alkylthio having a carbon number of 1-6 and optionally having substituent(s), alkylsulfinyl having a carbon number of 1-6 and optionally having substituent(s) or alkylsulfonyl having a carbon number of 1-6 and optionally having substituent(s), wherein $R^1$ and $R^2$ are not simultaneously hydrogen atoms, $R^3$ is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, cyano, alkylthio having a carbon number of 1-6 and optionally having substituent(s), alkylsulfinyl having a carbon number of 1-6 and optionally having substituent(s) or alkylsulfonyl having a carbon number of 1-6 and optionally having substituent(s), $R^{4a}$, $R^{4b}$ and $R^{4c}$ are each independently a hydrogen atom, alkyl having a carbon number of 1-6 and optionally having substituent(s) or oxo, $R^{5a}$, $R^{5b}$ and $R^{5c}$ are the same or different hydrogen atom, alkyl having a carbon number of 1-6 and optionally having substituent(s) or aryl having a carbon number of 6-10 and optionally having substituent(s), X is a nitrogen atom (nitrogen atom may be oxidized to foist N-oxide), Y is a single bond, $Z^1$ and $Z^2$ are each independently a carbon atom (substituent $R^3$ is optionally bonded to the carbon atom) or a nitrogen atom, and m is 1 or 2, a pharmacologically acceptable salt thereof, or a hydrate or solvate thereof.

9. The amide derivative of any of the above-mentioned 1. to 4. and 8., wherein $R^1$ and $R^2$ are the same or different and each is alkyl having a carbon number of 1-6 and optionally having substituent(s), cycloalkyl having a carbon number of 3-6 and optionally having substituent(s), alkoxy having a carbon number of 1-6 and optionally having substituent(s), a halogen atom or cyano, $R^3$ is a hydrogen atom, alkyl having a carbon number of 1-6 and optionally having substituent(s), cycloalkyl having a carbon number of 3-6 and optionally having substituent(s), alkoxy having a carbon number of 1-6 and optionally having substituent(s), a halogen atom or cyano, $R^{4a}$, $R^{4b}$ and $R^{4c}$ are each independently a hydrogen atom or alkyl having a carbon number of 1-6 and optionally having substituent(s), $R^{5a}$, $R^{5b}$ and $R^{5c}$ are the same or different and each is a hydrogen atom, alkyl having a carbon number of 1-6 and optionally having substituent(s) or aryl having a carbon number of 6-10 and optionally having substituent(s), X is a nitrogen atom (nitrogen atom may be oxidized to form N-oxide), Y is a single bond, $Z^1$ and $Z^2$ are each independently a carbon atom (substituent $R^3$ is optionally bonded to the carbon atom) or a nitrogen atom, and m is 1 or 2, a pharmacologically acceptable salt thereof, or a hydrate or solvate thereof.

10. A pharmaceutical composition comprising the amide derivative of any of the above-mentioned 1. to 9., a pharmacologically acceptable salt thereof, or a hydrate or solvate thereof and a pharmaceutically acceptable additive.

11. An agent for suppressing MMP-9 production, comprising the amide derivative of any of the above-mentioned 1. to 9., a pharmacologically acceptable salt thereof, or a hydrate or solvate thereof.

12. An agent for the prophylaxis and/or treatment of an autoimmune disease or inflammatory bowel disease comprising the amide derivative of any of the above-mentioned 1. to 9., a pharmacologically acceptable salt thereof, or a hydrate or solvate thereof.

13. The agent of the above-mentioned 12., wherein the autoimmune disease is rheumatoid arthritis, multiple sclerosis or systemic lupus erythematosus.

14. The agent of the above-mentioned 12., wherein the inflammatory bowel disease is Crohn's disease or ulcerative colitis.

15. An agent for the prophylaxis and/or treatment of osteoarthritis, comprising the amide derivative of the above-mentioned 1. to 9., a pharmacologically acceptable salt thereof, or a hydrate or solvate thereof.

Effect of the Invention

Since the compound of the present invention selectively suppresses production of induction type MMPs, particularly MMP-9, rather than production of hemostatic type MMP-2, it is useful as an agent for the prophylaxis and/or treatment of autoimmune diseases such as rheumatoid arthritis and the like, inflammatory bowel diseases (ulcerative colitis, Crohn's disease) and osteoarthritis.

DESCRIPTION OF EMBODIMENTS

The compound of the present invention is the above-mentioned amide derivative represented by the formula (I), a pharmacologically acceptable salt thereof or a hydrate or solvate thereof. In the following, the meanings of the terms used in the present specification are described, and the present invention is explained in more detail. The explanation of the following terms does not limit the present invention in any way.

The alkyl having a carbon number of 1-6 is straight chain or branched chain alkyl, and methyl, ethyl, propyl, isopropyl, butyl, isobutyl, secondary butyl, tertiary butyl, pentyl, 3-methylbutyl, neopentyl, hexyl, 2-ethylbutyl and the like can be mentioned.

The alkenyl having a carbon number of 2-6 is straight chain or branched chain alkenyl, and vinyl, allyl, 1-propenyl, isopropenyl, 2-butenyl, 3-butenyl, 2-pentenyl, 4-pentenyl, 3-methyl-2-butenyl, 5-hexenyl, 4-methyl-3-pentenyl and the like can be mentioned.

The alkynyl having a carbon number of 2-6 is straight chain or branched chain alkynyl, and ethynyl, propynyl, butynyl, pentynyl, hexynyl and the like can be mentioned.

As the cycloalkyl having a carbon number of 3-6, cyclopropyl, cyclobutyl, cyclopentyl, cyclohexyl and the like can be mentioned.

As the aryl having a carbon number of 6-10, phenyl, naphthyl and the like can be mentioned.

The heteroaryl containing 1 to 6 nitrogen atom(s), oxygen atom(s) and sulfur atom(s) and having a ring-constituting atom number of 5-10 is a monovalent group induced from a monocyclic aromatic heterocycle containing 1 to 3 from a nitrogen atom, an oxygen atom and a sulfur atom and having a ring-constituting atom number of 5 or 6, a fused ring of this monocyclic aromatic heterocycle and benzene and a fused ring of the same or different these two monocyclic aromatic heterocycles, which groups may be partially or entirely reduced. Specific examples include, pyrrolyl, furyl, thienyl, pyrazolyl, imidazolyl, triazolyl, oxazolyl, isoxazolyl, thiazolyl, isothiazolyl, furazanyl, pyridyl, pyranyl, thiopyranyl, pyridazinyl, pyrimidinyl, pyrazinyl, triazinyl, oxazinyl, tetrazinyl, indolyl, indolinyl, benzofuranyl, 2,3-dihydrobenzofuranyl, benzothienyl, benzoxazolyl, benzimidazolyl, benzothiazolyl, quinolyl, isoquinolyl, quinoxalinyl, quinazolinyl and the like.

The alkoxy having a carbon number of 1-6 is straight chain or branched chain alkoxy, and methoxy, ethoxy, propoxy, isopropoxy, butoxy, isobutoxy, secondary butoxy, tertiary butoxy, pentoxy, 3-methylbutoxy, neopentoxy, hexyloxy, 2-ethylbutoxy and the like can be mentioned.

As the acyl having a total carbon number of 2-7, alkanoyl such as acetyl, propionyl, butyryl, isobutyryl, valeryl, isovaleryl, hexanoyl and the like, cycloalkylcarbonyl such as cyclopropylcarbonyl, cyclopentylcarbonyl, cyclohexylcarbonyl and the like, benzoyl and the like can be mentioned.

As the acyloxy having a total carbon number of 2-7, acetoxy, ethylcarbonyloxy, propylcarbonyloxy, isopropylcarbonyloxy, butylcarbonyloxy, isobutylcarbonyloxy, secondary butylcarbonyloxy, tertiary butylcarbonyloxy, pentylcarbonyloxy, neopentylcarbonyloxy, hexylcarbonyloxy, cyclopentylcarbonyloxy, cyclohexylcarbonyloxy, benzoyloxy and the like can be mentioned.

The halogen atom means a fluorine atom, a chlorine atom, a bromine atom or an iodine atom.

The alkylthio having a carbon number of 1-6 is straight chain or branched chain alkylthio, and methylthio, ethylthio, propylthio, isopropylthio, butylthio, isobutylthio, secondary butylthio, tertiary butylthio, pentylthio, 3-methylbutylthio, neopentylthio, hexylthio, 2-ethylbutylthio and the like can be mentioned.

The alkylsulfinyl having a carbon number of 1-6 is straight chain or branched chain alkylsulfinyl, and methanesulfinyl, ethylsulfinyl, propylsulfinyl, butylsulfinyl, pentylsulfinyl, hexylsulfinyl and the like can be mentioned.

The alkylsulfonyl having a carbon number of 1-6 is straight chain or branched chain alkylsulfonyl, and methanesulfonyl, ethylsulfonyl, propylsulfonyl, butylsulfonyl, pentylsulfonyl, hexylsulfonyl and the like can be mentioned.

The alkylamino having a carbon number of 1-6 is straight chain or branched chain alkylamino, and methylamino, ethylamino, propylamino, isopropylamino, butylamino, pentylamino, hexylamino and the like can be mentioned.

The dialkylamino having a total carbon number of 2-12 is straight chain or branched chain dialkylamino, and dimethylamino, diethylamino, dipropylamino, diisopropylamino, methylethylamino and the like can be mentioned.

The cyclic amino is a 5-7-membered cyclic group containing a nitrogen atom, which is bonded via the nitrogen atom (ring constituting atoms other than nitrogen atom are selected from a carbon atom, an oxygen atom and a sulfur atom), and examples thereof include aziridinyl, azetidinyl, pyrrolidinyl, piperidyl, piperazinyl, azepanyl, morpholinyl, thiomorpholinyl, thiazolidinyl, isothiazolidinyl, oxazolidinyl, imidazolidinyl, 1,2-thiazinanyl and the like, which are bonded via a nitrogen atom. In addition to these, specific examples of the cyclic amino include 2-oxopyrrolidin-1-yl, 2-oxoimidazolidin-1-yl and 2-oxooxazolidin-3-yl, wherein the carbon atom on the ring is substituted by oxo, 1-oxoisothiazolidin-2-yl, 1,1-dioxoisothiazolidin-2-yl, 1-oxo-1,2-thiazinan-2-yl and 1,1-dioxo-1,2-thiazinan-2-yl, wherein the sulfur atom on the ring is mono-substituted or di-substituted by oxo, and the like.

The acylamino having a total carbon number of 2-7 is amino substituted by the aforementioned acyl having a carbon number of 2-7, and alkanoylamino such as acetylamino, propionylamino, butyrylamino, isobutyrylamino, valerylamino, isovalerylamino, hexanoylamino and the like; cycloalkylcarbonylamino such as cyclopropylcarbonylamino, cyclopentylcarbonylamino, cyclohexylcarbonylamino and the like; benzoylamino and the like can be mentioned.

The alkylaminocarbonyl having a total carbon number of 2-7 is straight chain or branched chain alkylaminocarbonyl, and methylaminocarbonyl, ethylaminocarbonyl, propylaminocarbonyl, isopropylaminocarbonyl, butylaminocarbonyl, pentylaminocarbonyl, hexylaminocarbonyl and the like can be mentioned.

As the cycloalkylaminocarbonyl having a total carbon number of 4-7, cyclopropylaminocarbonyl, cyclobutylaminocarbonyl, cyclopentylaminocarbonyl, cyclohexylaminocarbonyl and the like can be mentioned.

The cyclic aminocarbonyl is a group wherein the aforementioned cyclic amino and carbonyl are bonded, and aziridin-1-ylcarbonyl, azetidin-1-ylcarbonyl, pyrrolidin-1-ylcarbonyl, piperidinocarbonyl, piperazin-1-ylcarbonyl, 1H-azepan-1-ylcarbonyl, morpholinocarbonyl, thiomorpholin-4-ylcarbonyl, thiazolidin-3-ylcarbonyl, isothiazolidin-2-ylcarbonyl, oxazolidin-3-ylcarbonyl, imidazolidin-1-ylcarbonyl and the like can be mentioned.

The alkylsulfonylamino having a carbon number of 1-6 is amino substituted by the aforementioned alkylsulfonyl having a carbon number of 1-6, and methanesulfonylamino, ethylsulfonylamino, propylsulfonylamino, butylsulfonylamino, pentylsulfonylamino, hexylsulfonylamino and the like can be mentioned.

The cycloalkylsulfonylamino having a carbon number of 3-6 is the aforementioned alkylsulfonylamino having a carbon number of 1-6, wherein the alkyl moiety has been substituted by the aforementioned cycloalkyl having a carbon number of 3-6, and cyclopropylsulfonylamino, cyclobutylsulfonylamino, cyclopentylsulfonylamino, cyclohexylsulfonylamino and the like can be mentioned.

The alkylaminosulfonyl having a carbon number of 1-6 is straight chain or branched chain alkylaminosulfonyl, and methylaminosulfonyl, ethylaminosulfonyl, propylaminosulfonyl, isopropylaminosulfonyl, butylaminosulfonyl, pentylaminosulfonyl, hexylaminosulfonyl and the like can be mentioned.

The cycloalkylaminosulfonyl having a carbon number of 3-6 is the aforementioned alkylaminosulfonyl having a carbon number of 1-6, wherein the alkyl moiety has been substituted by the aforementioned cycloalkyl having a carbon number of 3-6, and cyclopropylaminosulfonyl, cyclobutylaminosulfonyl, cyclopentylaminosulfonyl, cyclohexylaminosulfonyl and the like can be mentioned.

The cyclic aminosulfonyl is the aforementioned cyclic aminocarbonyl, wherein the carbonyl moiety has been substituted by sulfonyl, and aziridin-1-ylsulfonyl, azetidin-1-ylsulfonyl, pyrrolidin-1-ylsulfonyl, piperidinosulfonyl, piperazin-1-ylsulfonyl, 1H-azepan-1-ylsulfonyl, morpholinosulfonyl, thiomorpholin-4-ylsulfonyl, thiazolidin-3-ylsulfonyl, isothiazolidin-2-ylsulfonyl and the like can be mentioned.

The alkoxycarbonyl having a total carbon number of 2-7 is a group wherein the aforementioned alkoxy having a carbon number of 1-6 is bonded to carbonyl, and methoxycarbonyl, ethoxycarbonyl, propoxycarbonyl, isopropoxycarbonyl, butoxycarbonyl, isobutoxycarbonyl, secondary butoxycarbonyl, tertiary butoxycarbonyl, pentoxycarbonyl, 3-methylbutoxycarbonyl, neopentoxycarbonyl, hexyloxycarbonyl, 2-ethylbutoxycarbonyl and the like can be mentioned.

As the substituent that alkyl having a carbon number of 1-6, alkenyl having a carbon number of 2-6, alkynyl having a carbon number of 2-6, cycloalkyl having a carbon number of 3-6, alkoxy having a carbon number of 1-6, acyl having a total carbon number of 2-7, acyloxy having a total carbon number of 2-7, alkylthio having a carbon number of 1-6, alkylsulfinyl having a carbon number of 1-6, alkylsulfonyl having a carbon number of 1-6, alkylamino having a carbon number of 1-6, dialkylamino having a total carbon number of 2-12, and alkoxycarbonyl having a total carbon number of 2-7 may have, the aforementioned aryl having a carbon number of 6-10, the aforementioned heteroaryl containing 1 to 3 from a nitrogen atom, an oxygen atom and a sulfur atom and having a ring-constituting atom number of 5 or 6, the aforementioned alkoxy having a carbon number of 1-6 optionally substituted by alkoxy having a carbon number of 1-6, the aforementioned acyloxy having a total carbon number of 2-7, the aforementioned halogen atom, a hydroxyl group, nitro, cyano, amino and the like can be mentioned.

As the substituent that aryl having a carbon number of 6-10, heteroaryl containing 1 to 6 nitrogen atom(s), oxygen atom(s) and sulfur atom(s) and having a ring-constituting atom number of 5-10, and cyclic amino may have, the aforementioned alkyl having a carbon number of 1-6, the aforementioned alkoxy having a carbon number of 1-6, the aforementioned acyl having a total carbon number of 2-7, the aforementioned acyloxy having a total carbon number of 2-7, the aforementioned halogen atom, a hydroxyl group, nitro, cyano, the aforementioned alkylsulfonyl having a carbon number of 1-6, amino, the aforementioned alkoxycarbonyl having a carbon number of 2-7, carboxy, carbamoyl, amide, sulfonamide, haloalkyl having a carbon number of 1-6, aralkyl having a carbon number of 7-16, oxo and the like can be mentioned.

The haloalkyl having a carbon number of 1-6 is the aforementioned alkyl having a carbon number of 1-6 which is substituted by the aforementioned halogen atom, and fluoromethyl, difluoromethyl, trifluoromethyl, fluoroethyl, difluoroethyl, trifluoroethyl, pentafluoroethyl, fluoropropyl, trifluoropropyl, pentafluoropropyl, fluoroisopropyl, difluoroisopropyl, fluorobutyl, trifluorobutyl, pentafluorobutyl, fluoropentyl, trifluoropentyl, fluorohexyl, trifluoro n-hexyl and the like, as well as the substituents exemplified here in which fluorine atom is partially or entirely substituted by other halogen atom and the like can be mentioned.

The aralkyl having a carbon number of 7-16 is the aforementioned alkyl having a carbon number of 1-6, which is substituted by the aforementioned aryl having a carbon number of 6-10, and benzyl, phenethyl, phenylpropyl, naphthylmethyl, naphthylethyl and the like can be mentioned.

In one embodiment, in the above-mentioned formula (I), A is preferably a group represented by the following formula

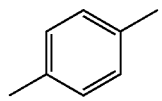

wherein benzene optionally has one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6 and cyclic aminosulfonyl, the right bond is bonded to carbonyl, and the left bond is bonded to a nitrogen atom.

In another embodiment, in the above-mentioned formula (I), A is preferably a group represented by the following formula

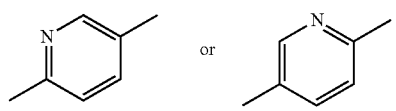

wherein pyridine optionally has one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6 and cyclic aminosulfonyl, the right bond is bonded to carbonyl, and the left bond is bonded to a nitrogen atom.

Preferably, in the above-mentioned formula (I), benzene and pyridine for A optionally have one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, hydroxyl group, nitro, cyano, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylsulfonylamino having a carbon number of 1-6 and cycloalkylsulfonylamino having a carbon number of 3-6.

The benzene and pyridine for A in the above-mentioned formula (I) are preferably unsubstituted or substituted by alkyl having a carbon number of 1-6, cycloalkyl having a carbon number of 3-6, alkoxy having a carbon number of 1-6, a halogen atom, nitro, cyano, alkylsulfonyl having a carbon number of 1-6, amino, cyclic amino, acylamino having a total carbon number of 2-7 or alkylsulfonylamino having a carbon number of 1-6, more preferably unsubstituted or substituted by alkyl having a carbon number of 1-6, a halogen atom, cyano, alkylsulfonyl having a carbon number of 1-6, 2-oxopyrrolidin-1-yl, 2-oxoimidazolidin-1-yl, 2-oxooxazolidin-3-yl or 1,1-dioxoisothiazolidin-2-yl. When substituents are present, the number thereof is preferably 1 or 2.

In one embodiment, in the above-mentioned formula (I), $R^1$ and $R^2$ are preferably are the same or different and each is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, cyano, alkylthio having a carbon number of 1-6 and optionally having substituent(s), alkylsulfinyl having a carbon number of 1-6 and optionally having substituent(s) or alkylsulfonyl having a carbon number of 1-6 and optionally having substituent(s), wherein $R^1$ and $R^2$ are not simultaneously hydrogen atoms, more preferably, the same or different and each is alkyl having a carbon number of 1-6 and optionally having substituent(s), cycloalkyl having a carbon number of 3-6 and optionally having substituent(s), alkoxy having a carbon number of 1-6 and optionally having substituent(s), a halogen atom or cyano.

More preferable examples of $R^1$ include a hydrogen atom, alkyl having a carbon number of 1-6, haloalkyl having a carbon number of 1-6, alkenyl having a carbon number of 2-6, cycloalkyl having a carbon number of 3-6, alkoxy having a carbon number of 1-6 and a halogen atom, still more preferable examples include a hydrogen atom, alkyl having a carbon number of 1-6, alkenyl having a carbon number of 2-6, cycloalkyl having a carbon number of 3-6 and a halogen atom, and particularly preferable examples include alkyl having a carbon number of 1-6 and cycloalkyl having a carbon number of 3-6. Most preferably examples include alkyl having a carbon number of 1-6.

More preferable examples of $R^2$ include a hydrogen atom, alkyl having a carbon number of 1-6, haloalkyl having a carbon number of 1-6, cycloalkyl having a carbon number of 3-6, aryl having a carbon number of 6-10, alkoxy having a carbon number of 1-6, a halogen atom and cyano, still more preferable examples include alkyl having a carbon number of 1-6, haloalkyl having a carbon number of 1-6, cycloalkyl having a carbon number of 3-6, a halogen atom and cyano, and particularly preferable examples include alkyl having a carbon number of 1-6 and cycloalkyl having a carbon number of 3-6. Most preferably examples include alkyl having a carbon number of 1-6.

In one embodiment, in the above-mentioned formula (I), $R^3$ is preferably a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, cyano, alkylthio having a carbon number of 1-6 and optionally having substituent(s), alkylsulfinyl having a carbon number of 1-6 and optionally having substituent(s) or alkylsulfonyl having a carbon number of 1-6 and optionally having substituent(s), more preferably, a hydrogen atom, alkyl having a carbon number of 1-6 and optionally having substituent(s), cycloalkyl having a carbon number of 3-6 and optionally having substituent(s), alkoxy having a carbon number of 1-6 and optionally having substituent(s), a halogen atom or cyano.

More preferable examples of $R^3$ include a hydrogen atom, alkyl having a carbon number of 1-6, cycloalkyl having a carbon number of 3-6, a halogen atom and cyano, more preferable examples include a hydrogen atom, alkyl having a carbon number of 1-6, and a halogen atom, and particularly preferable examples include a hydrogen atom. Preferable binding position of $R^3$ is

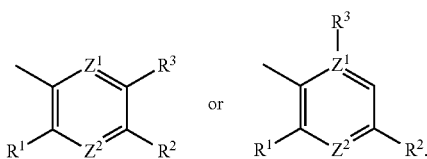

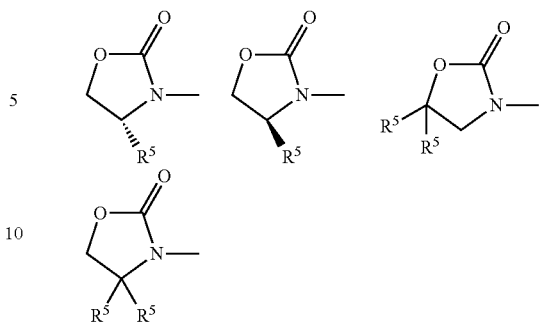

In one embodiment, in the above-mentioned formula (I), $R^{4a}$, $R^{4b}$ and $R^{4c}$ are preferably each independently a hydrogen atom or alkyl having a carbon number of 1-6 and optionally having substituent(s).

In another embodiment, in the above-mentioned formula (I), $R^{4a}$, $R^{4b}$ and $R^{4c}$ are preferably each independently a hydrogen atom, alkyl having a carbon number of 1-6 and optionally having substituent(s) or oxo.

More preferable examples of $R^{4a}$, $R^{4b}$ and $R^{4c}$ include a hydrogen atom, alkyl having a carbon number of 1-6 and oxo. More preferable examples include a hydrogen atom, alkyl having a carbon number of 1-6. Particularly preferable examples include a hydrogen atom.

In one embodiment, in the above-mentioned formula (I), $R^{5a}$, $R^{5b}$ and $R^{5c}$ are preferably the same or different and each is a hydrogen atom, alkyl having a carbon number of 1-6 and optionally having substituent(s) or aryl having a carbon number of 6-10 and optionally having substituent(s).

More preferably, $R^{5a}$, $R^{5b}$ and $R^{5c}$ are each a hydrogen atom, alkyl having a carbon number of 1-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxycarbonyl having a total carbon number of 2-7 and optionally having substituent(s) or oxo.

More preferable examples of $R^{5a}$, $R^{5b}$ and $R^{5c}$ include hydrogen atom, alkyl having a carbon number of 1-6 and optionally having substituent(s), and aryl having a carbon number of 6-10. Still more preferable examples include a hydrogen atom, alkyl having a carbon number of 1-6, aryl having a carbon number of 6-10, alkyl having a carbon number of 1-6, which is substituted by aryl having a carbon number of 6-10, alkyl having a carbon number of 1-6, which is substituted by a hydroxyl group, alkyl having a carbon number of 1-6 which is substituted by alkoxy having a carbon number of 1-6, alkyl having a carbon number of 1-6, which is substituted by alkoxy having a carbon number of 1-6 which is substituted by alkoxy having a carbon number of 1-6, alkyl having a carbon number of 1-6 which is substituted by acyloxy having a total carbon number of 2-7, most preferable examples include a hydrogen atom, alkyl having a carbon number of 1-6, alkyl having a carbon number of 1-6, which is substituted by a hydroxyl group, and alkyl having a carbon number of 1-6, which is substituted by alkoxy having a carbon number of 1-6. Particularly, most preferable examples include a hydrogen atom and alkyl having a carbon number of 1-6.

Oxazolidin-2-one is preferably unsubstituted or substituted at the following positions for substitution ($R^5$ in the chemical formulas is any of $R^{5a}$, $R^{5b}$ and $R^{5c}$, but is not a hydrogen atom),

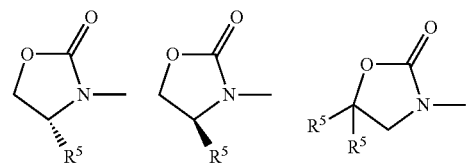

still more preferably, substituted at the following substitution,

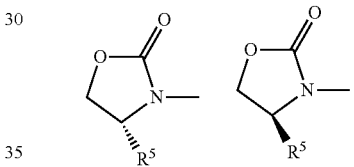

furthermore preferably, substituted at the following substitution positions,

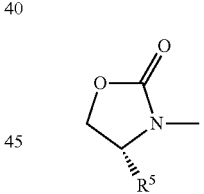

particularly preferably, substituted at the following substitution positions.

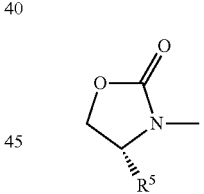

In one embodiment, in the above-mentioned formula (I), X is preferably a carbon atom (any of $R^{4a}$, $R^{4b}$ and $R^{4c}$ may be bonded to the carbon atom, and the carbon atom is not substituted by oxo).

In another embodiment, in the above-mentioned formula (I), X is preferably a nitrogen atom (nitrogen atom may be oxidized to form N-oxide).

In one embodiment, in the above-mentioned formula (I), Y is preferably carbonyl or an oxygen atom.

In another embodiment, in the above-mentioned formula (I), Y is preferably a single bond.

In one embodiment, in the above-mentioned formula (I), $Z^1$ and $Z^2$ are each preferably carbon atom (substituent $R^3$ is optionally bonded to the carbon atom).

When Y is carbonyl or an oxygen atom, X is preferably a carbon atom, $R^3$ is preferably a hydrogen atom, $Z^1$ and $Z^2$ are each preferably a carbon atom. When Y is a single bond, X is preferably a nitrogen atom, and $Z^2$ is preferably a carbon atom. When Y is a single bond, X is particularly preferably a nitrogen atom, $Z^1$ is particularly preferably a nitrogen atom, and $Z^2$ is particularly preferably a carbon atom.

m is preferably 1.

The "pharmacologically acceptable salt" is not particularly limited as long as it is acceptable as a medicament, and salt with inorganic acid, salt with organic acid, salt with alkali metal, salt with alkaline earth metal, salt with inorganic base, and salt with organic base can be mentioned.

The "pharmaceutically acceptable" in the present specification means being generally safe and harmless, and may be biologically undesirable but preferable in other aspects, and include those useful for the preparation of pharmaceutical compositions usable as medicament for human as well as veterinary medicine.

While the compound of the present invention can be produced by the following methods, the production methods are note limited.

The compound (I) of the present invention can be produced by the following Method A, B, C, D, E or F.

Method A (Step 1)

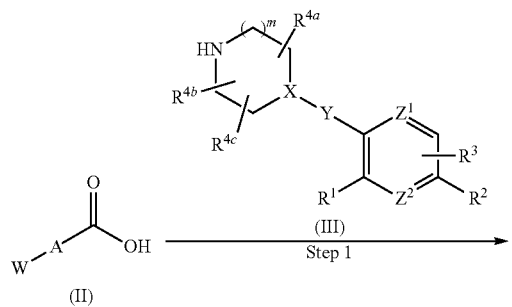

wherein W is a chlorine atom, a bromine atom or an iodine atom, and other symbols are as defined above.

By reacting a compound represented by the formula (II) with a compound represented by the formula (III), the corresponding compound represented by the formula (IV) can be obtained. The reaction proceeds using a condensing agent in a suitable solvent at 0° C.—at room temperature. As the condensing agent, 4-(4,6-dimethoxy[1.3.5]triazin-2-yl)-4-methylmorpholinium chloride hydrate (DMT-MM), 1-ethyl-3-(3'-dimethylaminopropyl)carbodiimide hydrochloride (WSC HCl) and the like can be mentioned. As the solvent, methanol, N,N-dimethylformamide, chloroform, tetrahydrofuran and the like can be mentioned. The reaction may be promoted by the addition of 1-hydroxybenzotriazole (HOBt). When a compound represented by the formula (III) forms a salt with an acid, the reaction proceeds by neutralization by the addition of a base.

Method A (Step 1, Alternative Method)

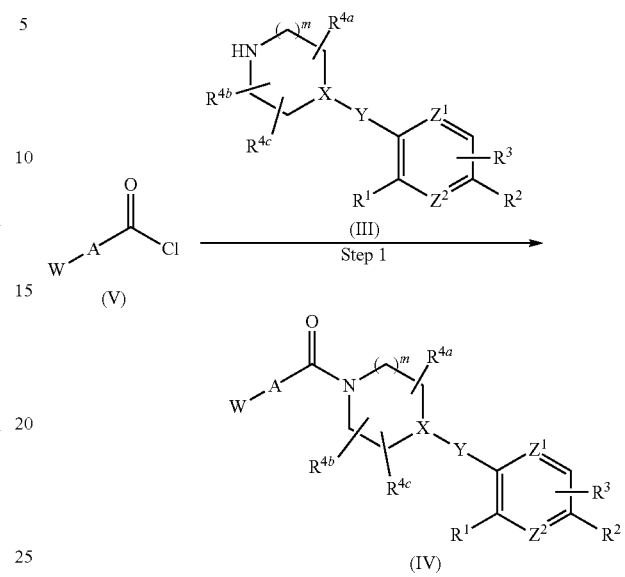

wherein the symbols are as defined above.

By reacting a compound represented by the formula (V) with a compound represented by the formula (III), the corresponding compound represented by the formula (IV) is obtained. The reaction proceeds by using a base in a suitable solvent at 0° C.—room temperature. Examples of the base include aqueous sodium hydroxide solution, triethylamine, N-methylmorpholine and the like. Examples of the solvent include tetrahydrofuran, dimethoxyethane, ethyl acetate and the like.

Method A (Step 2)

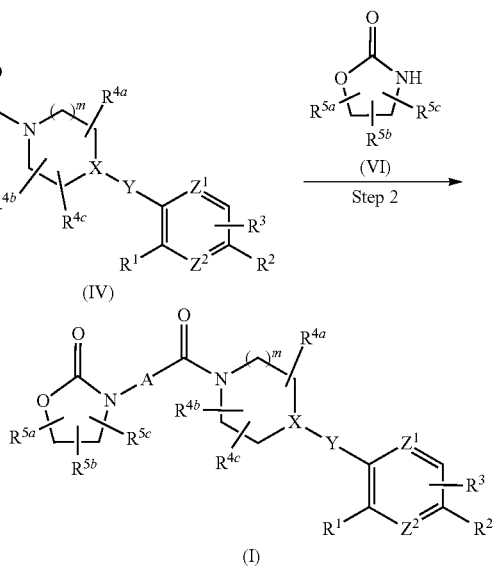

wherein the symbols are as defined above.

By reacting a compound represented by the formula (IV) with a compound represented by the formula (VI), the corresponding compound represented by the formula (I) is obtained. The reaction proceeds by heating with a copper catalyst, a ligand and a base in a suitable solvent. Examples of the copper catalyst include copper (I) iodide and the like. Examples of the ligand include N,N'-dimethylethylenediamine and the like. Examples of the base include potassium carbonate, tripotassium phosphate, cesium carbonate and the like. Examples of the solvent include toluene, 1,4-dioxane and the like. The reaction also proceeds by heating with a palladium catalyst, a phosphine ligand and a base in a suitable solvent. Examples of the palladium catalyst include palladium (II) acetate, tris(dibenzylideneacetone)dipalladium (0) and the like. Examples of the phosphine ligand include 2-dicyclohexylphosphinobiphenyl, 2-di-tert-butylphosphinobiphenyl and the like. Examples of the base include tripotassium phosphate, cesium carbonate and the like. Examples of the solvent include toluene, tetrahydrofuran, 1,4-dioxane and the like.

Method B (Step 1)

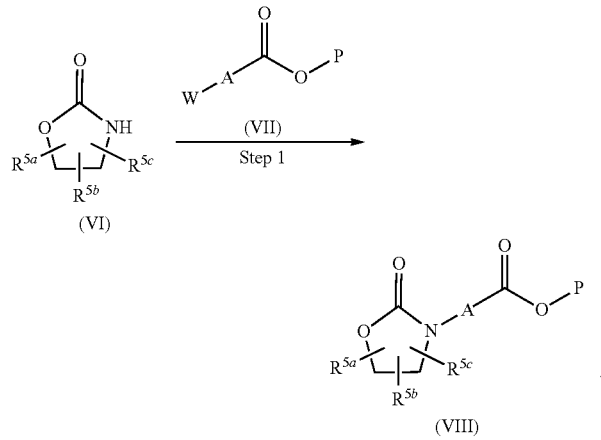

wherein P is a carboxyl-protecting group that can be removed by hydrolysis, and other symbols are as defined above.

By reacting a compound represented by the formula (VI) with a compound represented by the formula (VII), the corresponding compound represented by the formula (VIII) is obtained. The reaction proceeds by a method similar to Method A, Step 2.

Method B (Step 2)

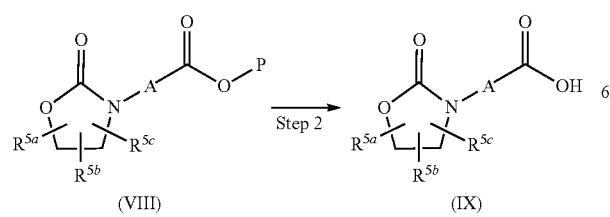

wherein the symbols are as defined above.

By subjecting a compound represented by the formula (VIII) to hydrolysis, the corresponding compound represented by the formula (IX) is obtained. The reaction proceeds by using a base in a suitable solvent at room temperature –80° C. Examples of the base include aqueous sodium hydroxide solution and the like. Examples of the solvent include methanol, ethanol, dioxane and the like.

Method B (Step 3)

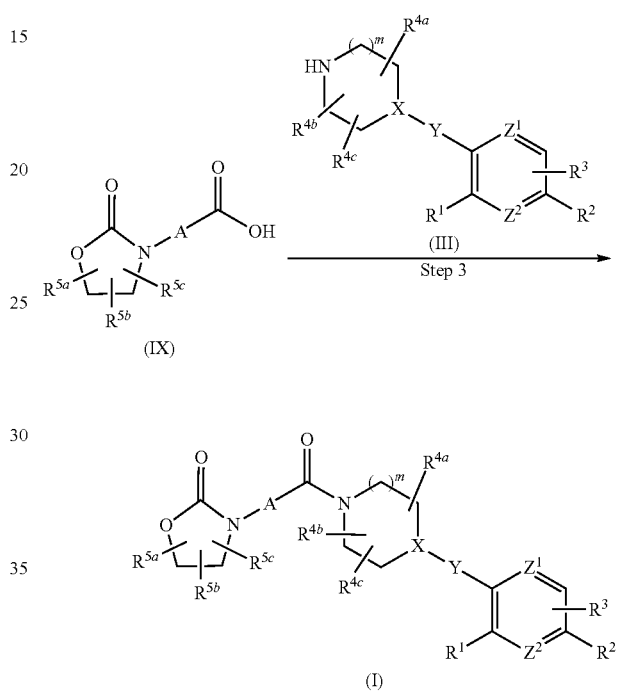

wherein the symbols are as defined above.

By reacting a compound represented by the formula (IX) with a compound represented by the formula (III), the corresponding compound represented by the formula (I) is obtained. The reaction proceeds by a method similar to Method A, Step 1. In addition, after hydrolysis of the formula (VIII), by reacting a compound represented by the formula (IX) with a compound represented by the formula (III) without isolation and purification, a compound represented by the formula (I) can also be obtained in one pot from the formula (VIII).

Method B (Step 3, Alternative Method)

A compound represented by the formula (I) wherein $R^1$, $R^2$ and $R^3$ are each a hydrogen atom, alkyl having a carbon number of 1-6 and optionally having substituent(s), alkenyl having a carbon number of 2-6 and optionally having substituent(s), cycloalkyl having a carbon number of 3-6 and optionally having substituent(s) or aryl having a carbon number of 6-10 and optionally having substituent(s) can also be produced by the following method.

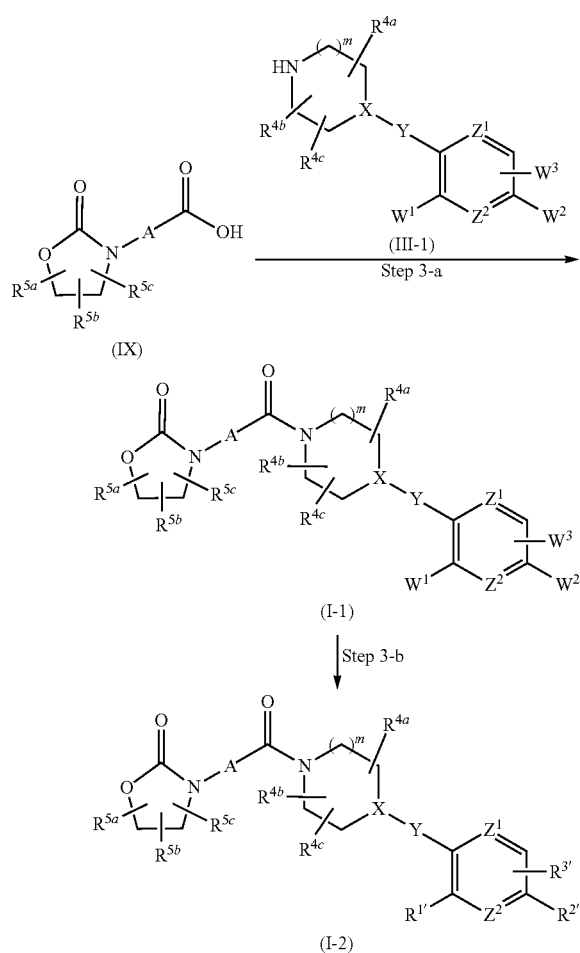

Method B (Step 3-b)

In this step, the chlorine atom, bromine atom and iodine atom of the substituents $W^1$, $W^2$ and $W^3$ in a compound represented by the formula (I-1) are each converted by Suzuki reaction to alkyl, alkenyl, cycloalkyl or aryl. The reaction proceeds by heating with a palladium catalyst, a phosphine ligand and a base in a suitable solvent. Examples of the palladium catalyst include palladium (II) acetate and the like. Examples of the phosphine ligand include 2-dicyclohexylphosphino-2,6-dimethoxybiphenyl and the like. A complex of a palladium catalyst and a phosphine ligand may also be used and, for example, [1,1'-bis(diphenylphosphino)ferrocene]palladium (II) dichloride dichloromethane complex, dichlorobis(tricyclohexylphosphine)palladium (II) and the like can be mentioned. Examples of the base include tripotassium phosphate, potassium fluoride and the like. Examples of the solvent include tetrahydrofuran, toluene, a mixed solvent of such organic solvent and water and the like.

Method C (Step 1)

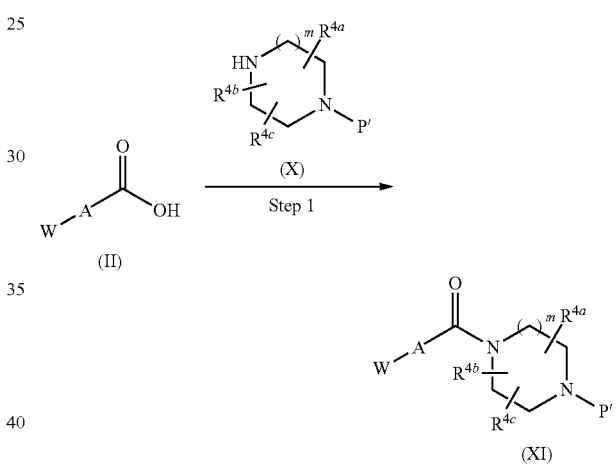

wherein P' is an amino-protecting group, and other symbols are as defined above.

By reacting a compound represented by the formula (II) with a compound represented by the formula (X), the corresponding compound represented by the formula (XI) is obtained. The reaction proceeds by a method similar to Method A, Step 1.

wherein $W^1$, $W^2$ and $W^3$ are each a hydrogen atom, a chlorine atom, a bromine atom, an iodine atom or alkyl having a carbon number of 1-6 and optionally having substituent(s), $R^{1'}$, $R^{2'}$ and $R^{3'}$ are each a hydrogen atom, alkyl having a carbon number of 1-6 and optionally having substituent(s), alkenyl having a carbon number of 2-6 and optionally having substituent(s), cycloalkyl having a carbon number of 3-6 and optionally having substituent(s) or aryl having a carbon number of 6-10 and optionally having substituent(s), provided that when $W^1$ is a hydrogen atom or alkyl having a carbon number of 1-6 and optionally having substituent(s), $R^{1'}$ is as defined for $W^1$, when $W^2$ is a hydrogen atom or alkyl having a carbon number of 1-6 and optionally having substituent(s), $R^{2'}$ is as defined for $W^2$, and when $W^3$ is a hydrogen atom or alkyl having a carbon number of 1-6 and optionally having substituent(s), $R^{3'}$ is as defined for $W^3$, and other symbols are as defined above.

Method B (Step 3-a)

By reacting a compound represented by the formula (IX) with a compound represented by the formula (III-1), the corresponding compound represented by the formula (I-1) is obtained. The reaction proceeds by a method similar to Method A, Step 1.

Method C (Step 2)

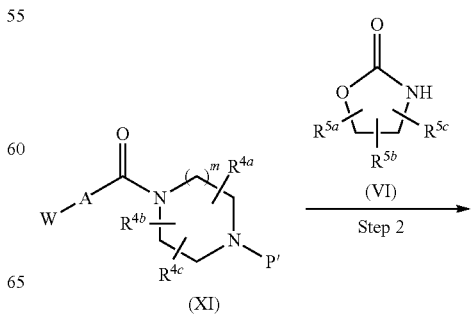

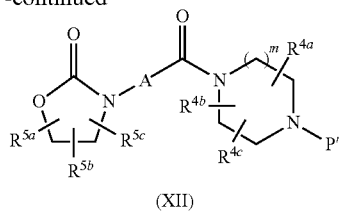

(XII)

wherein each symbol is as described above.

By reacting a compound represented by the formula (XI) with a compound represented by the formula (VI), the corresponding compound represented by the formula (XII) is obtained. The reaction proceeds by a method similar to Method A, Step 2.

Method C (Step 2, Alternative Method)

A compound represented by the formula (XII) wherein $R^{5a}$, $R^{5b}$ and $R^{5c}$ are each alkoxyalkyl (alkyl substituted by alkoxy) can also be produced by the following method. While a reaction scheme when the following $R^{5c}$ is alkoxyalkyl is shown as an example, the reaction also proceeds by a similar reaction scheme when $R^{5a}$ or $R^{5b}$ is alkoxyalkyl.

Method C (Step 2-b)

By subjecting only P''' of a compound represented by the formula (XII-1) to deprotection, the corresponding compound represented by the formula (XII-2) is obtained. When, for example, P''' is benzoyl, the reaction proceeds with a base in a suitable solvent at 0° C.-80° C. Examples of the base include aqueous sodium hydroxide solution and the like. Examples of the solvent include tetrahydrofuran, 1,4-dioxane, dimethoxyethane and the like.

Method C (Step 2-c)

By subjecting a compound represented by the formula (XII-2) to alkylation, the corresponding compound represented by the formula (XII-3) is obtained. The reaction proceeds with an alkylating agent and a base in a suitable solvent at 0° C.—room temperature. Examples of the alkylating agent include methyl iodide and the like. Examples of the base include sodium hydride and the like. Examples of the solvent include N,N-dimethylformamide and the like.

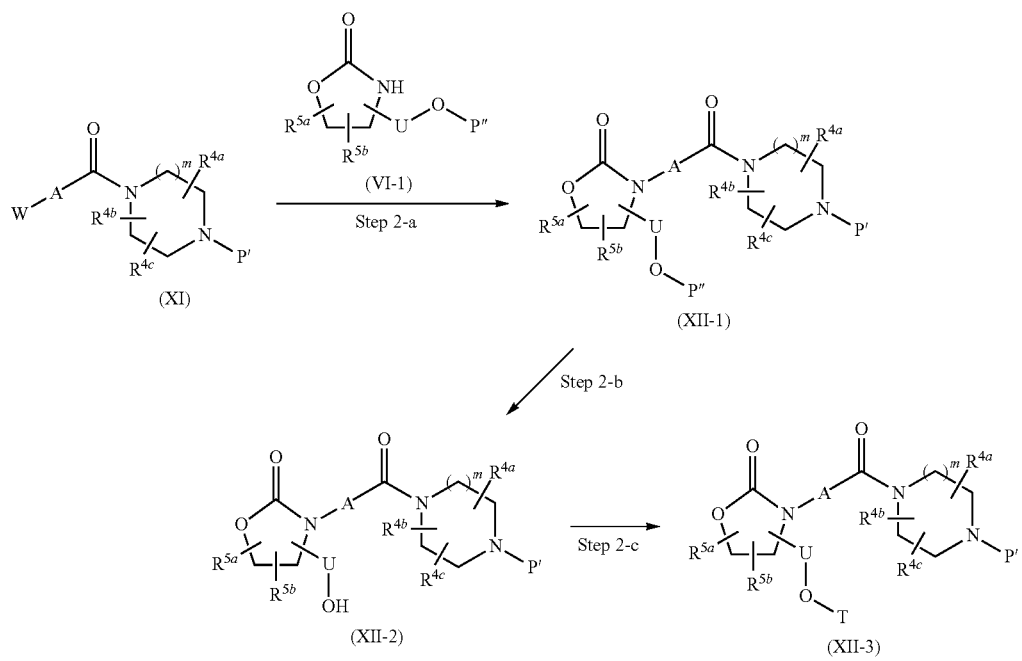

wherein P''' is a hydroxyl-protecting group, T is alkyl, U is alkylene, and other symbols are as defined above.

Method C (Step 2-a)

By reacting a compound represented by the formula (XI) with a compound represented by the formula (VI-1), the corresponding compound represented by the formula (XII-1) is obtained. The reaction proceeds by a method similar to Method A, Step 2.

Method C (Step 3)

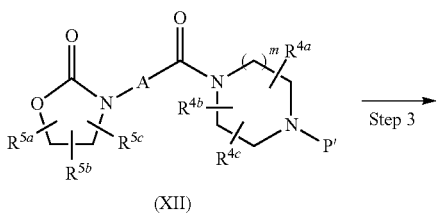

(XII)

-continued

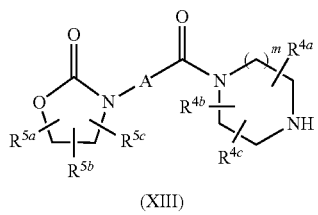

(XIII)

wherein the symbols are as defined above.

By removing the protecting group P' of a compound represented by the formula (XII), a compound represented by the formula (XIII) is obtained. When, for example, P' is a Boc group, the reaction proceeds with an acid in a suitable solvent at 0° C.—room temperature. Examples of the acid include hydrogen chloride/ethyl acetate and the like. Examples of the solvent include chloroform, ethyl acetate and the like.

Method C (Step 4)

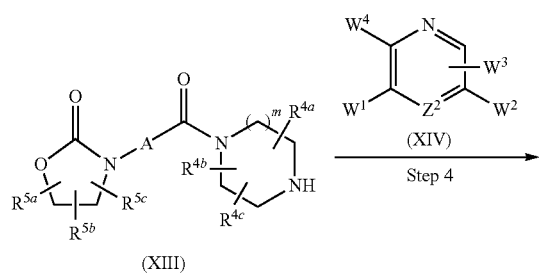

wherein $W^4$ is a fluorine atom, a chlorine atom, a bromine atom or an iodine atom, and other symbols are as defined above.

By reacting a compound represented by the formula (XIII) with a compound represented by the formula (XIV), the corresponding compound represented by the formula (XV) is obtained. The reaction proceeds by heating with a base in a suitable solvent. Examples of the base include potassium carbonate and the like. Examples of the solvent include N,N-dimethylformamide and the like.

Method C (Step 5)

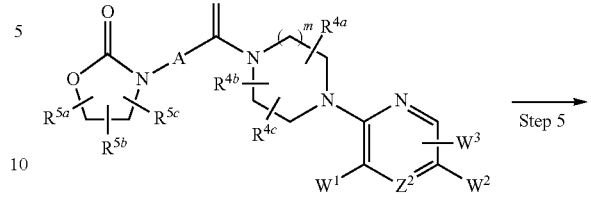

wherein each symbol is as described above.

By subjecting a compound represented by the formula (XV) to a Suzuki reaction, a compound represented by the formula (I-2) is obtained. The reaction proceeds by a method similar to Method B Step 3 alternative method, Step 3-b.

Method D (Step 1)

A compound represented by the formula (I) wherein A is a group represented by the following formula

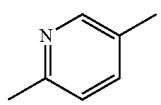

can also be produced by the following method.

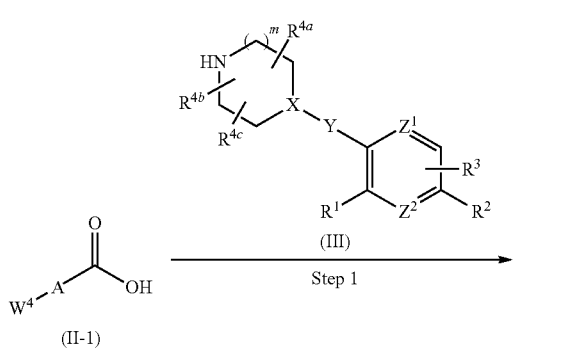

wherein $W^4$ is a fluorine atom, a chlorine atom, a bromine atom or an iodine atom, and other symbols are as defined above.

By reacting a compound represented by the formula (II-1) with a compound represented by the formula (III), the corresponding compound represented by the formula (IV-1) is obtained. The reaction proceeds by a method similar to Method A, Step 1.

Method D (Step 2)

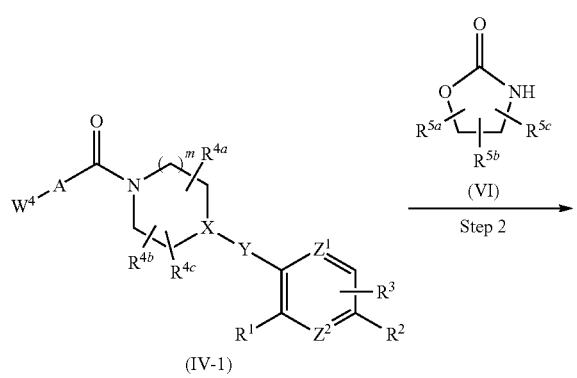

(IV-1)

(I)

wherein the symbols are as defined above.

By reacting a compound represented by the formula (IV-1) with a compound represented by the formula (VI), the corresponding compound represented by the formula (I) is obtained. The reaction proceeds by heating with a base in a suitable solvent. Examples of the base include sodium hydride and the like. Examples of the solvent include N,N-dimethylformamide and the like.

Method E (Step 1)

A compound represented by the formula (I) wherein A is cyclic amino optionally having substituent(s) can also be produced by the following method.

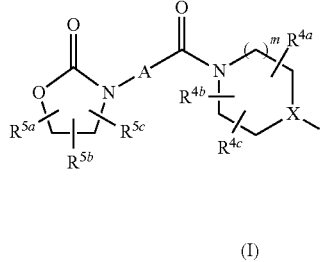

(IV-2)

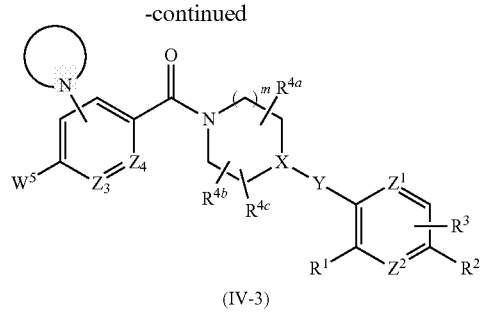

(IV-3)

wherein $W^5$ is a chlorine atom, $W^6$ is a bromine atom or an iodine atom, $Z^3$ and $Z^4$ are each independently a carbon atom (substituent is optionally bonded to the carbon atom) or a nitrogen atom and are not simultaneously nitrogen atoms, and other symbols are as defined above.

By reacting a compound represented by the formula (IV-2) with cyclic amine represented by the formula (VI-2) and optionally having substituent(s), the corresponding compound represented by the formula (IV-3) is obtained. The reaction proceeds by a method similar to Method A, Step 2.

Method E (Step 2)

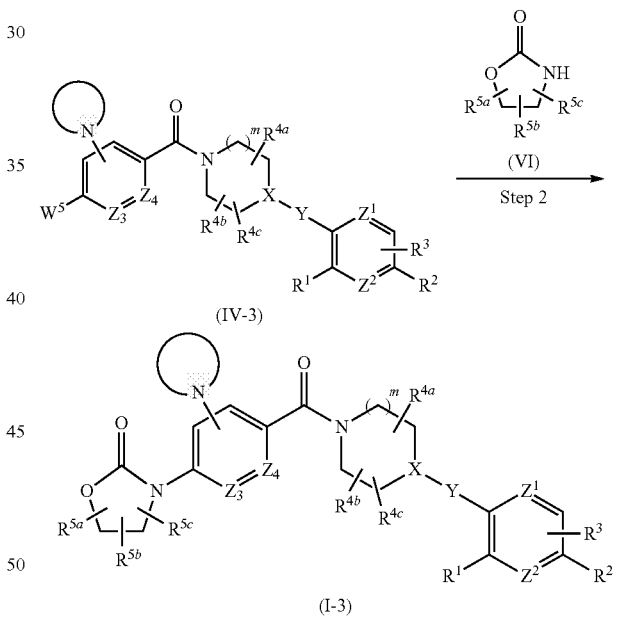

(I-3)

wherein the symbols are as defined above.

By reacting a compound represented by the formula (IV-3) with a compound represented by the formula (VI), the corresponding compound represented by the formula (I-3) is obtained. The reaction proceeds by a method similar to Method A, Step 2.

Method F (Step 1)

A compound represented by the formula (I), wherein $R^{5a}$, $R^{5b}$ and $R^{5c}$ are each alkoxyalkyl (alkyl substituted by alkoxy) can also be produced by the following method. While a reaction scheme when the following $R^{5c}$ is alkoxyalkyl is shown as an example, the reaction also proceeds by a similar reaction scheme when $R^{5a}$ and $R^{5b}$ are each alkoxyalkyl.

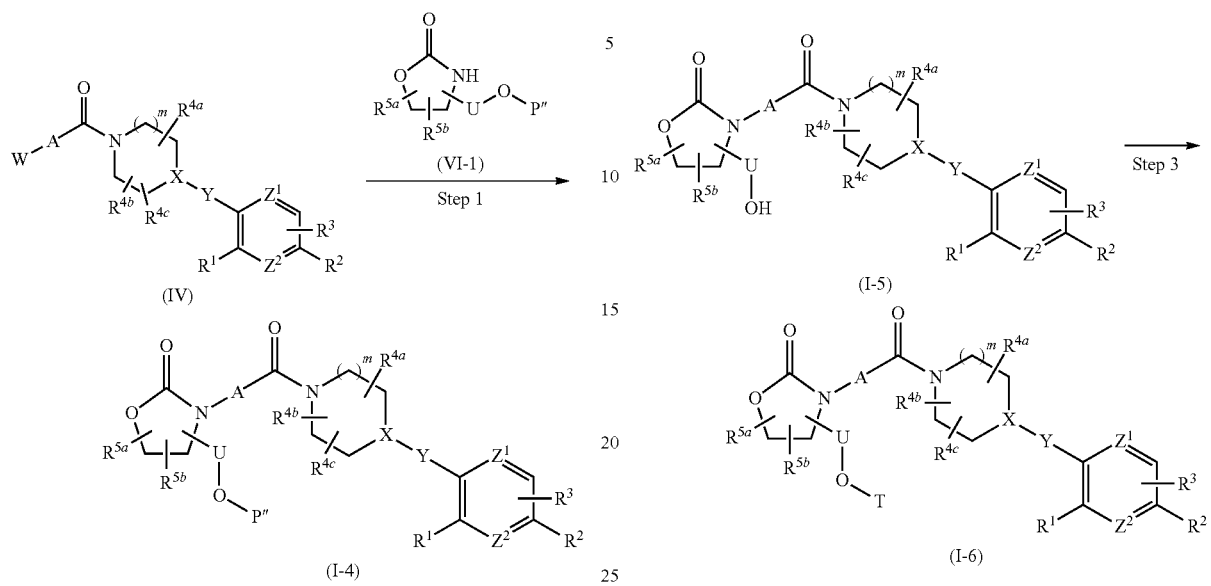

wherein the symbols are as defined above.

By reacting a compound represented by the formula (IV) with a compound represented by the formula (VI-1), the corresponding compound represented by the formula (I-4) is obtained. The reaction proceeds by a method similar to Method A, Step 2.

Method F (Step 2)


wherein the symbols are as defined above.

By subjecting only P''' of a compound represented by the formula (I-4) to deprotection, the corresponding compound represented by the formula (I-5) is obtained. The reaction proceeds by a method similar to Method C, Step 2-b.

Method F (Step 3)

wherein the symbols are as defined above.

By subjecting a compound represented by the formula (I-5) to alkylation, the corresponding compound represented by the formula (I-6) is obtained. The reaction proceeds by a method similar to Method C, Step 2-c.

A compound of the formula (I) wherein X is N-oxide and Y is a single bond (compound (I-8)) can be produced by the following method.

wherein the symbols are as defined above.

By subjecting a compound represented by the formula (I-7) to an oxidation reaction, a compound represented by the formula (I-8) is obtained. The reaction proceeds using an oxidant in a suitable solvent at 0° C.—room temperature. Examples of the oxidant include m-chloroperbenzoic acid and the like. Examples of the solvent include methylene chloride, chloroform and the like.

Preparation Method of Formula (III)

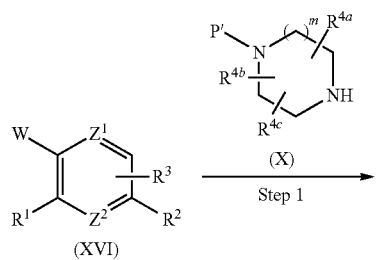

reaction proceeds by heating with a palladium catalyst, a phosphine ligand and a base in a suitable solvent. Examples of the palladium catalyst include palladium (II) acetate and the like. Examples of the phosphine ligand include 2-dicyclohexylphosphino-2,4,6-triisopropylbiphenyl and the like. A complex of a palladium catalyst and a phosphine ligand may be used and, for example, rac-2,2'-bis(diphenylphosphino)-1,1'-binaphthyl and the like can be mentioned. Examples of the base include sodium tert-butoxide and the like. Examples of the solvent include toluene and the like.

(Step 2)

A compound represented by the formula (III) is obtained by subjecting a compound represented by the formula (XVII) to a method similar to Method C, Step 3.

Alternative Preparation Method of Formula (III)

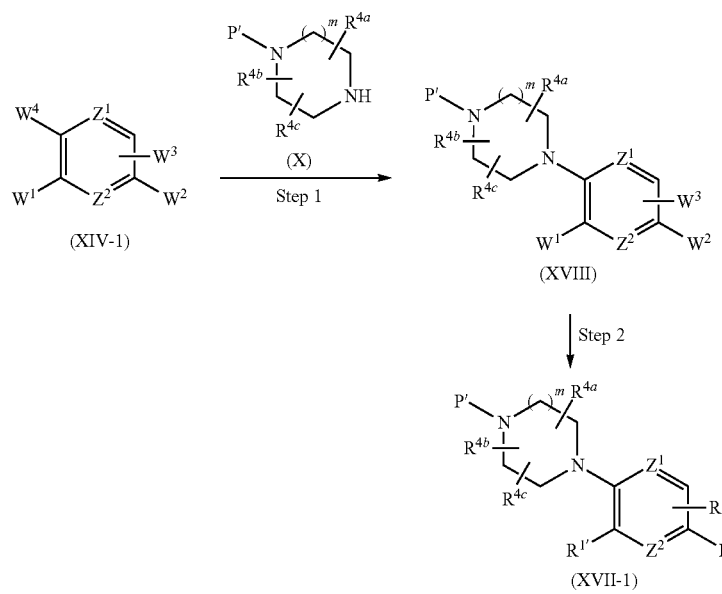

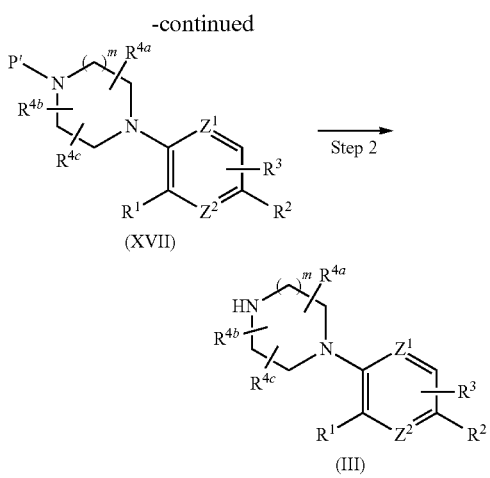

wherein the symbols are as defined above.

(Step 1)

By reacting a compound represented by the formula (XVI) with a compound represented by the formula (X), a compound represented by the formula (XVII) is obtained. The wherein the symbols are as defined above.

(Step 1)

By reacting a compound represented by the formula (XIV-1) with a compound represented by the formula (X), a compound represented by the formula (XVIII) is obtained. The reaction proceeds by a method similar to Method C, Step 4, or a method similar to Preparation method of formula (III), Step 1.

(Step 2)

In this step, the chlorine atom, bromine atom and iodine atom of the substituents $W^1$, $W^2$ and $W^3$ in a compound represented by the formula (XVIII) are each converted by Suzuki reaction to alkyl having a carbon number of 1-6 and optionally having substituent(s), alkenyl having a carbon number of 2-6 and optionally having substituent(s), cycloalkyl having a carbon number of 3-6 and optionally having substituent(s) or aryl having a carbon number of 6-10 and optionally having substituent(s). The reaction proceeds by a method similar to Method B, Step 3 alternative method, Step 3-b. Moreover, a compound of the formula (XVII-1) wherein $R^1$, $R^2$ and $R^3$ are each alkyl, which was produced in this step, can also be converted to alkyl by once converting these substituents to alkenyl, and thereafter performing a reduction reaction under a hydrogen atmosphere and using palladium carbon.

(Step 3)

By subjecting a compound represented by the formula (XVII-1) to a method similar to Method C, Step 3, a compound represented by the formula (III-1) is obtained.

Preparation Method of Formula (VI)

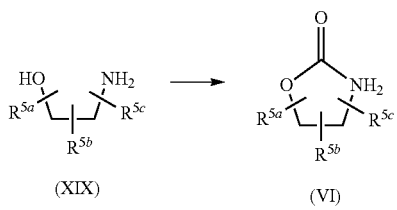

wherein each symbol is as defined above.

A compound represented by the formula (VI) is obtained by heating a compound represented by the formula (XIX) with diethyl carbonate and potassium carbonate.

The amide derivative of the formula (I), which was produced by the aforementioned method, can be purified to any purity by a conventionally-used purification means, for example, concentration, extraction, chromatography, reprecipitation, recrystallization and the like. In addition, it can be converted to a pharmacologically acceptable salt as necessary by treatment with an acid or base etc. in a suitable solvent (water, alcohol, ether etc.). Furthermore, the obtained compound of the present invention or a pharmacologically acceptable salt thereof can be converted to a hydrate or solvate thereof by treatment with water, water-containing solvent or other solvent (for example, alcohol etc.).

The amide compound and a pharmacologically acceptable salt thereof of the present invention include racemic compounds, stereoisomers, and mixture of these compounds, and includes isotope-labeled and radioactivity-labeled compounds. Such isomers can be isolated by a standard separation technique including fractional crystallization and chiral column chromatography. In addition, the compound of the present invention has an asymmetric carbon atom. Therefore, it includes enantiomer and diastereomer. A diastereomer mixture can be separated into each diastereomer based on their physical/chemical differences by a method well known in the art, for example, chromatography and/or fractional crystallization. Enantiomer can be separated by chiral column chromatography or by reacting an enantiomer compound with an appropriate optically active compound to give a diastereomer mixture, separating each diastereomer and converting each diastereomer to a corresponding enantiomer. All such isomers including diastereomer, enantiomer and a mixture thereof are a part of the compound of the present invention.

The compound of the present invention has a MMP-9 selective production suppressive action, and can be used as a prophylactic medicament or a therapeutic drug for autoimmune diseases represented by rheumatoid arthritis, multiple sclerosis, systemic lupus erythematosus and the like, inflammatory bowel diseases (ulcerative colitis, Crohn's disease) or osteoarthritis.

In the present invention, "prophylaxis" means an act of administering the compound of the present invention or a pharmaceutical composition containing the compound to an individual who has not developed a disease, condition or symptom. In addition, "treatment" means an act of administering the compound of the present invention or a pharmaceutical composition containing the compound to an individual who has developed a disease, condition or symptom. Therefore, an act of administration to an individual who has developed a disease, condition or symptom, for the prevention of aggravation of the symptom and the like, and for the prevention of attack and recurrence is one embodiment of the "treatment".

When the compound of the present invention is used as a medicament, the compound of the present invention is mixed with a pharmaceutically acceptable carrier (excipient, binder, disintegrant, corrigent, flavor, emulsifier, diluent, solubilizing agents and the like) to give a pharmaceutical composition which can be orally or parenterally administered. A pharmaceutical composition can be formulated by a general method.

In the present specification, parenteral includes subcutaneous injection, intravenous injection, intramuscular injection, intraperitoneal injection, drip or topical administration (transdermal administration, transocular administration, transpulmonary or bronchial administration, transnasal administration, transrectal administration and the like) and the like.

The dose of the compound of the present invention is determined according to the age, body weight, general health condition, sex, diet, administration time, administration method, clearance rate, and the level of disease for which patients are undergoing treatments at that time, or further in consideration of other factors. While the daily dose of the compound of the present invention varies depending on the condition and body weight of patient, the kind of the compound, administration route and the like, it is parenterally administered at, for example, 0.01 to 100 mg/patient/day by subcutaneous, intravenous, intramuscular, transdermal, transocular, transpulmonary or bronchial, transnasal or rectal administration, or about 0.01 to 1000 mg/patient/day by oral administration.

EXAMPLES

The present invention is explained in detail in the following by referring to Starting Material Synthesis Examples, Examples and Experimental Examples, which are not to be construed as limitative.

Preparation Example 1

Preparation of (4-bromo-2,6-difluorophenyl)[4-(2,4-dimethylphenyl)piperazin-1-yl]methanone 4-Bromo-2,6-difluorobenzoic acid (5 g) and 4-(4,6-dimethoxy[1.3.5]triazin-2-yl)-4-methylmorpholinium chloride hydrate (DMT-MM) (6.9 g) were dissolved in a mixture of chloroform (50 mL) and methanol (50 mL), 1-(2,4-dimethylphenyl)piperazine (4 g) was added, and the mixture was stirred at room temperature overnight. After evaporation of the solvent, ethyl acetate was added, and insoluble materials were filtered off. The solvent in the filtrate was evaporated to give the title compound (7 g).

Preparation Example 2

Preparation of (4-bromo-3-fluorophenyl)[4-(2,4-dimethylphenyl)piperazin-1-yl]methanone By reaction and treatment in the same manner as in Preparation Example 1 and using 4-bromo-3-fluorobenzoic acid (5 g) and 1-(2,4-dimethylphenyl)piperazine (4 g), the title compound (7 g) was obtained.

Preparation Example 3

Preparation of (4-bromo-3-chlorophenyl)[4-(2,4-dimethylphenyl)piperazin-1-yl]methanone By reaction and treatment in the same manner as in Preparation Example 1 and using 4-bromo-3-chlorobenzoic acid (2.4 g) and 1-(2,4-dimethylphenyl)piperazine (1.9 g), the title compound (4.1 g) was obtained.

Preparation Example 4

Preparation of (4-bromo-2-fluorophenyl)[4-(2,4-dimethylphenyl)piperazin-1-yl]methanone By reaction and treatment in the same manner as in Preparation Example 1 and using 4-bromo-2-fluorobenzoic acid (5 g) and 1-(2,4-dimethylphenyl)piperazine (4.4 g), the title compound (9 g) was obtained.

Preparation Example 5

Preparation of (4-bromo-2-methoxyphenyl)[4-(2,4-dimethylphenyl)piperazin-1-yl]methanone Methyl 4-bromo-2-methoxybenzoate (10 g) was dissolved in methanol (80 mL), 1N aqueous sodium hydroxide solution (80 mL) was added, and the mixture was refluxed for 3 hr. After cooling, 1N hydrochloric acid (80 mL) was added, and the mixture was filtered to give 4-bromo-2-methoxybenzoic acid (9.2 g). By reaction and treatment in the same manner as in Preparation Example 1 and using 4-bromo-2-methoxybenzoic acid (3.1 g) and 1-(2,4-dimethylphenyl)piperazine (2.7 g), the title compound (4.4 g) was obtained.

Preparation Example 6

Preparation of (4-bromo-2-methylphenyl) [4-(2,4-dimethylphenyl)piperazin-1-yl]methanone By reaction and treatment in the same manner as in Preparation Example 1 and using 4-bromo-2-methylbenzoic acid (5 g) and 1-(2,4-dimethylphenyl)piperazine (4.6 g), the title compound (8.9 g) was obtained.

Preparation Example 7

Preparation of (4-bromo-2-chloro-5-fluorophenyl)[4-(2,4-dimethylphenyl)-piperazin-1-yl]methanone By reaction and treatment in the same manner as in Preparation Example 1 and using 4-bromo-2-chloro-5-fluorobenzoic acid (5 g) and 1-(2,4-dimethylphenyl)piperazine (3.8 g), the title compound (8.5 g) was obtained.

Preparation Example 8

Preparation of [4-(2,4-dimethylphenyl)piperazin-1-yl](4-iodophenyl)methanone

To tetrahydrofuran (60 mL) were added 4-iodobenzoyl chloride (5 g), 1-(2,4-dimethylphenyl)piperazine (3.6 g) and 1N aqueous sodium hydroxide solution (20 mL), and the mixture was stirred at room temperature overnight. Ethyl acetate was added for partitioning, the organic layer was washed with saturated brine, and the solvent was evaporated. The title compound (8 g) was obtained.

Preparation Example 9

Preparation of (4-bromo-2-methanesulfonylphenyl) [4-(2,4-dimethylphenyl)piperazin-1-yl]methanone By reaction and treatment in the same manner as in Preparation Example 1 and using 4-bromo-2-methanesulfonylbenzoic acid (1 g) and 1-(2,4-dimethylphenyl)piperazine (684 mg), the title compound (1.3 g) was obtained.

Preparation Example 10

Preparation of (4-bromo-3-methylphenyl)[4-(2,4-dimethylphenyl)piperazin-1-yl]methanone By reaction and treatment in the same manner as in Preparation Example 1 and using 4-bromo-3-methylbenzoic acid (25 g) and 1-(2,4-dimethylphenyl)piperazine (22 g), the title compound (45 g) was obtained.

Preparation Example 11

Preparation of (4-bromo-2-chlorophenyl)[4-(2,4-dimethylphenyl)piperazin-1-yl]methanone By reaction and treatment in the same manner as in Preparation Example 1 and using 4-bromo-2-chlorobenzoic acid (5 g) and 1-(2,4-dimethylphenyl)piperazine (4 g), the title compound (9 g) was obtained.

Preparation Example 12

Preparation of ethyl 4-(2-oxooxazolidin-3-yl)benzoate

To a mixture of ethyl 4-iodobenzoate (1.5 mL), oxazolidin-2-one (940 mg), potassium carbonate (2.5 g) and copper (I) iodide (171 mg) were added toluene (9 mL) and N,N'-dimethylethylenediamine (195 µL), and the mixture was refluxed for 8 hr. After cooling, water was added to the reaction mixture, and the mixture was extracted with ethyl acetate. The organic layer was washed with saturated brine, and the solvent was evaporated. The residue was purified by column chromatography (chloroform) to give the title compound (1.2 g).

Preparation Example 13

Preparation of [4-(2,4-dimethylphenyl)piperazin-1-yl](4-bromophenyl)methanone

To tetrahydrofuran (120 mL) were added 4-bromobenzoyl chloride (25 g), 1-(2,4-dimethylphenyl)piperazine (22 g) and 1N aqueous sodium hydroxide solution (120 mL), and the mixture was stirred at room temperature for 6 hr. Ethyl acetate was added for partitioning, the organic layer was washed with saturated brine, and the solvent was evaporated. The title compound (31 g) was obtained.

Preparation Example 14

Preparation of 3-{4-[4-(2-chloro-5-fluoro-4-methylphenyl)piperazine-1-carbonyl]-3-methanesulfonylphenyl}oxazolidin-2-one To a mixture of 1-Boc-piperazine (1.9 g), 1-bromo-2-chloro-5-fluoro-4-methylbenzene (2.2 g), palladium acetate (112 mg), rac-2,2'-bis(diphenylphosphino)-1,1'-binaphthyl (312 mg) and sodium tert-butoxide (1.4 g) was added toluene (20 mL), and the mixture was refluxed for 8 hr. After cooling, water was added to the reaction mixture, and the mixture was extracted with ethyl acetate. The organic layer was washed with saturated brine, and the solvent was evaporated. The residue was purified by column chromatography (chloroform). The obtained compound was dissolved in chloroform (3 mL), 4N hydrogen chloride/ethyl acetate (3 mL) was added, and the mixture was stirred at room temperature for 3 hr. Filtration gave 1-(2-chloro-5-fluoro-4-methylphenyl)piperazine hydrochloride (2 g). To a mixture of 1-(2-chloro-5-fluoro-4-methylphenyl)piperazine hydrochloride (1.1 g), 4-bromo-2-methanesulfonylbenzoic acid (1.1 g) and 4-(4,6-dimethoxy[1.3.5]triazin-2-yl)-4-methylmorpholinium chloride hydrate (DMT-MM) (1.5 g) were added chloroform (50 mL), methanol (50 mL) and N-methylmorpholine (440 µL), and the mixture was stirred at room temperature overnight. After evaporation of the solvent, the residue was purified by column chromatography (chloroform:methanol) to give (4-bromo-2-methanesulfonylphenyl)[4-(2-chloro-5-fluoro-4-methylphenyl)piperazin-1-yl]methanone (1.9 g). To a mixture of (4-bromo-2-methanesulfonylphenyl)[4-(2-chloro-5-fluoro-4-methylphenyl)piperazin-1-yl]methanone (1.9 g), oxazolidin-2-one (418 mg), potassium carbonate (1.7 g) and copper (I) iodide (152 mg) were added toluene (4 mL) and N,N'-dimethylethylenediamine (180 µL), and the mixture was refluxed for 8 hr. After cooling, water was added to the reaction mixture, and the mixture was extracted with chloroform. The organic layer was washed with saturated brine, and the solvent was evaporated. The residue was purified by column chromatography (chloroform:methanol) to give the title compound (0.5 g).

Preparation Example 15

Preparation of (4-bromo-2-methanesulfonylphenyl)[4-(2-ethyl-4-methylphenyl)piperazin-1-yl]methanone A mixture of 4-bromo-2-ethylaniline (1.4 mL), diisopropylethylamine (4.4 mL) and N,N-bis(2-chloroethyl)-4-methylbenzenesulfonamide (3 g) was refluxed for 5 hr. After cooling, the solvent was evaporated, and the residue was purified by column chromatography (chloroform) to give 1-(4-bromo-2-ethylphenyl)-4-(toluene-4-sulfonyl)piperazine (3 g). To a mixture of 1-(4-bromo-2-ethylphenyl)-4-(toluene-4-sulfonyl)piperazine (3 g), methylboronic acid (1.2 g), palladium acetate (112 mg), 2-dicyclohexylphosphino-2',6'-dimethoxybiphenyl (411 mg) and potassium fluoride (2.3 g) was added tetrahydrofuran (30 mL), and the mixture was refluxed for 8 hr. After cooling, water was added to the reaction mixture, and the mixture was extracted with ethyl acetate. The organic layer was washed with saturated brine, and the solvent was evaporated. The residue was purified by column chromatography (chloroform) to give 1-(2-ethyl-4-methylphenyl)-4-(toluene-4-sulfonyl)piperazine (2.9 g). A mixture of 1-(2-ethyl-4-methylphenyl)-4-(toluene-4-sulfonyl)piperazine (2.9 g), hydrobromic acid (16 mL) and acetic acid (16 mL) was refluxed for 8 hr. After cooling, the reaction mixture was alkalified with 1N aqueous sodium hydroxide solution, and the mixture was extracted with chloroform. The organic layer was washed with saturated brine, and the solvent was evaporated. 4N hydrogen chloride/ethyl acetate (3 mL) was added and the mixture was filtered to give 1-(2-ethyl-4-methylphenyl)piperazine hydrochloride (1.7 g). To a mixture of 4-bromo-2-methanesulfonylbenzoic acid (1.1 g), 1-(2-ethyl-4-methylphenyl)piperazine hydrochloride (963 mg) and 4-(4,6-dimethoxy[1.3.5]triazin-2-yl)-4-methylmorpholinium chloride hydrate (DMT-MM) (1.5 g) were added chloroform (6 mL), methanol (6 mL) and N-methylmorpholine (440 µL), and the mixture was stirred at room temperature overnight. After evaporation of the solvent, the residue was purified by column chromatography (chloroform) to give the title compound (1.8 g).

Preparation Example 16

Preparation of (4-iodophenyl)[4-(4-methyl-2-vinylphenyl)piperazin-1-yl]methanone A mixture of 4-bromo-3-chlorotoluene (2.1 g), Boc-piperazine (1.9 g), palladium acetate (112 mg), rac-2,2'-bis(diphenylphosphino)-1,1'-binaphthyl (312 mg), sodium tert-butoxide (1.4 g) and toluene (20 mL) was refluxed for 5 hr. After cooling, water was added to the reaction mixture, and the mixture was extracted with ethyl acetate. The organic layer was washed with saturated brine, and the solvent was evaporated. The residue was purified by column chromatography (chloroform) to give 4-(2-chloro-4-methylphenyl)piperazine-1-carboxylic acid tert-butyl ester (3.1 g). To a mixture of 4-(2-chloro-4-methylphenyl)piperazine-1-carboxylic acid tert-butyl ester (932 mg), 2,4,6-trivinylcyclotriboroxane pyridine complex (1 g), palladium acetate (74 mg), 2-dicyclohexylphosphino-2',6'-dimethoxybiphenyl (271 mg) and potassium fluoride (697 mg) was added tetrahydrofuran (4 mL), and the mixture was refluxed for 8 hr. After cooling, water was added to the reaction mixture, and the mixture was extracted with ethyl acetate. The organic layer was washed with saturated brine, and the solvent was evaporated. The residue was purified by column chromatography (chloroform) to give 4-(4-methyl-2-vinylphenyl)piperazine-1-carboxylic acid tert-butyl ester (0.9 g). 4-(4-Methyl-2-vinylphenyl)piperazine-1-carboxylic acid tert-butyl ester (0.9 g) was dissolve in chloroform (2 mL), 4N hydrogen chloride/ethyl acetate (1 mL) was added, and the mixture was stirred at room temperature for 3 hr. 1N aqueous sodium hydroxide solution (8 mL) was added, and the mixture was extracted with chloroform. The organic layer was washed with saturated brine, and the solvent was evaporated to give 1-(4-methyl-2-vinylphenyl)piperazine (606 mg). 1-(4-Methyl-2-vinylphenyl)piperazine (606 mg) was dissolved in tetrahydrofuran (8 mL), 4-iodobenzoyl chloride (1.1 g) and 1N aqueous sodium hydroxide solution (4 mL) were added, and the mixture was stirred at room temperature overnight. The mixture was extracted with ethyl acetate, washed with saturated brine, and the solvent was evaporated. The residue was purified by column chromatography (chloroform) to give the title compound (1 g).

Preparation Example 17

Preparation of [4-(2-cyclopropyl-4-methylphenyl)piperazin-1-yl](4-iodophenyl)methanone To a mixture of 4-(2-chloro-4-methylphenyl)piperazine-1-carboxylic acid tert-butyl ester (932 mg), bis(tricyclohexylphosphine)palladium (II) dichloride (132 mg), tripotassium phosphate (3.8 g) and cyclopropylboronic acid (688 mg) were added toluene (10 mL) and water (500 µL) and the mixture was refluxed for 5 hr. After cooling, the mixture was extracted with ethyl acetate, washed with saturated brine, and the solvent was evaporated. The residue was purified by column chromatography (chloroform) to give 4-(2-cyclopropyl-4- methylphenyl)piperazine-1carboxylic acid tert-butyl ester (1 g). 4-(2-Cyclopropyl-4-methylphenyl)piperazine-1carboxylic acid tert-butyl ester (1 g) was dissolved in chloroform (1 mL), 4N hydrogen chloride/ethyl acetate (1 mL) was added, and the mixture was stirred at room temperature for 3 hr. Filtration gave 1-(2-cyclopropyl-4-methylphenyl)piperazine hydrochloride (160 mg). To tetrahydrofuran (2 mL) were added 4-iodobenzoyl chloride (169 mg), 1-(2-cyclopropyl-4-methylphenyl)piperazine hydrochloride (160 mg) and 1N aqueous sodium hydroxide solution (2 mL), and the mixture was stirred at room temperature overnight. Ethyl acetate was added for partitioning, the organic layer was washed with saturated brine, and the solvent was evaporated. The residue was purified by column chromatography (chloroform) to give the title compound (280 mg).

Preparation Example 18

Preparation of (R)-4-(4-isopropyl-2-oxooxazolidin-3-yl)benzoic acid

To a mixture of ethyl 4-iodobenzoate (5.8 mL), (R)-4-isopropyloxazolidin-2-one (5 g), potassium carbonate (15 g) and copper (I) iodide (1.3 g) were added toluene (35 mL) and N,N'-dimethylethylenediamine (1.5 mL), and the mixture was refluxed for 8 hr. After cooling, water was added to the reaction mixture, and the mixture was extracted with ethyl acetate. The organic layer was washed with saturated brine, and the solvent was evaporated. The residue was dissolved in methanol (35 mL) and 1,4-dioxane (35 mL), 1N aqueous sodium hydroxide solution (70 mL) was added, and the mixture was stirred at room temperature overnight. 1N hydrochloric acid (70 mL) was added, and the mixture was filtered to give the title compound (9 g).

Preparation Example 19

Preparation of (4-bromophenyl)[4-(2,4-dichlorophenyl)piperazin-1-yl]methanone

To tetrahydrofuran (30 mL) were added 4-bromobenzoyl chloride (2.5 g), 1-(2,4-chlorophenyl)piperazine dihydrochloride (3 g) and 1N aqueous sodium hydroxide solution (30 mL), and the mixture was stirred at room temperature overnight. Ethyl acetate was added for partitioning, the organic layer was washed with saturated brine, and the solvent was evaporated. The title compound (3.3 g) was obtained.

Preparation Example 20

Preparation of (6-bromopyridin-3-yl)[4-(2,4-dimethylphenyl)piperazin-1-yl]methanone By reaction and treatment in the same manner as in Preparation Example 1 and using 6-bromonicotinic acid (2 g) and 1-(2,4-dimethylphenyl)piperazine (1.9 g), the title compound (3.8 g) was obtained.

Preparation Example 21

Preparation of (5-bromopyridin-2-yl)[4-(2,4-dimethylphenyl)piperazin-1-yl]methanone By reaction and treatment in the same manner as in Preparation Example 1 and using 5-bromopyridine-2-carboxylic acid (5 g) and 1-(2,4-dimethylphenyl)piperazine (4.8 g), the title compound (9.4 g) was obtained.

Preparation Example 22

Preparation of methyl (R)-4-(4-benzyl-2-oxooxazolidin-3-yl)benzoate

To a mixture of p-(methoxycarbonyl)phenylboronic acid (2.45 g), (R)-4-benzyloxazolidin-2-one (1.205 g) and copper (II) acetate (1.23 g) were added methylene chloride (20 mL) and triethylamine (1.9 mL), and the mixture was stirred at room temperature overnight. Water was added to the reaction mixture, and insoluble materials were filtered off. The filtrate was extracted with chloroform. The solvent was evaporated, and the obtained residue was purified by column chromatography (chloroform) to give the title compound (0.19 g).

Preparation Example 23

Preparation of (6-bromopyridin-3-yl)[4-(4-chlorobenzoyl)piperidin-1-yl]methanone To chloroform (150 mL) were added (4-chlorophenyl)(piperidin-4-yl)methanone hydrochloride (13 g) and 1N aqueous sodium hydroxide solution (50 mL), and the mixture was stirred at room temperature for 10 min. The chloroform layer was partitioned, methanol (50 mL), 6-bromonicotinic acid (10 g) and 4-(4,6-dimethoxy[1.3.5]triazin-2-yl)-4-methylmorpholinium chloride hydrate (DMT-MM) (16.6 g) were added, and the mixture was stirred at room temperature overnight. After evaporation of the solvent, ethyl acetate was added, and insoluble materials were filtered off. The solvent in the filtrate was evaporated to give the title compound (16.4 g).

Preparation Example 24

Preparation of benzoic acid (R)-3-{4-[4-(4-chlorobenzoyl)piperidine-1-carbonyl]-3-methanesulfonylphenyl}-2-oxooxazolidin-4-ylmethyl ester By reaction and treatment in the same manner as in Preparation Example 1 and using 4-bromo-2-methylsulfonylbenzoic acid (2.8 g) and (4-chlorophenyl)piperidin-4-ylmethanone (2.6 g), (4-bromo-2-methanesulfonylphenyl)[4-(4-chlorobenzoyl)piperidin-1-yl]methanone (4.8 g) was obtained. By reaction and treatment in the same manner as in Preparation Example 12 and using (4-bromo-2-methanesulfonylphenyl)[4-(4-chlorobenzoyl)piperidin-1-yl]methanone (1.5 g) and benzoic acid (R)-2-oxooxazolidin-4-ylmethyl ester (796 mg), the title compound (938 mg) was obtained.

Preparation Example 25

Preparation of (R)-4-methyloxazolidin-2-one

A mixture of (R)-(−)-2-amino-1-propanol (30 mL), diethyl carbonate (51 mL) and potassium carbonate (6 g) was stirred at 150° C. for 3 hr. After cooling, water was added to the reaction mixture, and the mixture was extracted with ethyl acetate. The organic layer was washed with saturated brine, and the solvent was evaporated to give the title compound (36 g).

Preparation Example 26

Preparation of (R)-4-ethyloxazolidin-2-one

By reaction and treatment in the same manner as in Preparation Example 25 and using (R)-(−)-2-amino-1-butanol (5 mL), the title compound (6 g) was obtained.

Preparation Example 27

Preparation of (R)-3-{4-[4-(4-chlorobenzoyl)piperidine-1-carbonyl]phenyl}-4-isopropyloxazolidin-2-one To a mixture of (R)-4-(4-isopropyl-2-oxooxazolidin-3-yl)benzoic acid (499 mg) described in Preparation Example 18, (4-chlorophenyl)piperidin-4-ylmethanone hydrochloride (520 mg) and 4-(4,6-dimethoxy[1.3.5]triazin-2-yl)-4-methylmorpholinium chloride hydrate (DMT-MM)(829 mg) were added chloroform (3 mL), methanol (3 mL) and N-methylmorpholine (220 µL) and the mixture was stirred at room temperature overnight. After evaporation of the solvent, the residue was purified by column chromatography (chloroform:methanol) to give the title compound (728 mg).

Preparation Example 28

Preparation of (6-bromopyridin-3-yl)(4-p-tolyloxypiperidin-1-yl)methanone

To a mixture of 4-(p-tolyloxy)piperidine (765 mg), 6-bromonicotinic acid (808 mg) and 4-(4,6-dimethoxy[1.3.5]triazin-2-yl)-4-methylmorpholinium chloride hydrate (DMT-MM) (1.7 g) were added chloroform (5 mL) and methanol (5 mL), and the mixture was stirred at room temperature overnight. After evaporation of the solvent, the residue was purified by column chromatography (chloroform:methanol) to give the title compound (1.5 g).

Preparation Example 29

Preparation of (R)-4-propyloxazolidin-2-one

By reaction and treatment in the same manner as in Preparation Example 25 and using (R)-(−)-2-amino-1-pentanol (3 g), the title compound (3.4 g) was obtained.

Preparation Example 30

Preparation of (4-bromophenyl)[4-(4-chlorobenzoyl)piperidin-1-yl]methanone

To tetrahydrofuran (120 mL) were added 4-bromobenzoyl chloride (25 g), (4-chlorophenyl)piperidin-4-ylmethanone hydrochloride (30 g) and 1N aqueous sodium hydroxide solution (250 mL), and the mixture was stirred at room temperature for 3 hr. Ethyl acetate was added for partitioning, the organic layer was washed with saturated brine, and the solvent was evaporated. The residue was recrystallized to give the title compound (46 g).

Preparation Example 31

Preparation of 3-{4-[4-(4-chlorobenzoyl)piperidine-1-carbonyl]-3-methanesulfonylphenyl}oxazolidin-2-one To a mixture of (4-bromo-2-methanesulfonylphenyl)[4-(4-chlorobenzoyl)piperidin-1-yl]methanone (1.5 g), which is the intermediate described in Preparation Example 24, oxazolidin-2-one (313 mg), potassium carbonate (829 mg) and copper (I) iodide (114 mg) were added toluene (3 mL) and N,N'-dimethylethylenediamine (130 µL), and the mixture was refluxed for 8 hr. After cooling, water was added to the reaction mixture, and the mixture was extracted with chloroform. The organic layer was washed with saturated brine, and the solvent was evaporated. The residue was purified by column chromatography (chloroform:methanol) to give the title compound (982 mg).

Preparation Example 32

Preparation of 3-{5-[4-(4-chlorobenzoyl)piperidine-1-carbonyl]pyridin-2-yl}oxazolidin-2-one By reaction and treatment in the same manner as in Preparation Example 31 and using (6-bromopyridin-3-yl)[4-(4-chlorobenzoyl)piperidin-1-yl]methanone (2 g) described in Preparation Example 23 and oxazolidin-2-one (435 mg), the title compound (260 mg) was obtained.

Preparation Example 33

Preparation of (R)-3-{5-[4-(4-chlorobenzoyl)piperidine-1-carbonyl]pyridin-2-yl}-4-methyloxazolidin-2-one By reaction and treatment in the same manner as in Preparation Example 31 and using (6-bromopyridin-3-yl)[4-(4-chlorobenzoyl)piperidin-1-yl]methanone (2 g) described in Preparation Example 23 and (R)-4-methyloxazolidin-2-one (288 mg) described in Preparation Example 25, the title compound (510 mg) was obtained.

Preparation Example 34

Preparation of (R)-3-{5-[4-(4-chlorobenzoyl)piperidine-1-carbonyl]pyridin-2-yl}-4-ethyloxazolidin-2-one By reaction and treatment in the same manner as in Preparation Example 31 and using (6-bromopyridin-3-yl)[4-(4-chlorobenzoyl)piperidin-1-yl]methanone (2 g) described in Preparation Example 23 and (R)-4-ethyloxazolidin-2-one (300 mg) described in Preparation Example 26, the title compound (710 mg) was obtained.

Preparation Example 35

Preparation of (5-bromopyridin-2-yl)[4-(4-chlorobenzoyl)piperidin-1-yl]methanone By reaction and treatment in the same manner as in Preparation Example 27 and using 5-bromopyridine-2-carboxylic acid (1.2 g) and (4-chlorophenyl)piperidin-4-ylmethanone hydrochloride (1.6 g), the title compound (2.4 g) was obtained.

Preparation Example 36

Preparation of (R)-3-{6-[4-(4-chlorobenzoyl)piperidine-1-carbonyl]pyridin-3-yl}-4-methyloxazolidin-2-one By reaction and treatment in the same manner as in Preparation Example 31 and using (5-bromopyridin-2-yl)[4-(4-chlorobenzoyl)piperidin-1-yl]methanone (2.4 g) described in Preparation Example 35 and (R)-4-methyloxazolidin-2-one (728 mg) described in Preparation Example 25, the title compound (2.1 g) was obtained.

Preparation Example 37

Preparation of (R)-4-(4-methyl-2-oxooxazolidin-3-yl)benzoic acid

By reaction and treatment in the same manner as in Preparation Example 18 and using ethyl 4-iodobenzoate (1.4 mL) and (R)-4-methyloxazolidin-2-one (860 mg) described in Preparation Example 25, the title compound (0.9 g) was obtained.

Preparation Example 38

Preparation of (R)-4-methoxymethyloxazolidin-2-one

By reaction and treatment in the same manner as in Preparation Example 25 and using (S)-2-amino-3-methoxy-1-propanol (1 g), the title compound (550 mg) was obtained.

Preparation Example 39

Preparation of ethyl 4-(5-methoxymethyl-2-oxooxazolin-3-yl)benzoate

By reaction and treatment in the same manner as in Preparation Example 25 and using 1-amino-3-methoxypropan-2-ol (1 g), 5-methoxymethyloxazolidin-2-one (620 mg) was obtained. To a mixture of 5-methoxymethyloxazolidin-2-one (620 mg), ethyl 4-iodobenzoate (1.6 mL), potassium carbonate (2.6 g) and copper (I) iodide (552 mg) were added toluene (20 mL) and N,N'-dimethylethylenediamine (625 μL), and the mixture was refluxed for 8 hr. After cooling, water was added to the reaction mixture, and the mixture was extracted with ethyl acetate. The organic layer was washed with saturated brine, and the solvent was evaporated to give the title compound (830 mg).

Preparation Example 40

Preparation of 4-(5-methyl-2-oxooxazolidin-3-yl)benzoic acid

A mixture of 1-amino-2-propanol (1.4 g), diethyl carbonate (2.4 mL) and potassium carbonate (500 mg) was stirred at 150° C. for 3 hr. After cooling, water was added to the reaction mixture, and the mixture was extracted with ethyl acetate. The organic layer was washed with saturated brine, and the solvent was evaporated to give 5-methyloxazolidin-2-one (1.9 g). To a mixture of ethyl 4-iodobenzoate (3.2 mL), 5-methyloxazolidin-2-one (1.9 g), potassium carbonate (8 g) and copper (I) iodide (720 mg) were added toluene (20 mL) and N,N'-dimethylethylenediamine (800 μL), and the mixture was refluxed for 3 hr. After cooling, water was added to the reaction mixture, and the mixture was extracted with chloroform. The organic layer was washed with saturated brine, and the solvent was evaporated. The residue was dissolved in methanol (20 mL) and 1,4-dioxane (20 mL), 1N aqueous sodium hydroxide solution (40 mL) was added, and the mixture was stirred at room temperature for 3 hr. 1N hydrochloric acid (40 mL) was added, and the mixture was extracted with chloroform. The solvent was evaporated to give the title compound (3.9 g).

Preparation Example 41

Preparation of (R)-4-(5-methyl-2-oxooxazolidin-3-yl)benzoic acid

A mixture of (R)-1-amino-2-propanol (1 g), diethyl carbonate (1.7 mL) and potassium carbonate (350 mg) was stirred at 150° C. for 3 hr. After cooling, water was added to the reaction mixture, and the mixture was extracted with ethyl acetate. The organic layer was washed with saturated brine, and the solvent was evaporated to give (R)-5-methyloxazolidin-2-one (1.3 g).

By reaction and treatment in the same manner as in Preparation Example 40 and using ethyl 4-iodobenzoate and (R)-5-methyloxazolidin-2-one, the title compound (2 g) was obtained.

Preparation Example 42

Preparation of (S)-5-methyloxazolidin-2-one

By reaction and treatment in the same manner as in Preparation Example 25 and using (S)-(+)-1-amino-2-propanol (5 g), the title compound (6 g) was obtained.

Preparation Example 43

Preparation of 5,5-dimethyloxazolin-2-one

By reaction and treatment in the same manner as in Preparation Example 25 and using 1-amino-2-methylpropan-2-ol (5 g), the title compound (5 g) was obtained.

Preparation Example 44

Preparation of (S)-4-methyloxazolidin-2-one

By reaction and treatment in the same manner as in Preparation Example 25 and using (S)-(−)-2-amino-1-propanol (5 mL), the title compound (6.5 g) was obtained.

Preparation Example 45

Preparation of (R)-2-methoxy-4-(4-methyl-2-oxooxazolidin-3-yl)benzoic acid

To a mixture of methyl 4-bromo-2-methoxybenzoate (5.8 mL), (R)-4-methyloxazolidin-2-one (2 g) described in Preparation Example 25, potassium carbonate (2.8 g) and copper (I) iodide (760 mg) were added toluene (10 mL) and N,N'-dimethylethylenediamine (880 μL), and the mixture was refluxed for 8 hr. After cooling, water was added to the reaction mixture, and the mixture was extracted with chloroform. The organic layer was washed with saturated brine, and the solvent was evaporated. The residue was purified by column chromatography (hexane:ethyl acetate) to give methyl (R)-2-methoxy-4-(4-methyl-2-oxooxazolidin-3-yl)benzoate (2.1 g). Methyl (R)-2-methoxy-4-(4-methyl-2-oxooxazolidin-3-yl)benzoate (2.1 g) was dissolved in methanol (8 mL) and tetrahydrofuran (8 mL), 1N aqueous sodium hydroxide solution (16 mL) was added, and the mixture was stirred at room temperature for 3 hr. 1N hydrochloric acid (16 mL) was added, and the mixture was extracted with chloroform. The organic layer was washed with saturated brine, and the solvent was evaporated. The title compound (2.2 g) was obtained.

Preparation Example 46

Preparation of (R)-3-methoxy-4-(4-methyl-2-oxooxazolidin-3-yl)benzoic acid

By reaction and treatment in the same manner as in Preparation Example 45 and using methyl 4-bromo-3-methoxybenzoate (1 g) and (R)-4-methyloxazolidin-2-one (607 mg) described in Preparation Example 25, the title compound (1 g) was obtained.

Preparation Example 47

Preparation of 1-(3,5-dimethylpyridin-2-yl)piperazine

To 2,3,5-trichloropyridine (25 g) were added 1-BOC-piperazine (28.13 g), potassium carbonate (37.86 g), N,N-dimethylformamide (25 mL) and toluene (50 mL), and the mixture was stirred at 100° C. After completion of the reaction, water was added to the reaction mixture, and the mixture was extracted with ethyl acetate. The organic layer was washed with saturated brine, and the solvent was evaporated. The residue was purified by column chromatography (hexane:ethyl acetate) to give 4-(3,5-dichloropyridin-2-yl)piperazine-1-carboxylic acid tert-butyl ester (39.13 g). To 4-(3,5-dichloropyridin-2-yl)piperazine-1-carboxylic acid tert-butyl ester (6.35 g) were added palladium (II) acetate (0.46 g), 2-dicyclohexylphosphino-2',6'-dimethoxybiphenyl (1.71 g), potassium fluoride (9.556 g), methylboronic acid (5 g) and tetrahydrofuran (202 mL), and the mixture was refluxed under a nitrogen stream for 8 hr. Water was added to the reaction mixture, and the mixture was extracted with ethyl acetate. The organic layer was washed with saturated brine, and the solvent was evaporated. The residue was purified by column chromatography (hexane:ethyl acetate) to give 4-(3,5-dimethylpyridin-2-yl)piperazine-1-carboxylic acid tert-butyl ester (5.45 g). To 4-(3,5-dimethylpyridin-2-yl)piperazine-1-carboxylic acid tert-butyl ester (5.45 g) were added 4N hydrogen chloride/ethyl acetate (18.2 mL) and chloroform (45.5 mL), and the mixture was stirred at room temperature. After completion of the reaction, to the reaction mixture were added water and potassium carbonate, and the mixture was extracted with ethyl acetate. The solvent was evaporated to give the title compound (3.3 g).

Preparation Example 48

Preparation of 1-(3-cyclopropyl-5-methylpyridin-2-yl)piperazine hydrochloride

To a mixture of 1-Boc-piperazine (7.2 g), 2,3-dichloro-5-methylpyridine (5 g), palladium (II) acetate (179 mg), rac-2,2'-bis(diphenylphosphino)-1,1'-binaphthyl (499 mg) and sodium tert-butoxide (4.1 g) was added toluene (30 mL), and the mixture was refluxed for 5 hr. After cooling, water was added to the reaction mixture, and the mixture was extracted with ethyl acetate. The organic layer was washed with saturated brine, and the solvent was evaporated. The residue was purified by column chromatography (hexane:ethyl acetate) to give 4-(3-chloro-5-methylpyridin-2-yl)piperazine-1-carboxylic acid tert-butyl ester (9 g). To a mixture of 4-(3-chloro-5-methylpyridin-2-yl)piperazine-1-carboxylic acid tert-butyl ester (9 g), bis(tricyclohexylphosphine)palladium (II) dichloride (1 g), tripotassium phosphate (30 g) and cyclopropylboronic acid (5.5 g) were added toluene (80 mL) and water (4 mL), and the mixture was refluxed for 8 hr. After cooling, water was added to the reaction mixture, and the mixture was extracted with ethyl acetate. The organic layer was washed with saturated brine, and the solvent was evaporated. The residue was purified by column chromatography (hexane:ethyl acetate) to give 4-(3-cyclopropyl-5-methylpyridin-2-yl)piperazine-1-carboxylic acid tert-butyl ester (9 g). 4-(3-Cyclopropyl-5-methylpyridin-2-yl)piperazine-1-carboxylic acid tert-butyl ester (9 g) was dissolved in chloroform (25 mL), 4N hydrogen chloride/ethyl acetate (25 mL) was added, and the mixture was stirred at room temperature overnight. Ethyl acetate (100 mL) was added and the mixture was filtered to give the title compound (4.6 g).

Preparation Example 49

Preparation of 1-(5-cyclopropyl-3-methylpyridin-2-yl)piperazine hydrochloride

To a mixture of 4-(5-bromo-3-methylpyridin-2-yl)piperazine-1-carboxylic acid tert-butyl ester (3.6 g), bis(tricyclohexylphosphine)palladium (II) dichloride (396 mg), tripotassium phosphate (12 g) and cyclopropylboronic acid (2.1 g) were added toluene (30 mL) and water (1.5 mL), and the mixture was refluxed for 8 hr. After cooling, the mixture was extracted with ethyl acetate, washed with saturated brine, and the solvent was evaporated. The residue was purified by column chromatography (chloroform) to give 4-(5-cyclopropyl-3-methylpyridin-2-yl)piperazine-1-carboxylic acid tert-butyl ester (2.2 g). 4-(5-Cyclopropyl-3-methylpyridin-2-yl)piperazine-1-carboxylic acid tert-butyl ester (2.2 g) was dissolved in chloroform (5 mL), 4N hydrogen chloride/ethyl acetate (5 mL) was added, and the mixture was stirred at room temperature overnight. Ethyl acetate (20 mL) was added, and the mixture was filtered to give the title compound (1.3 g).

Preparation Example 50

Preparation of 1-(3,5-dicyclopropylpyridin-2-yl)piperazine hydrochloride

To a mixture of 2,3,5-tribromopyridine (10 g), 1-Boc-piperazine (6 g) and potassium carbonate (20 g) was added 2-butanone (80 mL), and the mixture was refluxed for 8 hr. After cooling, water was added to the reaction mixture, and the mixture was extracted with ethyl acetate. The organic layer was washed with saturated brine, and the solvent was evaporated to give 4-(3,5-dibromopyridin-2-yl)piperazine-1-carboxylic acid tert-butyl ester (13 g). To a mixture of 4-(3,5-dibromopyridin-2-yl)piperazine-1-carboxylic acid tert-butyl ester (13 g), bis(tricyclohexylphosphine)palladium (II) dichloride (1.3 g), tripotassium phosphate (38 g) and cyclopropylboronic acid (8.4 g) were added toluene (100 mL) and water (5 mL), and the mixture was refluxed for 8 hr. After cooling, the mixture was extracted with ethyl acetate. The organic layer was washed with saturated brine, and the solvent was evaporated. The residue was purified by column chromatography (hexane:ethyl acetate) to give 4-(3,5-dicyclopropylpyridin-2-yl)piperazine-1-carboxylic acid tert-butyl ester (7 g). 4-(3,5-Dicyclopropylpyridin-2-yl)piperazine-1-carboxylic acid tert-butyl ester (7 g) was dissolved in chloroform (25 mL), 4N hydrogen chloride/ethyl acetate (25 mL) was added, and the mixture was stirred at room temperature overnight. To the reaction mixture was added 1N aqueous sodium hydroxide solution (100 mL), and the mixture was extracted with chloroform. The organic layer was washed with saturated brine, and the solvent was evaporated. The residue was dissolved in ethyl acetate (50 mL), 4N hydrogen chloride/ethyl acetate (8 mL) was added, and the mixture was filtered to give the title compound (3.2 g).

Preparation Example 51

Preparation of 1-(3-methyl-5-trifluoromethylpyridin-2-yl)piperazine

To 2,3-dichloro-5-trifluoromethylpyridine (25 g) were added 1-BOC-piperazine (23.84 g), potassium carbonate (32.08 g), N,N-dimethylformamide (50 mL) and toluene (50 mL), and the mixture was stirred at 100° C. for 8 hr. Water was added to the reaction mixture, and the mixture was extracted with ethyl acetate. The organic layer was washed with water and saturated brine, and the solvent was evaporated. The residue was purified by column chromatography (hexane:ethyl acetate) to give 4-(3-chloro-5-trifluoromethylpyridin-2-yl)piperazine-1-carboxylic acid tert-butyl ester (45.71 g). To 4-(3-chloro-5-trifluoromethylpyridin-2-yl)piperazine-1-carboxylic acid tert-butyl ester (11 g) were added palladium (II) acetate (0.726 g), 2-dicyclohexylphosphino-2',6'-dimethoxybiphenyl (2.692 g), potassium fluoride (15.06 g), methylboronic acid (7.88 g) and tetrahydrofuran (300 mL), and the mixture was refluxed under a nitrogen stream for 8 hr. Water was added to the reaction mixture, and the mixture was extracted with ethyl acetate. The organic layer was washed with water and saturated brine, and the solvent was evaporated. The residue was purified by column chromatography (hexane:ethyl acetate) to give 4-(3-methyl-5-trifluoromethylpyridin-2-yl)piperazine-1-carboxylic acid tert-butyl ester (9.14 g). To 4-(3-methyl-5-trifluoromethylpyridin-2-yl)piperazine-1-carboxylic acid tert-butyl ester (9.14 g) were added 4N hydrogen chloride/ethyl acetate (26 mL) and chloroform (64 mL), and the mixture was stirred at room temperature overnight. To the reaction mixture were added water and sodium hydrogen carbonate, and the mixture was extracted with chloroform. The solvent was evaporated to give the title compound (6.38 g).
MS (ESI) m/z:246(M+H)$^+$.

Preparation Example 52

Preparation of 1-(3,5,6-trimethylpyridin-2-yl)piperazine hydrochloride

To a mixture of 2,3,5,6-tetrachloropyridine (10 g), 1-Boc-piperazine (8.6 g) and potassium carbonate (13 g) was added 2-butanone (140 mL), and the mixture was refluxed for 8 hr. After cooling, water was added to the reaction mixture, and the mixture was extracted with ethyl acetate. The organic layer was washed with saturated brine, and the solvent was evaporated to give 4-(3,5,6-trichloropyridin-2-yl)piperazine-1-carboxylic acid tert-butyl ester (17 g). To a mixture of 4-(3,5,6-trichloropyridin-2-yl)piperazine-1-carboxylic acid tert-butyl ester (17 g), palladium (II) acetate (516 mg), 2-dicyclohexylphosphino-2',6'-dimethoxybiphenyl (1.9 g), potassium fluoride (24 g) and methylboronic acid (12 g) was added tetrahydrofuran (140 mL), and the mixture was refluxed for 8 hr. After cooling, the mixture was extracted with ethyl acetate. The organic layer was washed with saturated brine, and the solvent was evaporated. The residue was purified by column chromatography (hexane:ethyl acetate) to give 4-(3,5,6-trimethylpyridin-2-yl)piperazine-1-carboxylic acid tert-butyl ester (14 g). 4-(3,5,6-Trimethylpyridin-2-yl)piperazine-1-carboxylic acid tert-butyl ester (14 g) was dissolved in chloroform (28 mL), 4N hydrogen chloride/ethyl acetate (25 mL) was added, and the mixture was stirred at room temperature overnight. Ethyl acetate (100 mL) was added, and the mixture was filtered to give the title compound (11 g).

Preparation Example 53

Preparation of 1-(5-ethyl-3-methylpyridin-2-yl)piperazine

To a mixture of 4-(5-bromo-3-methylpyridin-2-yl)piperazine-1-carboxylic acid tert-butyl ester (3.3 g), bis(tricyclohexylphosphine)palladium (II) dichloride (332 mg), tripotassium phosphate (11 g) and vinylboronic acid pinacol ester (3 g) were added toluene (27 mL) and water (1.4 mL), and the mixture was refluxed for 8 hr. After cooling, the mixture was extracted with ethyl acetate. The organic layer was washed with saturated brine, and the solvent was evaporated. The residue was purified by column chromatography (hexane:ethyl acetate) to give 4-(3-methyl-5-vinylpyridin-2-yl)piperazine-1-carboxylic acid tert-butyl ester (1.3 g). 4-(3-Methyl-5-vinylpyridin-2-yl)piperazine-1-carboxylic acid tert-butyl ester (1.3 g) was dissolved in ethanol (20 mL), 5% palladium carbon-ethylenediamine complex (600 mg) was added, and the mixture was stirred under a hydrogen atmosphere for 8 hr at room temperature. After celite filtration, the solvent in the filtrate was evaporated to give 4-(5-ethyl-3-methylpyridin-2-yl)piperazine-1-carboxylic acid tert-butyl ester (870 mg). 4-(5-Ethyl-3-methylpyridin-2-yl)piperazine-1-carboxylic acid tert-butyl ester (870 mg) was dissolved in chloroform (2 mL), 4N hydrogen chloride/ethyl acetate (1.5 mL) was added, and the mixture was stirred at room temperature overnight. 1N Aqueous sodium hydroxide solution (7 mL) was added, and the mixture was extracted with chloroform. The organic layer was washed with saturated brine, and the solvent was evaporated to give the title compound (441 mg).

Preparation Example 54

Preparation of 1-(3-ethyl-5-methylpyridin-2-yl)piperazine hydrochloride

By reaction and treatment in the same manner as in Example 53 and using 4-(3-chloro-5-methylpyridin-2-yl)piperazine-1-carboxylic acid tert-butyl ester (9 g), which is the intermediate described in Preparation Example 48, a compound was obtained, which was treated with 4N hydrogen chloride/ethyl acetate (2 mL) to give the title compound (1.1 g).

Preparation Example 55

Preparation of 1-(5-methyl-3-trifluoromethylpyridin-2-yl)piperazine hydrochloride By reaction and treatment in the same manner as in Preparation Example 52 and using 2,5-dichloro-3-(trifluoromethyl)pyridine (2 g) and 1-Boc-piperazine (1.7 g), the title compound (0.5 g) was obtained.

Preparation Example 56

Preparation of 1-(5-isopropyl-3-methylpyridin-2-yl)piperazine

By reaction and treatment in the same manner as in Preparation Example 53 and using 4-(5-bromo-3-methylpyridin-2-yl)piperazine-1-carboxylic acid tert-butyl ester (3.3 g) and 2-isopropenyl-4,4,5,5-tetramethyl-1,3,2-dioxaborane (3 g), the title compound (1.6 g) was obtained.

Preparation Example 57

Preparation of 1-(5-cyclopentyl-3-methylpyridin-2-yl)piperazine

To a mixture of 4-(5-bromo-3-methylpyridin-2-yl)piperazine-1-carboxylic acid tert-butyl ester (3.6 g), palladium (II) acetate (225 mg), 2-dicyclohexylphosphino-2',6'-diisopropoxy-1,1'-biphenyl (933 mg), tripotassium phosphate (6.4 g) and cyclopentylboronic acid (2 g) were added toluene (30 mL) and water (1.5 mL), and the mixture was refluxed for 8 hr. After cooling, the mixture was extracted with ethyl acetate, washed with saturated brine, and the solvent was evaporated. The residue was purified by column chromatography (hexane:ethyl acetate) to give 4-(5-cyclopentyl-3-methylpyridin-2-yl)piperazine-1-carboxylic acid tert-butyl ester (1.3 g). 4-(5-Cyclopentyl-3-methylpyridin-2-yl)piperazine-1-carboxylic acid tert-butyl ester (1.3 g) was dissolved in chloroform (5 mL), 4N hydrogen chloride/ethyl acetate (5 mL) was added, and the mixture was stirred at room temperature overnight. To the reaction mixture was added 1N aqueous sodium hydroxide solution (20 mL), and the mixture was extracted with chloroform. The organic layer was washed with saturated brine, and the solvent was evaporated to give the title compound (1 g).

Preparation Example 58

Preparation of 1-(5-cyclobutyl-3-methylpyridin-2-yl)piperazine

To a mixture of 4-(5-bromo-3-methylpyridin-2-yl)piperazine-1-carboxylic acid tert-butyl ester (4.8 g), bis(tricyclohexylphosphine)palladium (II) dichloride (515 mg), tripotassium phosphate (16 g) and cyclobutylboronic acid (2.6 g) were added toluene (39 mL) and water (2 mL), and the mixture was refluxed for 8 hr. After cooling, the mixture was extracted with ethyl acetate, washed with saturated brine, and the solvent was evaporated. The residue was purified by column chromatography (hexane:ethyl acetate) to give 4-(5-cyclobutyl-3-methylpyridin-2-yl)piperazine-1-carboxylic acid tert-butyl ester (560 mg). 4-(5-cyclobutyl-3-methylpyridin-2-yl)piperazine-1-carboxylic acid tert-butyl ester (560 mg) was dissolved in chloroform (1.5 mL), 4N hydrogen chloride/ethyl acetate (1.5 mL) was added, and the mixture was stirred at room temperature overnight. To the reaction mixture was added 1N aqueous sodium hydroxide solution (8 mL), and the mixture was extracted with chloroform. The organic layer was washed with saturated brine, and the solvent was evaporated to give the title compound (350 mg).

Preparation Example 59

1-(3,5-dimethylpyrazin-2-yl)piperazine hydrochloride

To a mixture of 2-chloro-3,5-dimethylpyrazine (2.8 g), 1-Boc-piperazine (3.7 g), palladium (II) acetate (225 mg), 2-(dicyclohexylphosphino)-2',4',6'-tri-isopropyl-1,1'-biphenyl (953 mg) and sodium tert-butoxide (2.7 g) was added toluene (40 mL), and the mixture was refluxed for 8 hr. After cooling, the mixture was extracted with ethyl acetate. The organic layer was washed with saturated brine, and the solvent was evaporated. The residue was purified by column chromatography (hexane:ethyl acetate) to give 3',5'-dimethyl-2,3,5,6-tetrahydro[1,2']bipyrazinyl-4-carboxylic acid tert-butyl ester (5 g). 3',5'-Dimethyl-2,3,5,6-tetrahydro[1,2']bipyrazinyl-4-carboxylic acid tert-butyl ester (5 g) was dissolved in chloroform (15 mL), 4N hydrogen chloride/ethyl acetate (15 mL) was added, and the mixture was stirred at room temperature overnight. Ethyl acetate (100 mL) was added, and the mixture was filtered to give the title compound (3.3 g).

Preparation Example 60

Preparation of (4-bromo-2,6-difluorophenyl)[4-(3,5-dimethylpyridin-2-yl)piperazin-1-yl]methanone 4-Bromo-2,6-difluorobenzoic acid (2.875 g) and 1-(3,5-dimethylpyridin-2-yl)piperazine (2.32 g) described in Preparation Example 47 and 1-hydroxybenzotriazole 1hydrate (1.64 g) were dissolve in N,N-dimethylformamide (50 mL), 1-ethyl-3-(3'-dimethylaminopropyl)carbodiimide hydrochloride (2.32 g) was added, and the mixture was stirred at room temperature overnight. To the reaction mixture was added saturated brine, and the mixture was extracted with ethyl acetate. The organic layer was washed with water and saturated brine, and the solvent was evaporated. The residue was purified by column chromatography (chloroform:methanol) to give the title compound (4.33 g).
MS (ESI) m/z:410(M+H)$^+$.

Preparation Example 61

Preparation of (4-bromo-2-methanesulfonylphenyl)[4-(3,5-dimethylpyridin-2-yl)piperazin-1-yl]methanone By reaction and treatment in the same manner as in Preparation Example 60 and using 4-bromo-2-methanesulfonylbenzoic acid (2.79 g) and 1-(3,5-dimethylpyridin-2-yl)piperazine (1.91 g) described in Preparation Example 47, the title compound (3.09 g) was obtained. MS (ESI) m/z:452(M+H)$^+$.

Preparation Example 62

Preparation of 1-(3,5-dicyclopropylpyridin-2-yl)piperazine 4-(3,5-Dicyclopropylpyridin-2-yl)piperazine-1-carboxylic acid tert-butyl ester (7.4 g), which is the intermediate described in Preparation Example 50, was dissolved in chloroform (54 mL), 4N hydrogen chloride/ethyl acetate (21.5 mL) was added, and the mixture was stirred at room temperature overnight. To the reaction mixture was added chloroform and saturated aqueous sodium hydrogen carbonate, and the mixture was extracted with chloroform. The solvent was evaporated to give the title compound (4.6 g).

Preparation Example 63

Preparation of (4-bromo-2-nitrophenyl)[4-(3,5-dimethylpyridin-2-yl)piperazin-1-yl]methanone By reaction and treatment in the same manner as in Preparation Example 60 and using 4-bromo-2-nitrobenzoic acid (2.3 g) and 1-(3,5-dimethylpyridin-2-yl)piperazine (1.91 g) described in Preparation Example 47, the title compound (3.54 g) was obtained.
MS (ESI) m/z:419(M+H)$^+$.

Preparation Example 64

Preparation of 1-(3,5-dimethylpyridin-2-yl)piperazine hydrochloride

To a mixture of 4-(5-bromo-3-methylpyridin-2-yl)piperazine-1-carboxylic acid tert-butyl ester (25 g), methylboronic acid (8.4 g), [1,1'-bis(diphenylphosphino)ferrocene]palladium (II) dichloride dichloromethane complex (1:1)(2.9 g) and potassium fluoride (16 g) was added tetrahydrofuran (140 mL), and the mixture was refluxed for 8 hr. After cooling, water was added to the reaction mixture, and the mixture was extracted with ethyl acetate. The organic layer was washed with saturated brine, and the solvent was evaporated. The residue was purified by column chromatography (hexane:ethyl acetate) to give 4-(3,5-dimethylpyridin-2-yl)piperazine-1-carboxylic acid tert-butyl ester (16 g). 4-(3,5-Dimethylpyridin-2-yl)piperazine-1-carboxylic acid tert-butyl ester (16 g) was dissolved in chloroform (100 mL), 4N hydrogen chloride/ethyl acetate (50 mL) was added, and the mixture was stirred at room temperature overnight. Ethyl acetate (200 mL) was added, and the mixture was filtered to give the title compound (10 g).

Preparation Example 65

Preparation of (4-bromo-2-fluorophenyl)[4-(3,5-dimethylpyridin-2-yl)piperazin-1-yl]methanone 1-(3,5-Dimethylpyridin-2-yl)piperazine (2.42 g) described in Preparation Example 47 was dissolve in tetrahydrofuran (32 mL), 4-bromo-2-fluorobenzoyl chloride (3.0 g) and 1N aqueous sodium hydroxide solution (15 mL) were added, and the mixture was stirred at room temperature. The reaction mixture poured into water under cooling, 4N aqueous sodium hydroxide solution and ethyl acetate were added and the mixture was extracted with ethyl acetate. The organic layer was washed with 4N aqueous sodium hydroxide solution and saturated brine, then washed with saturated brine, sodium sulfate was added and dried. The solvent was evaporated under reduced pressure. The residue was purified by column chromatography (ethyl acetate:hexane) to give the title compound (4.39 g).
MS (ESI) m/z:392(M+H)$^+$.

Preparation Example 66

Preparation of (4-bromo-3-fluorophenyl)[4-(3,5-dimethylpyridin-2-yl)piperazin-1-yl]methanone 1-(3,5-Dimethylpyridin-2-yl)piperazine (2.87 g) described in Preparation Example 47 was dissolved in N,N-dimethylformamide (38 ml), 4-bromo-3-fluorobenzoic acid (3.29 g), 1-hydroxybenzotriazole 1 hydrate (2.43 g) and 1-ethyl-3-(3'-dimethylaminopropyl)carbodiimide hydrochloride (3.45 g) were added, and the mixture was stirred at room temperature for 4 hr. The reaction mixture was poured into water under cooling, and extracted with ethyl acetate. The organic layer was washed twice with water, washed with saturated brine, and dried over sodium sulfate. The solvent was evaporated under reduced pressure and the residue was purified by column chromatography (ethyl acetate:hexane). Then, ethyl acetate and hexane were added and the mixture was stirred at room temperature. The solid was collected by filtration and dried under reduced pressure to give the title compound (3.97 g).
MS (ESI) m/z:392(M+H)$^+$.

Preparation Example 67

Preparation of (4-bromo-2-methylphenyl)[4-(3,5-dimethylpyridin-2-yl)piperazin-1-yl]methanone To a mixture of 1-(3,5-dimethylpyridin-2-yl)piperazine (3.8 g) described in Preparation Example 47, 4-bromo-2-methylbenzoic acid (4.3 g) and 4-(4,6-dimethoxy[1.3.5]triazin-2-yl)-4-methylmorpholinium chloride hydrate (DMT-MM) (8.8 g) were added chloroform (30 mL) and methanol (30 mL), and the mixture was stirred at room temperature overnight. After evaporation of the solvent, ethyl acetate was added, and insoluble materials were filtered off. The solvent in the filtrate was evaporated, and the residue was purified by column chromatography (hexane:ethyl acetate) to give the title compound (7 g).

Preparation Example 68

Preparation of (4-bromo-3-methylphenyl)[4-(3,5-dimethylpyridin-2-yl)piperazin-1-yl]methanone By reaction and treatment in the same manner as in Preparation Example 67 and using 4-bromo-3-methylbenzoic acid (4.3 g) and 1-(3,5-dimethylpyridin-2-yl)piperazine (3.8 g) described in Preparation Example 47, the title compound (7 g) was obtained.

Preparation Example 69

Preparation of (4-bromo-2-chlorophenyl)[4-(3,5-dimethylpyridin-2-yl)piperazin-1-yl]methanone To a mixture of 1-(3,5-dimethylpyridin-2-yl)piperazine hydrochloride (956 mg) described in Preparation Example 64, 4-bromo-2-chlorobenzoic acid (1 g) and 4-(4,6-dimethoxy[1.3.5]triazin-2-yl)-4-methylmorpholinium chloride hydrate (DMT-MM) (1.7 g) were added chloroform (6 mL), methanol (6 mL) and N-methylmorpholine (465 µL), and the mixture was stirred at room temperature overnight. Water was added to the reaction mixture, and the mixture was extracted with chloroform. The organic layer was washed with saturated brine, and the solvent was evaporated. The residue was purified by column chromatography (hexane:ethyl acetate) to give the title compound (1.7 g).

Preparation Example 70

Preparation of (4-bromo-3-chlorophenyl)[4-(3,5-dimethylpyridin-2-yl)piperazin-1-yl]methanone By reaction and treatment in the same manner as in Preparation Example 69 and using 4-bromo-3-chlorobenzoic acid (989 mg) and 1-(3,5-dimethylpyridin-2-yl)piperazine hydrochloride (956 mg) described in Preparation Example 64, the title compound (1.7 g) was obtained.

Preparation Example 71

Preparation of (5-chloro-4-iodo-2-methoxyphenyl)[4-(3,5-dimethylpyridin-2-yl)piperazin-1-yl]methanone By reaction and treatment in the same manner as in Preparation Example 67 and using 5-chloro-4-iodo-2-methoxybenzoic acid (1 g) and 1-(3,5-dimethylpyridin-2-yl)piperazine (612 mg) described in Preparation Example 47, the title compound (1.5 g) was obtained.

Preparation Example 72

Preparation of (4-bromo-2-chloro-5-fluorophenyl)[4-(3,5-dimethylpyridin-2-yl)piperazin-1-yl]methanone By reaction and treatment in the same manner as in Preparation Example 8 and using 4-bromo-2-chloro-5-fluorobenzoyl chloride (1 g) and 1-(3,5-dimethylpyridin-2-yl)piperazine hydrochloride (843 mg) described in Preparation Example 64, the title compound (1.5 g) was obtained.

Preparation Example 73

Preparation of (6-bromopyridin-3-yl)[4-(3,5-dimethylpyridin-2-yl)piperazin-1-yl]methanone By reaction and treatment in the same manner as in Preparation Example 67 and using 6-bromonicotinic acid (808 mg) and 1-(3,5-dimethylpyridin-2-yl)piperazine (765 mg) described in Preparation Example 47, the title compound (1.5 g) was obtained.

Preparation Example 74

Preparation of (4-bromo-2-methanesulfonylphenyl)[4-(3,5-dichloropyridin-2-yl)piperazin-1-yl]methanone By reaction and treatment in the same manner as in Preparation Example 1 and using 4-bromo-2-methanesulfonylbenzoic acid (279 mg) and 1-(3,5-dichloropyridin-2-yl)piperazine (232 mg), the title compound (0.5 g) was obtained.

Preparation Example 75

Preparation of ethyl (R)-4-(2-oxo-4-phenyloxazolidin-3-yl)benzoate

By reaction and treatment in the same manner as in Preparation Example 12 and using ethyl 4-iodobenzoate (1.7 mL) and (R)-(−)-4-phenyloxazolidin-2-one (2 g), the title compound (4 g) was obtained.

Preparation Example 76

Preparation of 1-(3-cyclopropyl-5-trifluoromethylpyridin-2-yl)piperazine hydrochloride By reaction and treatment in the same manner as in Preparation Example 49 and using 4-(3-chloro-5-trifluoromethylpyridin-2-yl)piperazine-1-carboxylic acid tert-butyl ester (7.3 g), which is the intermediate described in Preparation Example 51, and cyclopropylboronic acid (4.2 g), the title compound (5.8 g) was obtained.

Preparation Example 77

Preparation of [4-(3,5-dimethylpyridin-2-yl)piperazin-1-yl](4-iodophenyl)methanone By reaction and treatment in the same manner as in Preparation Example 8 and using 1-(3,5-dimethylpyridin-2-yl)piperazine (3.8 g) described in Preparation Example 47 and 4-iodobenzoyl chloride (5.3 g), the title compound (8 g) was obtained.

Preparation Example 78

Preparation of (R)-4-(4-ethyl-2-oxooxazolidin-3-yl)benzoic acid

By reaction and treatment in the same manner as in Preparation Example 18 and using ethyl 4-iodobenzoate (1.4 mL) and (R)-4-ethyloxazolidin-2-one (979 mg) described in Preparation Example 26, the title compound (2.6 g) was obtained.

Preparation Example 79

Preparation of (R)-4-(4-propyl-2-oxooxazolidin-3-yl)benzoic acid

By reaction and treatment in the same manner as in Preparation Example 18 and using ethyl 4-iodobenzoate (3.2 mL) and (R)-4-propyloxazolidin-2-one (2.5 g) described in Preparation Example 29, the title compound (5.7 g) was obtained.

Preparation Example 80

Preparation of (S)-4-(4-isopropyl-2-oxooxazolidin-3-yl)benzoic acid

By reaction and treatment in the same manner as in Preparation Example 18 and using ethyl 4-iodobenzoate (2.9 mL) and (S)-4-isopropyloxazolidin-2-one (2.5 g), the title compound (4.5 g) was obtained.

Preparation Example 81

Preparation of methyl (R)-3-fluoro-4-(4-methyl-2-oxooxazolidin-3-yl)benzoate

By reaction and treatment in the same manner as in Preparation Example 12 and using methyl 4-bromo-3-fluorobenzoate (1.2 g) and (R)-4-methyloxazolidin-2-one (607 mg) described in Preparation Example 25, the title compound (1.2 g) was obtained.

Preparation Example 82

Preparation of methyl (R)-3-methyl-4-(4-methyl-2-oxooxazolidin-3-yl)benzoate

By reaction and treatment in the same manner as in Preparation Example 12 and using methyl 4-bromo-3-methylbenzoate (1.1 g) and (R)-4-methyloxazolidin-2-one (607 mg) described in Preparation Example 25, the title compound (1.2 g) was obtained.

Preparation Example 83

Preparation of (4-bromo-2-methanesulfonylphenyl)[4-(3,5,6-trimethylpyridin-2-yl)piperazin-1-yl]methanone By reaction and treatment in the same manner as in Preparation Example 27 and using 4-bromo-2-methanesulfonylbenzoic acid (3.5 g) and 1-(3,5,6-trimethylpyridin-2-yl)piperazine hydrochloride (3 g) described in Preparation Example 52, the title compound (3 g) was obtained.

Preparation Example 84

Preparation of (4-bromo-2-methanesulfonylphenyl)[4-(3-cyclopropyl-5-methylpyridin-2-yl)piperazin-1-yl]methanone By reaction and treatment in the same manner as in Preparation Example 27 and using 4-bromo-2-methanesulfonylbenzoic acid (558 mg) and 1-(3-cyclopropyl-5-methylpyridin-2-yl)piperazine hydrochloride (508 mg) described in Preparation Example 48, the title compound (0.9 g) was obtained.

Preparation Example 85

Preparation of (4-bromo-2-methanesulfonylphenyl)[4-(5-cyclopropyl-3-methylpyridin-2-yl)piperazin-1-yl]methanone By reaction and treatment in the same manner as in Preparation Example 27 and using 4-bromo-2-methanesulfonylbenzoic acid (558 mg) and 1-(5-cyclopropyl-3-methylpyridin-2-yl)piperazine hydrochloride (508 mg) described in Preparation Example 49, the title compound (0.9 g) was obtained.

Preparation Example 86

Preparation of (4-bromo-2-fluorophenyl)[4-(5-cyclopropyl-3-methylpyridin-2-yl)piperazin-1-yl]methanone By reaction and treatment in the same manner as in Preparation Example 8 and using 4-bromo-2-fluorobenzoyl chloride (2.5 g) and 1-(5-cyclopropyl-3-methylpyridin-2-yl)piperazine hydrochloride (2.7 g) described in Preparation Example 49, the title compound (4.2 g) was obtained.

Preparation Example 87

Preparation of (4-bromo-2-fluorophenyl)[4-(3-cyclopropyl-5-trifluoromethylpyridin-2-yl)piperazin-1-yl]methanone By reaction and treatment in the same manner as in Preparation Example 8 and using 4-bromo-2-fluorobenzoyl chloride (2.5 g) and 1-(3-cyclopropyl-5-trifluoromethylpyridin-2-yl)piperazine hydrochloride (3.2 g) described in Preparation Example 76, the title compound (4.2 g) was obtained.

Preparation Example 88

Preparation of 1-(2,4-dimethylphenyl)-[1,4]diazepane hydrochloride

To 1-bromo-2,4-dimethylbenzene (1.85 g) were added 1-BOC-1,4]diazepane (2 g), palladium (II) acetate (0.115 g), rac-2,2'-bis(diphenylphosphino)-1,1'-binaphthyl (0.31 g), sodium tert-butoxide (1.34 g) and toluene (35 mL), and the mixture was refluxed for 9 hr. Water was added to the reaction mixture, and the mixture was extracted with ethyl acetate. The organic layer was washed with saturated brine, and the solvent was evaporated. The residue was purified by column chromatography (chloroform:methanol) to give 4-(2,4-dimethylphenyl)-[1,4]diazepane-1-carboxylic acid tert-butyl ester (2.16 g). To 4-(2,4-dimethylphenyl)-[1,4]diazepane-1-carboxylic acid tert-butyl ester (2.16 g) were added 4N hydrogen chloride/ethyl acetate (6.9 mL) and chloroform (17 mL), and the mixture was stirred at room temperature overnight. The solvent was evaporated to give the title compound (1.74 g).

Preparation Example 89

Preparation of (4-bromo-2-methanesulfonylphenyl)[4-(3,5-dicyclopropylpyridin-2-yl)piperazin-1-yl]methanone By reaction and treatment in the same manner as in Preparation Example 38 and using 4-bromo-2-methanesulfonylbenzoic acid (2.29 g) and 1-(3,5-dicyclopropylpyridin-2-yl)piperazine (2 g) described in Preparation Example 62, the title compound (3.02 g) was obtained.
MS (ESI) m/z:504(M+H)$^+$.

Preparation Example 90

Preparation of 4-(4-bromo-3-fluorobenzoyl)piperazine-1-carboxylic acid tert-butyl ester 4-Bromo-3-fluorobenzoic acid (4.38 g) was dissolve in tetrahydrofuran (50 mL), 1-ethyl-3-(3'-dimethylaminopropyl)carbodiimide hydrochloride (4.6 g), 1-hydroxybenzotriazole 1hydrate (3.24 g) and piperazine-1-carboxylic acid tert-butyl ester (4.47 g) were added, and the mixture was stirred at room temperature. The reaction mixture was poured into water under cooling, 4N aqueous sodium hydroxide solution and ethyl acetate were added and the mixture was extracted with ethyl acetate. The organic layer was washed with 4N aqueous sodium hydroxide solution and saturated brine, then washed with saturated brine, and dried over sodium sulfate. The solvent was evaporated under reduced pressure. The residue was purified by column chromatography (ethyl acetate:hexane) to give the title compound (7.01 g).

MS (ESI) m/z:287 (M+H−100)+ (detected as Boc-dissociated compound).

Preparation Example 91

Preparation of (R)-4-[4-(4-benzoyloxymethyl-2-oxooxazolidin-3-yl)-3-fluoro-benzoyl]piperazine-1-carboxylic acid tert-butyl ester To a mixture of 4-(4-bromo-3-fluorobenzoyl)piperazine-1-carboxylic acid tert-butyl ester (3.49 g) described in Preparation Example 90, benzoic acid (R)-2-oxooxazolidin-4-ylmethyl ester (1.99 g), potassium carbonate (2.49 g) and copper (I) iodide (343 mg) were added toluene (18 mL) and N,N'-dimethylethylenediamine (387 μL), and the mixture was refluxed for 3 hr. Since the starting materials were left, copper (I) iodide (343 mg) and N,N'-dimethylethylenediamine (387 μL) were added and the mixture was further refluxed for 4 hr. The reaction mixture was cooled, ethyl acetate and aqueous ammonium chloride solution were added and the mixture was extracted with ethyl acetate. The ethyl acetate layer was washed with a 1:1 mixture of saturated aqueous ammonium chloride solution and ammonia water, and the mixture was washed once with saturated aqueous ammonium chloride solution, once with saturated aqueous sodium chloride solution, and dried over sodium sulfate. The solvent was evaporated under reduced pressure. The residue was purified by column chromatography (chloroform:methanol) to give the title compound (1.48 g).

MS (ESI) m/z:528(M+H)+.

Preparation Example 92

Preparation of (R)-4-[3-fluoro-4-(4-hydroxymethyl-2-oxooxazolidin-3-yl)benzoyl]piperazine-1-carboxylic acid tert-butyl ester (R)-4-[4-(4-Benzoyloxymethyl-2-oxooxazolidin-3-yl)-3-fluoro-benzoyl]piperazine-1-carboxylic acid tert-butyl ester (1.45 g) described in Preparation Example 91 was dissolved in dimethoxyethane, 4N aqueous sodium hydroxide solution was added and the mixture was stirred at room temperature. Under ice-cooling, the reaction mixture was neutralized with 1N hydrochloric acid, ethyl acetate and sodium chloride were added and the mixture was extracted with ethyl acetate, and dried over sodium sulfate. The solvent was evaporated under reduced pressure. The residue was purified by column chromatography (chloroform:methanol) to give the title compound (859 mg).

MS (ESI) m/z:324 (M+H−100)+ (detected as Boc-dissociated compound).

Preparation Example 93

Preparation of (R)-4-[3-fluoro-4-(4-methoxymethyl-2-oxooxazolidin-3-yl)benzoyl]piperazine-1-carboxylic acid tert-butyl ester (R)-4-[3-fluoro-4-(4-hydroxymethyl-2-oxooxazolidin-3-yl)benzoyl]piperazine-1-carboxylic acid tert-butyl ester (494 mg) described in Preparation Example 92 was dissolved in N,N-dimethylformamide (3.7 mL), sodium hydride (51 mg, 60% in oil) was added under ice-cooling and the mixture was stirred. Then, under ice-cooling, methyl iodide (182 mg) was added and the mixture was stirred at room temperature. The reaction mixture was added to saturated brine under ice-cooling and the mixture was extracted with ethyl acetate. The organic layer was washed twice with saturated brine, and dried over sodium sulfate, and the solvent was evaporated under reduced pressure. The residue was purified by column chromatography (chloroform:methanol) to give the title compound (290 mg).

MS (ESI) m/z:338 (M+H−100)+ (detected as Boc-dissociated compound).

Preparation Example 94

Preparation of (R)-3-[2-fluoro-4-(piperazine-1-carbonyl)phenyl]-4-methoxymethyloxazolidin-2-one (R)-4-[3-Fluoro-4-(4-methoxymethyl-2-oxooxazolidin-3-yl)benzoyl]piperazine-1-carboxylic acid tert-butyl ester (506 mg) described in Preparation Example 93 was dissolved in ethyl acetate (5 mL), 4N hydrogen chloride/ethyl acetate (5 mL) was added and the mixture was stirred at room temperature. Under ice-cooling, the reaction mixture was neutralized with ethyl acetate and saturated aqueous sodium hydrogen carbonate solution, and extracted once with ethyl acetate and the aqueous layer was extracted with twice with chloroform. The organic layer was dried over sodium sulfate and the solvent was evaporated under reduced pressure to give the title compound (390 mg).

MS (ESI) m/z:338(M+H)+.

Preparation Example 95

Preparation of [4-(3,5-dicyclopropylpyridin-2-yl)piperazin-1-yl](4-iodophenyl)methanone By reaction and treatment in the same manner as in Preparation Example 65 and using 1-(3,5-dicyclopropylpyridin-2-yl)piperazine (5.52 g) described in Preparation Example 62, 4-iodobenzoyl chloride (6.35 g), the title compound (9.76 g) was obtained.

MS (ESI) m/z:474(M+H)+.

Preparation Example 96

Preparation of 1-(5-cyclopropyl-3-methylpyridin-2-yl)piperazine

To 1-(5-cyclopropyl-3-methylpyridin-2-yl)piperazine hydrochloride described in Preparation Example 49 was added ethyl acetate (50 mL), 1N aqueous sodium hydroxide solution (10 mL) was added under cooling and the mixture was stirred. To the reaction mixture were added sodium chloride and water under cooling, and the mixture was extracted twice with ethyl acetate. The organic layer was dried over sodium sulfate. The solvent was evaporated under reduced pressure to give the title compound (1.43 g).

MS (ESI) m/z:218(M+H)+.

Preparation Example 97

Preparation of [4-(5-cyclopropyl-3-methylpyridin-2-yl)piperazin-1-yl](4-iodophenyl)methanone By reaction and treatment in the same manner as in Preparation Example 65 and using 1-(5-cyclopropyl-3-methylpyridin-2-yl)piperazine (1.42 g) described in Preparation Example 96, 4-iodobenzoyl chloride (1.83 g), the title compound (2.63 g) was obtained.

MS (ESI) m/z:448(M+H)+.
The compounds obtained in Preparation Examples 1-97 are as described below.
Prepar. Ex. 1
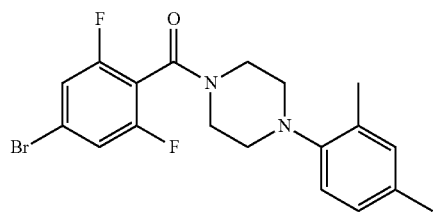
Prepar. Ex. 2
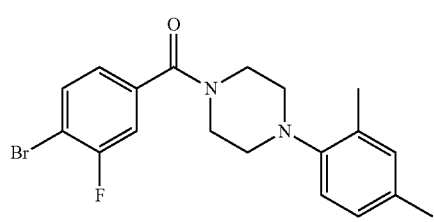
Prepar. Ex. 3
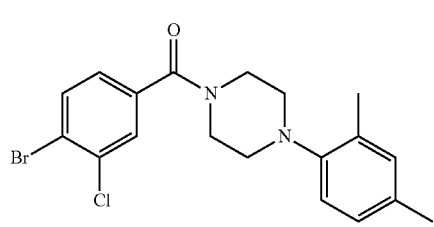
Prepar. Ex. 4
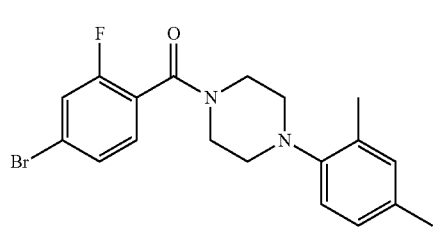
Prepar. Ex. 5
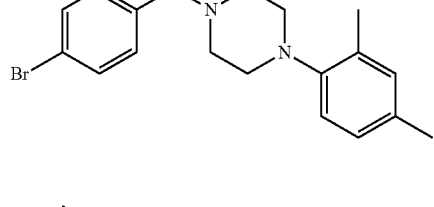
Prepar. Ex. 6
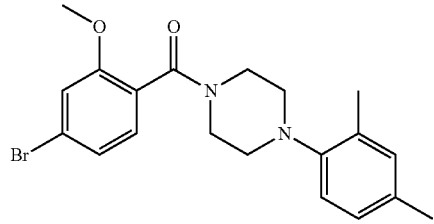
Prepar. Ex. 7
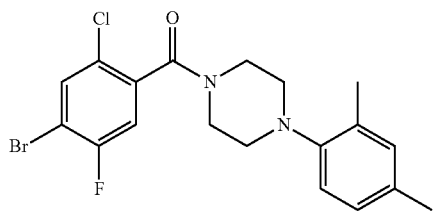
Prepar. Ex. 8
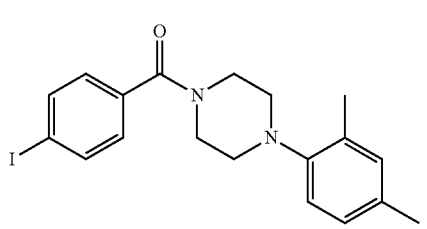
Prepar. Ex. 9
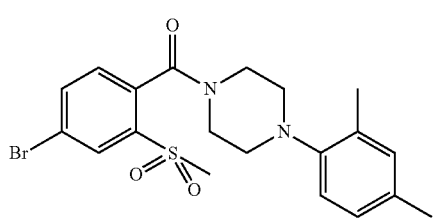
Prepar. Ex. 10
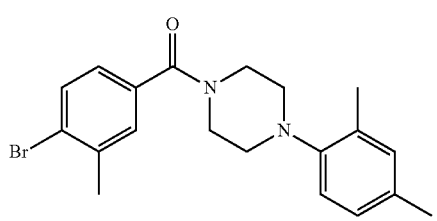
Prepar. Ex. 11
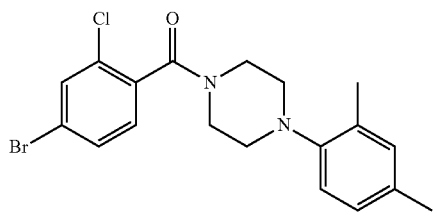
Prepar. Ex. 12
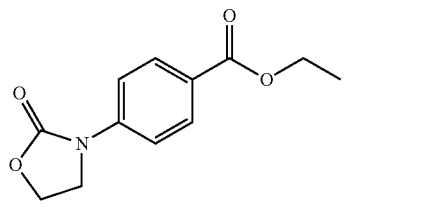
Prepar. Ex. 13
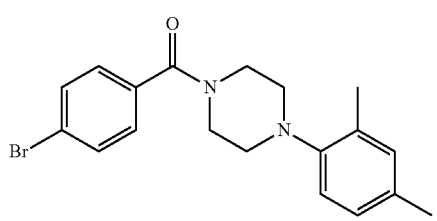

-continued
Prepar. Ex. 14
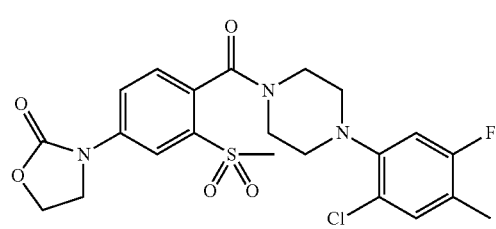
Prepar. Ex. 15
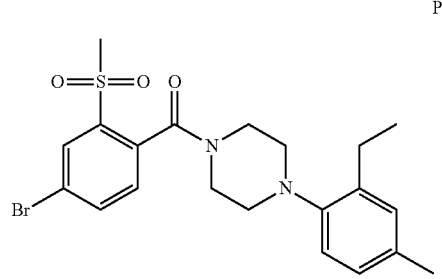
Prepar. Ex. 16
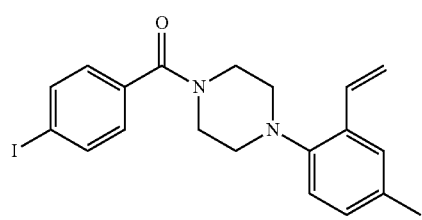
Prepar. Ex. 17
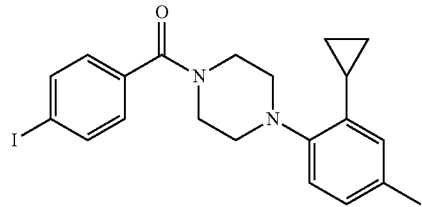
Prepar. Ex. 18
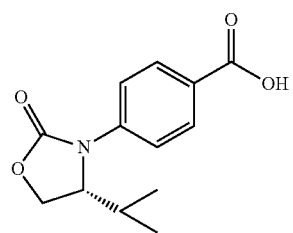
Prepar. Ex. 19
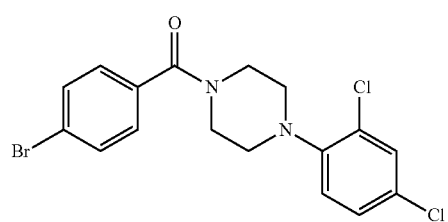
-continued
Prepar. Ex. 20
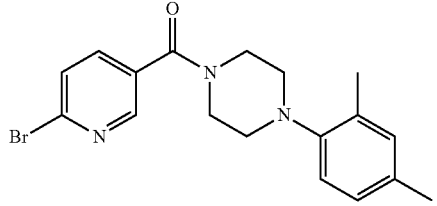
Prepar. Ex. 21
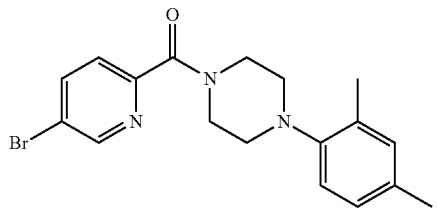
Prepar. Ex. 22
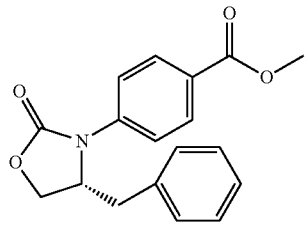
Prepar. Ex. 23
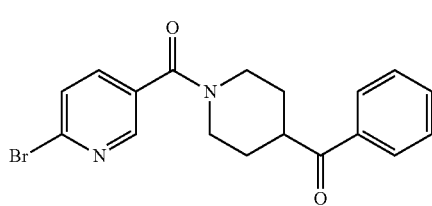
Prepar. Ex. 24
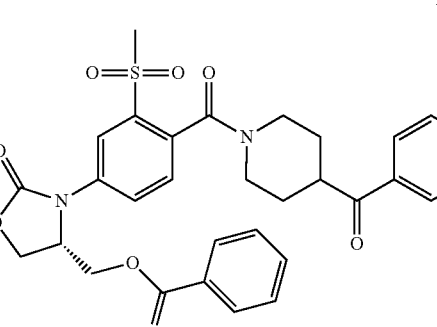
Prepar. Ex. 25
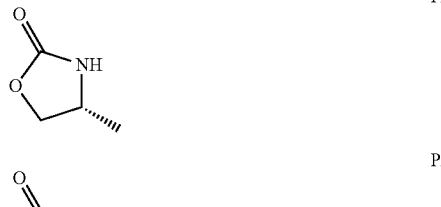
Prepar. Ex. 26
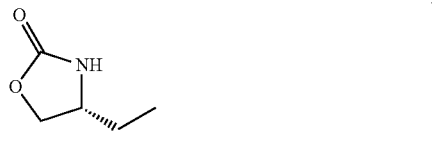

Prepar. Ex. 27
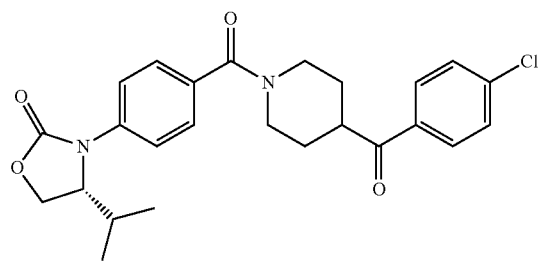
Prepar. Ex. 28
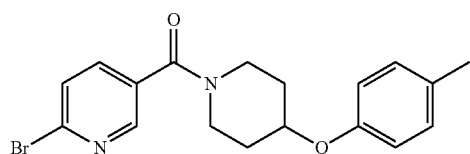
Prepar. Ex. 29
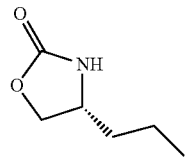
Prepar. Ex. 30
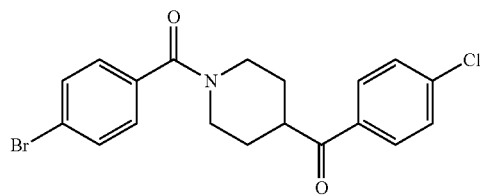
Prepar. Ex. 31
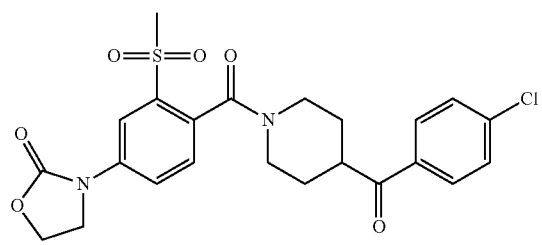
Prepar. Ex. 32
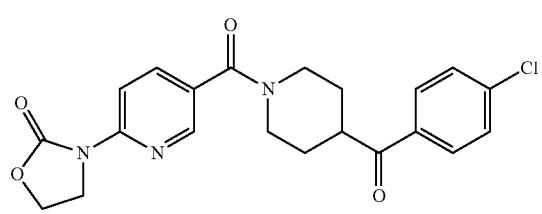
Prepar. Ex. 33
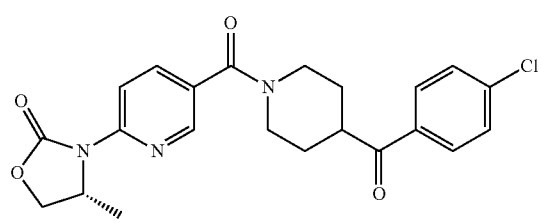
Prepar. Ex. 34
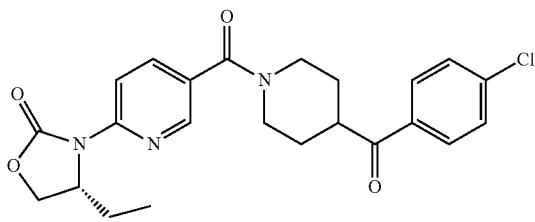
Prepar. Ex. 35
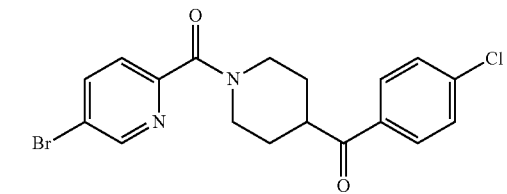
Prepar. Ex. 36
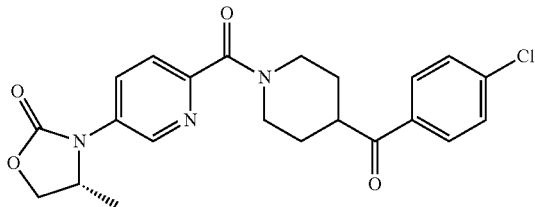
Prepar. Ex. 37
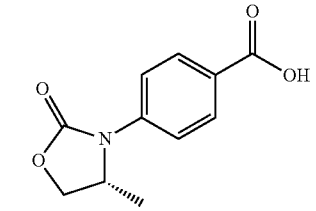
Prepar. Ex. 38
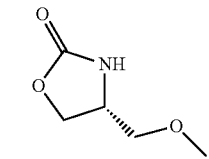
Prepar. Ex. 39
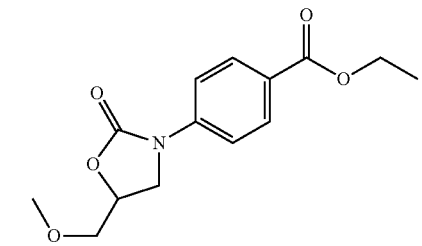
Prepar. Ex. 40
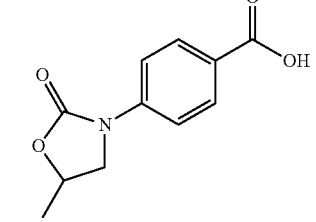

Prepar. Ex. 41
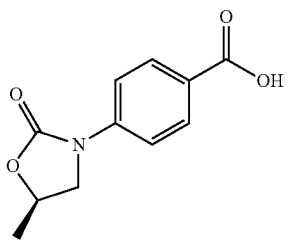
Prepar. Ex. 42
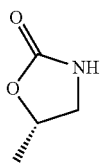
Prepar. Ex. 43
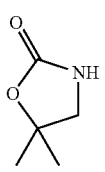
Prepar. Ex. 44
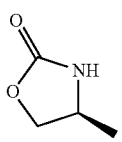
Prepar. Ex. 45
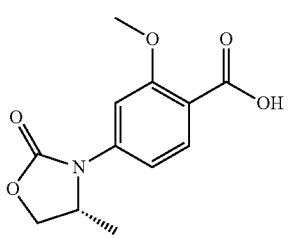
Prepar. Ex. 46
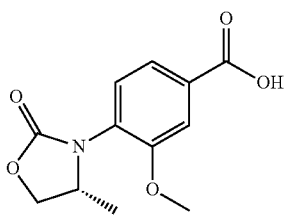
Prepar. Ex. 47
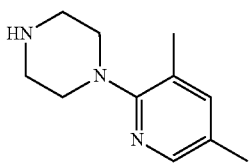
Prepar. Ex. 48
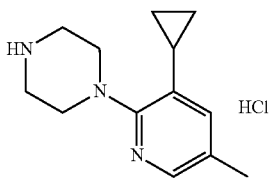
Prepar. Ex. 49
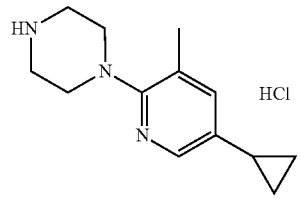
HCl
Prepar. Ex. 50
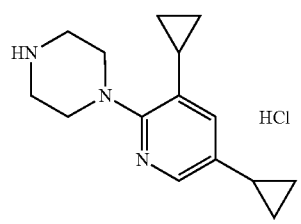
HCl
Prepar. Ex. 51
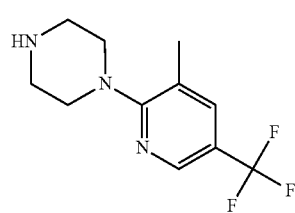
Prepar. Ex. 52
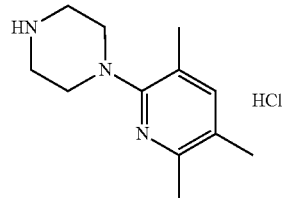
HCl
Prepar. Ex. 53
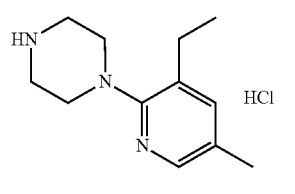
Prepar. Ex. 54
HCl
Prepar. Ex. 55
HCl
Prepar. Ex. 56
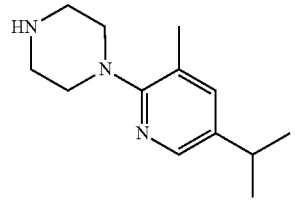

-continued
Prepar. Ex. 57
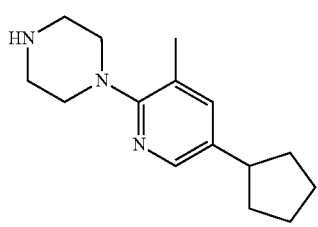
Prepar. Ex. 58
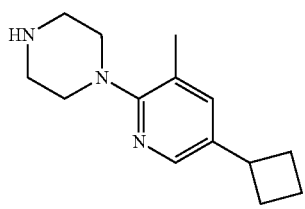
Prepar. Ex. 59
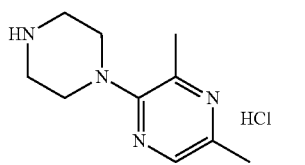
Prepar. Ex. 60
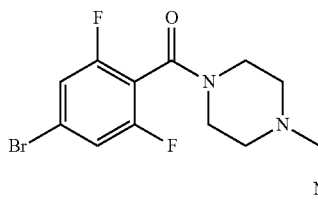
Prepar. Ex. 61
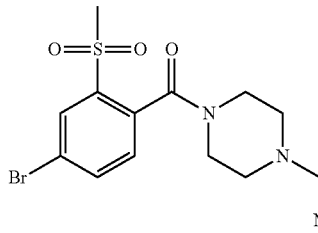
Prepar. Ex. 62
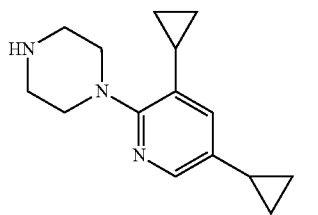
Prepar. Ex. 63
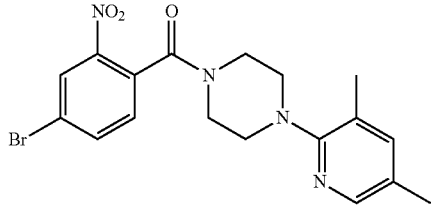
-continued
Prepar. Ex. 64
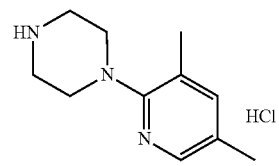
Prepar. Ex. 65
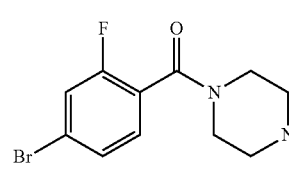
Prepar. Ex. 66
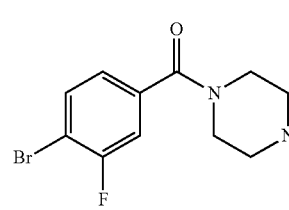
Prepar. Ex. 67
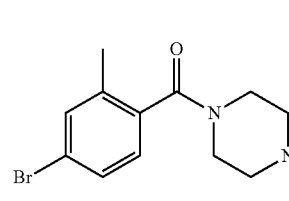
Prepar. Ex. 68
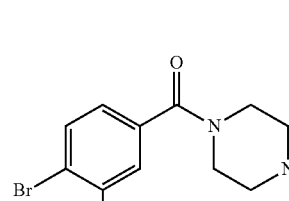
Prepar. Ex. 69
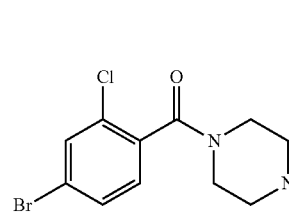
Prepar. Ex. 70
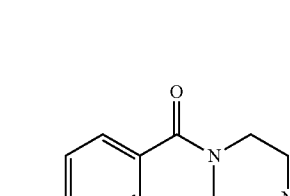

Prepar. Ex. 71, Prepar. Ex. 72, Prepar. Ex. 73, Prepar. Ex. 74, Prepar. Ex. 75, Prepar. Ex. 76, Prepar. Ex. 77, Prepar. Ex. 78, Prepar. Ex. 79, Prepar. Ex. 80, Prepar. Ex. 81, Prepar. Ex. 82

Prepar. Ex. 83
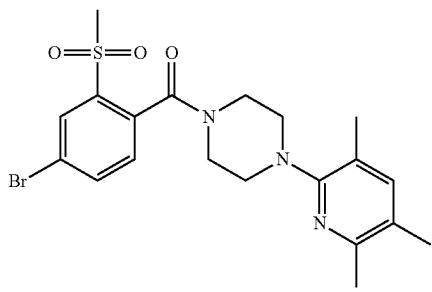
Prepar. Ex. 84
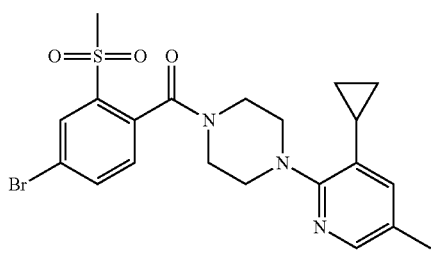
Prepar. Ex. 85
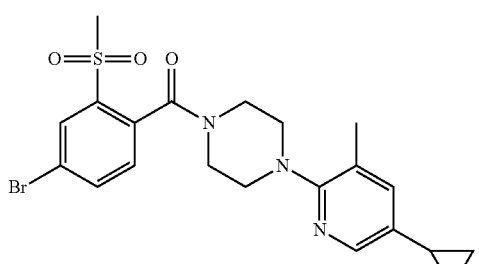
Prepar. Ex. 86
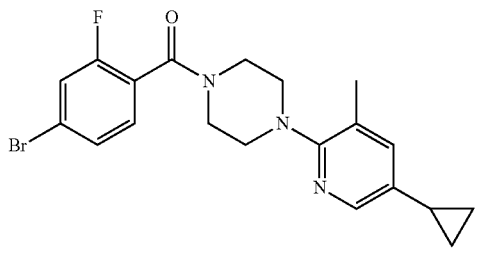
Prepar. Ex. 87
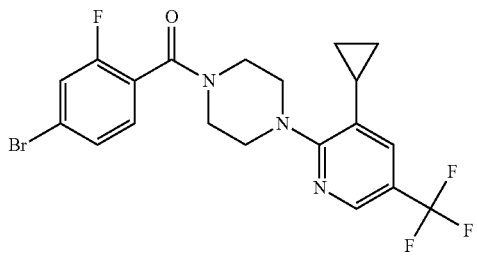
Prepar. Ex. 88
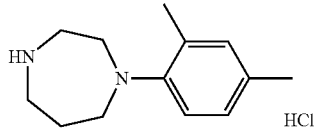
Prepar. Ex. 89
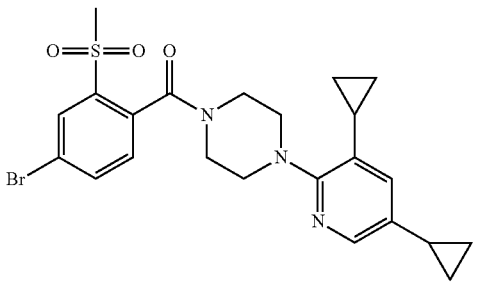
Prepar. Ex. 90
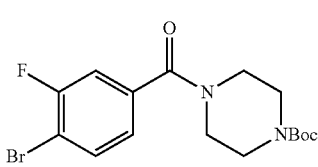
Prepar. Ex. 91
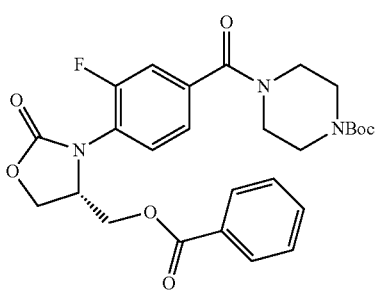
Prepar. Ex. 92
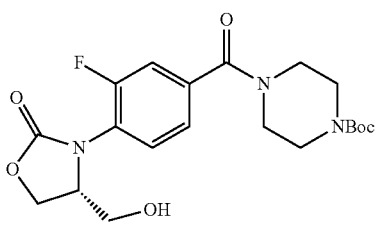
Prepar. Ex. 93
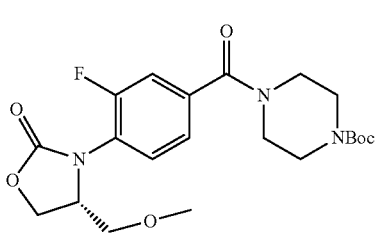
Prepar. Ex. 94
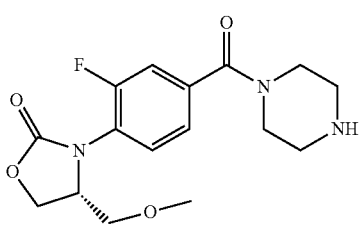

Prepar. Ex. 95

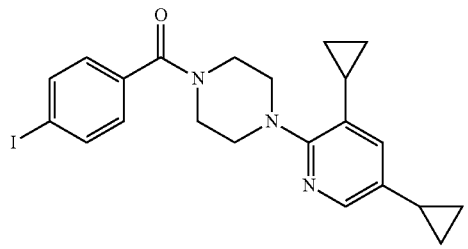

Prepar. Ex. 96

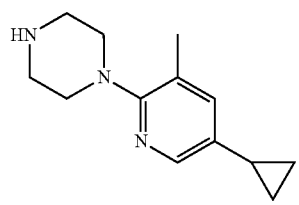

Prepar. Ex. 97

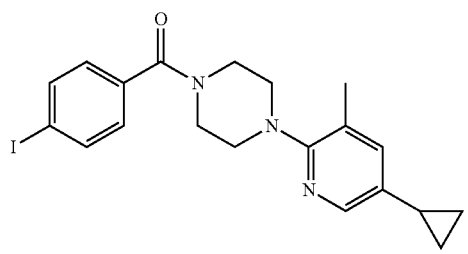

Preparation Example 98

Preparation of (4-bromo-2-fluorophenyl)[4-(3,5,6-trimethylpyridin-2-yl)piperazin-1-yl]methanone

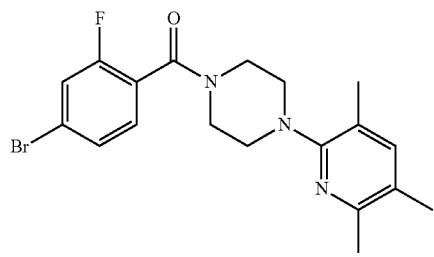

By reaction and treatment in the same manner as in Preparation Example 8 and using 4-bromo-2-fluorobenzoyl chloride (5 g) and 1-(3,5,6-trimethylpyridin-2-yl)piperazine hydrochloride (5 g) described in Preparation Example 52, the title compound (5 g) was obtained.

Preparation Example 99

Preparation of 1-(5-ethyl-3-methylpyridin-2-yl)piperazine hydrochloride

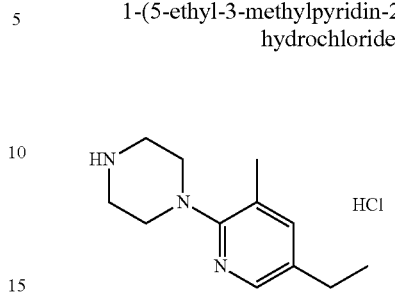

To a mixture of 4-(5-bromo-3-methylpyridin-2-yl)piperazine-1-carboxylic acid tert-butyl ester (11 g), bis(tricyclohexylphosphine)palladium (II) dichloride (1 g), tripotassium phosphate (13 g) and vinylboronic acid pinacol ester (10 g) were added toluene (90 mL) and water (4.5 mL), and the mixture was refluxed for 8 hr. After cooling, the mixture was extracted with ethyl acetate. The organic layer was washed with saturated brine, and the solvent was evaporated. The residue was purified by column chromatography (hexane:ethyl acetate) to give 4-(3-methyl-5-vinylpyridin-2-yl)piperazine-1-carboxylic acid tert-butyl ester (9 g). 4-(3-Methyl-5-vinylpyridin-2-yl)piperazine-1-carboxylic acid tert-butyl ester (9 g) was dissolved in ethanol (90 mL), 5% palladium carbon-ethylenediamine complex (2 g) was added, and the mixture was stirred under a hydrogen atmosphere at room temperature overnight. After celite filtration, the solvent in the filtrate was evaporated to give 4-(5-ethyl-3-methylpyridin-2-yl)piperazine-1-carboxylic acid tert-butyl ester (9 g). 4-(5-Ethyl-3-methylpyridin-2-yl)piperazine-1-carboxylic acid tert-butyl ester (9 g) was dissolved in chloroform (20 mL), 4N hydrogen chloride/ethyl acetate (20 mL) was added, and the mixture was stirred at room temperature overnight. Ethyl acetate (100 mL) was added, and the precipitate was collected by filtration to give the title compound (5 g).

Preparation Example 100

Preparation of (4-bromo-2-fluorophenyl)[4-(5-ethyl-3-methylpyridin-2-yl)piperazin-1-yl]methanone

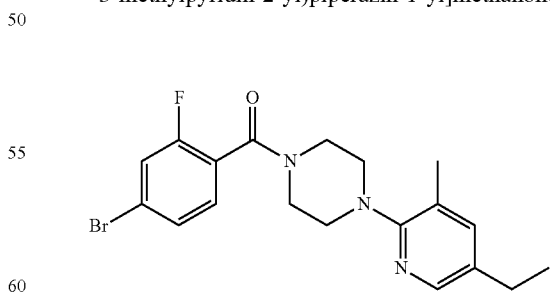

By reaction and treatment in the same manner as in Preparation Example 8 and using 4-bromo-2-fluorobenzoyl chloride (2.4 g) and 1-(5-ethyl-3-methylpyridin-2-yl)piperazine hydrochloride (2.4 g) described in Preparation Example 99, the title compound (4 g) was obtained.

Preparation Example 101

Preparation of (4-bromo-2-methanesulfonylphenyl)[4-(5-ethyl-3-methylpyridin-2-yl)piperazin-1-yl]methanone

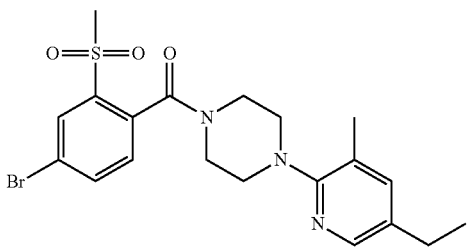 [SMILES: CCc1cnc(N2CCN(C(=O)c3ccc(Br)cc3S(C)(=O)=O)CC2)c(C)c1]

By reaction and treatment in the same manner as in Preparation Example 1 and using 4-bromo-2-(methanesulfonyl)benzoic acid (2.8 g) and 1-(5-ethyl-3-methylpyridin-2-yl)piperazine hydrochloride (2.4 g) described in Preparation Example 99, the title compound (4.6 g) was obtained.

Preparation Example 102

Preparation of 1-(3-methyl-5-propylpyridin-2-yl)piperazine

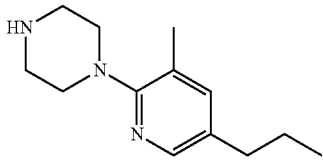 [SMILES: CCCc1cnc(N2CCNCC2)c(C)c1]

To a mixture of 4-(5-bromo-3-methylpyridin-2-yl)piperazine-1-carboxylic acid tert-butyl ester (6.7 g), bis(tricyclohexylphosphine)palladium (II) dichloride (148 mg), tripotassium phosphate (13 g) and cis-1-propene-1-boronic acid (2.6 g) were added toluene (60 mL) and water (3 mL), and the mixture was refluxed for 8 hr. After cooling, the mixture was extracted with ethyl acetate. The organic layer was washed with saturated brine, and the solvent was evaporated. The residue was purified by column chromatography (hexane: ethyl acetate) to give 4-[3-methyl-5-propenylpyridin-2-yl]piperazine-1-carboxylic acid tert-butyl ester (6 g). 4-[3-Methyl-5-propenylpyridin-2-yl]piperazine-1-carboxylic acid tert-butyl ester (6 g) was dissolved in ethanol (40 mL), 5% palladium carbon-ethylenediamine complex (1.2 g) was added, and the mixture was stirred under a hydrogen atmosphere at room temperature overnight. After celite filtration, the solvent in the filtrate was evaporated to give 4-[3-methyl-5-propylpyridin-2-yl]piperazine-1-carboxylic acid tert-butyl ester (6 g). 4-[3-Methyl-5-propylpyridin-2-yl]piperazine-1-carboxylic acid tert-butyl ester (6 g) was dissolved in chloroform (10 mL), 4N hydrogen chloride/ethyl acetate (10 mL) was added, and the mixture was stirred at room temperature overnight. To the reaction mixture was added 1N aqueous sodium hydroxide solution (40 mL), and the mixture was extracted with chloroform. The organic layer was washed with saturated brine, and the solvent was evaporated to give the title compound (2.9 g).

Preparation Example 103

Preparation of 5-ethyloxazolidin-2-one

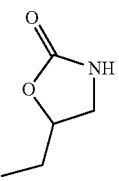

By reaction and treatment in the same manner as in Preparation Example 25 and using 1-amino-2-butanol (5 mL), the title compound (4 g) was obtained.

Preparation Example 104

Preparation of (4-bromo-2-fluorophenyl)[4-(3-ethyl-5-methylpyridin-2-yl)piperazin-1-yl]methanone

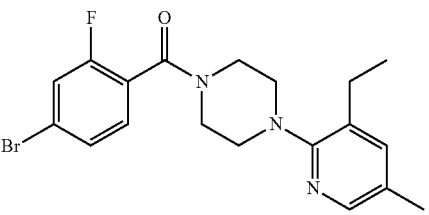 [SMILES: CCc1cc(C)cnc1N1CCN(C(=O)c2ccc(Br)cc2F)CC1]

By reaction and treatment in the same manner as in Preparation Example 8 and using 4-bromo-2-fluorobenzoyl chloride (1.1 g) and 1-(3-ethyl-5-methylpyridin-2-yl)piperazine hydrochloride (1 g) described in Preparation Example 54, the title compound (1.1 g) was obtained.

Preparation Example 105

Preparation of (4-bromo-2-fluorophenyl)[4-(3,5-dimethylpyrazin-2-yl)piperazin-1-yl]methanone

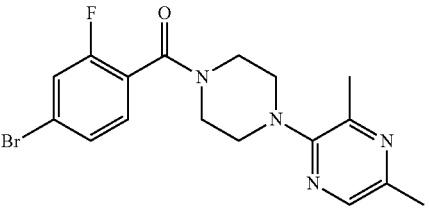 [SMILES: Cc1cnc(N2CCN(C(=O)c3ccc(Br)cc3F)CC2)c(C)n1]

By reaction and treatment in the same manner as in Preparation Example 8 and using 4-bromo-2-fluorobenzoyl chloride (1.1 g) and 1-(3,5-dimethylpyrazin-2-yl)piperazine hydrochloride (915 mg) described in Preparation Example 59, the title compound (1.1 g) was obtained.

Preparation Example 106

Preparation of (6-bromopyridin-3-yl)[4-(5-cyclopropyl-3-methylpyridin-2-yl)piperazin-1-yl]methanone

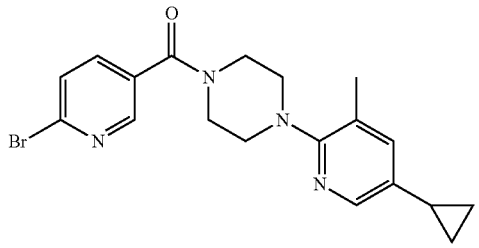 [SMILES: Cc1cc(C2CC2)cnc1N1CCN(C(=O)c2ccc(Br)nc2)CC1]

By reaction and treatment in the same manner as in Preparation Example 27 and using 6-bromonicotinic acid (2 g) and 1-(5-cyclopropyl-3-methylpyridin-2-yl)piperazine hydrochloride (2.5 g) described in Preparation Example 49, the title compound (3.4 g) was obtained.

Preparation Example 107

Preparation of 1-(3-fluoro-5-methylpyridin-2-yl)piperazine 2hydrochloride

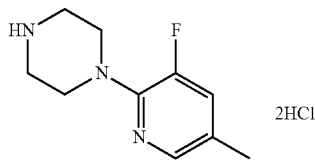

A mixture of 2-chloro-3-fluoro-5-methylpyridine (5 g), 1-Boc-piperazine (6.5 g), palladium acetate (382 mg), 2-(dicyclohexylphosphino)-2',4',6'-tri-isopropyl-1,1'-biphenyl (1.6 g), sodium tert-butoxide (4.6 g) and toluene was refluxed for 5 hr. After cooling, water was added and the mixture was extracted with ethyl acetate. The organic layer was washed with saturated brine, and the solvent was evaporated. The residue was purified by column chromatography (hexane:ethyl acetate). The obtained compound was dissolved in chloroform (20 mL), 4N hydrogen chloride/ethyl acetate (20 mL) was added, and the mixture was stirred at room temperature overnight. Ethyl acetate was added, and the precipitate was collected by filtration to give the title compound (4.7 g).

Preparation Example 108

Preparation of (4-bromo-2-fluorophenyl)[4-(3-fluoro-5-methylpyridin-2-yl)piperazin-1-yl]methanone

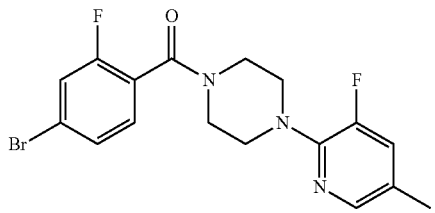 [SMILES: Cc1cnc(N2CCN(C(=O)c3ccc(Br)cc3F)CC2)c(F)c1]

By reaction and treatment in the same manner as in Preparation Example 8 and using 4-bromo-2-fluorobenzoyl chloride (2.7 g) and (2.6 g) described in Preparation Example 107, the title compound (3.5 g) was obtained.

Preparation Example 109

Preparation of (4-bromo-2-fluorophenyl)[4-(3-cyclopropyl-5-methylpyridin-2-yl)piperazin-1-yl]methanone

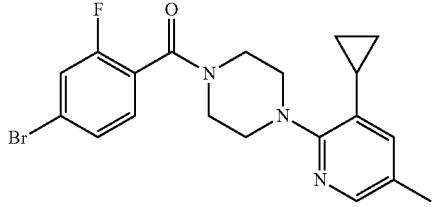 [SMILES: Cc1cnc(N2CCN(C(=O)c3ccc(Br)cc3F)CC2)c(C2CC2)c1]

By reaction and treatment in the same manner as in Preparation Example 8 and using 4-bromo-2-fluorobenzoyl chloride (2.6 g) and 1-(3-cyclopropyl-5-methylpyridin-2-yl)piperazine hydrochloride (2.8 g) described in Preparation Example 48, the title compound (2.5 g) was obtained.

Preparation Example 110

Preparation of (4-bromo-2-fluorophenyl)[4-(3-chloro-5-methylpyridin-2-yl)piperazin-1-yl]methanone

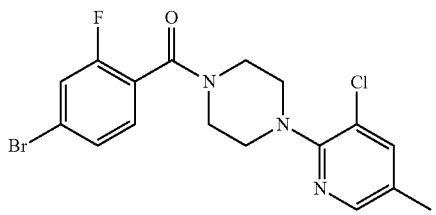

4-(3-Chloro-5-methylpyridin-2-yl)piperazine-1-carboxylic acid tert-butyl ester (1.4 g), which is the intermediate described in Preparation Example 48, was dissolved in chloroform (2.5 mL), trifluoroacetic acid (2 mL) was added, and the mixture was stirred at room temperature overnight. The reaction mixture was alkalified with 1N aqueous sodium hydroxide solution, and extracted with chloroform. The organic layer was washed with saturated brine, and the solvent was evaporated. By reaction and treatment in the same manner as in Preparation Example 8 and using the obtained residue and 4-bromo-2-fluorobenzoyl chloride (1.1 g), the title compound (1.9 g) was obtained.

Preparation Example 111

Preparation of (6-bromopyridin-3-yl)[4-(3-cyclopropyl-5-trifluoromethylpyridin-2-yl)piperazin-1-yl]methanone

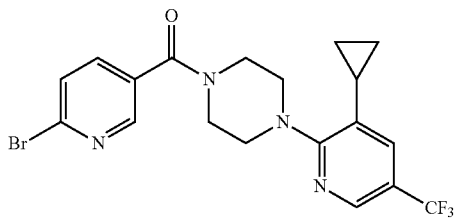 [SMILES: O=C(c1ccc(Br)nc1)N1CCN(c2ncc(C(F)(F)F)cc2C2CC2)CC1]

By reaction and treatment in the same manner as in Preparation Example 27 and using 6-bromonicotinic acid (667 mg) and 1-(3-cyclopropyl-5-trifluoromethylpyridin-2-yl)piperazine hydrochloride (1.2 g) described in Preparation Example 76, the title compound (1.6 g) was obtained.

Preparation Example 112

Preparation of (6-bromopyridin-3-yl)[4-(3,5-dicyclopropylpyridin-2-yl)piperazin-1-yl]methanone

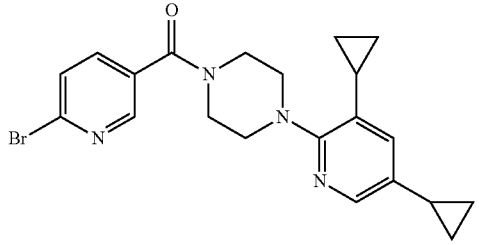 [SMILES: O=C(c1ccc(Br)nc1)N1CCN(c2ncc(C3CC3)cc2C2CC2)CC1]

By reaction and treatment in the same manner as in Preparation Example 1 and using 6-bromonicotinic acid (2 g) and 1-(3,5-dicyclopropylpyridin-2-yl)piperazine hydrochloride (3.2 g) described in Preparation Example 50, the title compound (4.1 g) was obtained.

Preparation Example 113

Preparation of [4-(5-bromo-3-methylpyridin-2-yl)piperazin-1-yl](6-fluoro-4-methylpyridin-3-yl)methanone

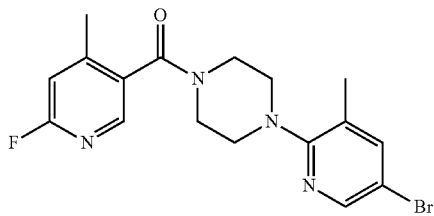 [SMILES: Cc1cc(F)ncc1C(=O)N1CCN(c2ncc(Br)cc2C)CC1]

By reaction and treatment in the same manner as in Preparation Example 69 and using 6-fluoro-4-methylnicotinic acid (931 mg) and 1-(5-bromo-3-methylpyridin-2-yl)piperazine (1.5 g), the title compound (1 g) was obtained.

Preparation Example 114

Preparation of 4-methyloxazolidin-2-one

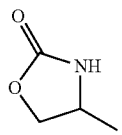

By reaction and treatment in the same manner as in Preparation Example 25 and using 2-amino-1-propanol (5 mL), the title compound (6.7 g) was obtained.

Preparation Example 115

Preparation of (6-bromopyridin-3-yl)[4-(5-ethyl-3-methylpyridin-2-yl)piperazin-1-yl]methanone

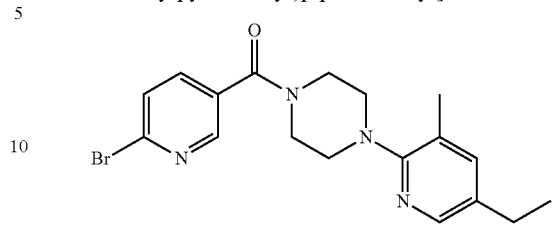

By reaction and treatment in the same manner as in Preparation Example 1 and using 6-bromonicotinic acid (2 g) and 1-(5-ethyl-3-methylpyridin-2-yl)piperazine (3.1 g) described in Preparation Example 53, the title compound (5 g) was obtained.

Preparation Example 116

Preparation of methyl 4-bromo-2-(1,1-dioxoisothiazolidin-2-yl)benzoate

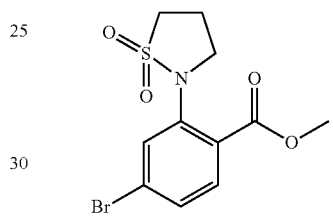

To a mixture of methyl 2-amino-4-bromobenzoate (5 g), triethylamine (5.73 mL), methylene chloride (39 mL) was added 3-chloropropanesulfonyl chloride (3.44 mL) under ice-cooling, and the mixture was stirred at room temperature. Water was added to the reaction mixture, and the mixture was extracted with chloroform. The organic layer was washed with diluted hydrochloric acid and saturated brine, and the solvent was evaporated. To the residue were added 1,8-diazabicyclo[5.4.0]undec-7-ene (DBU) (3.9 mL) and DMF (29 mL), and the mixture was stirred at room temperature. Water was added to the reaction mixture, and the mixture was extracted with ethyl acetate. The organic layer was washed with diluted hydrochloric acid and saturated brine, and the solvent was evaporated. To the residue was added isopropyl ether, and the precipitated solid was collected by filtration to give the title compound (5.045 g).

Preparation Example 117

Preparation of methyl 2-(1,1-dioxoisothiazolidin-2-yl)-4-(2-oxooxazolidin-3-yl)benzoate

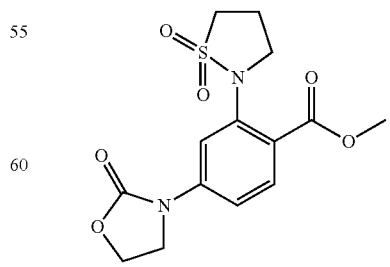

By reaction and treatment in the same manner as in Preparation Example 12 and using methyl 4-bromo-2-(1,1-dioxoisothiazolidin-2-yl)benzoate (2 g) described in Preparation Example 116 and oxazolidin-2-one (515 mg), the title compound (758 mg) was obtained.

Preparation Example 118

Preparation of [4-bromo-2-(1,1-dioxoisothiazolidin-2-yl)phenyl][4-(3,5-dimethylpyridin-2-yl)piperazin-1-yl]methanone

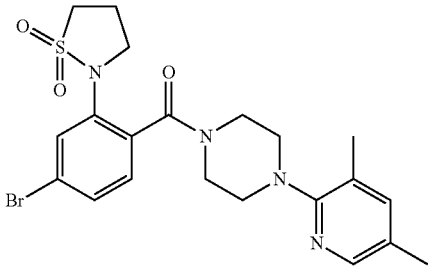 [SMILES: Cc1cnc(N2CCN(C(=O)c3ccc(Br)cc3N3CCCS3(=O)=O)CC2)c(C)c1]

To methyl 4-bromo-2-(1,1-dioxoisothiazolidin-2-yl)benzoate (2 g) described in Preparation Example 116 were added 1N aqueous sodium hydroxide solution (9 mL) and methanol (18 mL), and the mixture was stirred at 60-70° C. 1N hydrochloric acid (9 mL) was added, a solution of 1-(3,5-dimethylpyridin-2-yl)piperazine (1.14 g) described in Preparation Example 47 in methanol (2 mL) and 4-(4,6-dimethoxy[1.3.5]triazin-2-yl)-4-methylmorpholinium chloride hydrate (DMT-MM) (1.65 g) were added, and the mixture was stirred at room temperature overnight. Water was added to the reaction mixture, and the mixture was extracted with ethyl acetate. After evaporation of the solvent, the residue was purified by column chromatography (hexane:ethyl acetate) to give the title compound (2.4 g).

MS(ESI)m/z:493(M+H)$^+$.

Preparation Example 119

Preparation of (2-bromo-4-chlorophenyl)[4-(3,5-dimethylpyridin-2-yl)piperazin-1-yl]methanone

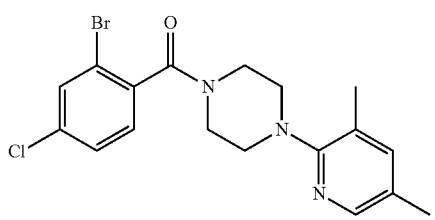 [SMILES: Cc1cnc(N2CCN(C(=O)c3ccc(Cl)cc3Br)CC2)c(C)c1]

By reaction and treatment in the same manner as in Preparation Example 60 and using 2-bromo-4-chlorobenzoic acid (2.09 g) and 1-(3,5-dimethylpyridin-2-yl)piperazine (1.7 g) described in Preparation Example 47, the title compound (3.58 g) was obtained.

MS(ESI)m/z:408(M+H)$^+$.

Preparation Example 120

Preparation of 3-{5-chloro-2-[4-(3,5-dimethylpyridin-2-yl)piperazine-1-carbonyl]phenyl}oxazolidin-2-one

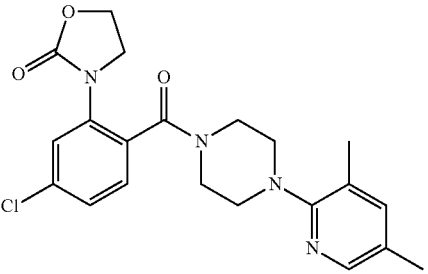 [SMILES: Cc1cnc(N2CCN(C(=O)c3ccc(Cl)cc3N3CCOC3=O)CC2)c(C)c1]

By reaction and treatment in the same manner as in Preparation Example 12 and using (2-bromo-4-chlorophenyl)[4-(3,5-dimethylpyridin-2-yl)piperazin-1-yl]methanone (1.79 g) described in Preparation Example 119 and oxazolidin-2-one (0.381 g), the title compound (1.023 g) was obtained.

MS(ESI)m/z:415(M+H)$^+$.

Preparation Example 121

Preparation of 1-{5-chloro-2-[4-(3,5-dimethylpyridin-2-yl)piperazine-1-carbonyl]phenyl}pyrrolidin-2-one

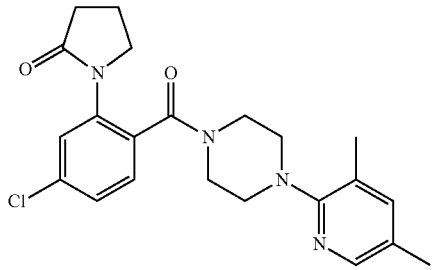 [SMILES: Cc1cnc(N2CCN(C(=O)c3ccc(Cl)cc3N3CCCC3=O)CC2)c(C)c1]

By reaction and treatment in the same manner as in Preparation Example 12 and using (2-bromo-4-chlorophenyl)[4-(3,5-dimethylpyridin-2-yl)piperazin-1-yl]methanone (1.57 g) described in Preparation Example 119 and 2-pyrrolidone (0.33 g), the title compound (0.72 g) was obtained.

MS(ESI)m/z:413(M+H)$^+$.

Preparation Example 122

Preparation of 4-bromo-2-methanesulfonylaminobenzoic acid

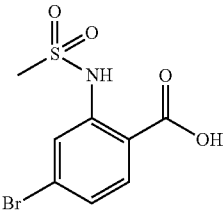

Methyl 2-amino-4-bromobenzoate (1 g) was dissolve in tetrahydrofuran (15 mL), triethylamine (4.2 mL) and methanesulfonyl chloride (0.74 mL) were added, and the mixture was stirred at room temperature for 6 hr. Water was added to the reaction mixture, and the mixture was extracted with chloroform. After evaporation of the solvent, to the residue were added methanol (20 mL) and 1N aqueous sodium hydroxide solution (13 mL), and the mixture was stirred at 50-60° C. The mixture was acidified with 1N hydrochloric acid, and the precipitated solid was collected by filtration to give the title compound (0.964 g).

Preparation Example 123

Preparation of N-{5-bromo-2-[4-(3,5-dimethylpyridin-2-yl)piperazine-1-carbonyl]phenyl}methanesulfonamide

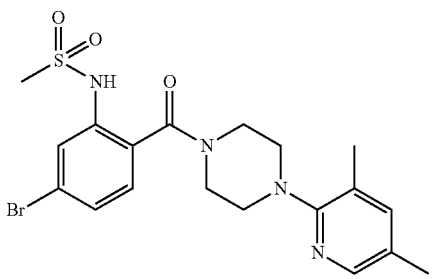 [SMILES: Cc1cnc(N2CCN(C(=O)c3ccc(Br)cc3NS(C)(=O)=O)CC2)c(C)c1]

By reaction and treatment in the same manner as in Preparation Example 60 and using 4-bromo-2-methanesulfonylaminobenzoic acid (0.964 g) described in Preparation Example 122 and 1-(3,5-dimethylpyridin-2-yl)piperazine (0.629 g) described in Preparation Example 47, the title compound (0.321 g) was obtained.

MS(ESI)m/z:467(M+H)⁺.

Preparation Example 124

Preparation of N-{5-bromo-2-[4-(5-cyclopropyl-3-methylpyridin-2-yl)piperazine-1-carbonyl]phenyl}methanesulfonamide

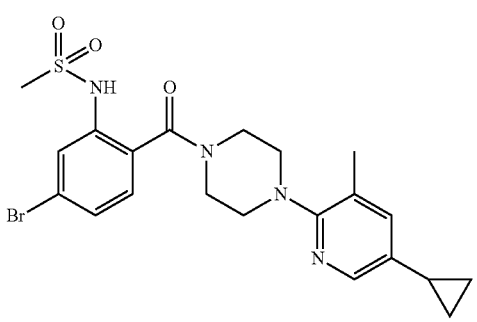 [SMILES: Cc1cc(C2CC2)cnc1N1CCN(C(=O)c2ccc(Br)cc2NS(C)(=O)=O)CC1]

By reaction and treatment in the same manner as in Preparation Example 60 and using 4-bromo-2-methanesulfonylaminobenzoic acid (1 g) described in Preparation Example 122 and 1-(5-cyclopropyl-3-methylpyridin-2-yl)piperazine (0.739 g) described in Preparation Example 96, the title compound (1.34 g) was obtained.

MS(ESI)m/z:493(M+H)⁺.

Preparation Example 125

Preparation of (R)-[4-chloro-2-(3-methyl-1,1-dioxoisothiazolidin-2-yl)phenyl][4-(3,5-dimethylpyridin-2-yl)piperazin-1-yl]methanone

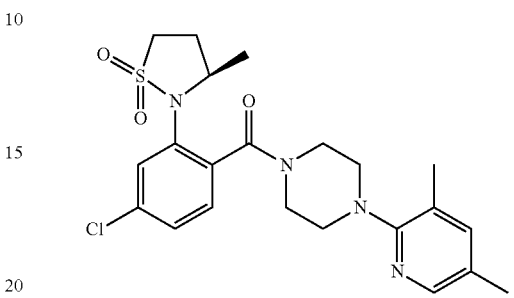

By reaction and treatment in the same manner as in Preparation Example 12 and using (2-bromo-4-chlorophenyl)[4-(3,5-dimethylpyridin-2-yl)piperazin-1-yl]methanone (408.7 mg) described in Preparation Example 119 and 3-methylisothiazolidine-1,1-dioxide (135 mg), the title compound (95.1 mg) was obtained.

MS(ESI)m/z:463(M+H)⁺.

Preparation Example 126

Preparation of 1-acetyl-3-{5-chloro-2-[4-(3,5-dimethylpyridin-2-yl)piperazine-1-carbonyl]phenyl}imidazolidin-2-one

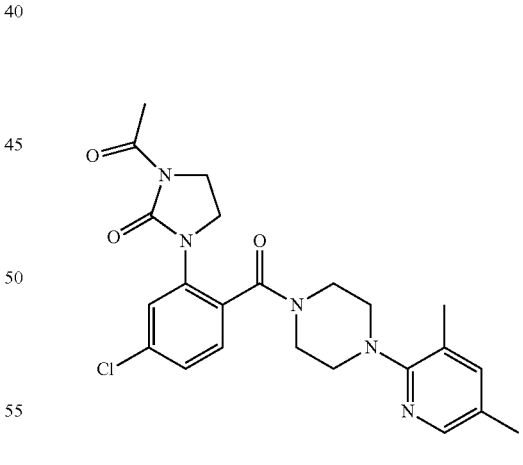

By reaction and treatment in the same manner as in Preparation Example 12 and using (2-bromo-4-chlorophenyl)[4-(3,5-dimethylpyridin-2-yl)piperazin-1-yl]methanone (408.7 mg) described in Preparation Example 119 and 1-acetyl-2-imidazolidinone (128 mg), the title compound (221.5 mg) was obtained.

MS(ESI)m/z:456(M+H)⁺.

Preparation Example 127

Preparation of 1-{5-chloro-2-[4-(3,5-dimethylpyridin-2-yl)piperazine-1-carbonyl]phenyl}-3-methylimidazolidin-2-one

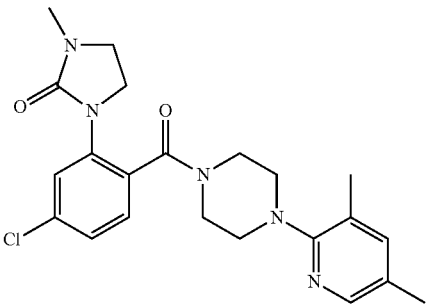 [SMILES: Cc1cnc(N2CCN(C(=O)c3ccc(Cl)cc3N3CCN(C)C3=O)CC2)c(C)c1]

By reaction and treatment in the same manner as in Preparation Example 12 and using (2-bromo-4-chlorophenyl)[4-(3,5-dimethylpyridin-2-yl)piperazin-1-yl]methanone (960 mg) described in Preparation Example 119 and 1-methyl-2-imidazolidinone (235 mg), the title compound (184 mg) was obtained.
MS(ESI)m/z:428(M+H)$^+$.

Preparation Example 128

Preparation of [4-chloro-2-(1,1-dioxo-1,2-thiazinan-2-yl)phenyl][4-(3,5-dimethylpyridin-2-yl)piperazin-1-yl]methanone

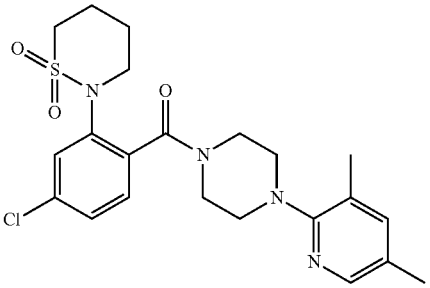 [SMILES: Cc1cnc(N2CCN(C(=O)c3ccc(Cl)cc3N3CCCCS3(=O)=O)CC2)c(C)c1]

By reaction and treatment in the same manner as in Preparation Example 12 and using (2-bromo-4-chlorophenyl)[4-(3,5-dimethylpyridin-2-yl)piperazin-1-yl]methanone (1.19 mg) described in Preparation Example 119 and 1,4-butanesultam (0.394 g), the title compound (0.389 g) was obtained.
MS(ESI)m/z:463(M+H)$^+$.

Preparation Example 129

Preparation of (4-bromo-2-methylphenyl)[4-(5-ethyl-3-methylpyridin-2-yl)piperazin-1-yl]methanone

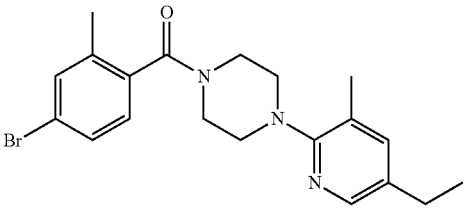 [SMILES: CCc1cnc(N2CCN(C(=O)c3ccc(Br)cc3C)CC2)c(C)c1]

By reaction and treatment in the same manner as in Preparation Example 60 and using 4-bromo-2-methylbenzoic acid (1.00 g) and 1-(5-ethyl-3-methylpyridin-2-yl)piperazine (1.05 g) described in Preparation Example 53, the title compound (1.06 g) was obtained.
MS(ESI)m/z:402 (M+H)$^+$.

Preparation Example 130

Preparation of (4-bromo-2-methylphenyl)[4-(5-cyclopropyl-3-methylpyridin-2-yl)piperazin-1-yl]methanone

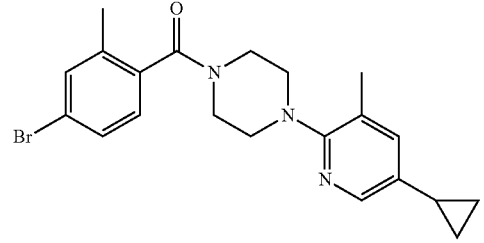

By reaction and treatment in the same manner as in Preparation Example 60 and using 4-bromo-2-methylbenzoic acid (1.00 g) and 1-(5-cyclopropyl-3-methylpyridin-2-yl)piperazine (1.52 g) described in Preparation Example 96, the title compound (1.04 g) was obtained.
MS(ESI)m/z:414 (M+H)$^+$.

Preparation Example 131

Preparation of 6-[4-(6-bromopyridine-3-carbonyl)piperazin-1-yl]-5-methylnicotinonitrile

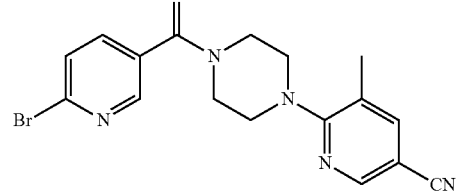

By reaction and treatment in the same manner as in Preparation Example 60 and using 6-bromonicotinic acid (500 mg) and 5-methyl-6-piperazin-1-ylnicotinonitrile (501 mg), the title compound (709 mg) was obtained.
MS(ESI)m/z:386 (M+H)$^+$.

Preparation Example 132

Preparation of (4-bromo-2-methylphenyl)[4-(3,5,6-trimethylpyridin-2-yl)piperazin-1-yl]methanone

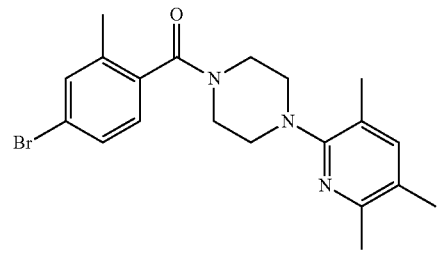 [SMILES: Cc1cc(Br)ccc1C(=O)N1CCN(c2nc(C)c(C)cc2C)CC1]

By reaction and treatment in the same manner as in Preparation Example 60 and using 4-bromo-2-methylbenzoic acid (215 mg) and 1-(3,5,6-trimethylpyridin-2-yl)piperazine (205 mg) obtained by neutralizing 1-(3,5,6-trimethylpyridin-2-yl)

piperazine hydrochloride described in Preparation Example 52 and converting same to a free form, the title compound (346 mg) was obtained.

Preparation Example 133

Preparation of 6-[4-(4-bromo-2-methylbenzoyl)piperazin-1-yl]-5-methylnicotinonitrile

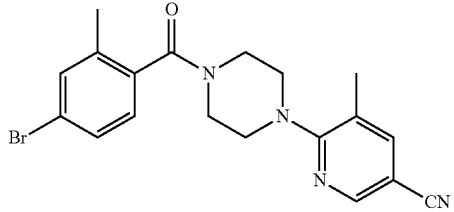 [SMILES: Cc1cc(Br)ccc1C(=O)N1CCN(c2ncc(C#N)cc2C)CC1]

By reaction and treatment in the same manner as in Preparation Example 60 and using 4-bromo-2-methylbenzoic acid (215 mg) and 5-methyl-6-piperazin-1-ylnicotinonitrile (202 mg), the title compound (426 mg) was obtained.

Preparation Example 134

Preparation of 6-[4-(4-bromo-2-fluorobenzoyl)piperazin-1-yl]-5-methylnicotinonitrile

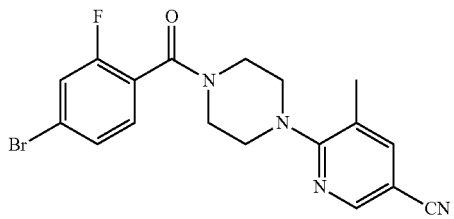 [SMILES: Cc1cc(C#N)cnc1N1CCN(C(=O)c2ccc(Br)cc2F)CC1]

By reaction and treatment in the same manner as in Preparation Example 60 and using 4-bromo-2-fluorobenzoic acid (215 mg) and 5-methyl-6-piperazin-1-ylnicotinonitrile (202 mg), the title compound (433 mg) was obtained.

Preparation Example 135

Preparation of [4-(2,4-dimethylphenyl)piperazin-1-yl](6-fluoro-4-methylpyridin-3-yl)methanone

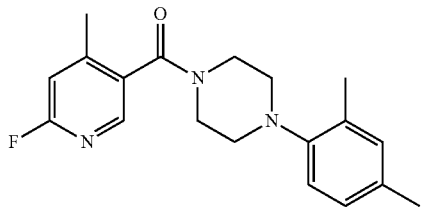 [SMILES: Cc1ccc(N2CCN(C(=O)c3cnc(F)cc3C)CC2)c(C)c1]

By reaction and treatment in the same manner as in Preparation Example 60 and using 6-fluoro-4-methylnicotinic acid (500 mg) and 1-(2,4-dimethylphenyl)piperazine (607 mg), the title compound (870 mg) was obtained.
MS(ESI)m/z:328(M+H)$^+$.

Preparation Example 136

Preparation of [4-(5-cyclopropyl-3-methylpyridin-2-yl)piperazin-1-yl](6-fluoro-4-methylpyridin-3-yl)methanone

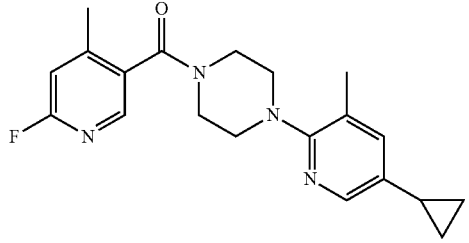 [SMILES: Cc1cc(F)ncc1C(=O)N1CCN(c2ncc(C3CC3)cc2C)CC1]

To a solution of [4-(5-bromo-3-methylpyridin-2-yl)piperazin-1-yl](6-fluoro-4-methylpyridin-3-yl)methanone (2.2 g) described in Preparation Example 113 in tetrahydrofuran (15 mL) were added 2-dicyclohexylphosphino-2',6'-dimethoxybiphenyl (229 mg), palladium acetate (125 mg), tripotassium phosphate (3.12 g) and cyclopropylboronic acid (721 mg), and the mixture was refluxed for 7 hr. After cooling, the mixture was extracted with ethyl acetate, washed with saturated brine, and the solvent was evaporated. The residue was purified by column chromatography to give the title compound (2.39 g).
MS(ESI)m/z:355(M+H)$^+$.

Preparation Example 137

Preparation of [4-(5-ethyl-3-methylpyridin-2-yl)piperazin-1-yl](6-fluoro-4-methylpyridin-3-yl)methanone

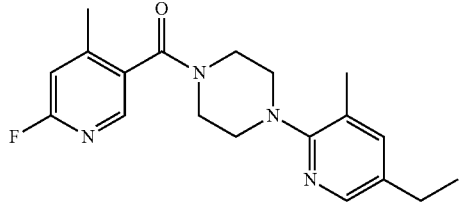 [SMILES: CCc1cnc(N2CCN(C(=O)c3cnc(F)cc3C)CC2)c(C)c1]

By reaction and treatment in the same manner as in Preparation Example 60 and using 6-fluoro-4-methylnicotinic acid (500 mg) and 1-(5-ethyl-3-methylpyridin-2-yl)piperazine (649 mg) described in Preparation Example 53, the title compound (640 mg) was obtained.
MS(ESI)m/z:343(M+H)$^+$.

Preparation Example 138

Preparation of 6-(2-oxooxazolidin-3-yl)nicotinic acid methyl ester

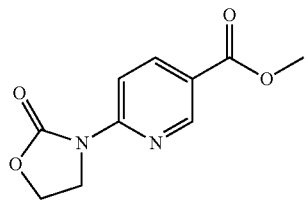 [SMILES: COC(=O)c1ccc(N2CCOC2=O)nc1]

By reaction and treatment in the same manner as in Preparation Example 12 and using methyl 6-bromonicotinate (1 g)

Preparation Example 139

Preparation of [4-(3,5-dicyclopropylpyridin-2-yl)piperazin-1-yl](6-fluoro-4-methylpyridin-3-yl)methanone

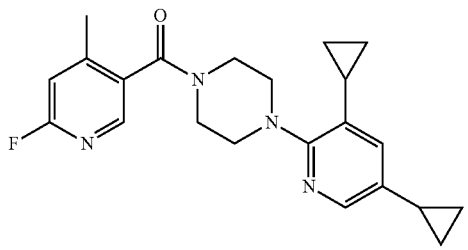 [SMILES: Cc1cc(F)ncc1C(=O)N1CCN(c2ncc(C3CC3)cc2C2CC2)CC1]

By reaction and treatment in the same manner as in Preparation Example 60 and using 6-fluoro-4-methylnicotinic acid (600 mg) and 1-(3,5-dicyclopropylpyridin-2-yl)piperazine (922 mg) described in Preparation Example 62, the title compound (1.23 g) was obtained.

MS(ESI)m/z:381(M+H)$^+$.

Preparation Example 140

Preparation of (6-bromopyridin-3-yl)[4-(4-cyclopropyl-2-methylphenyl)piperazin-1-yl]methanone

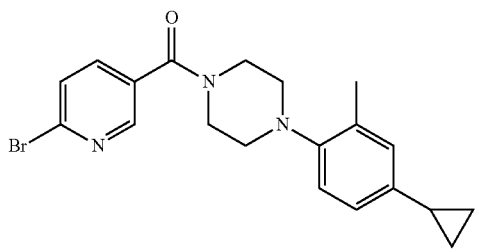 [SMILES: Cc1cc(C2CC2)ccc1N1CCN(C(=O)c2ccc(Br)nc2)CC1]

By reaction and treatment in the same manner as in Preparation Example 15 and using 4-bromo-2-methylaniline (3 g), N,N-bis(2-chloroethyl)-4-methylbenzenesulfonamide (5.65 g) and cyclopropylboronic acid (721 mg), 1-(4-cyclopropyl-2-methylphenyl)piperazine (640 mg) was obtained. To a solution (7 mL) of 6-bromonicotinic acid (132 mg) in methanol were added 1-(4-cyclopropyl-2-methylphenyl)piperazine (150 mg) and 4-(4,6-dimethoxy[1.3.5]triazin-2-yl)-4-methylmorpholinium chloride hydrate (DMT-MM) (217 mg), and the mixture was stirred at room temperature overnight. Water was added to the reaction mixture, and the mixture was extracted with ethyl acetate. The organic layer was washed with saturated brine, and the solvent was evaporated. The residue was purified by column chromatography (ethyl acetate:hexane) to give the title compound (260 mg).

MS(ESI)m/z:400(M+H)$^+$.

Preparation Example 141

Preparation of (6-bromopyridin-3-yl)[4-(2,4-dicyclopropylphenyl)piperazin-1-yl]methanone

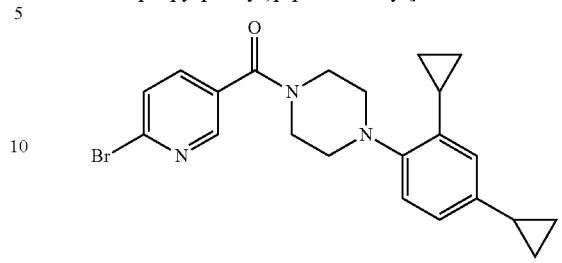

A mixture of 1-(2,4-dichlorophenyl)piperazine (3 g), di-tert-butyl dicarbonate (3.23 g), triethylamine (5.5 mL) and methanol (30 mL) was stirred at room temperature for 5 hr. Water and ethyl acetate were added for partitioning, the organic layer was washed with saturated brine, and the solvent was evaporated. The residue was purified by column chromatography (hexane:ethyl acetate) to give 4-(2,4-dichlorophenyl)piperazine-1-carboxylic acid tert-butyl ester (3.3 g). To a solution of 4-(2,4-dichlorophenyl)piperazine-1-carboxylic acid tert-butyl ester (3.3 g) in tetrahydrofuran (15 mL) were added 2-dicyclohexylphosphino-2',6'-dimethoxybiphenyl (809 mg), palladium acetate (442 mg), tripotassium phosphate (11 g) and cyclopropylboronic acid (2.54 g), and the mixture was refluxed for 7 hr. After cooling, the mixture was extracted with ethyl acetate, washed with saturated brine, and the solvent was evaporated. The residue was purified by column chromatography (hexane:ethyl acetate) to give 4-(2,4-dicyclopropylphenyl)piperazine-1-carboxylic acid tert-butyl ester (3.3 g). 4-(2,4-Dicyclopropylphenyl)piperazine-1-carboxylic acid tert-butyl ester (3.3 g) was dissolved in dichloromethane (20 mL), 4N hydrogen chloride/dioxane (10 mL) was added, and the mixture was stirred at room temperature for 3.5 hr. Diethyl ether (100 mL) was added, and the precipitate was collected by filtration. To the obtained precipitate were added ethyl acetate and 1N aqueous sodium hydroxide solution, and the mixture was extracted with ethyl acetate and washed with saturated brine. The solvent was evaporated to give 1-(2,4-dicyclopropylphenyl)piperazine (1.6 g). By reaction and treatment in the same manner as in Preparation Example 27 and using 6-bromonicotinic acid (237 mg) and 1-(2,4-dicyclopropylphenyl)piperazine (300 mg), the title compound (500 mg) was obtained.

MS(ESI)m/z:426(M+H)+.

Preparation Example 142

Preparation of [4-(2,4-dicyclopropylphenyl)piperazin-1-yl](6-fluoro-4-methylpyridin-3-yl)methanone

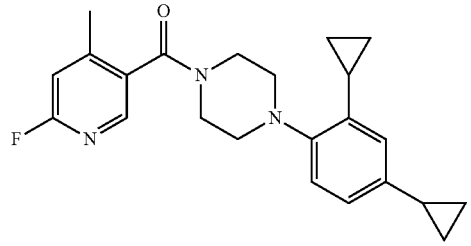 [SMILES: Cc1cc(F)ncc1C(=O)N1CCN(c2ccc(C3CC3)cc2C2CC2)CC1]

By reaction and treatment in the same manner as in Preparation Example 27 and using 6-fluoro-4-methylnicotinic acid (386 mg) and 1-(2,4-dicyclopropylphenyl)piperazine (650 mg), the title compound (980 mg) was obtained.
MS(ESI)m/z:380(M+H)⁺.

Preparation Example 143

Preparation of (6-bromopyridin-3-yl)[4-(2,4,5-trimethylphenyl)piperazin-1-yl]methanone

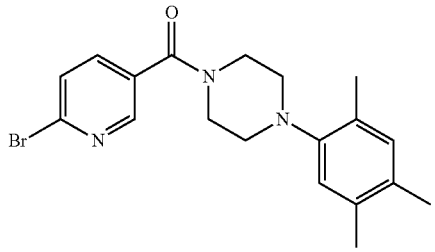 [SMILES: Cc1cc(C)c(N2CCN(C(=O)c3ccc(Br)nc3)CC2)cc1C]

To a mixture of 1-Boc-piperazine (1.39 g), 1-bromo-2,4,5-trimethylbenzene (1 g), tris(dibenzylideneacetone)dipalladium (0) (257 mg), rac-2,2'-bis(diphenylphosphino)-1,1'-binaphthyl (481 mg) and sodium tert-butoxide (669 mg) was added toluene (10 mL), and the mixture was refluxed for 3 hr. After cooling, water was added to the reaction mixture, and the mixture was extracted with ethyl acetate. The organic layer was washed with saturated brine, and the solvent was evaporated. The residue was purified by column chromatography (ethyl acetate:hexane) to give 4-(2,4,5-trimethylphenyl)piperazine-1-carboxylic acid tert-butyl ester (1.53 g). 4-(2,4,5-trimethylphenyl)piperazine-1-carboxylic acid tert-butyl ester (1.53 g) was dissolved in dichloromethane (10 mL), 4N hydrogen chloride/dioxane (5 mL) was added, and the mixture was stirred at room temperature for 3 hr. Diethyl ether (100 mL) was added, and the precipitate was collected by filtration. To the obtained precipitate were added ethyl acetate and 1N aqueous sodium hydroxide solution, and the mixture was extracted with ethyl acetate and washed with saturated brine. The solvent was evaporated to give 1-(2,4,5-trimethylphenyl)piperazine (920 mg). By reaction and treatment in the same manner as in Preparation Example 27 and using 6-bromonicotinic acid (412 mg) and 1-(2,4,5-trimethylphenyl)piperazine (440 mg), the title compound (800 mg) was obtained.
MS(ESI)m/z:388(M+H)⁺.

Preparation Example 144

Preparation of (6-bromopyridin-3-yl)[4-(3-cyclopropyl-5-methylpyridin-2-yl)piperazin-1-yl]methanone

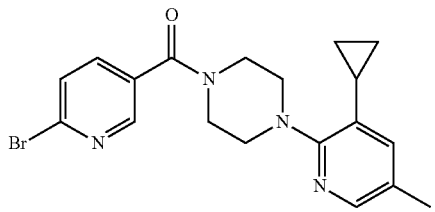 [SMILES: Cc1cnc(N2CCN(C(=O)c3ccc(Br)nc3)CC2)c(C2CC2)c1]

By reaction and treatment in the same manner as in Preparation Example 27 and using 6-bromonicotinic acid (185 mg) and 1-(3-cyclopropyl-5-methylpyridin-2-yl)piperazine (210 mg), the title compound (170 mg) was obtained.
MS(ESI)m/z:401(M+H)⁺.

Preparation Example 145

Preparation of (6-bromopyridin-3-yl)[4-(5-ethyl-3-methylpyridin-2-yl)piperazin-1-yl]methanone

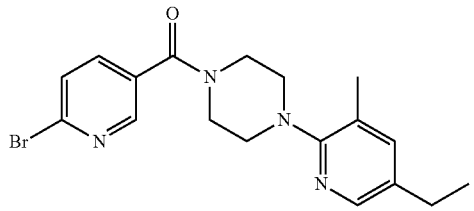 [SMILES: CCc1cnc(N2CCN(C(=O)c3ccc(Br)nc3)CC2)c(C)c1]

By reaction and treatment in the same manner as in Preparation Example 27 and using 6-bromonicotinic acid (500 mg) and 1-(5-ethyl-3-methylpyridin-2-yl)piperazine (586 mg) described in Preparation Example 53, the title compound (530 mg) was obtained.
MS(ESI)m/z:389(M+H)⁺.

Preparation Example 146

Preparation of (6-bromopyridin-3-yl)[4-(3,5,6-trimethylpyridin-2-yl)piperazin-1-yl]methanone

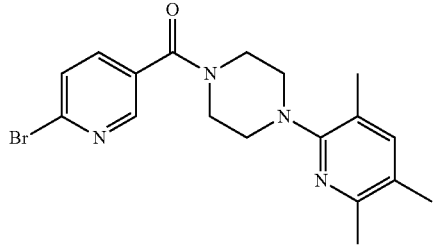 [SMILES: Cc1cc(C)c(N2CCN(C(=O)c3ccc(Br)nc3)CC2)nc1C]

To 1-(3,5,6-trimethylpyridin-2-yl)piperazine hydrochloride described in Preparation Example 52 were added ethyl acetate and 1N aqueous sodium hydroxide solution, and the mixture was extracted with ethyl acetate and washed with saturated brine. The solvent was evaporated to give 1-(3,5,6-trimethylpyridin-2-yl)piperazine (470 mg). By reaction and treatment in the same manner as in Preparation Example 27 and using 6-bromonicotinic acid (407 mg) and 1-(3,5,6-trimethylpyridin-2-yl)piperazine (470 mg), the title compound (620 mg) was obtained.
MS(ESI)m/z:389(M+H)⁺.

Preparation Example 147

Preparation of [4-(5-cyclopropyl-3-methylpyridin-2-yl)piperazin-1-yl](6-fluoro-5-methylpyridin-3-yl)methanone

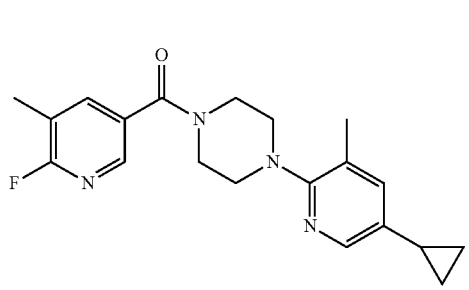 [SMILES: Cc1cc(C(=O)N2CCN(c3ncc(C4CC4)cc3C)CC2)cnc1F]

By reaction and treatment in the same manner as in Preparation Example 60 and using 6-fluoro-5-methylnicotinic acid (1 g) and 1-(5-cyclopropyl-3-methylpyridin-2-yl)piperazine (1.4 g) described in Preparation Example 96, the title compound (1.2 g) was obtained.
MS(ESI)m/z:355(M+H)⁺.

Preparation Example 148

Preparation of [4-(3,5-dimethylpyridin-2-yl)piperazin-1-yl](6-fluoro-5-methylpyridin-3-yl)methanone

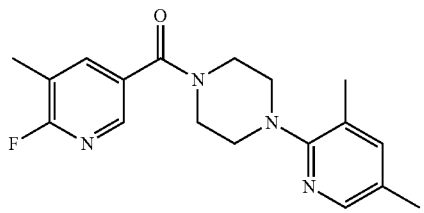 [SMILES: Cc1cnc(N2CCN(C(=O)c3cnc(F)c(C)c3)CC2)c(C)c1]

By reaction and treatment in the same manner as in Preparation Example 60 and using 6-fluoro-5-methylnicotinic acid (500 mg) and 1-(3,5-dimethylpyridin-2-yl)piperazine (620 mg) described in Preparation Example 47, the title compound (1.1 g) was obtained.
MS(ESI)m/z:329(M+H)⁺.

Preparation Example 149

Preparation of [4-(5-ethyl-3-methylpyridin-2-yl)piperazin-1-yl](6-fluoro-5-methylpyridin-3-yl)methanone

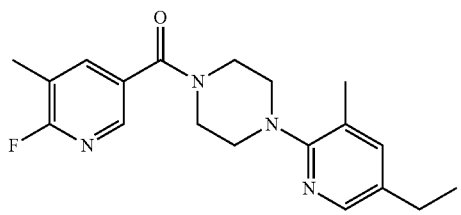 [SMILES: CCc1cnc(N2CCN(C(=O)c3cnc(F)c(C)c3)CC2)c(C)c1]

By reaction and treatment in the same manner as in Preparation Example 60 and using 6-fluoro-5-methylnicotinic acid (500 mg) and 1-(5-ethyl-3-methylpyridin-2-yl)piperazine (661 mg) described in Preparation Example 53, the title compound (440 mg) was obtained.
MS(ESI)m/z:343(M+H)⁺.

Preparation Example 150

Preparation of (5-bromopyridin-2-yl)[4-(3,5-dimethylpyridin-2-yl)piperazin-1-yl]methanone

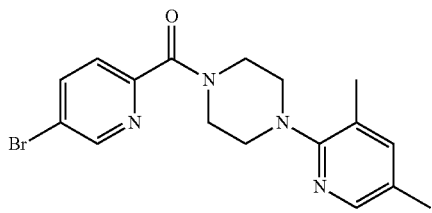 [SMILES: Cc1cnc(N2CCN(C(=O)c3ccc(Br)cn3)CC2)c(C)c1]

By reaction and treatment in the same manner as in Preparation Example 60 and using 5-bromo-2-picolinic acid (5.0 g) and 1-(3,5-dimethylpyridin-2-yl)piperazine (4.7 g) described in Preparation Example 47, the title compound (7.6 g) was obtained.
MS(ESI)m/z:375(M+H)⁺.

Preparation Example 151

Preparation of (5-bromopyridin-2-yl)[4-(5-cyclopropyl-3-methylpyridin-2-yl)piperazin-1-yl]methanone

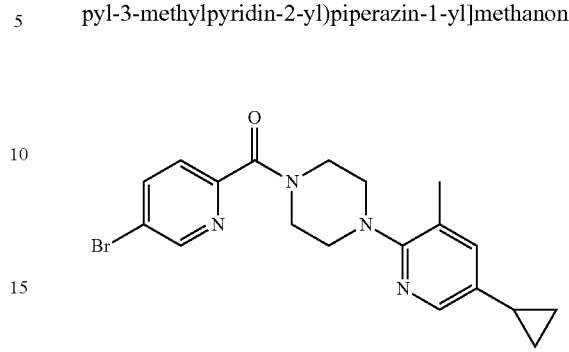

By reaction and treatment in the same manner as in Preparation Example 60 and using 5-bromo-2-picolinic acid (1.5 g) and 1-(5-cyclopropyl-3-methylpyridin-2-yl)piperazine (1.8 g) described in Preparation Example 96, the title compound (1.4 g) was obtained.
MS(ESI)m/z:401(M+H)⁺.

Preparation Example 152

Preparation of (6-bromopyridin-3-yl)[4-(4-cyclopropylphenoxy)piperidin-1-yl]methanone

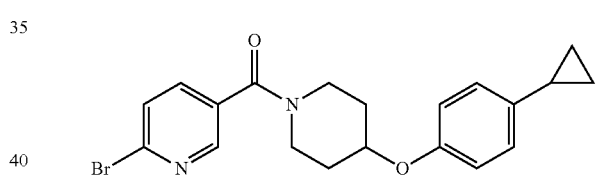

To a solution of 1-Boc-4-(4-bromophenoxy)piperidine (5 g) in toluene (70 mL) were added dichlorobis(tricyclohexylphosphine)palladium (II) (725 mg), tripotassium phosphate (14.9 g) and cyclopropylboronic acid (1.81 g), and the mixture was refluxed for 7 hr. After cooling, water was added, insoluble materials were filtered off, and the mixture was extracted with ethyl acetate and washed with saturated brine. The solvent was evaporated and the residue was purified by column chromatography to give 4-(4-cyclopropylphenoxy) piperidine-1-carboxylic acid tert-butyl ester. 4-(4-Cyclopropylphenoxy)piperidine-1-carboxylic acid tert-butyl ester was dissolve in ethyl acetate (3 mL), 4N hydrogen chloride/ethyl acetate (7 mL) was added, and the mixture was stirred at room temperature overnight. Water was added, and the mixture was washed with ethyl acetate. To the aqueous solution was added 1N aqueous sodium hydroxide solution, and the mixture was extracted with ethyl acetate. The organic layer was washed with saturated brine, and the solvent was evaporated to give 4-(4-cyclopropylphenoxy)piperidine (2.49 g). By reaction and treatment in the same manner as in Preparation Example 60 and using 6-bromonicotinic acid (1.2 g) and 4-(4-cyclopropylphenoxy)piperidine (1.4 g), the title compound (2.4 g) was obtained.
MS(ESI)m/z:401(M+H)⁺.

Preparation Example 153

Preparation of 1-(2,6-dimethylpyridin-3-yl)piperazine

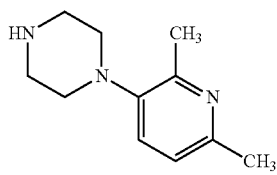

By reaction and treatment in the same manner as in Preparation Example 88 and using 1-Boc-piperazine (2.0 g) and 3-bromo-2,6-dimethylpyridine (2.0 g), a compound was obtained. To the compound were added water and potassium carbonate, and the mixture was extracted with ethyl acetate. The solvent was evaporated to give the title compound (2.01 g).

Preparation Example 154

Preparation of 4-(4-bromo-2-fluorobenzoyl)piperazine-1-carboxylic acid tert-butyl ester

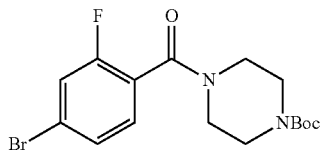 [SMILES: CC(C)(C)OC(=O)N1CCN(C(=O)c2ccc(Br)cc2F)CC1]

By reaction and treatment in the same manner as in Preparation Example 90 and using 4-bromo-2-fluorobenzoic acid (8.76 g) and piperazine-1-carboxylic acid tert-butyl ester (8.2 g), the title compound (14.7 g) was obtained.
MS(ESI)m/z:387(M+H)+.

Preparation Example 155

Preparation of (R)-4-[4-(4-benzoyloxymethyl-2-oxooxazolidin-3-yl)2-fluoro-benzoyl]piperazine-1-carboxylic acid tert-butyl ester

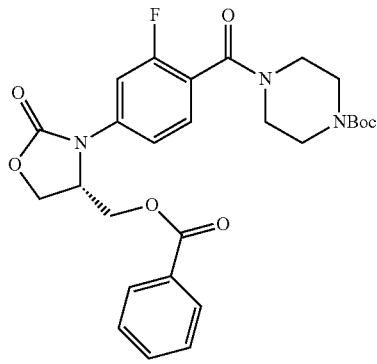 [SMILES: CC(C)(C)OC(=O)N1CCN(C(=O)c2ccc(N3C(=O)OC[C@H]3COC(=O)c3ccccc3)cc2F)CC1]

By reaction and treatment in the same manner as in Preparation Example 91 and using 4-(4-bromo-2-fluorobenzoyl)piperazine-1-carboxylic acid tert-butyl ester (3.49 g) described in Preparation Example 154 and benzoic acid (R)-2-oxooxazolidin-4-ylmethyl ester (1.99 g), the title compound (2.37 g) was obtained.
MS(ESI)m/z:528(M+H)+.

Preparation Example 156

Preparation of (R)-4-[2-fluoro-4-(4-hydroxymethyl-2-oxooxazolidin-3-yl)benzoyl]piperazine-1-carboxylic acid tert-butyl ester

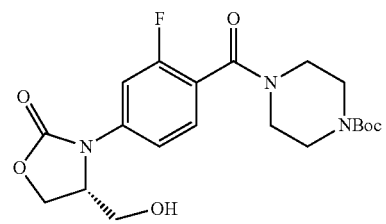

By reaction and treatment in the same manner as in Preparation Example 92 and using (R)-4-[4-(4-benzoyloxymethyl-2-oxooxazolidin-3-yl)2-fluoro-benzoyl]piperazine-1-carboxylic acid tert-butyl ester (5.04 g) described in Preparation Example 155, the title compound (4.14 g) was obtained.
MS(ESI)m/z:424(M+H)+.

Preparation Example 157

Preparation of (R)-4-[2-fluoro-4-(4-methoxymethyl-2-oxooxazolidin-3-yl)benzoyl]piperazine-1-carboxylic acid tert-butyl ester

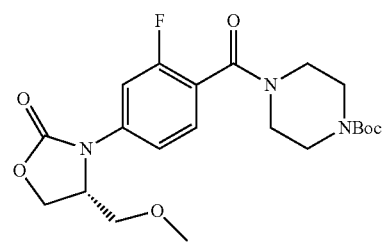 [SMILES: COC[C@@H]1COC(=O)N1c1ccc(C(=O)N2CCN(C(=O)OC(C)(C)C)CC2)c(F)c1]

By reaction and treatment in the same manner as in Preparation Example 93 and using (R)-4-[2-fluoro-4-(4-hydroxymethyl-2-oxooxazolidin-3-yl)benzoyl]piperazine-1-carboxylic acid tert-butyl ester (1.64 g) described in Preparation Example 156 and methyl iodide (658 mg), the title compound (1.17 g) was obtained.
MS(ESI)m/z:438(M+H)+.

Preparation Example 158

Preparation of (R)-3-[3-fluoro-4-(piperazine-1-carbonyl)phenyl]-4-methoxymethyloxazolidin-2-one

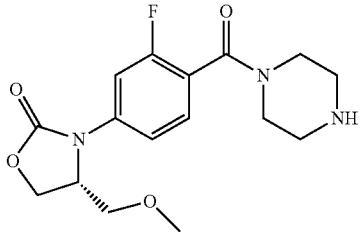 [SMILES: COC[C@@H]1COC(=O)N1c1ccc(C(=O)N2CCNCC2)c(F)c1]

By reaction and treatment in the same manner as in Preparation Example 94 and using (R)-4-[2-fluoro-4-(4-methoxymethyl-2-oxooxazolidin-3-yl)benzoyl]piperazine-1-carboxylic acid tert-butyl ester (1.14 g) described in Preparation Example 157, the title compound (892 mg) was obtained.
MS(ESI)m/z:338(M+H)$^+$.

Preparation Example 159

Preparation of (R)-4-[4-(4-ethoxymethyl-2-oxooxazolidin-3-yl)-2-fluorobenzoyl]piperazine-1-carboxylic acid tert-butyl ester

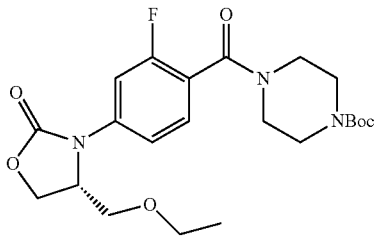 [SMILES: CCOC[C@@H]1COC(=O)N1c1ccc(C(=O)N2CCN(C(=O)OC(C)(C)C)CC2)c(F)c1]

By reaction and treatment in the same manner as in Preparation Example 93 and using (R)-4-[2-fluoro-4-(4-hydroxymethyl-2-oxooxazolidin-3-yl)benzoyl]piperazine-1-carboxylic acid tert-butyl ester (2.20 g) described in Preparation Example 156 and ethyl iodide (972 mg), the title compound (1.67 g) was obtained.
MS(ESI)m/z:452(M+H)$^+$.

Preparation Example 160

Preparation of (R)-4-ethoxymethyl-3-[3-fluoro-4-(piperazine-1-carbonyl)phenyl]oxazolidin-2-one

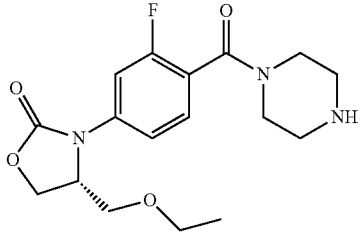 [SMILES: CCOC[C@@H]1COC(=O)N1c1ccc(C(=O)N2CCNCC2)c(F)c1]

By reaction and treatment in the same manner as in Preparation Example 94 and using (R)-4-[4-(4-ethoxymethyl-2-oxooxazolidin-3-yl)-2-fluorobenzoyl]piperazine-1-carboxylic acid tert-butyl ester (2.06 g) described in Preparation Example 159, the title compound (1.62 g) was obtained.
MS(ESI)m/z:352(M+H)$^+$.

Preparation Example 161

Preparation of 4-(4-iodobenzoyl)piperazine-1-carboxylic acid tert-butyl ester

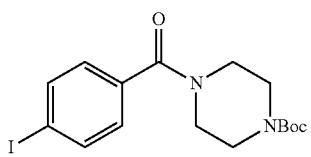 [SMILES: CC(C)(C)OC(=O)N1CCN(C(=O)c2ccc(I)cc2)CC1]

4-Iodobenzoyl chloride (7.99 g) and piperazine-1-carboxylic acid tert-butyl ester (5.87 g) were dissolved in tetrahydrofuran (75 ml), 1N aqueous sodium hydroxide solution (36 mL) was added, and the mixture was stirred at room temperature. The reaction mixture was poured into water under cooling and 1N aqueous sodium hydroxide solution and ethyl acetate were added, and the mixture was extracted with ethyl acetate. The organic layer was washed with 1N aqueous sodium hydroxide solution and saturated brine, then washed with saturated brine, and dried over sodium sulfate. The solvent was evaporated under reduced pressure. To the residue was added hexane and the mixture was stirred at room temperature. The crystals were collected by filtration to give the title compound (11.67 g).
MS(ESI)m/z:417(M+H)$^+$.

Preparation Example 162

Preparation of (R)-4-[4-(4-benzoyloxymethyl-2-oxooxazolidin-3-yl)benzoyl]piperazine-1-carboxylic acid tert-butyl ester

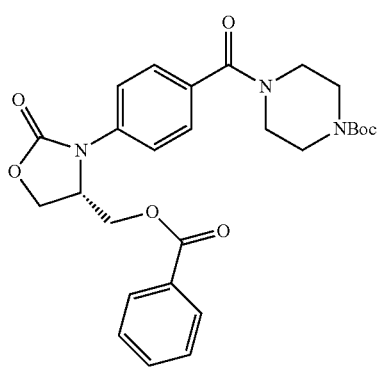 [SMILES: CC(C)(C)OC(=O)N1CCN(C(=O)c2ccc(N3C(=O)OC[C@H]3COC(=O)c3ccccc3)cc2)CC1]

By reaction and treatment in the same manner as in Preparation Example 91 and using 4-(4-iodobenzoyl)piperazine-1-carboxylic acid tert-butyl ester (3.75 g) described in Preparation Example 161 and benzoic acid (R)-2-oxooxazolidin-4-ylmethyl ester (1.99 g), the title compound (4.14 g) was obtained.
MS(ESI)m/z:510(M+H)$^+$.

Preparation Example 163

Preparation of (R)-4-[4-(4-hydroxymethyl-2-oxooxazolidin-3-yl)benzoyl]piperazine-1-carboxylic acid tert-butyl ester

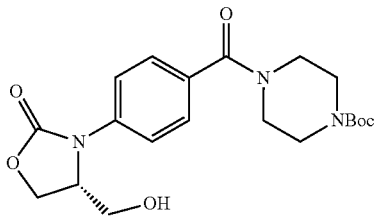 [SMILES: CC(C)(C)OC(=O)N1CCN(C(=O)c2ccc(N3C(=O)OC[C@H]3CO)cc2)CC1]

By reaction and treatment in the same manner as in Preparation Example 92 and using (R)-4-[4-(4-benzoyloxymethyl-2-oxooxazolidin-3-yl)benzoyl]piperazine-1-carboxylic acid tert-butyl ester (1.02 g) described in Preparation Example 162, the title compound (737 mg) was obtained.
MS(ESI)m/z:406(M+H)$^+$.

Preparation Example 164

Preparation of (R)-4-[4-(4-methoxymethyl-2-oxooxazolidin-3-yl)benzoyl]piperazine-1-carboxylic acid tert-butyl ester

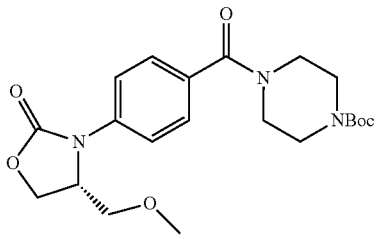 [SMILES: COC[C@@H]1COC(=O)N1c1ccc(C(=O)N2CCN(C(=O)OC(C)(C)C)CC2)cc1]

By reaction and treatment in the same manner as in Preparation Example 93 and using (R)-4-[4-(4-hydroxymethyl-2-oxooxazolidin-3-yl)benzoyl]piperazine-1-carboxylic acid tert-butyl ester (739 mg) described in Preparation Example 163 and methyl iodide (259 mg), the title compound (544 mg) was obtained.
MS(ESI)m/z:420(M+H)$^+$.

Preparation Example 165

Preparation of (R)-4-methoxymethyl-3-[4-(piperazine-1-carbonyl)phenyl]oxazolidin-2-one

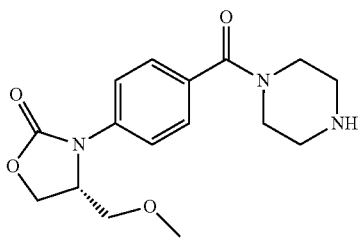 [SMILES: COC[C@@H]1COC(=O)N1c1ccc(C(=O)N2CCNCC2)cc1]

By reaction and treatment in the same manner as in Preparation Example 94 and using (R)-4-[4-(4-methoxymethyl-2-oxooxazolidin-3-yl)benzoyl]piperazine-1-carboxylic acid tert-butyl ester (715 mg) described in Preparation Example 164, the title compound (524 mg) was obtained.
MS(ESI)m/z:320(M+H)$^+$.

Preparation Example 166

Preparation of (R)-4-[4-(4-ethoxymethyl-2-oxooxazolidin-3-yl)benzoyl]piperazine-1-carboxylic acid tert-butyl ester

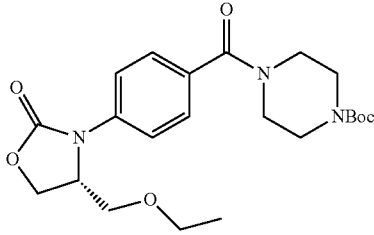 [SMILES: CCOC[C@@H]1COC(=O)N1c1ccc(C(=O)N2CCN(C(=O)OC(C)(C)C)CC2)cc1]

By reaction and treatment in the same manner as in Preparation Example 93 and using (R)-4-[4-(4-hydroxymethyl-2-oxooxazolidin-3-yl)benzoyl]piperazine-1-carboxylic acid tert-butyl ester (2.43 g) described in Preparation Example 163 and ethyl iodide (1.12 g), the title compound (1.97 g) was obtained.
MS(ESI)m/z:434(M+H)$^+$.

Preparation Example 167

Preparation of (R)-4-ethoxymethyl-3-[4-(piperazine-1-carbonyl)phenyl]oxazolidin-2-one

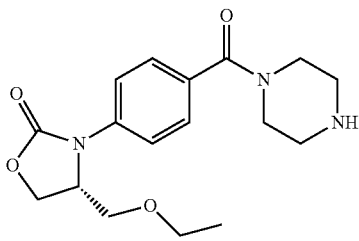 [SMILES: CCOC[C@@H]1COC(=O)N1c1ccc(C(=O)N2CCNCC2)cc1]

By reaction and treatment in the same manner as in Preparation Example 94 and using (R)-4-[4-(4-ethoxymethyl-2-oxooxazolidin-3-yl)benzoyl]piperazine-1-carboxylic acid tert-butyl ester (2.51 g) described in Preparation Example 166, the title compound (1.98 g) was obtained.
MS(ESI)m/z:334(M+H)$^+$.

Preparation Example 168

Preparation of 4-(4-bromo-2-methanesulfonylbenzoyl)piperazine-1-carboxylic acid tert-butyl ester

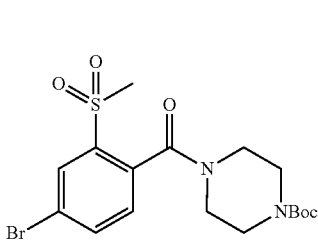 [SMILES: CC(C)(C)OC(=O)N1CCN(C(=O)c2ccc(Br)cc2S(C)(=O)=O)CC1]

By reaction and treatment in the same manner as in Preparation Example 90 and using 4-bromo-2-methanesulfonylbenzoic acid (10.2 g) and piperazine-1-carboxylic acid tert-butyl ester (7.49 g), the title compound (15.4 g) was obtained.
MS(ESI)m/z:347(M+H−100)$^+$ (detected as Boc-dissociated compound).

Preparation Example 169

Preparation of (R)-4-[4-(4-benzoyloxymethyl-2-oxooxazolidin-3-yl)-2-methanesulfonylbenzoyl]piperazine-1-carboxylic acid tert-butyl ester

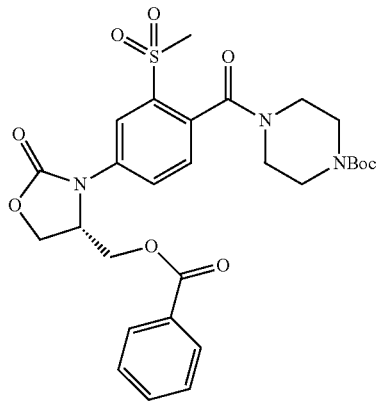 [SMILES: CC(C)(C)OC(=O)N1CCN(C(=O)c2ccc(N3C(=O)OC[C@H]3COC(=O)c3ccccc3)cc2S(C)(=O)=O)CC1]

By reaction and treatment in the same manner as in Preparation Example 91 and using 4-(4-bromo-2-methanesulfonylbenzoyl)piperazine-1-carboxylic acid tert-butyl ester (2.24 g) described in Preparation Example 168 and benzoic acid (R)-2-oxooxazolidin-4-ylmethyl ester (1.11 g), the title compound (2.34 g) was obtained.

MS(ESI)m/z:588(M+H)⁺.

Preparation Example 170

Preparation of (R)-4-[4-(4-hydroxymethyl-2-oxooxazolidin-3-yl)-2-methanesulfonylbenzoyl]piperazine-1-carboxylic acid tert-butyl ester

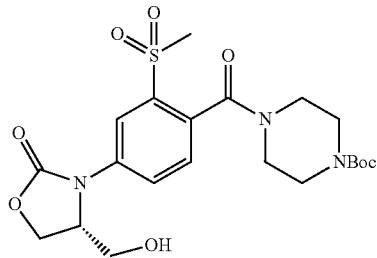 [SMILES: CC(C)(C)OC(=O)N1CCN(C(=O)c2ccc(N3C(=O)OC[C@H]3CO)cc2S(C)(=O)=O)CC1]

By reaction and treatment in the same manner as in Preparation Example 92 and using (R)-4-[4-(4-benzoyloxymethyl-2-oxooxazolidin-3-yl)-2-methanesulfonylbenzoyl]piperazine-1-carboxylic acid tert-butyl ester (2.31 g) described in Preparation Example 169, the title compound (1.27 g) was obtained.

MS(ESI)m/z:384(M+H−100)⁺ (detected as Boc-dissociated compound).

Preparation Example 171

Preparation of (R)-4-[2-methanesulfonyl-4-(4-methoxymethyl-2-oxooxazolidin-3-yl)benzoyl]piperazine-1-carboxylic acid tert-butyl ester

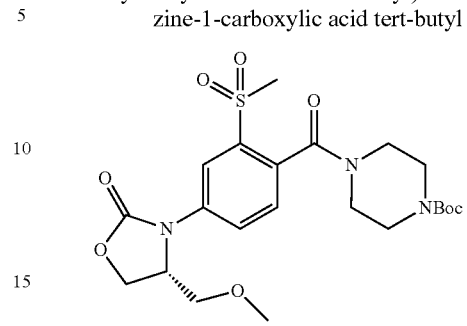

By reaction and treatment in the same manner as in Preparation Example 93 and using (R)-4-[4-(4-hydroxymethyl-2-oxooxazolidin-3-yl)-2-methanesulfonylbenzoyl]piperazine-1-carboxylic acid tert-butyl ester (908 mg) described in Preparation Example 170 and methyl iodide (320 mg), the title compound (738 mg) was obtained.

MS(ESI)m/z:498(M+H)⁺.

Preparation Example 172

Preparation of (R)-3-[3-methanesulfonyl-4-(piperazine-1-carbonyl)phenyl]-4-methoxymethyloxazolidin-2-one

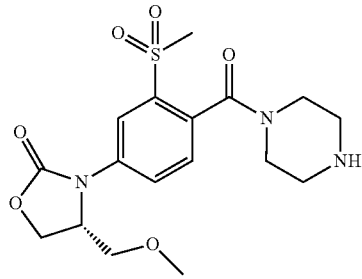 [SMILES: COC[C@@H]1COC(=O)N1c1ccc(C(=O)N2CCNCC2)c(S(C)(=O)=O)c1]

By reaction and treatment in the same manner as in Preparation Example 94 and using (R)-4-[2-methanesulfonyl-4-(4-methoxymethyl-2-oxooxazolidin-3-yl)benzoyl]piperazine-1-carboxylic acid tert-butyl ester (1.49 g) described in Preparation Example 171, the title compound (1.19 g) was obtained.

MS(ESI)m/z:398(M+H)⁺.

Preparation Example 173

Preparation of 4-(3,5,6-trichloropyridin-2-yl)piperazine-1-carboxylic acid tert-butyl ester

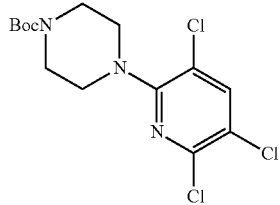 [SMILES: CC(C)(C)OC(=O)N1CCN(c2nc(Cl)c(Cl)cc2Cl)CC1]

To a mixture of 2,3,5,6-tetrachloropyridine (6.51 g), 1-Boc-piperazine (6.71 g) and potassium carbonate (9.95 g)

were added dimethylformamide (15 mL) and toluene (30 mL), and the mixture was stirred at 100° C. for 2 hr. After cooling, water was added to the reaction mixture, and the mixture was extracted with ethyl acetate. The organic layer was washed with saturated brine, and dried over sodium sulfate. The solvent was evaporated under reduced pressure and the residue was purified by column chromatography (ethyl acetate:hexane) to give the title compound (9.42 g).

Preparation Example 174

Preparation of 4-(3,5,6-trimethylpyridin-2-yl)piperazine-1-carboxylic acid tert-butyl ester

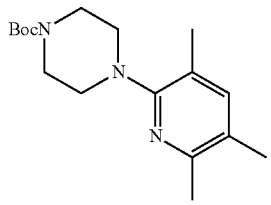

To a mixture of 4-(3,5,6-trichloropyridin-2-yl)piperazine-1-carboxylic acid tert-butyl ester (9.27 g) described in Preparation Example 173, palladium (II) acetate (851 mg), 2-dicyclohexylphosphino-2',6'-dimethoxybiphenyl (3.11 g), potassium fluoride (17.6 g) and methylboronic acid (9.08 g) was added tetrahydrofuran (190 mL), and the mixture was refluxed for 5.5 hr. After cooling, to the reaction mixture were added ethyl acetate and saturated brine and the mixture was extracted with ethyl acetate. The organic layer was washed with saturated brine, and dried over sodium sulfate. The solvent was evaporated under reduced pressure and the residue was purified by column chromatography (hexane:ethyl acetate) to give the title compound (7.08 g).

MS(ESI)m/z:306(M+H)$^+$.

Preparation Example 175

Preparation of 1-(3,5,6-trimethylpyridin-2-yl)piperazine

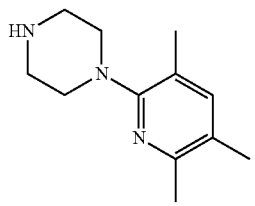

By reaction and treatment in the same manner as in Preparation Example 94 and using 4-(3,5,6-trimethylpyridin-2-yl)piperazine-1-carboxylic acid tert-butyl ester (7.06 g) described in Preparation Example 174, the title compound (4.39 g) was obtained.

MS(ESI)m/z:206(M+H)$^+$.

Preparation Example 176

Preparation of (4-iodophenyl)[4-(3,5,6-trimethylpyridin-2-yl)piperazin-1-yl]methanone

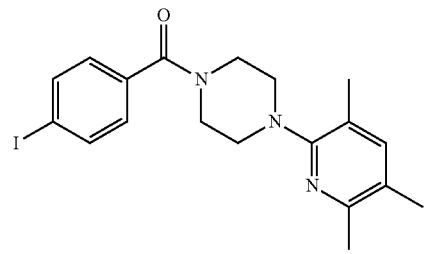 [SMILES: Cc1cc(C)c(N2CCN(C(=O)c3ccc(I)cc3)CC2)nc1C]

By reaction and treatment in the same manner as in Preparation Example 161 and using 1-(3,5,6-trimethylpyridin-2-yl)piperazine (4.39 g) described in Preparation Example 175 and 4-iodobenzoyl chloride (5.98 g), the title compound (8.82 g) was obtained.

MS(ESI)m/z:436(M+H)$^+$.

Preparation Example 177

Preparation of [4-(5-ethyl-3-methylpyridin-2-yl)piperazin-1-yl](4-iodophenyl)methanone

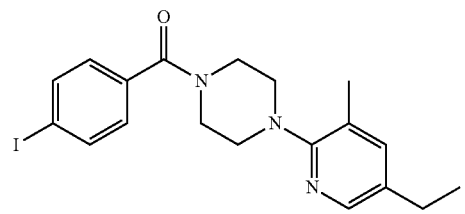 [SMILES: CCc1cnc(N2CCN(C(=O)c3ccc(I)cc3)CC2)c(C)c1]

By reaction and treatment in the same manner as in Preparation Example 161 and using 1-(5-ethyl-3-methylpyridin-2-yl)piperazine (2.46 g) described in Preparation Example 53 and 4-iodobenzoyl chloride (3.36 g), the title compound (4.72 g) was obtained.

MS(ESI)m/z:436(M+H)$^+$.

Preparation Example 178

Preparation of 4-bromo-2-(1,1-dioxoisothiazolidin-2-yl)benzoic acid

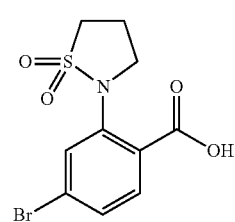 [SMILES: O=C(O)c1ccc(Br)cc1N1CCCS1(=O)=O]

To methyl 4-bromo-2-(1,1-dioxoisothiazolidin-2-yl)benzoate (5.57 g) described in Preparation Example 116 were added ethanol (43 mL) and 1N aqueous sodium hydroxide solution (21.7 mL) and the mixture was stirred at 60° C. for 40 min. Ethanol was evaporated and the mixture was neutralized with water and 1N hydrochloric acid under ice-cooling and the mixture was stirred. The precipitated crystal were collected by filtration to give the title compound (5.25 g).

MS(ESI)m/z:320(M+H)$^+$.

Preparation Example 179

Preparation of [4-bromo-2-(1,1-dioxoisothiazolidin-2-yl)phenyl][4-(5-cyclopropyl-3-methylpyridin-2-yl)piperazin-1-yl]methanone

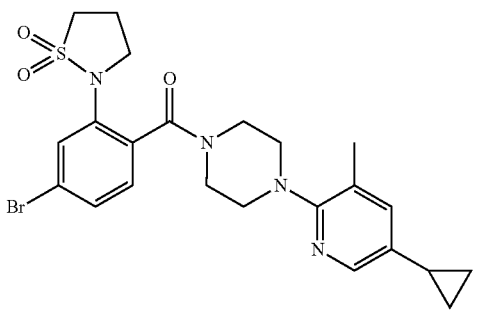 [SMILES: Cc1cc(C2CC2)cnc1N1CCN(C(=O)c2ccc(Br)cc2N2CCCS2(=O)=O)CC1]

By reaction and treatment in the same manner as in Preparation Example 90 and using 4-bromo-2-(1,1-dioxoisothiazolidin-2-yl)benzoic acid (6.72 g) described in Preparation Example 178 and 1-(5-cyclopropyl-3-methylpyridin-2-yl)piperazine (4.56 g) described in Preparation Example 96, the title compound (9.68 g) was obtained.

MS(ESI)m/z:519(M+H)$^+$.

Preparation Example 180

Preparation of [4-bromo-2-(1,1-dioxoisothiazolidin-2-yl)phenyl][4-(5-ethyl-3-methylpyridin-2-yl)piperazin-1-yl]methanone

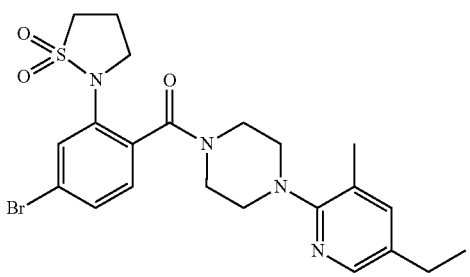 [SMILES: CCc1cnc(N2CCN(C(=O)c3ccc(Br)cc3N3CCCS3(=O)=O)CC2)c(C)c1]

By reaction and treatment in the same manner as in Preparation Example 90 and using 4-bromo-2-(1,1-dioxoisothiazolidin-2-yl)benzoic acid (4.80 g) described in Preparation Example 178 and 1-(5-ethyl-3-methylpyridin-2-yl)piperazine (3.08 g) described in Preparation Example 53, the title compound (7.16 g) was obtained.

MS(ESI)m/z:507(M+H)$^+$.

Preparation Example 181

Preparation of [4-bromo-2-(1,1-dioxoisothiazolidin-2-yl)phenyl][4-(2,4-dimethylphenyl)piperazin-1-yl]methanone

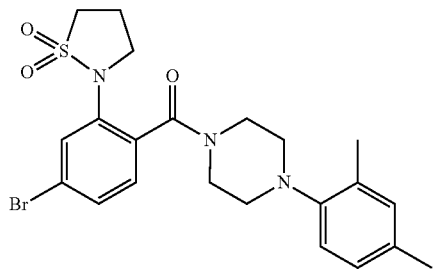 [SMILES: Cc1ccc(N2CCN(C(=O)c3ccc(Br)cc3N3CCCS3(=O)=O)CC2)c(C)c1]

By reaction and treatment in the same manner as in Preparation Example 90 and using 4-bromo-2-(1,1-dioxoisothiazolidin-2-yl)benzoic acid (661 mg) described in Preparation Example 178 and 1-(2,4-dimethylphenyl)piperazine (431 mg), the title compound (1.03 g) was obtained.

MS(ESI)m/z:492(M+H)$^+$.

Preparation Example 182

Preparation of 4-(5-methylpyridin-2-yl)piperazine-1-carboxylic acid tert-butyl ester

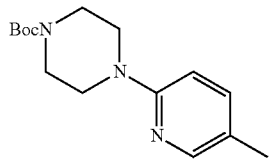

To a mixture of 4-(5-bromopyridin-2-yl)piperazine-1-carboxylic acid tert-butyl ester (5.33 g), palladium (II) acetate (175 mg), 2-dicyclohexylphosphino-2',6'-dimethoxybiphenyl (639 mg), potassium fluoride (5.43 g) and methylboronic acid (2.80 g) was added tetrahydrofuran (120 mL), and the mixture was refluxed under a nitrogen stream for 3 hr. To the reaction mixture were added ethyl acetate and saturated brine, and the mixture was extracted with ethyl acetate. The organic layer was washed with saturated brine, and dried over sodium sulfate. The solvent was evaporated under reduced pressure and the residue was purified by column chromatography (hexane:ethyl acetate) to give the title compound (3.93 g).

MS(ESI)m/z:278(M+H)$^+$.

Preparation Example 183

Preparation of 1-(5-methylpyridin-2-yl)piperazine

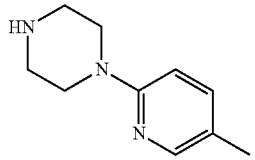

By reaction and treatment in the same manner as in Preparation Example 94 and using 4-(5-methylpyridin-2-yl)piperazine-1-carboxylic acid tert-butyl ester (3.94 g) described in Preparation Example 182, the title compound (2.26 g) was obtained.

Preparation Example 184

Preparation of (4-bromo-2-fluorophenyl)[4-(5-methylpyridin-2-yl)piperazin-1-yl]methanone

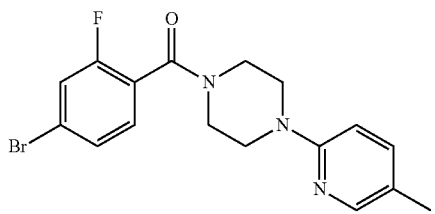 [SMILES: Cc1ccc(N2CCN(C(=O)c3ccc(Br)cc3F)CC2)nc1]

By reaction and treatment in the same manner as in Preparation Example 90 and using 4-bromo-2-fluorobenzoic acid (1.45 g) and 1-(5-methylpyridin-2-yl)piperazine (1.06 g) described in Preparation Example 183, the title compound (2.01 g) was obtained.

MS(ESI)m/z:378(M+H)$^+$.

Preparation Example 185

Preparation of (4-bromo-2,6-difluorophenyl)[4-(5-methylpyridin-2-yl)piperazin-1-yl]methanone

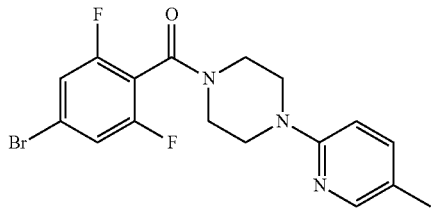 [SMILES: Cc1ccc(N2CCN(C(=O)c3c(F)cc(Br)cc3F)CC2)nc1]

By reaction and treatment in the same manner as in Preparation Example 90 and using 4-bromo-2,6-difluorobenzoic acid (1.56 g) and 1-(5-methylpyridin-2-yl)piperazine (1.06 g) described in Preparation Example 183, the title compound (1.57 g) was obtained.

MS(ESI)m/z:396(M+H)$^+$.

Preparation Example 186

Preparation of 4-(5-cyclopropylpyridin-2-yl)piperazine-1-carboxylic acid tert-butyl ester

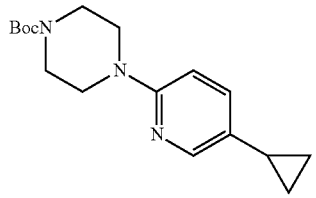 [SMILES: CC(C)(C)OC(=O)N1CCN(c2ccc(C3CC3)cn2)CC1]

To a mixture of 4-(5-bromopyridin-2-yl)piperazine-1-carboxylic acid tert-butyl ester (5.37 g), bis(tricyclohexylphosphine)palladium (II) dichloride (347 mg), tripotassium phosphate (9.99 g) and cyclopropylboronic acid (2.02 g) were added toluene (49 mL) and water (2.5 mL), and the mixture was refluxed. After cooling, ethyl acetate and saturated aqueous sodium hydrogen carbonate solution were added, and the mixture was extracted with ethyl acetate. The organic layer was washed with saturated brine and dried over sodium sulfate, and the solvent was evaporated. The residue was purified by column chromatography (hexane:ethyl acetate) to give the title compound (3.41 g).

MS(ESI)m/z:304(M+H)$^+$.

Preparation Example 187

Preparation of 1-(5-cyclopropylpyridin-2-yl)piperazine

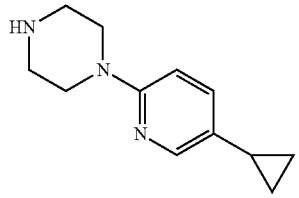 [SMILES: c1cc(N2CCNCC2)ncc1C1CC1]

By reaction and treatment in the same manner as in Preparation Example 94 and using 4-(5-cyclopropylpyridin-2-yl)piperazine-1-carboxylic acid tert-butyl ester (3.40 g) described in Preparation Example 186, the title compound (2.22 g) was obtained.

MS(ESI)m/z:204(M+H)$^+$.

Preparation Example 188

Preparation of (4-bromo-2-fluorophenyl)[4-(5-cyclopropylpyridin-2-yl)piperazin-1-yl]methanone

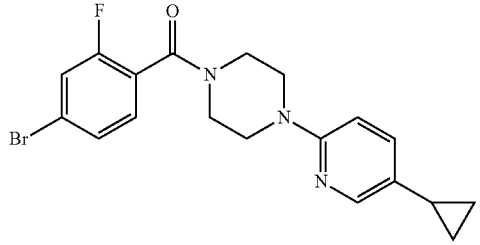

By reaction and treatment in the same manner as in Preparation Example 90 and using 4-bromo-2-fluorobenzoic acid (1.2 g) and 1-(5-cyclopropylpyridin-2-yl)piperazine (1.02 g)

described in Preparation Example 187, the title compound (1.73 g) was obtained.
MS(ESI)m/z:404(M+H)+.

Preparation Example 189

Preparation of (4-bromo-2,6-difluorophenyl)[4-(5-cyclopropylpyridin-2-yl)piperazin-1-yl]methanone

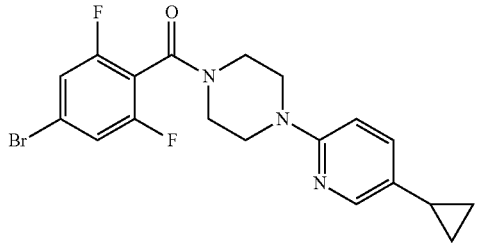 [SMILES: O=C(c1c(F)cc(Br)cc1F)N1CCN(c2ccc(C3CC3)cn2)CC1]

By reaction and treatment in the same manner as in Preparation Example 90 and using 4-bromo-2,6-difluorobenzoic acid (1.20 g) and 1-(5-cyclopropylpyridin-2-yl)piperazine (1.15 g) described in Preparation Example 187, the title compound (1.90 g) was obtained.
MS(ESI)m/z:422(M+H)+.

Preparation Example 190

Preparation of methyl 4-bromo-2-iodobenzoate

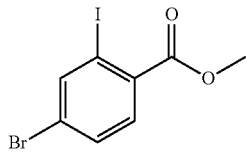

To methyl 2-amino-4-bromobenzoate (5.75 g) was added ice-cooled 20% sulfuric acid (75 mL), sodium nitrite (2.07 g) was added by small portions under ice-cooling and the mixture was stirred for 40 min. To this reaction mixture was added dropwise a solution obtained by dissolving potassium iodide (8.3 g) in water (25 mL) under ice-cooling, 20% sulfuric acid (30 mL) was added and the mixture was stirred for 2 hr. This reaction mixture was neutralized with 4N aqueous sodium hydroxide solution under ice-cooling, and the mixture was extracted with ethyl acetate, 10% aqueous sodium sulfite solution (45 mL) and sodium chloride. The organic layer was washed once with saturated brine and 10% aqueous sodium sulfite solution, with saturated brine, and dried over sodium sulfate. The solvent was evaporated and the residue was purified by column chromatography (hexane:ethyl acetate) to give the title compound (7.05 g).

Preparation Example 191

Preparation of methyl 4-bromo-2-cyanobenzoate

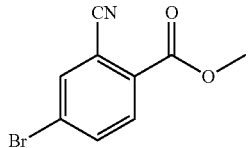

To methyl 4-bromo-2-iodobenzoate (3.52 g) described in Preparation Example 190 were added copper cyanide (1.16 g) and N-methylpyrrolidone (21 mL) and the mixture was stirred at 60° C. for 1 hr. Under cooling with water, ethyl acetate, saturated aqueous ammonium chloride solution and aqueous ammonia were added and the mixture was extracted with ethyl acetate. The organic layer was washed once with saturated aqueous ammonium chloride solution and aqueous ammonia, once with saturated aqueous ammonium chloride solution and once with saturated brine, and dried over sodium sulfate. The solvent was evaporated to give the title compound (2.39 g).
MS(ESI)m/z:240(M+H)+.

Preparation Example 192

Preparation of 4-bromo-2-cyano-benzoic acid

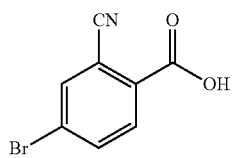

To methyl 4-bromo-2-cyanobenzoate (4.76 g) described in Preparation Example 191 was added dimethoxyethane (78 mL), a solution obtained by dissolving lithium hydroxide monohydrate (1.25 g) in water (30 mL) under ice-cooling was added dropwise, and the mixture was stirred for 1 hr. Under ice-cooling, the mixture was neutralized with 1N hydrochloric acid and dimethoxyethane was evaporated. Water was added and the mixture was stirred under ice-cooling. The precipitated crystals were collected by filtration to give the title compound (4.19 g).
MS(ESI)m/z:226(M+H)+.

Preparation Example 193

Preparation of 5-bromo-2-[4-(3,5-dimethylpyridin-2-yl)piperazine-1-carbonyl]benzonitrile

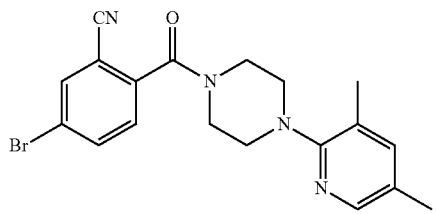

By reaction and treatment in the same manner as in Preparation Example 90 and using 4-bromo-2-cyanobenzoic acid (2.03 g) described in Preparation Example 192 and 1-(3,5-dimethylpyridin-2-yl)piperazine (1.81 g) described in Preparation Example 47, the title compound (2.98 g) was obtained.
MS(ESI)m/z:399(M+H)+.

Preparation Example 194

Preparation of 5-bromo-2-[4-(5-cyclopropyl-3-methylpyridin-2-yl)piperazine-1-carbonyl]benzonitrile

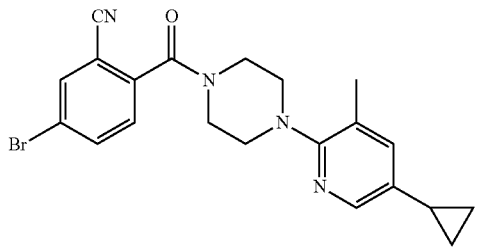 [SMILES: Cc1cc(C2CC2)cnc1N1CCN(C(=O)c2ccc(Cl)cc2Br)CC1]

By reaction and treatment in the same manner as in Preparation Example 90 and using 4-bromo-2-cyanobenzoic acid (2.14 g) described in Preparation Example 192 and 1-(5-cyclopropyl-3-methylpyridin-2-yl)piperazine (2.16 g) described in Preparation Example 96, the title compound (3.31 g) was obtained.

MS(ESI)m/z:425(M+H)⁺.

Preparation Example 195

Preparation of (2-bromo-4-chlorophenyl)[4-(5-cyclopropyl-3-methylpyridin-2-yl)piperazin-1-yl]methanone

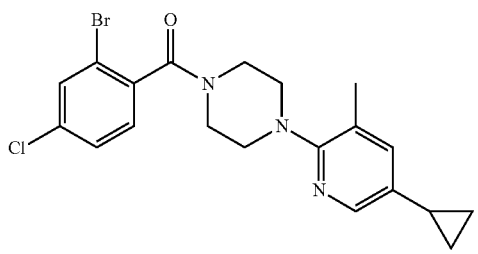

By reaction and treatment in the same manner as in Preparation Example 60 and using 2-bromo-4-chlorobenzoic acid (1 g) and 1-(5-cyclopropyl-3-methylpyridin-2-yl)piperazine (0.923 g) described in Preparation Example 96, the title compound (1.91 g) was obtained.

MS(ESI)m/z:434(M+H)⁺.

Preparation Example 196

Preparation of 1-acetyl-3-{5-chloro-2-[4-(5-cyclopropyl-3-methylpyridin-2-yl)piperazine-1-carbonyl]phenyl}imidazolidin-2-one

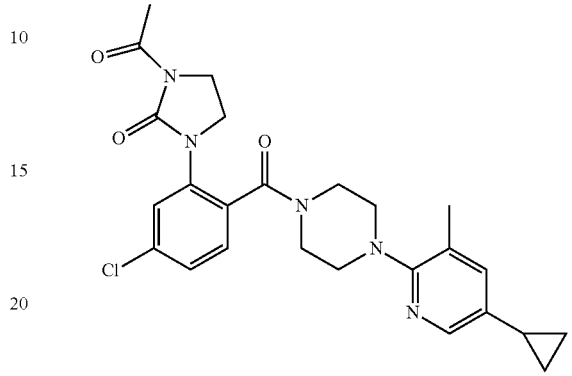

By reaction and treatment in the same manner as in Preparation Example 12 and using (2-bromo-4-chlorophenyl)[4-(5-cyclopropyl-3-methylpyridin-2-yl)piperazin-1-yl]methanone (1.91 g) described in Preparation Example 195 and 1-acetyl-2-imidazolidinone (0.563 g), the title compound (1.3 g) was obtained.

MS (ESI)m/z:482 (M+H)⁺.

Preparation Example 197

Preparation of methyl (S)-4-(4-benzyl-2-oxooxazolidin-3-yl)benzoate

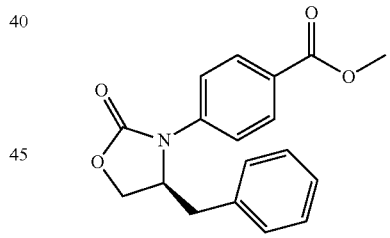

By reaction and treatment in the same manner as in Preparation Example 22 and using p-(methoxycarbonyl)phenylboronic acid (2.45 g) and (S)-4-benzyloxazolidin-2-one (1.205 g), the title compound (0.142 g) was obtained.

Example 1

Synthesis of 3-{4-[4-(2,4-dimethylphenyl)piperazine-1-carbonyl]-3,5-difluorophenyl}oxazolidin-2-one To a mixture of (4-bromo-2,6-difluorophenyl)[4-(2,4-dimethylphenyl)piperazin-1-yl]methanone (819 mg) described in Preparation Example 1, oxazolidin-2-one (174 mg), potassium carbonate (553 mg) and copper (I) iodide (76 mg) were added toluene (2 mL) and N,N'-dimethylethylenediamine (100 μL), and the mixture was refluxed for 8 hr. After cooling, water was added to the reaction mixture, and the mixture was extracted with chloroform. The organic layer was washed with saturated brine, and the solvent was evaporated. The residue was purified by column chromatography (chloroform:methanol) to give the title compound (118 mg).

Example 2

Synthesis of 3-{4-[4-(2,4-dimethylphenyl)piperazine-1-carbonyl]-2-fluorophenyl}oxazolidin-2-one By reaction and treatment in the same manner as in Example 1 and using (4-bromo-3-fluorophenyl)[4-(2,4-dimethylphenyl)piperazin-1-yl]methanone (783 mg) described in Preparation Example 2 and oxazolidin-2-one (174 mg), the title compound (273 mg) was obtained.

Example 3

Synthesis of 3-{2-chloro-4-[4-(2,4-dimethylphenyl)piperazine-1-carbonyl]phenyl}oxazolidin-2-one By reaction and treatment in the same manner as in Example 1 and using (4-bromo-3-chlorophenyl)[4-(2,4-dimethylphenyl)piperazin-1-yl]methanone (815 mg) described in Preparation Example 3 and oxazolidin-2-one (174 mg), the title compound (478 mg) was obtained.

Example 4

Synthesis of 3-{4-[4-(2,4-dimethylphenyl)piperazine-1-carbonyl]-3-fluorophenyl}oxazolidin-2-one By reaction and treatment in the same manner as in Example 1 and using (4-bromo-2-fluorophenyl)[4-(2,4-dimethylphenyl)piperazin-1-yl]methanone (783 mg) described in Preparation Example 4 and oxazolidin-2-one (174 mg), the title compound (383 mg) was obtained.

Example 5

Synthesis of 3-{4-[4-(2,4-dimethylphenyl)piperazine-1-carbonyl]-3-methoxyphenyl}oxazolidin-2-one By reaction and treatment in the same manner as in Example 1 and using (4-bromo-2-methoxyphenyl)[4-(2,4-dimethylphenyl)piperazin-1-yl]methanone (807 mg) described in Preparation Example 5 and oxazolidin-2-one (174 mg), the title compound (409 mg) was obtained.

Example 6

Synthesis of 3-{4-[4-(2,4-dimethylphenyl)piperazine-1-carbonyl]-3-methylphenyl}oxazolidin-2-one By reaction and treatment in the same manner as in Example 1 and using (4-bromo-2-methylphenyl)[4-(2,4-dimethylphenyl)piperazin-1-yl]methanone (775 mg) described in Preparation Example 6 and oxazolidin-2-one (174 mg), the title compound (224 mg) was obtained.

Example 7

Synthesis of 3-{5-chloro-4-[4-(2,4-dimethylphenyl)piperazine-1-carbonyl]-2-fluorophenyl}oxazolidin-2-one By reaction and treatment in the same manner as in Example 1 and using (4-bromo-2-chloro-5-fluorophenyl)[4-(2,4-dimethylphenyl)piperazin-1-yl]methanone (851 mg) described in Preparation Example 7 and oxazolidin-2-one (174 mg), the title compound (506 mg) was obtained.

Example 8

Synthesis of 3-{4-[4-(2,4-dimethylphenyl)piperazine-1-carbonyl]phenyl}oxazolidin-2-one By reaction and treatment in the same manner as in Example 1 and using [4-(2,4-dimethylphenyl)piperazin-1-yl](4-iodophenyl)methanone (7.7 g) described in Preparation Example 8 and oxazolidin-2-one (1.6 g), the title compound (4 g) was obtained.

Example 9

Synthesis of (R)-4-tert-butyl-3-{4-[4-(2,4-dimethylphenyl)piperazine-1-carbonyl]phenyl}oxazolidin-2-one To a mixture of [4-(2,4-dimethylphenyl)piperazin-1-yl](4-iodophenyl)methanone (841 mg) described in Preparation Example 8, (R)-(+)-4-tert-butyloxazolidin-2-one (214 mg), potassium carbonate (553 mg) and copper (I) iodide (76 mg) were added toluene (2 mL) and N,N'-dimethylethylenediamine (100 µL), and the mixture was refluxed for 8 hr. After cooling, water was added to the reaction mixture, and the mixture was extracted with chloroform. The organic layer was washed with saturated brine, and the solvent was evaporated. The residue was purified by column chromatography (chloroform:methanol) to give the title compound (7 mg).

Example 10

Synthesis of (R)-3-{4-[4-(2,4-dimethylphenyl)piperazine-1-carbonyl]phenyl}-4-phenyloxazolidin-2-one By reaction and treatment in the same manner as in Example 1 and using [4-(2,4-dimethylphenyl)piperazin-1-yl](4-iodophenyl)methanone (841 mg) described in Preparation Example 8 and (R)-(−)-4-phenyloxazolidin-2-one (326 mg), the title compound (88 mg) was obtained.

Example 11

Synthesis of 3-{4-[4-(2,4-dimethylphenyl)piperazine-1-carbonyl]-3-methanesulfonylphenyl}oxazolidin-2-one By reaction and treatment in the same manner as in Example 1 and using (4-bromo-2-methanesulfonylphenyl)[4-(2,4-dimethylphenyl)piperazin-1-yl]methanone (451 mg) described in Preparation Example 9 and oxazolidin-2-one (87 mg), the title compound (269 mg) was obtained.

Example 12

Synthesis of 3-{4-[4-(2,4-dimethylphenyl)piperazine-1-carbonyl]-3-methanesulfonylphenyl}-4,4-dimethyloxazolidin-2-one By reaction and treatment in the same manner as in Example 1 and using (4-bromo-2-methanesulfonylphenyl)[4-(2,4-dimethylphenyl)piperazin-1-yl]methanone (785 mg) described in Preparation Example 9 and 4,4-dimethyloxazolidin-2-one (200 mg), the title compound (126 mg) was obtained.

Example 13

Synthesis of (R)-3-{4-[4-(2,4-dimethylphenyl)piperazine-1-carbonyl]-3-methanesulfonylphenyl}-4-isopropyloxazolidin-2-one By reaction and treatment in the same manner as in Example 1 and using (4-bromo-2-methanesulfonylphenyl)[4-(2,4-dimethylphenyl)piperazin-1-yl]methanone (903 mg) described in Preparation Example 9 and (R)-4-isopropyloxazolidin-2-one (258 mg), the title compound (487 mg) was obtained.

Example 14

Synthesis of (R)-3-{4-[4-(2,4-dimethylphenyl)piperazine-1-carbonyl]-3-methanesulfonylphenyl}-4-phenyloxazolidin-2-one By reaction and treatment in the same manner as in Example 1 and using (4-bromo-2-methanesulfonylphenyl)[4-(2,4-dimethylphenyl)piperazin-1-yl]methanone (903 mg) described in Preparation Example 9 and (R)-(−)-4-phenyloxazolidin-2-one (326 mg), the title compound (163 mg) was obtained.

Example 15

Synthesis of 4-tert-butyl-3-{4-[4-(2,4-dimethylphenyl)piperazine-1-carbonyl]-3-methanesulfonylphenyl}oxazolidin-2-one By reaction and treatment in the same manner as in Example 1 and using (4-bromo-2-methanesulfonylphenyl)[4-(2,4-dimethylphenyl)piperazin-1-yl]methanone (903 mg) described in Preparation Example 9 and (R)-4-tert-butyloxazolidin-2-one (286 mg), the title compound (9 mg) was obtained.

Example 16

Synthesis of (R)-4-benzyl-3-{4-[4-(2,4-dimethylphenyl)piperazine-1-carbonyl]-3-methanesulfonylphenyl}oxazolidin-2-one By reaction and treatment in the same manner as in Example 1 and using (4-bromo-2-methanesulfonylphenyl)[4-(2,4-dimethylphenyl)piperazin-1-yl]methanone (903 mg) described in Preparation Example 9 and (R)-4-benzyloxazolidin-2-one (354 mg), the title compound (38 mg) was obtained.

Example 17

Synthesis of (R)-3-{4-[4-(2,4-dimethylphenyl)piperazine-1-carbonyl]-3-methanesulfonylphenyl}-4-isopropyl-5,5-dimethyloxazolidin-2-one By reaction and treatment in the same manner as in Example 1 and using (4-bromo-2-methanesulfonylphenyl)[4-(2,4-dimethylphenyl)piperazin-1-yl]methanone (722 mg) described in Preparation Example 9 and (R)-(+)-4-isopropyl-5,5-dimethyloxazolidin-2-one (250 mg), the title compound (359 mg) was obtained.

Example 18

Synthesis of (4R,5S)-3-{4-[4-(2,4-dimethylphenyl)piperazine-1-carbonyl]-3-methanesulfonylphenyl}-4-methyl-5-phenyloxazolidin-2-one By reaction and treatment in the same manner as in Example 1 and using (4-bromo-2-methanesulfonylphenyl)[4-(2,4-dimethylphenyl)piperazin-1-yl]methanone (903 mg) described in Preparation Example 9 and (4R,5S)-(+)-4-methyl-5-phenyloxazolidin-2-one (354 mg), the title compound (134 mg) was obtained.

Example 19

Synthesis of (R)-3-{4-[4-(2,4-dimethylphenyl)piperazine-1-carbonyl]-3-methanesulfonylphenyl}-4-hydroxymethyloxazolidin-2-one To a mixture of (4-bromo-2-methanesulfonylphenyl)[4-(2,4-dimethylphenyl)piperazin-1-yl]methanone (903 mg) described in Preparation Example 9, benzoic acid (R)-2-oxooxazolidin-4-ylmethyl ester (442 mg), potassium carbonate (553 mg) and copper (I) iodide (76 mg) were added toluene (4 mL) and N,N'-dimethylethylenediamine (100 μL), and the mixture was refluxed for 8 hr. After cooling, water was added to the reaction mixture, and the mixture was extracted with chloroform. The organic layer was washed with saturated brine, and the solvent was evaporated. The residue was purified by column chromatography (chloroform:methanol). To a solution of the obtained compound in dioxane (2 mL) and methanol (2 mL) was added 1 M aqueous sodium hydroxide solution (2 mL), and the mixture was stirred at room temperature for 3 hr. The mixture was extracted with chloroform, washed with saturated brine, and the solvent was evaporated. The residue was purified by column chromatography (chloroform:methanol) to give the title compound (344 mg).

Example 20

Synthesis of 3-{4-[4-(2,4-dimethylphenyl)piperazine-1-carbonyl]-2-methylphenyl}oxazolidin-2-one By reaction and treatment in the same manner as in Example 1 and using (4-bromo-3-methylphenyl)[4-(2,4-dimethylphenyl)piperazin-1-yl]methanone (775 mg) described in Preparation Example 10 and oxazolidin-2-one (174 mg), the title compound (266 mg) was obtained.

Example 21

Synthesis of 3-{3-chloro-4-[4-(2,4-dimethylphenyl) piperazine-1-carbonyl]phenyl}oxazolidin-2-one By reaction and treatment in the same manner as in Example 1 and using (4-bromo-2-chlorophenyl)[4-(2,4-dimethylphenyl)piperazin-1-yl]methanone (814 mg) described in Preparation Example 11 and oxazolidin-2-one (174 mg), the title compound (437 mg) was obtained.

Example 22

Synthesis of 3-{3-cyclopropyl-4-[4-(2,4-dimethylphenyl)piperazine-1-carbonyl]phenyl}oxazolidin-2-one To a mixture of 3-{3-chloro-4-[4-(2,4-dimethylphenyl)piperazine-1-carbonyl]phenyl}oxazolidin-2-one (347 mg) described in Example 21, bis(tricyclohexylphosphine)palladium (II) dichloride (33 mg), tripotassium phosphate (956 mg) and cyclopropylboronic acid (172 mg) were added toluene (4 mL) and water (200 μL), and the mixture was refluxed for 6 hr. After cooling, water was added to the reaction mixture, and the mixture was extracted with chloroform. The organic layer was washed with saturated brine, and the solvent was evaporated. The residue was purified by column chromatography (chloroform:methanol) to give the title compound (81 mg).

Example 23

Synthesis of 3-{4-[4-(2,4,6-trimethylphenyl)piperazine-1-carbonyl]phenyl}oxazolidin-2-one To ethyl 4-(-2-oxooxazolidin-3-yl)benzoate (0.235 g) described in Preparation Example 12 were added 1 M aqueous sodium hydroxide solution (1.3 mL) and ethanol (5 mL), and the mixture was stirred at 50° C. 1N hydrochloric acid (1.3 mL) was added, 1-(2,4,6-trimethylphenyl)piperazine (0.215 g) and 4-(4,6-dimethoxy[1.3.5]triazin-2-yl)-4-methylmorpholinium chloride hydrate (0.277 g) were added, and the mixture was stirred at room temperature overnight. The mixture was extracted with ethyl acetate, washed with saturated brine, and the solvent was evaporated. The residue was purified by HPLC (ODS, 0.05% TFA aqueous solution-acetonitrile) to give the title compound (37.7 mg).

Example 24

Synthesis of (R)-3-{4-[4-(2,4-dimethylphenyl)piperazine-1-carbonyl]phenyl}-4-hydroxymethyloxazolidin-2-one By reaction and treatment in the same manner as in Example 19 and using [4-(2,4-dimethylphenyl)piperazin-1-yl](4-bromophenyl)methanone (1.1 g) described in Preparation Example 13, the title compound (381 mg) was obtained.

Example 25

Synthesis of 3-{4-[4-(5-fluoro-2,4-dimethylphenyl) piperazine-1-carbonyl]-3-methanesulfonylphenyl}oxazolidin-2-one To a mixture of 3-{4-[4-(2-chloro-5-fluoro-4-methylphenyl)piperazine-1-carbonyl]-3-methanesulfonylphenyl}-oxazolidin-2-one (0.5 g) described in Preparation Example 14, methylboronic acid (479 mg), palladium (II) acetate (90 mg), 2-dicyclohexylphosphino-2',6'-dimethoxybiphenyl (328 mg) and potassium fluoride (930 mg) was added tetrahydrofuran (12 mL), and the mixture was refluxed for 18 hr. After cooling, water was added to the reaction mixture, and the mixture was extracted with chloroform. The organic layer was washed with saturated brine, and the solvent was evaporated. The residue was purified by column chromatography (chloroform:methanol) to give the title compound (55 mg).

Example 26

Synthesis of 3-{4-[4-(2-ethyl-4-methylphenyl)piperazine-1-carbonyl]-3-methanesulfonylphenyl}oxazolidin-2-one By reaction and treatment in the same manner as in Example 1 and using (4-bromo-2-methanesulfonylphenyl) [4-(2-ethyl-4-methylphenyl)piperazin-1-yl]methanone (1.8 g) described in Preparation Example 15 and oxazolidin-2-one (418 mg), the title compound (22 mg) was obtained.

Example 27

Synthesis of 3-{4-[4-(methyl-2-vinylphenyl)piperazine-1-carbonyl]phenyl}oxazolidin-2-one By reaction and treatment in the same manner as in Example 1 and using (4-iodophenyl)[4-(4-methyl-2-vinylphenyl)piperazin-1-yl]methanone (1 g) described in Preparation Example 16 and oxazolidin-2-one (313 mg), the title compound (53 mg) was obtained.

Example 28

Synthesis of 3-{4-[4-(2-cyclopropyl-4-methylphenyl)piperazine-1-carbonyl]phenyl}oxazolidin-2-one By reaction and treatment in the same manner as in Example 1 and using [4-(2-cyclopropyl-4-methylphenyl)piperazin-1-yl](4-iodophenyl)methanone (280 mg) described in Preparation Example 17 and oxazolidin-2-one (313 mg), the title compound (69 mg) was obtained.

Example 29

Synthesis of (R)-3-{4-[4-(2-ethyl-4-methylphenyl) piperazine-1-carbonyl]phenyl}-4-isopropyloxazolidin-2-one To a mixture of (R)-4-(4-isopropyl-2-oxooxazolidin-3-yl) benzoic acid (482 mg) described in Preparation Example 18, 1-(2-ethyl-4-methylphenyl)piperazine hydrochloride (499 mg), which is the intermediate described in Preparation Example 15, and 4-(4,6-dimethoxy[1.3.5]triazin-2-yl)-4-methylmorpholinium chloride hydrate (DMT-MM) (829 mg) were added chloroform (3 mL), methanol (3 mL) and N-methylmorpholine (220 μL), and the mixture was stirred at room temperature overnight. After evaporation of the solvent, the residue was purified by column chromatography (hexane: ethyl acetate) to give the title compound (88 mg).

Example 30

Synthesis of 3-{4-[4-(2,4-dichlorophenyl)piperazine-1-carbonyl]phenyl}oxazolidin-2-one By reaction and treatment in the same manner as in Example 1 and using (4-bromophenyl)[4-(2,4-dichlorophenyl)piperazin-1-yl]methanone (828 mg) described in Preparation Example 19 and oxazolidin-2-one (174 mg), the title compound (492 mg) was obtained.

Example 31

Synthesis of 3-{4-[4-(2,4-dimethylphenyl)-4-oxypiperazine-1-carbonyl]phenyl}oxazolidin-2-one 3-{4-[4-(2,4-Dimethylphenyl)piperazine-1-carbonyl]phenyl}oxazolidin-2-one (379 mg) described in Example 8 was dissolved in methylene chloride (4 mL), m-chloroperbenzoic acid (230 mg) was added, and the mixture was stirred at 5° C. for 2 hr. Water was added to the reaction mixture, and the mixture was extracted with chloroform. The organic layer was washed with saturated aqueous sodium hydrogen carbonate solution and saturated brine, and the solvent was evaporated. The residue was purified by column chromatography (chloroform:methanol) to give the title compound (249 mg).

Example 32

Synthesis of (R)-3-{4-[4-(2,4-dimethylphenyl)-4-oxypiperazine-1-carbonyl]-3-methanesulfonylphenyl}-4-hydroxymethyloxazolidin-2-one By reaction and treatment in the same manner as in Example 31 and using (R)-3-{4-[4-(2,4-dimethylphenyl)piperazine-1-carbonyl]-3-methanesulfonylphenyl}-4-hydroxymethyloxazolidin-2-one (310 mg) described in Example 19, the title compound (234 mg) was obtained.

Example 33

Synthesis of (R)-3-{4-[4-(2,4-dimethylphenyl)-4-oxypiperazine-1-carbonyl]-3-methanesulfonylphenyl}-4-isopropyloxazolidin-2-one By reaction and treatment in the same manner as in Example 31 and using (R)-3-{4-[4-(2,4-dimethylphenyl)piperazine-1-carbonyl]-3-methanesulfonylphenyl}-4-isopropyloxazolidin-2-one (110 mg) described in Example 13, the title compound (48 mg) was obtained.

Example 34

Synthesis of (R)-4-benzyl-3-{4-[4-(2,4-dimethylphenyl)piperazine-1-carbonyl]phenyl}oxazolidin-2-one To methyl (R)-4-(4-benzyl-2-oxooxazolidin-3-yl)benzoate (0.19 g) described in Preparation Example 22 were added 1N aqueous sodium hydroxide solution (0.92 mL), methanol (5 mL) and 1,4-dioxane (1 mL), and the mixture was stirred at 65° C. for 7 hr. 1N hydrochloric acid (0.92 mL) was added, 1-(2,4-dimethylphenyl)piperazine (0.116 g) and 4-(4,6-dimethoxy[1.3.5]triazin-2-yl)-4-methylmorpholinium chloride hydrate (0.17 g) were added, and the mixture was stirred at room temperature. After completion of the reaction, the mixture was extracted with ethyl acetate, washed with saturated brine, and the solvent was evaporated. The residue was purified by column chromatography (chloroform) to give the title compound (175.4 mg).

Example 35

Synthesis of 3-{5-[4-(2,4-dimethylphenyl)piperazine-1-carbonyl]pyridin-2-yl}oxazolidin-2-one By reaction and treatment in the same manner as in Example 1 and using (6-bromopyridin-3-yl)[4-(2,4-dimethylphenyl)piperazin-1-yl]methanone (749 mg) described in Preparation Example 20 and oxazolidin-2-one (174 mg), the title compound (473 mg) was obtained.

Example 36

Synthesis of (R)-3-{5-[4-(2,4-dimethylphenyl)piperazine-1-carbonyl]pyridin-2-yl}-4-phenyloxazolidin-2-one By reaction and treatment in the same manner as in Example 1 and using (6-bromopyridin-3-yl)[4-(2,4-dimethylphenyl)piperazin-1-yl]methanone (749 mg) described in Preparation Example 20 and (R)-(−)-4-phenyloxazolidin-2-one (222 mg), the title compound (25 mg) was obtained.

Example 37

Synthesis of 3-{5-[4-(2,4-dimethylphenyl)-4-oxypiperazine-1-carbonyl]pyridin-2-yl}oxazolidin-2-one By reaction and treatment in the same manner as in Example 31 and using 3-{5-[4-(2,4-dimethylphenyl)piperazine-1-carbonyl]pyridin-2-yl}oxazolidin-2-one (290 mg) described in Example 35, the title compound (239 mg) was obtained.

Example 38

Synthesis of 3-{6-[4-(2,4-dimethylphenyl)piperazine-1-carbonyl]pyridin-3-yl}oxazolidin-2-one By reaction and treatment in the same manner as in Example 1 and using (5-bromopyridin-2-yl)[4-(2,4-dimethylphenyl)piperazin-1-yl]methanone (749 mg) described in Preparation Example 21 and oxazolidin-2-one (174 mg), the title compound (449 mg) was obtained.

Example 39

Synthesis of (R)-3-{6-[4-(2,4-dimethylphenyl)piperazine-1-carbonyl]pyridin-3-yl}-4-phenyloxazolidin-2-one By reaction and treatment in the same manner as in Example 1 and using (5-bromopyridin-2-yl)[4-(2,4-dimethylphenyl)piperazin-1-yl]methanone (749 mg) described in Preparation Example 21 and (R)-(−)-4-phenyloxazolidin-2-one (326 mg), the title compound (183 mg) was obtained.

Example 40

Synthesis of 3-{4-[4-(4-chlorobenzoyl)piperidine-1-carbonyl]phenyl}oxazolidin-2-one To a mixture of (4-bromophenyl)[4-(4-chlorobenzoyl)piperidin-1-yl]methanone (1.6 g) described in Preparation Example 30, oxazolidin-2-one (348 mg), potassium carbonate (1.1 g) and copper (I) iodide (152 mg) were added toluene (4 mL) and N,N'-dimethylethylenediamine (200 µL), and the mixture was refluxed for 8 hr. After cooling, water was added to the reaction mixture, and the mixture was extracted with chloroform. The organic layer was washed with saturated brine, and the solvent was evaporated. The residue was purified by column chromatography (chloroform:methanol) to give the title compound (991 mg).

Example 41

Synthesis of 3-{4-[4-(4-methylbenzoyl)piperidine-1-carbonyl]phenyl}oxazolidin-2-one To a mixture of 3-{4-[4-(4-chlorobenzoyl)piperidine-1-carbonyl]phenyl}oxazolidin-2-one (413 mg) described in Example 40, methylboronic acid (120 mg), palladium (II) acetate (11 mg), 2-dicyclohexylphosphino-2',6'-dimethoxybiphenyl (41 mg) and potassium fluoride (232 mg) was added tetrahydrofuran (3 mL), and the mixture was refluxed for 5 hr. After cooling, water was added to the reaction mixture, and the mixture was extracted with chloroform. The organic layer was washed with saturated brine, and the solvent was evaporated. The residue was purified by column chromatography (chloroform:methanol) to give the title compound (112 mg).

Example 42

Synthesis of 3-{5-[4-(4-methylbenzoyl)piperidine-1-carbonyl]pyridin-2-yl}oxazolidin-2-one By reaction and treatment in the same manner as in Example 41 and using 3-{5-[4-(4-chlorobenzoyl)piperidine-1-carbonyl]pyridin-2-yl}oxazolidin-2-one (260 mg) described in Preparation Example 32, the title compound (148 mg) was obtained.

Example 43

Synthesis of (R)-4-hydroxymethyl-3-{3-methanesulfonyl-4-[4-(4-methylbenzoyl)piperidine-1-carbonyl]phenyl}oxazolidin-2-one To a mixture of benzoic acid (R)-3-{4-[4-(4-chlorobenzoyl)piperidine-1-carbonyl]-3-methanesulfonylphenyl}-2-oxooxazolidin-4-ylmethyl ester (938 mg) described in Preparation Example 24, methylboronic acid (359 mg), palladium (II) acetate (34 mg), 2-dicyclohexylphosphino-2',6'-dimethoxybiphenyl (123 mg) and potassium fluoride (697 mg) was added tetrahydrofuran (9 mL), and the mixture was refluxed for 8 hr. After cooling, water was added to the reaction mixture, and the mixture was extracted with chloroform. The organic layer was washed with saturated brine, and the solvent was evaporated. The obtained residue was dissolved in methanol (3 mL) and 1,4-dioxane (3 mL) and 1N aqueous sodium hydroxide solution (6 mL) were added, and the mixture was stirred at room temperature for 3 hr. Water was added to the reaction mixture, and the mixture was extracted with chloroform. The organic layer was washed with saturated brine, and the solvent was evaporated. The residue was purified by column chromatography (chloroform:methanol) to give the title compound (113 mg).

Example 44

Synthesis of 3-{3-methanesulfonyl-4-[4-(4-methylbenzoyl)piperidine-1-carbonyl]phenyl}oxazolidin-2-one By reaction and treatment in the same manner as in Example 41 and using 3-{4-[4-(4-chlorobenzoyl)piperidine-1-carbonyl]-3-methanesulfonylphenyl}oxazolidin-2-one (982 mg) described in Preparation Example 31, the title compound (607 mg) was obtained.

Example 45

Synthesis of (R)-4-isopropyl-3-{4-[4-(4-methylbenzoyl)piperidine-1-carbonyl]phenyl}oxazolidin-2-one By reaction and treatment in the same manner as in Example 41 and using (R)-3-{4-[4-(4-chlorobenzoyl)piperidine-1-carbonyl]phenyl}-4-isopropyloxazolidin-2-one (728 mg) described in Preparation Example 27, the title compound (274 mg) was obtained.

Example 46

Synthesis of (R)-4-methyl-3-{5-[4-(4-methylbenzoyl)piperidine-1-carbonyl]pyridin-2-yl}oxazolidin-2-one By reaction and treatment in the same manner as in Example 41 and using (R)-3-{5-[4-(4-chlorobenzoyl)piperidine-1-carbonyl]pyridin-2-yl}-4-methyloxazolidin-2-one (510 mg) described in Preparation Example 33, the title compound (340 mg) was obtained.

Example 47

Synthesis of (R)-4-ethyl-3-{5-[4-(4-methylbenzoyl)piperidine-1-carbonyl]pyridin-2-yl}oxazolidin-2-one By reaction and treatment in the same manner as in Example 41 and using (R)-3-{5-[4-(4-chlorobenzoyl)piperidine-1-carbonyl]pyridin-2-yl}-4-ethyloxazolidin-2-one (710 mg) described in Preparation Example 34, the title compound (439 mg) was obtained.

Example 48

Synthesis of (R)-4-methyl-3-{6-[4-(4-methylbenzoyl)piperidine-1-carbonyl]pyridin-3-yl}oxazolidin-2-one By reaction and treatment in the same manner as in Example 41 and using (R)-3-{6-[4-(4-chlorobenzoyl)piperidine-1-carbonyl]pyridin-3-yl}-4-methyloxazolidin-2-one (2.1 g) described in Preparation Example 36, the title compound (2 g) was obtained.

Example 49

Synthesis of (R)-4-methyl-3-{4-[4-(4-methylbenzoyl)piperidine-1-carbonyl]phenyl}oxazolidin-2-one To a mixture of (R)-4-(4-methyl-2-oxooxazolidin-3-yl)benzoic acid (633 mg) described in Preparation Example 37, (4-methylphenyl)piperidin-4-ylmethanone hydrochloride (719 mg) and 4-(4,6-dimethoxy[1.3.5]triazin-2-yl)-4-methylmorpholinium chloride hydrate (DMT-MM) (1.2 g) were added chloroform (3 mL), methanol (3 mL) and N-methylmorpholine (330 μL), and the mixture was stirred at room temperature overnight. To the reaction mixture was added 1N aqueous sodium hydroxide solution, and the mixture was extracted with chloroform. The organic layer was washed with saturated brine, and the solvent was evaporated. The residue was purified by column chromatography (hexane:ethyl acetate) to give the title compound (989 mg).

Example 50

Synthesis of (R)-3-{4-[4-(2,4-dimethylbenzoyl)piperidine-1-carbonyl]phenyl}-4-methyloxazolidin-2-one By reaction and treatment in the same manner as in Example 49 and using (2,4-dimethylphenyl)piperidin-4-ylmethanone hydrochloride (253 mg) and (R)-4-(4-methyl-2-oxooxazolidin-3-yl)benzoic acid (211 mg) described in Preparation Example 37, the title compound (419 mg) was obtained.

Example 51

Synthesis of 3-[5-(4-p-tolyloxypiperidine-1-carbonyl)pyridin-2-yl]oxazolidin-2-one By reaction and treatment in the same manner as in Example 40 and using (6-bromopyridin-3-yl)(4-p-tolyloxypiperidin-1-yl)methanone (1.5 g) described in Preparation Example 28, the title compound (1.3 g) was obtained.

Example 52

Synthesis of (R)-4-isopropyl-3-[4-(4-p-tolyloxypiperidine-1-carbonyl)phenyl]oxazolidin-2-one To a mixture of (R)-4-(4-isopropyl-2-oxooxazolidin-3-yl)benzoic acid (499 mg) described in Preparation Example 18, 4-(p-tolyloxy)piperidine (383 mg) and 4-(4,6-dimethoxy[1.3.5]triazin-2-yl)-4-methylmorpholinium chloride hydrate (DMT-MM) (829 mg) were added chloroform (3 mL) and methanol (3 mL), and the mixture was stirred at room temperature overnight. After evaporation of the solvent, the residue was purified by column chromatography (hexane:ethyl acetate) to give the title compound (196 mg).

Example 53

Synthesis of (R)-4-methyl-3-[5-(4-p-tolyloxypiperidine-1-carbonyl)pyridin-2-yl]oxazolidin-2-one By reaction and treatment in the same manner as in Example 40 and using (6-bromopyridin-3-yl)(4-p-tolyloxypiperidin-1-yl)methanone (1.2 g) described in Preparation Example 28 and (R)-4-methyloxazolidin-2-one (364 mg) described in Preparation Example 25, the title compound (200 mg) was obtained.

Example 54

Synthesis of (R)-4-ethyl-3-[5-(4-p-tolyloxypiperidine-1-carbonyl)pyridin-2-yl]oxazolidin-2-one By reaction and treatment in the same manner as in Example 40 and using (6-bromopyridin-3-yl)(4-p-tolyloxypiperidin-1-yl)methanone (1.2 g) described in Preparation Example 28 and (R)-4-ethyloxazolidin-2-one (525 mg) described in Preparation Example 26, the title compound (262 mg) was obtained.

Example 55

Synthesis of (R)-4-methyl-3-[4-(4-p-tolyloxypiperidine-1-carbonyl)phenyl]oxazolidin-2-one By reaction and treatment in the same manner as in Example 52 and using 4-(p-tolyloxy)piperidine (1 g) and (R)-4-(4-methyl-2-oxooxazolidin-3-yl)benzoic acid (1.2 g) described in Preparation Example 37, the title compound (1.6 g) was obtained.

Example 56

Synthesis of 3-{4-[4-(3,5-dichloropyridin-2-yl)piperazine-1-carbonyl]-3-methanesulfonylphenyl}oxazolidin-2-one By reaction and treatment in the same manner as in Example 1 and using (4-bromo-2-methanesulfonylphenyl)[4-(3,5-dichloropyridin-2-yl)piperazin-1-yl]methanone (0.5 g) described in Preparation Example 74 and oxazolidin-2-one (130 mg), the title compound (429 mg) was obtained.

Example 57

Synthesis of 3-{4-[4-(3,5-dimethylpyridin-2-yl)piperazine-1-carbonyl]-3-methanesulfonylphenyl}oxazolidin-2-one To a mixture of 3-{4-[4-(3,5-dichloropyridin-2-yl)piperazine-1-carbonyl]-3-methanesulfonylphenyl}oxazolidin-2-one (400 mg) described in Example 56, methylboronic acid (239 mg), palladium (II) acetate (17 mg), 2-dicyclohexylphosphino-2',6'-dimethoxybiphenyl (62 mg) and potassium fluoride (465 mg) was added tetrahydrofuran (3 mL), and the mixture was refluxed for 8 hr. After cooling, water was added to the reaction mixture, and the mixture was extracted with chloroform. The organic layer was washed with saturated brine, and the solvent was evaporated. The residue was purified by column chromatography (chloroform:methanol) to give the title compound (337 mg).

Example 58

Synthesis of 3-{4-[4-(3,5-dimethylpyridin-2-yl)piperazine-1-carbonyl]phenyl}oxazolidin-2-one By reaction and treatment in the same manner as in Example 1 and using [4-(3,5-dimethylpyridin-2-yl)piperazin-1-yl](4-iodophenyl)methanone (591 mg) described in Preparation Example 77 and oxazolidin-2-one (134 mg), the title compound (396 mg) was obtained.

Example 59

Synthesis of (R)-3-{4-[4-(3,5-dimethylpyridin-2-yl)piperazine-1-carbonyl]phenyl}-4-isopropyloxazolidin-2-one By reaction and treatment in the same manner as in Example 1 and using [4-(3,5-dimethylpyridin-2-yl)piperazin-1-yl](4-iodophenyl)methanone (567 mg) described in Preparation Example 77 and (R)-4-isopropyloxazolidin-2-one (192 mg), the title compound (210 mg) was obtained.

Example 60

Synthesis of 3-{4-[4-(3,5-dimethylpyridin-2-yl)piperazine-1-carbonyl]-3-fluorophenyl}oxazolidin-2-one By reaction and treatment in the same manner as in Example 1 and using (4-bromo-2-fluorophenyl)[4-(3,5-dimethylpyridin-2-yl)piperazin-1-yl]methanone (780 mg) described in Preparation Example 65 and oxazolidin-2-one (209 mg), the title compound (219 mg) was obtained.

Example 61

Synthesis of 3-{4-[4-(3,5-dimethylpyridin-2-yl)piperazine-1-carbonyl]-3-methylphenyl}oxazolidin-2-one By reaction and treatment in the same manner as in Example 1 and using (4-bromo-2-methylphenyl)[4-(3,5-dimethylpyridin-2-yl)piperazin-1-yl]methanone (777 mg) described in Preparation Example 67 and oxazolidin-2-one (209 mg), the title compound (390 mg) was obtained.

Example 62

Synthesis of (R)-3-{4-[4-(3,5-dimethylpyridin-2-yl)piperazine-1-carbonyl]-3-methanesulfonylphenyl}-4-isopropyloxazolidin-2-one By reaction and treatment in the same manner as in Example 1 and using (4-bromo-2-methanesulfonylphenyl)[4-(3,5-dimethylpyridin-2-yl)piperazin-1-yl]methanone (451 mg) described in Preparation Example 61 and (R)-4-isopropyloxazolidin-2-one (155 mg), the title compound (20 mg) was obtained.

Example 63

Synthesis of (R)-3-{4-[4-(3,5-dimethylpyridin-2-yl)piperazine-1-carbonyl]phenyl}-4-phenyloxazolidin-2-one Ethyl (R)-4-(2-oxo-4-phenyl-oxazolidin-3-yl)benzoate (623 mg) described in Preparation Example 75 was dissolve in methanol (3 mL) and 1,4-dioxane (3 mL), 1N aqueous sodium hydroxide solution (5 mL) was added, and the mixture was stirred at room temperature for 3 hr. The mixture was neutralized with 1N hydrochloric acid (5 mL), 1-(3,5-dimethylpyridin-2-yl)piperazine (383 mg) described in Preparation Example 47 and 4-(4,6-dimethoxy[1.3.5]triazin-2-yl)-4-methylmorpholinium chloride hydrate (DMT-MM) (829 mg) were added, and the mixture was stirred at room temperature overnight. Water was added to the reaction mixture, and the mixture was extracted with chloroform. The organic layer was washed with saturated brine, and the solvent was evaporated. The residue was purified by column chromatography (chloroform:methanol) to give the title compound (144 mg).

Example 64

Synthesis of 3-{4-[4-(3,5-dimethylpyridin-2-yl)piperazine-1-carbonyl]phenyl}-4,4-dimethyloxazolidin-2-one To a mixture of ethyl 4-iodobenzoate (290 µL), 4,4-dimethyloxazolidin-2-one (200 mg), potassium carbonate (739 mg) and copper (I) iodide (66 mg) were added toluene (2 mL) and N,N'-dimethylethylenediamine (75 µL), and the mixture was refluxed for 8 hr. After cooling, water was added to the reaction mixture, and the mixture was extracted with ethyl acetate. The organic layer was washed with saturated brine, and the solvent was evaporated. The residue was dissolved in methanol (4 mL) and 1,4-dioxane (4 mL) and 1N aqueous sodium hydroxide solution (3.5 mL) were added, and the mixture was stirred at room temperature for 3 hr. The mixture was neutralized with 1N hydrochloric acid (3.5 mL), 1-(3,5-dimethylpyridin-2-yl)piperazine (333 mg) described in Preparation Example 47 and 4-(4,6-dimethoxy[1.3.5]triazin-2-yl)-4-methylmorpholinium chloride hydrate (DMT-MM) (721 mg) were added, and the mixture was stirred at room temperature overnight. Water was added to the reaction mixture, and the mixture was extracted with chloroform. The organic layer was washed with saturated brine, and the solvent was evaporated. The residue was purified by column chromatography (chloroform:methanol) to give the title compound (151 mg).

Example 65

Synthesis of (R)-3-{4-[4-(3,5-dimethylpyridin-2-yl)piperazine-1-carbonyl]phenyl}-4-isopropyl-5,5-dimethyloxazolidin-2-one By reaction and treatment in the same manner as in Example 64 and using ethyl 4-iodobenzoate (500 µL) and (R)-(+)-4-isopropyl-5,5-dimethyloxazolidin-2-one (472 mg), the title compound (1 g) was obtained.

Example 66

Synthesis of (R)-4-isopropyl-3-{4-[4-(3-methyl-5-trifluoromethylpyridin-2-yl)piperazine-1-carbonyl]phenyl}oxazolidin-2-one By reaction and treatment in the same manner as in Example 29 and using (R)-4-(4-isopropyl-2-oxooxazolidin-3-yl)benzoic acid (499 mg) described in Preparation Example 18 and 1-(3-methyl-5-trifluoromethylpyridin-2-yl)piperazine (490 mg) described in Preparation Example 51, the title compound (292 mg) was obtained.

Example 67

Synthesis of (R)-3-{4-[4-(3,5-dimethylpyridin-2-yl)piperazine-1-carbonyl]phenyl}-5,5-dimethyl-4-phenyloxazolidin-2-one By reaction and treatment in the same manner as in Example 64 and using ethyl 4-iodobenzoate (285 µL) and (R)-(−)-5,5-dimethyl-4-phenyloxazolidin-2-one (325 mg), the title compound (114 mg) was obtained.

Example 68

Synthesis of (R)-4-isopropyl-3-{4-[4-(5-methylpyridin-2-yl)piperazine-1-carbonyl]phenyl}oxazolidin-2-one By reaction and treatment in the same manner as in Example 29 and using (R)-4-(4-isopropyl-2-oxooxazolidin-3-yl)benzoic acid (374 mg) described in Preparation Example 18 and 1-(5-methylpyridin-2-yl)piperazine (250 mg), the title compound (185 mg) was obtained.

Example 69

Synthesis of (R)-4-tert-butyl-3-{4-[4-(3,5-dimethylpyridin-2-yl)piperazine-1-carbonyl]phenyl}oxazolidin-2-one By reaction and treatment in the same manner as in Example 64 and using ethyl 4-iodobenzoate (285 μL) and (R)-(+)-4-tert-butyloxazolidin-2-one (250 mg), the title compound (160 mg) was obtained.

Example 70

Synthesis of (R)-3-{4-[4-(5-cyclopropyl-3-methylpyridin-2-yl)piperazine-1-carbonyl]phenyl}-4-isopropyloxazolidin-2-one By reaction and treatment in the same manner as in Example 29 and using 1-(5-cyclopropyl-3-methylpyridin-2-yl)piperazine hydrochloride (381 mg) described in Preparation Example 49 and (R)-4-(4-isopropyl-2-oxooxazolidin-3-yl)benzoic acid (374 mg) described in Preparation Example 18, the title compound (286 mg) was obtained.

Example 71

Synthesis of (R)-3-{4-[4-(3,5-dimethylpyridin-2-yl)piperazine-1-carbonyl]phenyl}-4-methyloxazolidin-2-one By reaction and treatment in the same manner as in Example 49 and using (R)-4-(4-methyl-2-oxooxazolidin-3-yl)benzoic acid (442 mg) described in Preparation Example 37 and 1-(3,5-dimethylpyridin-2-yl)piperazine hydrochloride (455 mg) described in Preparation Example 64, the title compound (571 mg) was obtained.

Example 72

Synthesis of (R)-3-{4-[4-(3,5-dimethylpyridin-2-yl)piperazine-1-carbonyl]phenyl}-4-hydroxymethyloxazolidin-2-one By reaction and treatment in the same manner as in Example 19 and using [4-(3,5-dimethylpyridin-2-yl)piperazin-1-yl](4-iodophenyl)methanone (2.1 g) described in Preparation Example 77 and benzoic acid (R)-2-oxooxazolidin-4-ylmethyl ester (1.3 g), the title compound (1 g) was obtained.

Example 73

Synthesis of (R)-3-{4-[4-(3,5-dimethylpyridin-2-yl)piperazine-1-carbonyl]phenyl}-4-methoxymethyloxazolidin-2-one (R)-3-{4-[4-(3,5-dimethylpyridin-2-yl)piperazine-1-carbonyl]phenyl}-4-hydroxymethyloxazolidin-2-one (205 mg) described in Example 72 was dissolved in N,N-dimethylformamide (1 mL), sodium hydride (32 mg) was added, and the mixture was stirred at room temperature for 30 min. Iodomethane (142 mg) was added, and the mixture was stirred at room temperature overnight. Water was added to the reaction mixture, and the mixture was extracted with ethyl acetate. The organic layer was washed with saturated brine, and the solvent was evaporated. The residue was purified by column chromatography (chloroform:methanol) to give the title compound (19 mg).

Example 74

Synthesis of (R)-3-{4-[4-(3,5-dimethylpyridin-2-yl)piperazine-1-carbonyl]phenyl}-4-ethyloxazolidin-2-one By reaction and treatment in the same manner as in Example 49 and using (R)-4-(4-ethyl-2-oxooxazolidin-3-yl)benzoic acid (470 mg) described in Preparation Example 78 and 1-(3,5-dimethylpyridin-2-yl)piperazine hydrochloride (455 mg) described in Preparation Example 64, the title compound (312 mg) was obtained.

Example 75

Synthesis of (R)-3-{4-[4-(3,5-dimethylpyridin-2-yl)piperazine-1-carbonyl]phenyl}-4-propyloxazolidin-2-one By reaction and treatment in the same manner as in Example 49 and using (R)-4-(2-oxo-4-propyloxazolidin-3-yl)benzoic acid (498 mg) described in Preparation Example 79 and 1-(3,5-dimethylpyridin-2-yl)piperazine hydrochloride (455 mg) described in Preparation Example 64, the title compound (239 mg) was obtained.

Example 76

Synthesis of (R)-3-{4-[4-(3,5-dimethylpyridin-2-yl)piperazine-1-carbonyl]-3-fluorophenyl}-4-methyloxazolidin-2-one By reaction and treatment in the same manner as in Example 1 and using (4-bromo-2-fluorophenyl)[4-(3,5-dimethylpyridin-2-yl)piperazin-1-yl]methanone (893 mg) described in Preparation Example 65 and (R)-4-methyloxazolidin-2-one (231 mg) described in Preparation Example 25, the title compound (215 mg) was obtained.

Example 77

Synthesis of (R)-3-{4-[4-(3,5-dimethylpyridin-2-yl)piperazine-1-carbonyl]-3-fluorophenyl}-4-ethyloxazolidin-2-one By reaction and treatment in the same manner as in Example 1 and using (4-bromo-2-fluorophenyl)[4-(3,5-dimethylpyridin-2-yl)piperazin-1-yl]methanone (1.6 g)

described in Preparation Example 65 and (R)-4-ethyloxazolidin-2-one (553 mg) described in Preparation Example 26, the title compound (336 mg) was obtained.

Example 78

Synthesis of (R)-3-{4-[4-(3,5-dimethylpyridin-2-yl)piperazine-1-carbonyl]-3-methylphenyl}-4-methyloxazolidin-2-one By reaction and treatment in the same manner as in Example 1 and using (4-bromo-2-methylphenyl)[4-(3,5-dimethylpyridin-2-yl)piperazin-1-yl]methanone (822 mg) described in Preparation Example 67 and (R)-4-methyloxazolidin-2-one (364 mg) described in Preparation Example 25, the title compound (82 mg) was obtained.

Example 79

Synthesis of (R)-3-{4-[4-(3,5-dimethylpyridin-2-yl)piperazine-1-carbonyl]-3-methylphenyl}-4-ethyloxazolidin-2-one hydrochloride To a mixture of (4-bromo-2-methylphenyl)[4-(3,5-dimethylpyridin-2-yl)piperazin-1-yl]methanone (935 mg) described in Preparation Example 67, (R)-4-ethyloxazolidin-2-one (300 mg) described in Preparation Example 26, potassium carbonate (1 g) and copper (I) iodide (95 mg) were added toluene (3 mL) and N,N'-dimethylethylenediamine (110 µL), and the mixture was refluxed for 16 hr. After cooling, water was added to the reaction mixture, and the mixture was extracted with chloroform. The organic layer was washed with saturated brine, and the solvent was evaporated. The residue was purified by column chromatography (hexane:ethyl acetate). The obtained compound was dissolved in ethyl acetate (5 mL), 4N hydrogen chloride/ethyl acetate (0.6 mL) was added, and the mixture was filtered to give the title compound (118 mg).

Example 80

Synthesis of (R)-3-{4-[4-(3,5-dimethylpyridin-2-yl)piperazine-1-carbonyl]-3-methylphenyl}-4-isopropyl-5,5-dimethyloxazolidin-2-one By reaction and treatment in the same manner as in Example 1 and using (4-bromo-2-methylphenyl)[4-(3,5-dimethylpyridin-2-yl)piperazin-1-yl]methanone (867 mg) described in Preparation Example 67 and (R)-(+)-4-isopropyl-5,5-dimethyloxazolidin-2-one (409 mg), the title compound (35 mg) was obtained.

Example 81

Synthesis of (R)-3-{4-[4-(3,5-dimethylpyridin-2-yl)piperazine-1-carbonyl]-3-methanesulfonylphenyl}-4-methyloxazolidin-2-one By reaction and treatment in the same manner as in Example 1 and using (4-bromo-2-methanesulfonylphenyl)[4-(3,5-dimethylpyridin-2-yl)piperazin-1-yl]methanone (839 mg) described in Preparation Example 61 and (R)-4-methyloxazolidin-2-one (288 mg) described in Preparation Example 25, the title compound (269 mg) was obtained.

Example 82

Synthesis of (R)-3-{4-[4-(3,5-dimethylpyridin-2-yl)piperazine-1-carbonyl]-3-methanesulfonylphenyl}-4-ethyloxazolidin-2-one By reaction and treatment in the same manner as in Example 1 and using (4-bromo-2-methanesulfonylphenyl)[4-(3,5-dimethylpyridin-2-yl)piperazin-1-yl]methanone (874 mg) described in Preparation Example 61 and (R)-4-ethyloxazolidin-2-one (300 mg) described in Preparation Example 26, the title compound (399 mg) was obtained.

Example 83

Synthesis of 3-{4-[4-(3,5-dimethylpyridin-2-yl)piperazine-1-carbonyl]phenyl}-5-methyloxazolidin-2-one By reaction and treatment in the same manner as in Example 49 and using 4-(5-methyl-2-oxooxazolidin-3-yl)benzoic acid (442 mg) described in Preparation Example 40 and 1-(3,5-dimethylpyridin-2-yl)piperazine hydrochloride (455 mg) described in Preparation Example 64, the title compound (272 mg) was obtained.

Example 84

Synthesis of (S)-3-{4-[4-(3,5-dimethylpyridin-2-yl)piperazine-1-carbonyl]phenyl}-4-isopropyloxazolidin-2-one By reaction and treatment in the same manner as in Example 49 and using (S)-4-(4-isopropyl-2-oxooxazolidin-3-yl)benzoic acid (496 mg) described in Preparation Example 80 and 1-(3,5-dimethylpyridin-2-yl)piperazine hydrochloride (455 mg) described in Preparation Example 64, the title compound (583 mg) was obtained.

Example 85

Synthesis of (R)-3-{4-[4-(3,5-dimethylpyridin-2-yl)piperazine-1-carbonyl]-3-methanesulfonylphenyl}-4-isopropyl-5,5-dimethyloxazolidin-2-one By reaction and treatment in the same manner as in Example 1 and using (4-bromo-2-methanesulfonylphenyl)[4-(3,5-dimethylpyridin-2-yl)piperazin-1-yl]methanone (890 mg) described in Preparation Example 61 and (R)-(+)-4-isopropyl-5,5-dimethyloxazolidin-2-one (409 mg), the title compound (51 mg) was obtained.

Example 86

Synthesis of (R)-3-{4-[4-(3,5-dimethylpyridin-2-yl)piperazine-1-carbonyl]-2-fluorophenyl}-4-methyloxazolidin-2-one hydrochloride Methyl (R)-3-fluoro-4-(4-methyl-2-oxooxazolidin-3-yl)benzoate (1.2 g) described in Preparation Example 81 was dissolve in methanol (5 mL) and 1,4-dioxane (5 mL), 1N aqueous sodium hydroxide solution (10 mL) was added, and the mixture was stirred at room temperature overnight. The mixture was neutralized with 1N hydrochloric acid (10 mL), and extracted with chloroform. The organic layer was washed with saturated brine, and the solvent was evaporated. The residue was dissolved in chloroform (8 mL) and methanol (8 mL), 1-(3,5-dimethylpyridin-2-yl)piperazine hydrochloride (1.1 g) described in Preparation Example 64, 4-(4,6-dimethoxy[1.3.5]triazin-2-yl)-4-methylmorpholinium chloride hydrate (DMT-MM) (829 mg) and N-methylmorpholine (550 μL) were added, and the mixture was stirred at room temperature overnight. To the reaction mixture was added 1N aqueous sodium hydroxide solution, and the mixture was extracted with chloroform. The organic layer was washed with saturated brine, and the solvent was evaporated. The residue was purified by column chromatography (hexane:ethyl acetate). The obtained compound was dissolved in ethyl acetate (50 mL), 4N hydrogen chloride/ethyl acetate (1.3 mL) was added, and the mixture was filtered to give the title compound (494 mg).

Example 87

Synthesis of (R)-3-{4-[4-(3-cyclopropyl-5-methylpyridin-2-yl)piperazine-1-carbonyl]phenyl}-4-methyloxazolidin-2-one hydrochloride (R)-4-(4-methyl-2-oxooxazolidin-3-yl)benzoic acid (442 mg) described in Preparation Example 37, 1-(3-cyclopropyl-5-methylpyridin-2-yl)piperazine hydrochloride (435 mg) described in Preparation Example 48 and 4-(4,6-dimethoxy[1.3.5]triazin-2-yl)-4-methylmorpholinium chloride hydrate (DMT-MM) (829 mg) were dissolved in chloroform (3 mL) and methanol (3 mL), N-methylmorpholine (220 μL) was added, and the mixture was stirred at room temperature overnight. To the reaction mixture was added 1N aqueous sodium hydroxide solution, and the mixture was extracted with chloroform. The organic layer was washed with saturated brine, and the solvent was evaporated. The residue was purified by column chromatography (hexane:ethyl acetate). The obtained compound was dissolved in ethyl acetate (20 mL), 4N hydrogen chloride/ethyl acetate (0.5 mL) was added, and the mixture was filtered to give the title compound (652 mg).

Example 88

Synthesis of (R)-3-{4-[4-(5-cyclopropyl-3-methylpyridin-2-yl)piperazine-1-carbonyl]phenyl}-4-methyloxazolidin-2-one By reaction and treatment in the same manner as in Example 49 and using (R)-4-(4-methyl-2-oxooxazolidin-3-yl)benzoic acid (221 mg) described in Preparation Example 37 and 1-(5-cyclopropyl-3-methylpyridin-2-yl)piperazine hydrochloride (254 mg) described in Preparation Example 49, the title compound (296 mg) was obtained.

Example 89

Synthesis of (R)-3-{4-[4-(3,5-dimethylpyridin-2-yl)piperazine-1-carbonyl]-2-methylphenyl}-4-methyloxazolidin-2-one hydrochloride By reaction and treatment in the same manner as in Example 86 and using methyl (R)-3-methyl-4-(4-methyl-2-oxooxazolidin-3-yl)benzoate (1.2 g) described in Preparation Example 82, the title compound (398 mg) was obtained.

Example 90

Synthesis of (R)-4-methyl-3-{4-[4-(3-methyl-5-trifluoromethylpyridin-2-yl)piperazine-1-carbonyl]phenyl}oxazolidin-2-one hydrochloride To a mixture of (R)-4-(4-methyl-2-oxooxazolidin-3-yl)benzoic acid (664 mg) described in Preparation Example 37, 1-(3-methyl-5-trifluoromethylpyridin-2-yl)piperazine (736 mg) described in Preparation Example 51 and 4-(4,6-dimethoxy[1.3.5]triazin-2-yl)-4-methylmorpholinium chloride hydrate (DMT-MM) (1.2 g) were added chloroform (5 mL) and methanol (5 mL), and the mixture was stirred at room temperature overnight. Water was added to the reaction mixture, and the mixture was extracted with chloroform. The organic layer was washed with saturated brine, and the solvent was evaporated. The residue was purified by column chromatography (hexane:ethyl acetate). The obtained compound was dissolved in ethyl acetate (20 mL), 4N hydrogen chloride/ethyl acetate (1 mL) was added, and the mixture was filtered to give the title compound (310 mg).

Example 91

Synthesis of (R)-3-{4-[4-(3-cyclopropyl-5-trifluoromethylpyridin-2-yl)piperazine-1-carbonyl]phenyl}-4-methyloxazolidin-2-one hydrochloride By reaction and treatment in the same manner as in Example 87 and using (R)-4-(4-methyl-2-oxooxazolidin-3-yl)benzoic acid (221 mg) described in Preparation Example 37 and 1-(3-cyclopropyl-5-trifluoromethylpyridin-2-yl)piperazine hydrochloride (615 mg) described in Preparation Example 76, the title compound (571 mg) was obtained.

Example 92

Synthesis of (R)-3-{4-[4-(3,5-dimethylpyridin-2-yl)piperazine-1-carbonyl]-2-methoxyphenyl}-4-methyloxazolidin-2-one hydrochloride By reaction and treatment in the same manner as in Example 87 and using (R)-3-methoxy-4-(4-methyl-2-oxooxazolidin-3-yl)benzoic acid (1 g) described in Preparation Example 46 and 1-(3,5-dimethylpyridin-2-yl)piperazine hydrochloride (956 mg) described in Preparation Example 64, the title compound (838 mg) was obtained.

Example 93

Synthesis of (R)-3-{3-chloro-4-[4-(3,5-dimethylpyridin-2-yl)piperazine-1-carbonyl]phenyl}-4-methyloxazolidin-2-one hydrochloride By reaction and treatment in the same manner as in Example 79 and using (4-bromo-2-chlorophenyl)[4-(3,5-dimethylpyridin-2-yl)piperazin-1-yl]methanone (1.7 g) described in Preparation Example 69 and (R)-4-methyloxazolidin-2-one (510 mg) described in Preparation Example 25, the title compound (299 mg) was obtained.

Example 94

Synthesis of (R)-3-{4-[4-(3,5-dicyclopropylpyridin-2-yl)piperazine-1-carbonyl]phenyl}-4-methyloxazolidin-2-one hydrochloride By reaction and treatment in the same manner as in Example 87 and using (R)-4-(4-methyl-2-oxooxazolidin-3-yl)benzoic acid (221 mg) described in Preparation Example 37 and 1-(3,5-dicyclopropylpyridin-2-yl)piperazine hydrochloride (487 mg) described in Preparation Example 50, the title compound (736 mg) was obtained.

Example 95

Synthesis of (R)-3-{4-[4-(3,5-dimethylpyridin-2-yl)piperazine-1-carbonyl]-3-methanesulfonylphenyl}-4-propyloxazolidin-2-one hydrochloride By reaction and treatment in the same manner as in Example 79 and using (4-bromo-2-methanesulfonylphenyl)[4-(3,5-dimethylpyridin-2-yl)piperazin-1-yl]methanone (1.3 g) described in Preparation Example 61 and (R)-4-propyloxazolidin-2-one (483 mg) described in Preparation Example 29, the title compound (400 mg) was obtained.

Example 96

Synthesis of (R)-3-{4-[4-(3,5-dimethylpyridin-2-yl)piperazine-1-carbonyl]-3,5-difluorophenyl}-4-methyloxazolidin-2-one hydrochloride By reaction and treatment in the same manner as in Example 79 and using (4-bromo-2,6-difluorophenyl)[4-(3,5-dimethylpyridin-2-yl)piperazin-1-yl]methanone (1.6 g) described in Preparation Example 60 and (R)-4-methyloxazolidin-2-one (607 mg) described in Preparation Example 25, the title compound (337 mg) was obtained.

Example 97

Synthesis of (R)-3-{2-chloro-4-[4-(3,5-dimethylpyridin-2-yl)piperazine-1-carbonyl]phenyl}-4-methyloxazolidin-2-one By reaction and treatment in the same manner as in Example 1 and using (4-bromo-3-chlorophenyl)[4-(3,5-dimethylpyridin-2-yl)piperazin-1-yl]methanone (1.7 g) described in Preparation Example 70 and (R)-4-methyloxazolidin-2-one (607 mg) described in Preparation Example 25, the title compound (288 mg) was obtained.

Example 98

Synthesis of (R)-4-methyl-3-{4-[4-(3,5,6-trimethylpyridin-2-yl)piperazine-1-carbonyl]phenyl}oxazolidin-2-one hydrochloride By reaction and treatment in the same manner as in Example 87 and using (R)-4-(4-methyl-2-oxooxazolidin-3-yl)benzoic acid (422 mg) described in Preparation Example 37 and 1-(3,5,6-trimethylpyridin-2-yl)piperazine hydrochloride (483 mg) described in Preparation Example 52, the title compound (675 mg) was obtained.

Example 99

Synthesis of (R)-3-{5-chloro-4-[4-(3,5-dimethylpyridin-2-yl)piperazine-1-carbonyl]-2-fluorophenyl}-4-methyloxazolidin-2-one hydrochloride By reaction and treatment in the same manner as in Example 79 and using (4-bromo-2-chloro-5-fluorophenyl)[4-(3,5-dimethylpyridin-2-yl)piperazin-1-yl]methanone (1.5 g) described in Preparation Example 72 and (R)-4-methyloxazolidin-2-one (400 mg) described in Preparation Example 25, the title compound (347 mg) was obtained.

Example 100

Synthesis of (R)-3-{4-[4-(3,5-dimethylpyrazin-2-yl)piperazine-1-carbonyl]phenyl}-4-methyloxazolidin-2-one By reaction and treatment in the same manner as in Example 49 and using (R)-4-(4-methyl-2-oxooxazolidin-3-yl)benzoic acid (422 mg) described in Preparation Example 37 and 1-(3,5-dimethylpyrazin-2-yl)piperazine hydrochloride (457 mg) described in Preparation Example 59, the title compound (484 mg) was obtained.

Example 101

Synthesis of (R)-3-{4-[4-(3,5-dimethylpyridin-2-yl)piperazine-1-carbonyl]-3-methanesulfonylphenyl}-4-hydroxymethyloxazolidin-2-one By reaction and treatment in the same manner as in Example 19 and using (4-bromo-2-methanesulfonylphenyl)[4-(3,5-dimethylpyridin-2-yl)piperazin-1-yl]methanone (1.6 g) described in Preparation Example 61 and benzoic acid (R)-2-oxooxazolidin-4-ylmethyl ester (903 mg), the title compound (1 g) was obtained.

Example 102

Synthesis of (R)-3-{4-[4-(3,5-dimethylpyridin-2-yl)piperazine-1-carbonyl]-3-fluorophenyl}-4-hydroxymethyloxazolidin-2-one By reaction and treatment in the same manner as in Example 19 and using (4-bromo-2-fluorophenyl)[4-(3,5-dimethylpyridin-2-yl)piperazin-1-yl]methanone (1.2 g) described in Preparation Example 65 and benzoic acid (R)-2-oxooxazolidin-4-ylmethyl ester (849 mg), the title compound (278 mg) was obtained.

Example 103

Synthesis of (R)-3-{3-methanesulfonyl-4-[4-(3,5,6-trimethylpyridin-2-yl)piperazine-1-carbonyl]phenyl}-4-methyloxazolidin-2-one hydrochloride By reaction and treatment in the same manner as in Example 79 and using (4-bromo-2-methanesulfonylphenyl)[4-(3,5,6-trimethylpyridin-2-yl)piperazin-1-yl]methanone (1.1 g) described in Preparation Example 83 and (R)-4-methyloxazolidin-2-one (313 mg) described in Preparation Example 25, the title compound (896 mg) was obtained.

Example 104

Synthesis of (R)-3-{4-[4-(5-cyclobutyl-3-methylpyridin-2-yl)piperazine-1-carbonyl]phenyl}-4-methyloxazolidin-2-one hydrochloride By reaction and treatment in the same manner as in Example 90 and using (R)-4-(4-methyl-2-oxooxazolidin-3-yl)benzoic acid (422 mg) described in Preparation Example 37 and 1-(5-cyclobutyl-3-methylpyridin-2-yl)piperazine (350 mg) described in Preparation Example 58, the title compound (429 mg) was obtained.

Example 105

Synthesis of (R)-3-{4-[4-(3,5-dimethylpyridin-2-yl)piperazine-1-carbonyl]phenyl}-5-methyloxazolidin-2-one hydrochloride By reaction and treatment in the same manner as in Example 90 and using (R)-4-(5-methyl-2-oxooxazolidin-3-yl)benzoic acid (422 mg) described in Preparation Example 41 and 1-(3,5-dimethylpyridin-2-yl)piperazine (383 mg) described in Preparation Example 47, the title compound (40 mg) was obtained.

Example 106

Synthesis of (R)-3-{4-[4-(5-ethyl-3-methylpyridin-2-yl)piperazine-1-carbonyl]phenyl}-4-methyloxazolidin-2-one hydrochloride By reaction and treatment in the same manner as in Example 90 and using (R)-4-(4-methyl-2-oxooxazolidin-3-yl)benzoic acid (422 mg) described in Preparation Example 37 and 1-(5-ethyl-3-methylpyridin-2-yl)piperazine (441 mg) described in Preparation Example 53, the title compound (502 mg) was obtained.

Example 107

Synthesis of (R)-4-methyl-3-{4-[4-(5-methyl-3-trifluoromethylpyridin-2-yl)piperazine-1-carbonyl]phenyl}oxazolidin-2-one hydrochloride By reaction and treatment in the same manner as in Example 87 and using (R)-4-(4-methyl-2-oxooxazolidin-3-yl)benzoic acid (422 mg) described in Preparation Example 37 and 1-(5-methyl-3-trifluoromethylpyridin-2-yl)piperazine hydrochloride (282 mg) described in Preparation Example 55, the title compound (51 mg) was obtained.

Example 108

Synthesis of (R)-3-{2-chloro-4-[4-(3,5-dimethylpyridin-2-yl)piperazine-1-carbonyl]-5-methoxyphenyl}-4-methyloxazolidin-2-one hydrochloride By reaction and treatment in the same manner as in Example 79 and using (5-chloro-4-iodo-2-methoxyphenyl)[4-(3,5-dimethylpyridin-2-yl)piperazin-1-yl]methanone (1.5 g) described in Preparation Example 71 and (R)-4-methyloxazolidin-2-one (400 mg) described in Preparation Example 25, the title compound (225 mg) was obtained.

Example 109

Synthesis of (R)-3-{5-[4-(3,5-dimethylpyridin-2-yl)piperazine-1-carbonyl]pyridin-2-yl}-4-methyloxazolidin-2-one 2hydrochloride By reaction and treatment in the same manner as in Example 79 and using (6-bromopyridin-3-yl)[4-(3,5-dimethylpyridin-2-yl)piperazin-1-yl]methanone (1.5 g) described in Preparation Example 73 and (R)-4-methyloxazolidin-2-one (510 mg) described in Preparation Example 25, the title compound (315 mg) was obtained.

Example 110

Synthesis of (R)-3-{4-[4-(3,5-dimethylpyridin-2-yl)piperazine-1-carbonyl]-3,5-difluorophenyl}-4-ethyloxazolidin-2-one To a mixture of (4-bromo-2,6-difluorophenyl)[4-(3,5-dimethylpyridin-2-yl)piperazin-1-yl]methanone (410 mg) described in Preparation Example 60, (R)-4-ethyloxazolidin-2-one (138 mg) described in Preparation Example 26, potassium carbonate (276 mg) and copper (I) iodide (38 mg) were added toluene (1.5 mL) and N,N'-dimethylethylenediamine (43 μL), and the mixture was refluxed for 2.5 hr. Since the starting materials were left, copper (I) iodide (38 mg) and N,N'-dimethylethylenediamine (43 μL) were added and the mixture was further refluxed for 2 hr. The reaction mixture was cooled, ethyl acetate and aqueous ammonium chloride solution were added and the mixture was extracted with ethyl acetate. The ethyl acetate layer was washed with a 1:1 mixture of saturated aqueous ammonium chloride solution and ammonia water, and the mixture was washed once with saturated aqueous ammonium chloride solution, once with saturated aqueous sodium chloride solution, and dried over sodium sulfate. The solvent was evaporated under reduced pressure. The residue was purified by column chromatography (chloroform:methanol) to give the title compound (279 mg).

Example 111

Synthesis of 3-{4-[4-(3,5-dimethylpyridin-2-yl)piperazine-1-carbonyl]-3,5-difluorophenyl}oxazolidin-2-one To a mixture of (4-bromo-2,6-difluorophenyl)[4-(3,5-dimethylpyridin-2-yl)piperazin-1-yl]methanone (410 mg) described in Preparation Example 60, oxazolidin-2-one (87 mg), potassium carbonate (277 mg) and copper (I) iodide (95.8 mg) were added toluene (1 mL) and N,N'-dimethylethylenediamine (101 μL), and the mixture was refluxed for 8 hr. Water was added to the reaction mixture, the mixture was extracted with chloroform, and the solvent was evaporated. The residue was purified by column chromatography (chloroform:methanol) to give the title compound (229.3 mg).

Example 112

Synthesis of 3-{4-[4-(3,5-dimethylpyridin-2-yl)piperazine-1-carbonyl]phenyl}-5-methoxymethyloxazolidin-2-one hydrochloride Ethyl 4-(5-methoxymethyl-2-oxooxazolin-3-yl)benzoate (830 mg) described in Preparation Example 39 was dissolved in methanol (3 mL) and tetrahydrofuran (3 mL), 1N aqueous sodium hydroxide solution (5 mL) was added, and the mixture was stirred at room temperature for 3 hr. The mixture was neutralized with 1N hydrochloric acid (5 mL), and extracted with chloroform. The organic layer was washed with saturated brine, and the solvent was evaporated. The residue was dissolved in chloroform (5 mL) and methanol (5 mL), 1-(3,5-dimethylpyridin-2-yl)piperazine (574 mg) described in Preparation Example 47 and 4-(4,6-dimethoxy[1.3.5]triazin-2-yl)-4-methylmorpholinium chloride hydrate (DMT-MM) (1.3 g) were added, and the mixture was stirred at room temperature overnight. After evaporation of the solvent, the residue was purified by column chromatography (hexane: ethyl acetate), and dissolved in ethyl acetate (10 mL). 4N hydrogen chloride/ethyl acetate (0.8 mL) was added and the mixture was filtered to give the title compound (484 mg).

Example 113

Synthesis of (R)-3-{4-[4-(3,5-dimethylpyridin-2-yl)piperazine-1-carbonyl]-3-methoxyphenyl}-4-methyloxazolidin-2-one hydrochloride By reaction and treatment in the same manner as in Example 87 and using (R)-2-methoxy-4-(4-methyl-2-oxooxazolidin-3-yl)benzoic acid (1.1 g) described in Preparation Example 45 and 1-(3,5-dimethylpyridin-2-yl)piperazine hydrochloride (956 mg) described in Preparation Example 64, the title compound (731 mg) was obtained.

Example 114

Synthesis of (R)-3-{4-[4-(5-isopropyl-3-methylpyridin-2-yl)piperazine-1-carbonyl]phenyl}-4-methyloxazolidin-2-one hydrochloride By reaction and treatment in the same manner as in Example 90 and using (R)-4-(4-methyl-2-oxooxazolidin-3-yl)benzoic acid (855 mg) described in Preparation Example 37 and 1-(5-isopropyl-3-methylpyridin-2-yl)piperazine (848 mg) described in Preparation Example 56, the title compound (1.1 g) was obtained.

Example 115

Synthesis of (S)-3-{4-[4-(3,5-dimethylpyridin-2-yl)piperazine-1-carbonyl]phenyl}-4-methyloxazolidin-2-one hydrochloride By reaction and treatment in the same manner as in Example 79 and using [4-(3,5-dimethylpyridin-2-yl)piperazin-1-yl](4-iodophenyl)methanone (842 mg) described in Preparation Example 77 and (S)-4-methyloxazolidin-2-one (303 mg) described in Preparation Example 44, the title compound (758 mg) was obtained.

Example 116

Synthesis of (R)-3-{4-[4-(3-cyclopropyl-5-methylpyridin-2-yl)piperazine-1-carbonyl]-3-methanesulfonylphenyl}-4-methyloxazolidin-2-one hydrochloride By reaction and treatment in the same manner as in Example 79 and using (4-bromo-2-methanesulfonylphenyl)[4-(3-cyclopropyl-5-methylpyridin-2-yl)piperazin-1-yl]methanone (0.9 g) described in Preparation Example 84 and (R)-4-methyloxazolidin-2-one (300 mg) described in Preparation Example 25, the title compound (516 mg) was obtained.

Example 117

Synthesis of (R)-3-{4-[4-(5-cyclopropyl-3-methylpyridin-2-yl)piperazine-1-carbonyl]-3-methanesulfonylphenyl}-4-methyloxazolidin-2-one hydrochloride By reaction and treatment in the same manner as in Example 79 and using (4-bromo-2-methanesulfonylphenyl)[4-(5-cyclopropyl-3-methylpyridin-2-yl)piperazin-1-yl]methanone (0.9 g) described in Preparation Example 85 and (R)-4-methyloxazolidin-2-one (300 mg) described in Preparation Example 25, the title compound (427 mg) was obtained.

Example 118

Synthesis of (R)-3-{4-[4-(3-ethyl-5-methylpyridin-2-yl)piperazine-1-carbonyl]phenyl}-4-methyloxazolidin-2-one hydrochloride By reaction and treatment in the same manner as in Example 87 and using (R)-4-(4-methyl-2-oxooxazolidin-3-yl)benzoic acid (332 mg) described in Preparation Example 37 and 1-(3-ethyl-5-methylpyridin-2-yl)piperazine hydrochloride (363 mg) described in Preparation Example 54, the title compound (446 mg) was obtained.

Example 119

Synthesis of (S)-3-{4-[4-(3,5-dimethylpyridin-2-yl)piperazine-1-carbonyl]phenyl}-5-methyloxazolidin-2-one hydrochloride By reaction and treatment in the same manner as in Example 79 and using [4-(3,5-dimethylpyridin-2-yl)piperazin-1-yl](4-iodophenyl)methanone (842 mg) described in Preparation Example 77 and (S)-5-methyloxazolidin-2-one (303 mg) described in Preparation Example 42, the title compound (684 mg) was obtained.

Example 120

Synthesis of (R)-3-{4-[4-(3,5-dicyclopropylpyridin-2-yl)piperazine-1-carbonyl]phenyl}-4-isopropyloxazolidin-2-one hydrochloride By reaction and treatment in the same manner as in Example 87 and using (R)-4-(4-isopropyl-2-oxooxazolidin-3-yl)benzoic acid (499 mg) described in Preparation Example 18 and 1-(3,5-dicyclopropylpyridin-2-yl)piperazine hydrochloride (560 mg) described in Preparation Example 50, the title compound (469 mg) was obtained.

Example 121

Synthesis of 3-{4-[4-(3,5-dimethylpyridin-2-yl)piperazine-1-carbonyl]-3-methylphenyl}-4,4-dimethyloxazolidin-2-one hydrochloride By reaction and treatment in the same manner as in Example 79 and using (4-bromo-2-methylphenyl)[4-(3,5-dimethylpyridin-2-yl)piperazin-1-yl]methanone (680 mg) described in Preparation Example 67 and 4,4-dimethyloxazolidin-2-one (294 mg), the title compound (100 mg) was obtained.

Example 122

Synthesis of (R)-3-{4-[4-(3,5-dicyclopropylpyridin-2-yl)piperazine-1-carbonyl]-3-methanesulfonylphenyl}-4-methyloxazolidin-2-one hydrochloride By reaction and treatment in the same manner as in Example 79 and using (4-bromo-2-methanesulfonylphenyl)[4-(3,5-dicyclopropylpyridin-2-yl)piperazin-1-yl]methanone (1 g) described in Preparation Example 89 and (R)-4-methyloxazolidin-2-one (303 mg) described in Preparation Example 25, the title compound (422 mg) was obtained.

Example 123

Synthesis of (R)-3-{4-[4-(3,5-dimethylpyridin-2-yl) piperazine-1-carbonyl]-2-methylphenyl}-5-methyloxazolidin-2-one hydrochloride By reaction and treatment in the same manner as in Example 79 and using (4-bromo-3-methylphenyl)[4-(3,5-dimethylpyridin-2-yl)piperazin-1-yl]methanone (685 mg) described in Preparation Example 68 and intermediate (R)-5-methyloxazolidin-2-one (258 mg) described in Preparation Example 41, the title compound (119 mg) was obtained.

Example 124

Synthesis of (R)-3-{4-[4-(3,5-dimethylpyridin-2-yl) piperazine-1-carbonyl]-2-fluorophenyl}-4-ethyloxazolidin-2-one By reaction and treatment in the same manner as in Example 110 and using (4-bromo-3-fluorophenyl)[4-(3,5-dimethylpyridin-2-yl)piperazin-1-yl]methanone (392 mg) described in Preparation Example 66 and (R)-4-ethyloxazolidin-2-one (138 mg) described in Preparation Example 26, the title compound (246 mg) was obtained.

Example 125

Synthesis of benzoic acid (R)-3-{4-[4-(3,5-dimethylpyridin-2-yl)piperazine-1-carbonyl]-2-fluorophenyl}-2-oxooxazolidin-4-ylmethyl ester By reaction and treatment in the same manner as in Example 110 and using (4-bromo-3-fluorophenyl)[4-(3,5-dimethylpyridin-2-yl)piperazin-1-yl]methanone (1.96 g) described in Preparation Example 66 and benzoic acid (R)-2-oxooxazolidin-4-ylmethyl ester (1.33 g), the title compound (367 mg) was obtained.

Example 126

Synthesis of (R)-3-{4-[4-(3,5-dimethylpyridin-2-yl) piperazine-1-carbonyl]-2-fluorophenyl}-4-hydroxymethyloxazolidin-2-one benzoic acid (R)-3-{4-[4-(3,5-dimethylpyridin-2-yl)piperazine-1-carbonyl]-2-fluorophenyl}-2-oxooxazolidin-4-ylmethyl ester (309 mg) described in Example 125 was dissolved in dimethoxyethane, 4N aqueous sodium hydroxide solution was added and the mixture was stirred at room temperature. Under ice-cooling, the mixture was neutralized with 1N hydrochloric acid, ethyl acetate and sodium chloride were added and the mixture was extracted with ethyl acetate. The ethyl acetate layer was washed once with saturated aqueous sodium chloride solution, and dried over sodium sulfate. The solvent was evaporated under reduced pressure. The residue was purified by column chromatography (chloroform:methanol) to give the title compound (181 mg).

Example 127

Synthesis of 3-{4-[4-(3,5-dimethylpyridin-2-yl)piperazine-1-carbonyl]-2-fluorophenyl}oxazolidin-2-one By reaction and treatment in the same manner as in Example 111 and using (4-bromo-3-fluorophenyl)[4-(3,5-dimethylpyridin-2-yl)piperazin-1-yl]methanone (392 mg) described in Preparation Example 66 and oxazolidin-2-one (87 mg), the title compound (271.1 mg) was obtained.

Example 128

Synthesis of 3-{4-[4-(3,5-dimethylpyridin-2-yl)piperazine-1-carbonyl]-2-methylphenyl}oxazolidin-2-one By reaction and treatment in the same manner as in Example 111 and using (4-bromo-3-methylphenyl)[4-(3,5-dimethylpyridin-2-yl)piperazin-1-yl]methanone (388 mg) described in Preparation Example 68 and oxazolidin-2-one (87 mg), the title compound (52.7 mg) was obtained.

Example 129

Synthesis of 3-{4-[4-(3,5-dimethylpyridin-2-yl)piperazine-1-carbonyl]-3-nitrophenyl}oxazolidin-2-one By reaction and treatment in the same manner as in Example 111 and using (4-bromo-2-nitrophenyl)[4-(3,5-dimethylpyridin-2-yl)piperazin-1-yl]methanone (1.5 g) described in Preparation Example 63 and oxazolidin-2-one (0.3115 g), the title compound (1.105 g) was obtained.

Example 130

Synthesis of 3-{4-[4-(3,5-dimethylpyridin-2-yl)piperazine-1-carbonyl]phenyl}-5,5-dimethyloxazolidin-2-one By reaction and treatment in the same manner as in Example 111 and using [4-(3,5-dimethylpyridin-2-yl)piper- Example 131

Synthesis of (R)-3-{4-[4-(5-cyclopentyl-3-methylpyridin-2-yl)piperazine-1-carbonyl]phenyl}-4-methyloxazolidin-2-one hydrochloride azin-1-yl](4-iodophenyl)methanone (842 mg) described in Preparation Example 77 and 5,5-dimethyloxazolin-2-one (345 mg) described in Preparation Example 43, the title compound (312 mg) was obtained.

Example 131

Synthesis of (R)-3-{4-[4-(5-cyclopentyl-3-methylpyridin-2-yl)piperazine-1-carbonyl]phenyl}-4-methyloxazolidin-2-one hydrochloride By reaction and treatment in the same manner as in Example 90 and using (R)-4-(4-methyl-2-oxooxazolidin-3-yl)benzoic acid (221 mg) described in Preparation Example 37 and 1-(5-cyclopentyl-3-methylpyridin-2-yl)piperazine (203 mg) described in Preparation Example 57, the title compound (127 mg) was obtained.

Example 132

Synthesis of (R)-3-{3-methanesulfonyl-4-[4-(3,5,6-trimethylpyridin-2-yl)piperazine-1-carbonyl]phenyl}-4-methoxymethyloxazolidin-2-one hydrochloride By reaction and treatment in the same manner as in Example 79 and using (4-bromo-2-methanesulfonylphenyl)[4-(3,5,6-trimethylpyridin-2-yl)piperazin-1-yl]methanone (466 mg) described in Preparation Example 83 and (R)-4-methoxymethyloxazolidin-2-one (131 mg) described in Preparation Example 38, the title compound (296 mg) was obtained.

Example 133

Synthesis of 3-{3-amino-4-[4-(3,5-dimethylpyridin-2-yl)piperazine-1-carbonyl]phenyl}oxazolidin-2-one A mixture of ammonium chloride (0.779 g), reduced iron (0.56 g), ethanol (16 mL) and water (4.3 mL) was stirred with heating at 60-70° C., and 3-{4-[4-(3,5-dimethylpyridin-2-yl)piperazine-1-carbonyl]-3-nitrophenyl}oxazolidin-2-one (1.105 g) described in Example 129 was added. After completion of the reaction, the mixture was extracted with ethyl acetate. The organic layer was washed with saturated brine, and the solvent was evaporated. The residue was purified by column chromatography (chloroform:methanol) to give the title compound (0.177 g).

Example 134

Synthesis of (R)-3-{4-[4-(3,5-dimethylpyridin-2-yl)piperazine-1-carbonyl]-3,5-difluorophenyl}-4-hydroxymethyloxazolidin-2-one By reaction and treatment in the same manner as in Example 125 and then Example 126 and using (4-bromo-2,6-difluorophenyl)[4-(3,5-dimethylpyridin-2-yl)piperazin-1-yl]methanone (759 mg) described in Preparation Example 60, the title compound (215 mg) was obtained.

Example 135

Synthesis of 3-{3-acetylamino-4-[4-(3,5-dimethylpyridin-2-yl)piperazine-1-carbonyl]phenyl}oxazolidin-2-one To a mixture of 3-{3-amino-4-[4-(3,5-dimethylpyridin-2-yl)piperazine-1-carbonyl]phenyl}oxazolidin-2-one (80 mg) described in Example 133, triethylamine (0.1 mL) and methylene chloride (2 mL) was added acetyl chloride (0.03 mL), and the mixture was stirred overnight. Water was added to the reaction mixture, and the mixture was extracted with ethyl acetate. The organic layer was washed with saturated brine, and the solvent was evaporated. The residue was purified by column chromatography (chloroform:methanol) to give the title compound (55.3 mg).

Example 136

Synthesis of 3-{4-[4-(3,5-dicyclopropylpyridin-2-yl)piperazine-1-carbonyl]-3-methanesulfonylphenyl}oxazolidin-2-one By reaction and treatment in the same manner as in Example 111 and using (4-bromo-2-methanesulfonylphenyl)[4-(3,5-dicyclopropylpyridin-2-yl)piperazin-1-yl]methanone (451 mg) described in Preparation Example 89 and oxazolidin-2-one (78 mg), the title compound (226.6 mg) was obtained.

Example 137

Synthesis of 3-{4-[4-(3,5-dicyclopropylpyridin-2-yl)piperazine-1-carbonyl]-3-methanesulfonylphenyl}-4,4-dimethyloxazolidin-2-one By reaction and treatment in the same manner as in Example 111 and using (4-bromo-2-methanesulfonylphenyl)[4-(3,5-dicyclopropylpyridin-2-yl)piperazin-1-yl]methanone (463 mg) described in Preparation Example 89 and 4,4-dimethyloxazolidin-2-one (106 mg), the title compound (85.6 mg) was obtained.

Example 138

Synthesis of 3-{4-[4-(3,5-dimethylpyridin-2-yl)piperazine-1-carbonyl]-3-(1,1-dioxo-isothiazolidin-2-yl)phenyl}oxazolidin-2-one To a mixture of 3-{3-amino-4-[4-(3,5-dimethylpyridin-2-yl)piperazine-1-carbonyl]phenyl}oxazolidin-2-one (93.1 mg) described in Example 133, triethylamine (63 µL) and tetrahydrofuran (1 mL) was added 3-chloropropanesulfonyl chloride (38 µL), and the mixture was stirred overnight. Water was added to the reaction mixture, and the mixture was extracted with ethyl acetate. The organic layer was washed with saturated brine, and the solvent was evaporated. To the residue were added 1,8-diazabicyclo[5.4.0]undec-7-ene (DBU) (42 µL) and DMF (1 mL), and the mixture was stirred at room temperature. Water was added to the reaction mixture, and the mixture was extracted with ethyl acetate. The organic layer was washed with saturated brine, and the solvent was evaporated. To the residue was added a mixed solvent of isopropyl ether and ethyl acetate, and the precipitated crystals were collected by filtration to give the title compound (62.1 mg).

Example 139

Synthesis of (R)-3-{4-[4-(3,5-dicyclopropylpyridin-2-yl)piperazine-1-carbonyl]-3-methanesulfonylphenyl}-4-ethyloxazolidin-2-one By reaction and treatment in the same manner as in Example 111 and using (4-bromo-2-methanesulfonylphenyl) [4-(3,5-dicyclopropylpyridin-2-yl)piperazin-1-yl]methanone (400 mg) described in Preparation Example 89 and (R)-4-ethyloxazolidin-2-one (91.3 mg) described in Preparation Example 26, the title compound (109.5 mg) was obtained.

Example 140

Synthesis of (R)-3-{4-[4-(5-cyclopropyl-3-methylpyridin-2-yl)piperazine-1-carbonyl]-3-fluorophenyl}-4-methyloxazolidin-2-one hydrochloride By reaction and treatment in the same manner as in Example 79 and using (4-bromo-2-fluorophenyl)[4-(5-cyclopropyl-3-methylpyridin-2-yl)piperazin-1-yl]methanone (770 mg) described in Preparation Example 86 and (R)-4-methyloxazolidin-2-one (273 mg) described in Preparation Example 25, the title compound (586 mg) was obtained.

Example 141

Synthesis of (R)-3-{4-[4-(3-cyclopropyl-5-trifluoromethylpyridin-2-yl)piperazine-1-carbonyl]-3-fluorophenyl}-4-methyloxazolidin-2-one hydrochloride By reaction and treatment in the same manner as in Example 79 and using (4-bromo-2-fluorophenyl)[4-(3-cyclopropyl-5-trifluoromethylpyridin-2-yl)piperazin-1-yl] methanone (600 mg) described in Preparation Example 87 and (R)-4-methyloxazolidin-2-one (170 mg) described in Preparation Example 25, the title compound (321 mg) was obtained.

Example 142

Synthesis of (R)-3-{4-[4-(3,5-dicyclopropylpyridin-2-yl)piperazine-1-carbonyl]-3-methanesulfonylphenyl}-4-methoxymethyloxazolidin-2-one By reaction and treatment in the same manner as in Example 111 and using (4-bromo-2-methanesulfonylphenyl) [4-(3,5-dicyclopropylpyridin-2-yl)piperazin-1-yl]methanone (400 mg) described in Preparation Example 89 and (R)-4-methoxymethyloxazolidin-2-one (104 mg) described in Preparation Example 38, the title compound (138.6 mg) was obtained.

Example 143

Synthesis of (S)-3-{4-[4-(3,5-dicyclopropylpyridin-2-yl)piperazine-1-carbonyl]-3-methanesulfonylphenyl}-4-methyloxazolidin-2-one hydrochloride By reaction and treatment in the same manner as in Example 79 and using (4-bromo-2-methanesulfonylphenyl) [4-(3,5-dicyclopropylpyridin-2-yl)piperazin-1-yl]methanone (400 mg) described in Preparation Example 89 and (S)-4-methyloxazolidin-2-one (80.2 mg) described in Preparation Example 44, the title compound (286.5 mg) was obtained.

Example 144

Synthesis of (S)-3-{4-[4-(3,5-dicyclopropylpyridin-2-yl)piperazine-1-carbonyl]-3-methanesulfonylphenyl}-5-methyloxazolidin-2-one By reaction and treatment in the same manner as in Example 111 and using (4-bromo-2-methanesulfonylphenyl) [4-(3,5-dicyclopropylpyridin-2-yl)piperazin-1-yl]methanone (400 mg) described in Preparation Example 89 and (S)-5-methyloxazolidin-2-one (80.2 mg) described in Preparation Example 42, the title compound (258.4 mg) was obtained.

Example 145

Synthesis of 3-{4-[4-(3,5-dicyclopropylpyridin-2-yl)piperazine-1-carbonyl]-3-methanesulfonylphenyl}-5,5-dimethyloxazolidin-2-one hydrochloride By reaction and treatment in the same manner as in Example 79 and using (4-bromo-2-methanesulfonylphenyl) [4-(3,5-dicyclopropylpyridin-2-yl)piperazin-1-yl]methanone (400 mg) described in Preparation Example 89 and 5,5-dimethyloxazolidin-2-one (91.3 mg) described in Preparation Example 43, the title compound (15.9 mg) was obtained.

Example 146

Synthesis of 3-{4-[4-(2,4-dimethylphenyl)-[1,4]diazepane-1-carbonyl]phenyl}oxazolidin-2-one To ethyl 4-(2-oxooxazolidin-3-yl)benzoate (0.235 g) described in Preparation Example 12 were added 1N aqueous sodium hydroxide solution (1.3 mL) and ethanol (5 mL), and the mixture was stirred at 50° C. 1N hydrochloric acid (1.3 mL) was added, 1-(2,4-dimethylphenyl)-[1,4]diazepane hydrochloride (0.241 g) described in Preparation Example 88, 4-(4,6-dimethoxy[1.3.5]triazin-2-yl)-4-methylmorpholinium chloride hydrate (0.277 g) and N-methylmorpholine (0.13 mL) were added, and the mixture was stirred at room temperature overnight. Water was added to the reaction mixture, and the mixture was extracted with ethyl acetate. The organic layer was washed with saturated brine, and the solvent was evaporated. The residue was purified by column chromatography (hexane:ethyl acetate) to give the title compound (41.8 mg).

Example 147

Synthesis of (R)-3-{4-[4-(3,5-dichloropyridin-2-yl) piperazine-1-carbonyl]-2-fluorophenyl}-4-methoxymethyloxazolidin-2-one (R)-3-[2-fluoro-4-(piperazine-1-carbonyl)phenyl]-4-methoxymethyloxazolidin-2-one (343 mg) described in Preparation Example 94 was dissolve in N,N-dimethylformamide (2 mL), 2,3,5-trichloropyridine (275 mg) and potassium carbonate (562 mg) were added and the mixture was stirred at 100° C. To the reaction mixture was added ethyl acetate under ice-cooling and insoluble materials were filtered off. Water was added to the filtrate and the mixture was extracted with ethyl acetate. The organic layer was washed twice with saturated brine, and dried over sodium sulfate. The solvent was evaporated under reduced pressure and the residue was purified by column chromatography (chloroform:methanol) to give the title compound (240 mg).

Example 148

Synthesis of (R)-3-{4-[4-(3,5-dimethylpyridin-2-yl)piperazine-1-carbonyl]-2-fluorophenyl}-4-methoxymethyloxazolidin-2-one (R)-3-{4-[4-(3,5-dichloropyridin-2-yl)piperazine-1-carbonyl]-2-fluorophenyl}-4-methoxymethyloxazolidin-2-one (216 mg) described in Example 147, palladium (II) acetate (10.2 mg), 2-dicyclohexylphosphino-2',6'-dimethoxybiphenyl (37.5 mg), potassium fluoride (212 mg), methylboronic acid (109 mg) and tetrahydrofuran (2.3 mL) were added, and the mixture was refluxed under a nitrogen stream for 2 hr. Under ice-cooling, saturated brine was added to the reaction mixture, and the mixture was extracted with ethyl acetate. The organic layer was dried over sodium sulfate and the solvent was evaporated under reduced pressure. The residue was purified by column chromatography (chloroform:methanol). Under ice-cooling, ethyl acetate, 1N hydrochloric acid and water were added and the mixture was extracted with water. The aqueous layer was washed with ethyl acetate, neutralized with sodium hydrogen carbonate, and extracted with ethyl acetate. The organic layer was washed with saturated brine, and dried over sodium sulfate. The solvent was evaporated under reduced pressure to give the title compound (173 mg).

Example 149

Synthesis of (R)-3-{4-[4-(3,5-dicyclopropylpyridin-2-yl)piperazine-1-carbonyl]phenyl}-4-ethyloxazolidin-2-one To a mixture of [4-(3,5-dicyclopropylpyridin-2-yl)piperazin-1-yl](4-iodophenyl)methanone (473 mg) described in Preparation Example 95, (R)-4-ethyloxazolidin-2-one (138 mg) described in Preparation Example 26, potassium carbonate (415 mg) and copper (I) iodide (38 mg) were added toluene (2 mL) and N,N'-dimethylethylenediamine (43 µL), and the mixture was heated under reflux for 3 hr. The reaction mixture was cooled, ethyl acetate and aqueous ammonium chloride solution were added and the mixture was extracted with ethyl acetate. The ethyl acetate layer was washed with a 1:1 mixture of saturated aqueous ammonium chloride solution and ammonia water, washed once with saturated aqueous ammonium chloride solution, once with saturated aqueous sodium chloride solution, and dried over sodium sulfate. The solvent was evaporated under reduced pressure. The residue was purified by column chromatography (chloroform:methanol) to give the title compound (377 mg).

Example 150

Synthesis of 3-{4-[4-(3,5-dicyclopropylpyridin-2-yl)piperazine-1-carbonyl]phenyl}oxazolidin-2-one By reaction and treatment in the same manner as in Example 149 and using [4-(3,5-dicyclopropylpyridin-2-yl)piperazin-1-yl](4-iodophenyl)methanone (473 mg) described in Preparation Example 95, oxazolidin-2-one (104 mg), the title compound (367 mg) was obtained.

Example 151

(S)-3-{4-[4-(3,5-dicyclopropylpyridin-2-yl)piperazine-1-carbonyl]phenyl}-5-methyloxazolidin-2-one By reaction and treatment in the same manner as in Example 149 and using [4-(3,5-dicyclopropylpyridin-2-yl)piperazin-1-yl](4-iodophenyl)methanone (473 mg) described in Preparation Example 95 and (S)-5-methyloxazolidin-2-one (121 mg) described in Preparation Example 42, the title compound (343 mg) was obtained.

Example 152

Synthesis of 3-{4-[4-(3,5-dicyclopropylpyridin-2-yl)piperazine-1-carbonyl]phenyl}-4,4-dimethyloxazolidin-2-one By reaction and treatment in the same manner as in Example 110 and using [4-(3,5-dicyclopropylpyridin-2-yl)piperazin-1-yl](4-iodophenyl)methanone (473 mg) described in Preparation Example 95 and 4,4-dimethyloxazolidin-2-one (138 mg), the title compound (198 mg) was obtained.

Example 153

Synthesis of (R)-3-{4-[4-(5-cyclopropyl-3-methylpyridin-2-yl)piperazine-1-carbonyl]phenyl}-4-ethyloxazolidin-2-one By reaction and treatment in the same manner as in Example 149 and using [4-(5-cyclopropyl-3-methylpyridin-2-yl)piperazin-1-yl](4-iodophenyl)methanone (447 mg) described in Preparation Example 97 and (R)-4-ethyloxazolidin-2-one (138 mg) described in Preparation Example 26, the title compound (292 mg) was obtained.

Example 154

Synthesis of 3-{4-[4-(5-cyclopropyl-3-methylpyridin-2-yl)piperazine-1-carbonyl]phenyl}oxazolidin-2-one By reaction and treatment in the same manner as in Example 149 and using [4-(5-cyclopropyl-3-methylpyridin-2-yl)piperazin-1-yl](4-iodophenyl)methanone (447 mg) described in Preparation Example 97 and oxazolidin-2-one (104 mg)), the title compound (327 mg) was obtained.

Example 155

Synthesis of (S)-3-{4-[4-(5-cyclopropyl-3-methylpyridin-2-yl)piperazine-1-carbonyl]phenyl}-5-methyloxazolidin-2-one By reaction and treatment in the same manner as in Example 149 and using [4-(5-cyclopropyl-3-methylpyridin-2-yl)piperazin-1-yl](4-iodophenyl)methanone (447 mg) described in Preparation Example 97 and (S)-5-methyloxazolidin-2-one (121 mg) described in Preparation Example 42, the title compound (344 mg) was obtained.

The compounds obtained in Examples 1-155 are as described below.

| Ex. | R5a/R5b/R5c (oxazolidinone) | —A— (Note 1) | (Note 2) | Y-aryl | salt | MS (ESI) m/z (M+H)+ |
|---|---|---|---|---|---|---|
| 1 | 3-methyl-oxazolidin-2-one | 2,5-dimethyl-3,4-difluorophenyl | 4-methylpiperazin-1-yl | 2,4-dimethylphenyl | | 416 |
| 2 | 3-methyl-oxazolidin-2-one | 2,5-dimethyl-3-fluorophenyl | 4-methylpiperazin-1-yl | 2,4-dimethylphenyl | | 398 |
| 3 | 3-methyl-oxazolidin-2-one | 2,5-dimethyl-3-chlorophenyl | 4-methylpiperazin-1-yl | 2,4-dimethylphenyl | | 414 |
| 4 | 3-methyl-oxazolidin-2-one | 2,5-dimethyl-4-fluorophenyl | 4-methylpiperazin-1-yl | 2,4-dimethylphenyl | | 398 |
| 5 | 3-methyl-oxazolidin-2-one | 2,5-dimethyl-4-methoxyphenyl | 4-methylpiperazin-1-yl | 2,4-dimethylphenyl | | 410 |
| 6 | 3-methyl-oxazolidin-2-one | 2,4,5-trimethylphenyl | 4-methylpiperazin-1-yl | 2,4-dimethylphenyl | | 394 |
| 7 | 3-methyl-oxazolidin-2-one | 2,5-dimethyl-4-fluoro-3-chlorophenyl | 4-methylpiperazin-1-yl | 2,4-dimethylphenyl | | 432 |

-continued

| Ex. | R5a, R5b, R5c (oxazolidinone) | —A— (Note 1) | R4a, R4b, R4c, X (Note 2) | Y, Z1, Z2, R1, R2, R3 | salt | MS (ESI) m/z (M + H)+ |
|---|---|---|---|---|---|---|
| 8 | oxazolidin-2-one, N-Me | 1,4-phenylene | 4-methylpiperazin-1-yl | 2,4-dimethylphenyl | | 380 |
| 9 | 4-t-Bu-oxazolidin-2-one, N-Me | 1,4-phenylene | 4-methylpiperazin-1-yl | 2,4-dimethylphenyl | | 436 |
| 10 | 4-Ph-oxazolidin-2-one, N-Me | 1,4-phenylene | 4-methylpiperazin-1-yl | 2,4-dimethylphenyl | | 456 |
| 11 | oxazolidin-2-one, N-Me | 2-SO2CH3-1,4-phenylene | 4-methylpiperazin-1-yl | 2,4-dimethylphenyl | | 458 |
| 12 | 4,4-diMe-oxazolidin-2-one, N-Me | 2-SO2CH3-1,4-phenylene | 4-methylpiperazin-1-yl | 2,4-dimethylphenyl | | 486 |
| 13 | 4-i-Pr-oxazolidin-2-one, N-Me | 2-SO2CH3-1,4-phenylene | 4-methylpiperazin-1-yl | 2,4-dimethylphenyl | | 500 |

-continued

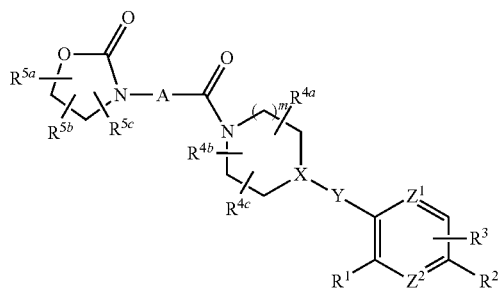

| Ex. | R5a R5b R5c | —A— (Note 1) | (Note 2) | R1 R2 R3 Y Z1 Z2 | salt | MS (ESI) m/z (M + H)+ |
|---|---|---|---|---|---|---|
| 14 | oxazolidinone, N-CH3, 4-Ph | 2,5-disubst phenyl SO2CH3, CH3 | N-methylpiperazine | 2,4-dimethylphenyl | | 534 |
| 15 | oxazolidinone, N-CH3, 4-t-Bu | 2,5-disubst phenyl SO2CH3, CH3 | N-methylpiperazine | 2,4-dimethylphenyl | | 514 |
| 16 | oxazolidinone, N-CH3, 4-CH2Ph | 2,5-disubst phenyl SO2CH3, CH3 | N-methylpiperazine | 2,4-dimethylphenyl | | 548 |
| 17 | oxazolidinone, N-CH3, 5,5-diCH3, 4-i-Pr | 2,5-disubst phenyl SO2CH3, CH3 | N-methylpiperazine | 2,4-dimethylphenyl | | 528 |
| 18 | oxazolidinone, N-CH3, 5-Ph, 4-CH3 | 2,5-disubst phenyl SO2CH3, CH3 | N-methylpiperazine | 2,4-dimethylphenyl | | 548 |
| 19 | oxazolidinone, N-CH3, 4-CH2OH | 2,5-disubst phenyl SO2CH3, CH3 | N-methylpiperazine | 2,4-dimethylphenyl | | 488 |

-continued

| Ex. | R5a, R5b, R5c | —A— (Note 1) | (Note 2) | Y, Z1, Z2, R1, R2, R3 | salt | MS (ESI) m/z (M + H)+ |
|---|---|---|---|---|---|---|
| 20 | oxazolidinone, N-Me | 2,4-dimethylphenyl (with CH3) | N-methylpiperazine | 2,4-dimethylphenyl | | 394 |
| 21 | oxazolidinone, N-Me | 2-Cl-4-methylphenyl | N-methylpiperazine | 2,4-dimethylphenyl | | 414 |
| 22 | oxazolidinone, N-Me | 2-cyclopropyl-5-methylphenyl | N-methylpiperazine | 2,4-dimethylphenyl | | 420 |
| 23 | oxazolidinone, N-Me | 4-methylphenyl | N-methylpiperazine | 2,4,6-trimethylphenyl | | 394 |
| 24 | oxazolidinone, N-Me, 4-CH2OH | 4-methylphenyl | N-methylpiperazine | 2,4-dimethylphenyl | | 410 |
| 25 | oxazolidinone, N-Me | 2-SO2CH3-5-methylphenyl | N-methylpiperazine | 4-F-2,5-dimethylphenyl | | 476 |
| 26 | oxazolidinone, N-Me | 2-SO2CH3-5-methylphenyl | N-methylpiperazine | 2-CH2CH3-5-methylphenyl | | 472 |

-continued

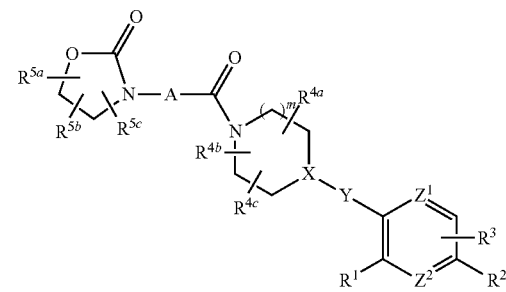

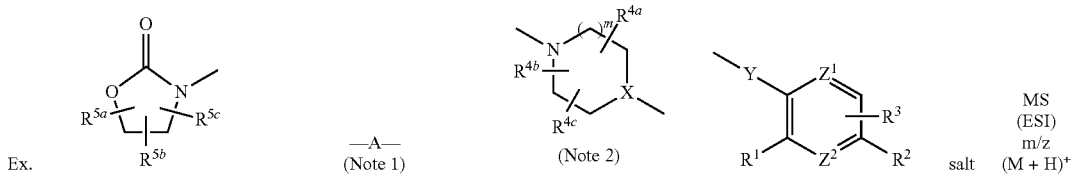

| Ex. | R5a, R5b, R5c structure | —A— (Note 1) | (Note 2) | Y-Z1/R1/Z2/R2/R3 | salt | MS (ESI) m/z (M + H)+ |
|---|---|---|---|---|---|---|
| 27 | oxazolidinone, N-Me | 1,4-phenylene | N-methylpiperazine | 2,5-dimethyl, vinyl | | 392 |
| 28 | oxazolidinone, N-Me | 1,4-phenylene | N-methylpiperazine | 2,5-dimethyl, cyclopropyl | | 406 |
| 29 | oxazolidinone, N-Me, 4-i-Pr | 1,4-phenylene | N-methylpiperazine | 2,5-dimethyl, Et | | 436 |
| 30 | oxazolidinone, N-Me | 1,4-phenylene | N-methylpiperazine | 2,4-dichloro | | 420 |
| 31 | oxazolidinone, N-Me | 1,4-phenylene | N-methylpiperazine N-oxide | 2,5-dimethyl | | 396 |
| 32 | oxazolidinone, N-Me, 4-CH2OH | 2-SO2CH3, 5-Me phenylene | N-methylpiperazine N-oxide | 2,5-dimethyl | | 504 |

-continued

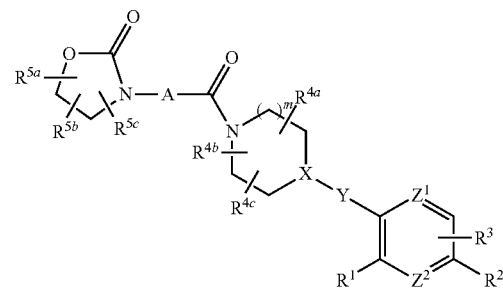

| Ex. | R5a R5b R5c | —A— (Note 1) | (Note 2) | Y Z1 Z2 R1 R2 R3 | salt | MS (ESI) m/z (M + H)+ |
|---|---|---|---|---|---|---|
| 33 | oxazolidinone, N-Me, i-Pr | 2,5-dimethylphenyl-SO2CH3 | N-methylpiperazine N-oxide | 2,4-dimethylphenyl | | 516 |
| 34 | oxazolidinone, N-Me, CH2-Ph | 4-methylphenyl | N-methylpiperazine | 2,4-dimethylphenyl | | 470 |
| 35 | oxazolidinone, N-Me | 2,5-dimethylpyridyl | N-methylpiperazine | 2,4-dimethylphenyl | | 381 |
| 36 | oxazolidinone, N-Me, Ph | 2,5-dimethylpyridyl | N-methylpiperazine | 2,4-dimethylphenyl | | 457 |
| 37 | oxazolidinone, N-Me | 2,5-dimethylpyridyl | N-methylpiperazine N-oxide | 2,4-dimethylphenyl | | 397 |
| 38 | oxazolidinone, N-Me | 2,5-dimethylpyridyl | N-methylpiperazine | 2,4-dimethylphenyl | | 381 |

-continued
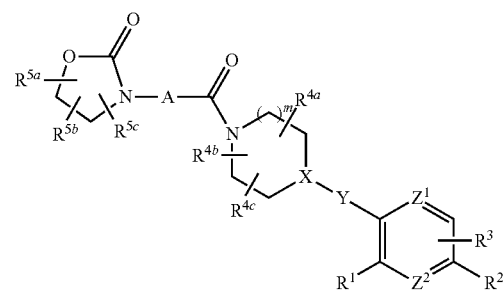
| Ex. | 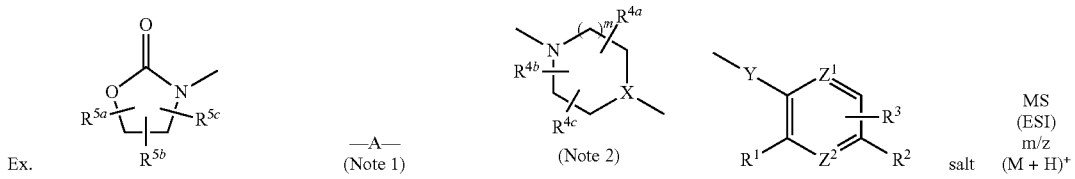 R⁵ᵃ R⁵ᵇ R⁵ᶜ | —A— (Note 1) | R⁴ᵇ R⁴ᶜ X (Note 2) R⁴ᵃ | Y Z¹ Z² R¹ R² R³ | salt | MS (ESI) m/z (M + H)⁺ |
|---|---|---|---|---|---|---|
| 39 | 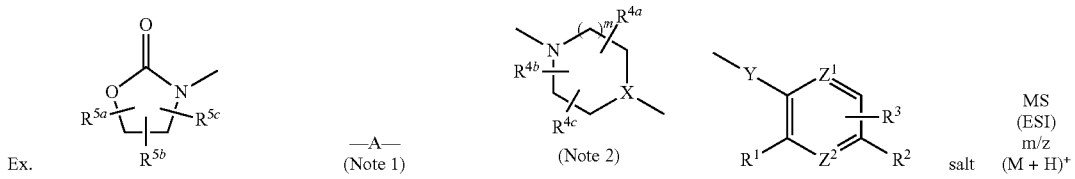 | | | | | 457 |
| 40 | 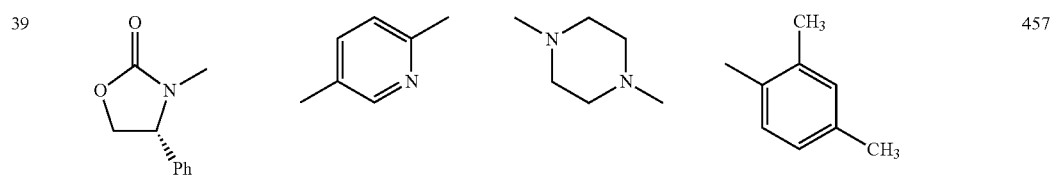 | | | | | 413 |
| 41 | 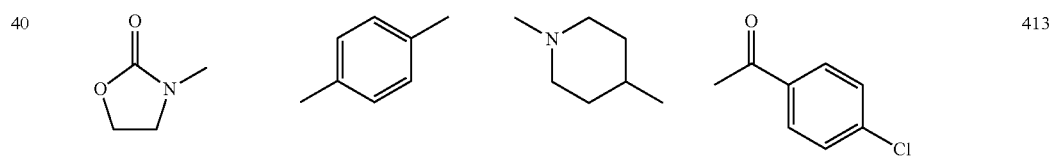 | | | | | 393 |
| 42 | 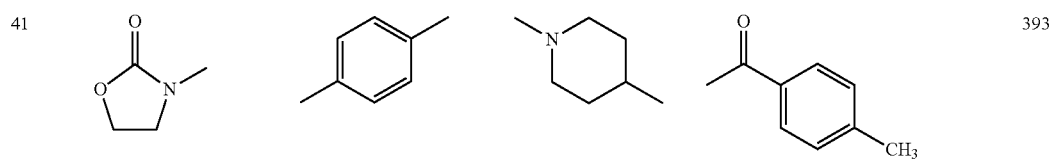 | | | | | 394 |
| 43 | 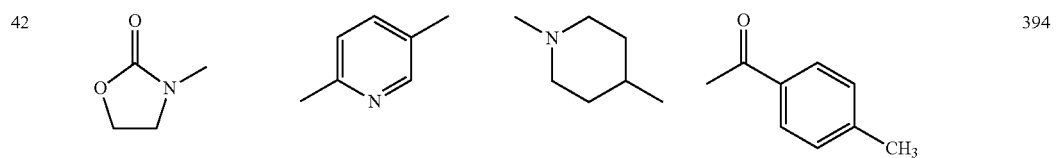 | | | | | 501 |
| 44 | 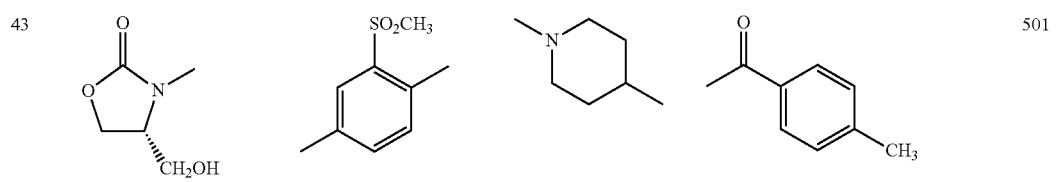 | | | | | 471 |

-continued

| Ex. | R5a, R5b, R5c | —A— (Note 1) | (Note 2) | Y, Z1, Z2, R1, R2, R3 | salt | MS (ESI) m/z (M + H)+ |
|---|---|---|---|---|---|---|
| 45 | oxazolidinone, i-Pr | 1,4-phenylene | N-methyl piperidine | 4-acetylphenyl | | 435 |
| 46 | oxazolidinone, CH3 | 2,5-pyridine | N-methyl piperidine | 4-acetylphenyl | | 408 |
| 47 | oxazolidinone, CH2CH3 | 2,5-pyridine | N-methyl piperidine | 4-acetylphenyl | | 422 |
| 48 | oxazolidinone, CH3 | 2,5-pyridine | N-methyl piperidine | 4-acetylphenyl | | 408 |
| 49 | oxazolidinone, CH3 | 1,4-phenylene | N-methyl piperidine | 4-acetylphenyl | | 407 |
| 50 | oxazolidinone, CH3 | 1,4-phenylene | N-methyl piperidine | 2,4-dimethyl-acetylphenyl | | 421 |

-continued

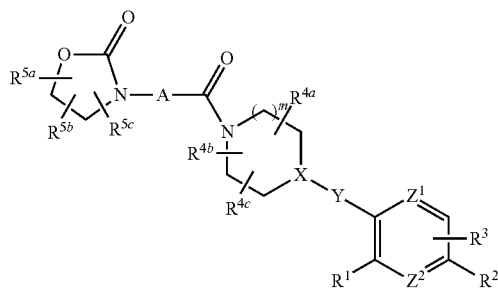

| Ex. | R5a R5b R5c | —A— (Note 1) | (Note 2) | Y Z1 Z2 R1 R2 R3 | salt | MS (ESI) m/z (M + H)+ |
|---|---|---|---|---|---|---|
| 51 | oxazolidinone, N-Me | 2,5-pyridyl (Me) | 4-Me-piperidine, N-Me | 4-MeO-C6H4-CH3 | | 382 |
| 52 | oxazolidinone, N-Me, i-Pr | 1,4-phenylene (Me) | 4-Me-piperidine, N-Me | 4-MeO-C6H4-CH3 | | 423 |
| 53 | oxazolidinone, N-Me, CH3 | 2,5-pyridyl (Me) | 4-Me-piperidine, N-Me | 4-MeO-C6H4-CH3 | | 396 |
| 54 | oxazolidinone, N-Me, CH2CH3 | 2,5-pyridyl (Me) | 4-Me-piperidine, N-Me | 4-MeO-C6H4-CH3 | | 410 |
| 55 | oxazolidinone, N-Me, CH3 | 1,4-phenylene (Me) | 4-Me-piperidine, N-Me | 4-MeO-C6H4-CH3 | | 395 |
| 56 | oxazolidinone, N-Me | 2-SO2CH3-phenyl | N-Me-piperazine | 3,5-diCl-2-Me-pyridyl | | 499 |

-continued

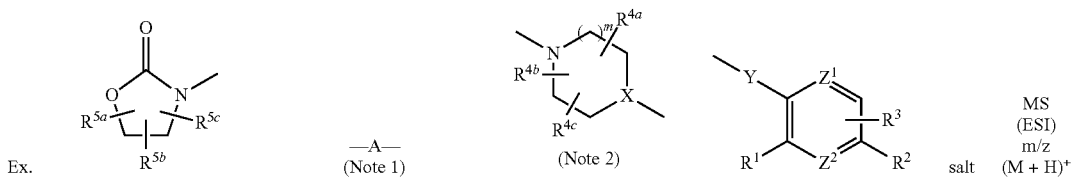

| Ex. | 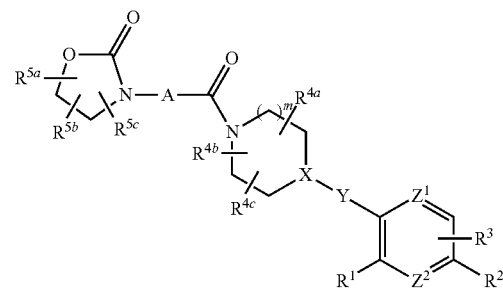 | —A— (Note 1) | (Note 2) | Y Z¹ Z² R¹ R² R³ | salt | MS (ESI) m/z (M + H)⁺ |
|---|---|---|---|---|---|---|
| 57 | oxazolidinone N-Me | 2,5-di-Me-SO₂CH₃-phenyl | N-Me piperazine | 2,5-diMe-pyridyl | | 459 |
| 58 | oxazolidinone N-Me | 1,4-phenyl | N-Me piperazine | 2,5-diMe-pyridyl | | 381 |
| 59 | oxazolidinone N-Me, i-Pr | 1,4-phenyl | N-Me piperazine | 2,5-diMe-pyridyl | | 423 |
| 60 | oxazolidinone N-Me | 2-F-phenyl | N-Me piperazine | 2,5-diMe-pyridyl | | 399 |
| 61 | oxazolidinone N-Me | 2-CH₃-phenyl | N-Me piperazine | 2,5-diMe-pyridyl | | 396 |
| 62 | oxazolidinone N-Me, i-Pr | 2,5-di-Me-SO₂CH₃-phenyl | N-Me piperazine | 2,5-diMe-pyridyl | | 501 |

| Ex. | 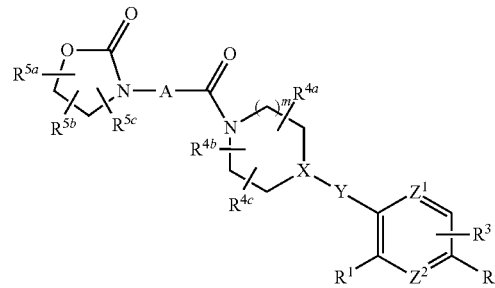 R5b R5a R5c | —A— (Note 1) | 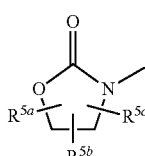 (Note 2) | Y Z1 R1 Z2 R2 R3 | salt | MS (ESI) m/z (M + H)+ |
|---|---|---|---|---|---|---|
| 63 | 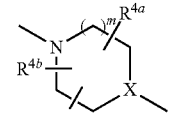 | 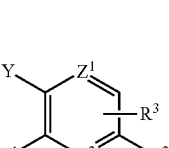 | 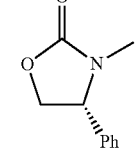 | 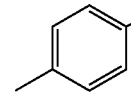 | | 457 |
| 64 | 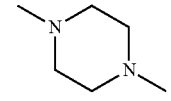 | 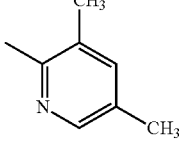 | 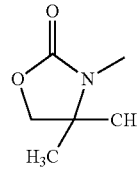 | 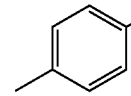 | | 409 |
| 65 | 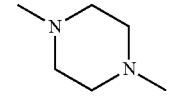 | 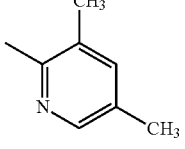 | 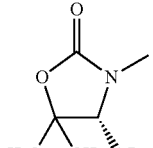 | 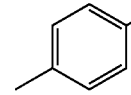 | | 451 |
| 66 | 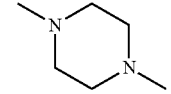 | 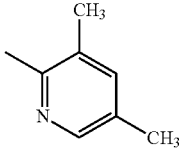 | 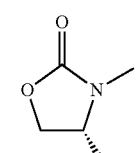 | 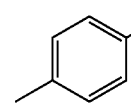 | | 477 |
| 67 | 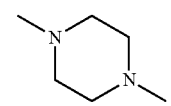 | 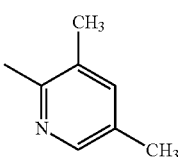 | 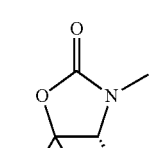 | 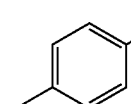 | | 485 |
| 68 | 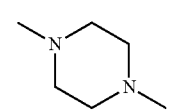 | 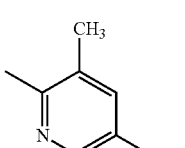 | 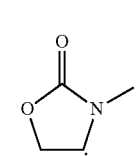 | 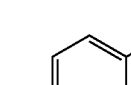 | | 409 |

-continued

| Ex. | (R⁵ᵃ,R⁵ᵇ,R⁵ᶜ group) | —A— (Note 1) | (Note 2) | Y, Z¹, Z², R¹, R², R³ | salt | MS (ESI) m/z (M + H)⁺ |
|---|---|---|---|---|---|---|
| 69 | oxazolidinone, t-Bu | 1,4-phenylene | N-methylpiperazine | 2,5-dimethylpyridin-3-yl (CH₃, CH₃) | | 437 |
| 70 | oxazolidinone, i-Pr | 1,4-phenylene | N-methylpiperazine | 5-cyclopropyl-2-methylpyridin-3-yl (CH₃) | | 449 |
| 71 | oxazolidinone, CH₃ | 1,4-phenylene | N-methylpiperazine | 2,5-dimethylpyridin-3-yl | | 395 |
| 72 | oxazolidinone, CH₂OH | 1,4-phenylene | N-methylpiperazine | 2,5-dimethylpyridin-3-yl | | 411 |
| 73 | oxazolidinone, CH₂OCH₃ | 1,4-phenylene | N-methylpiperazine | 2,5-dimethylpyridin-3-yl | | 425 |
| 74 | oxazolidinone, CH₂CH₃ | 1,4-phenylene | N-methylpiperazine | 2,5-dimethylpyridin-3-yl | | 409 |

-continued
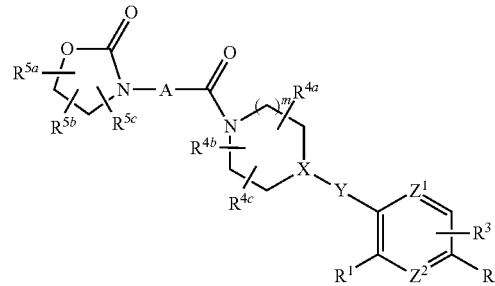
| Ex. | 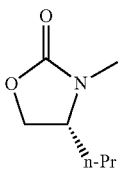 | —A— (Note 1) | 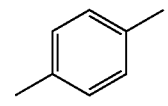 (Note 2) | Y, Z¹, Z², R¹, R², R³ | salt | MS (ESI) m/z (M + H)⁺ |
|---|---|---|---|---|---|---|
| 75 | 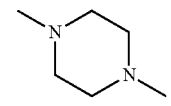 | 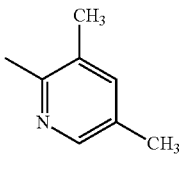 | 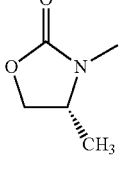 | 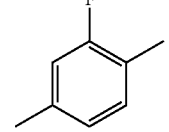 | | 423 |
| 76 | 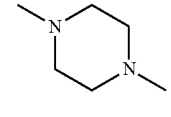 | 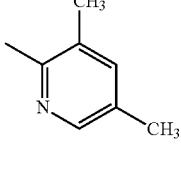 | 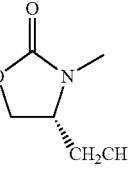 | 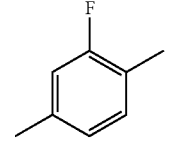 | | 413 |
| 77 | 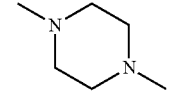 | 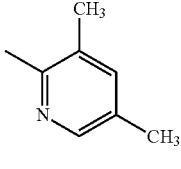 | 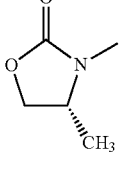 | 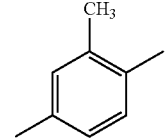 | | 427 |
| 78 | 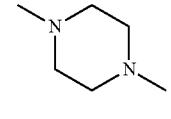 | 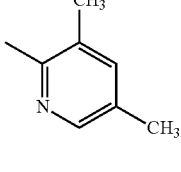 | 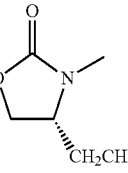 | 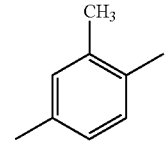 | | 409 |
| 79 | 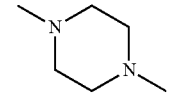 | 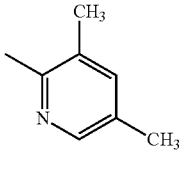 | 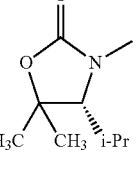 | 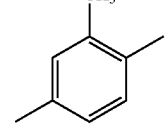 | HCl salt | 423 |
| 80 | 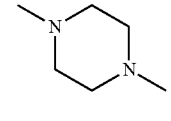 | | | 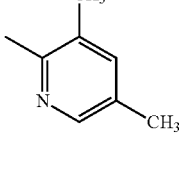 | | 465 |

-continued

| Ex. | (carbamate) | —A— (Note 1) | (amine) (Note 2) | (aryl) | salt | MS (ESI) m/z (M + H)+ |
|---|---|---|---|---|---|---|
| 81 | oxazolidinone, 4-CH₃ | 2,5-dimethylphenyl, SO₂CH₃ | N-methylpiperazine | 2,5-dimethylpyridine | | 473 |
| 82 | oxazolidinone, 4-CH₂CH₃ | 2,5-dimethylphenyl, SO₂CH₃ | N-methylpiperazine | 2,5-dimethylpyridine | | 487 |
| 83 | oxazolidinone, 5-CH₃ | 1,4-phenyl | N-methylpiperazine | 2,5-dimethylpyridine | | 395 |
| 84 | oxazolidinone, 4-i-Pr | 1,4-phenyl | N-methylpiperazine | 2,5-dimethylpyridine | | 423 |
| 85 | oxazolidinone, 5,5-diMe, 4-i-Pr | 2,5-dimethylphenyl, SO₂CH₃ | N-methylpiperazine | 2,5-dimethylpyridine | | 529 |
| 86 | oxazolidinone, 4-CH₃ | 2-F-4-methylphenyl | N-methylpiperazine | 2,5-dimethylpyridine | HCl salt | 413 |

-continued

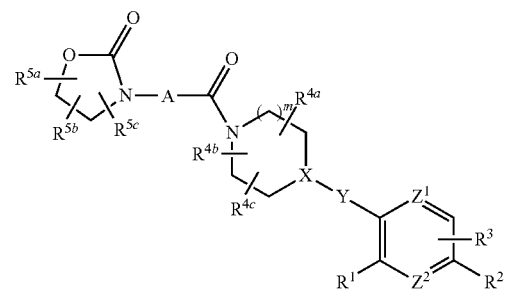

| Ex. | R5a, R5b, R5c structure | —A— (Note 1) | (Note 2) | Y, Z1, Z2, R1, R2, R3 | salt | MS (ESI) m/z (M + H)+ |
|---|---|---|---|---|---|---|
| 87 | (S)-4-methyl-oxazolidin-2-one, N-Me | 1,4-phenylene, Me | N-methylpiperazine | 3-cyclopropyl-5-methylpyridin-2-yl | HCl salt | 421 |
| 88 | (S)-4-methyl-oxazolidin-2-one, N-Me | 1,4-phenylene, Me | N-methylpiperazine | 5-cyclopropyl-3-methylpyridin-2-yl | | 421 |
| 89 | (S)-4-methyl-oxazolidin-2-one, N-Me | 3,4-dimethylphenylene | N-methylpiperazine | 3,5-dimethylpyridin-2-yl | HCl salt | 409 |
| 90 | (S)-4-methyl-oxazolidin-2-one, N-Me | 2-methyl-1,4-phenylene | N-methylpiperazine | 3,5-dimethylpyridin-2-yl | HCl salt | 449 |
| 91 | (S)-4-methyl-oxazolidin-2-one, N-Me | 1,4-phenylene | N-methylpiperazine | 3-cyclopropyl-5-methylpyridin-2-yl | HCl salt | 475 |
| 92 | (S)-4-methyl-oxazolidin-2-one, N-Me | 2-methoxy-5-methylphenylene | N-methylpiperazine | 3,5-dimethylpyridin-2-yl | HCl salt | 425 |

-continued

| Ex. | ![R5a,R5b,R5c oxazolidinone] | —A— (Note 1) | (Note 2) | Y-Z1,Z2,R1,R2,R3 | salt | MS (ESI) m/z (M + H)+ |
|---|---|---|---|---|---|---|
| 93 | oxazolidinone, CH3 | 2-Cl, 4-yl phenyl | N-methylpiperazine | 2,5-dimethylpyridin-3-yl | HCl salt | 429 |
| 94 | oxazolidinone, CH3 | 1,4-phenylene | N-methylpiperazine | 2-methyl-5-cyclopropyl-3-cyclopropylpyridinyl | HCl salt | 447 |
| 95 | oxazolidinone, n-Pr | 2-SO2CH3, 4-yl phenyl | N-methylpiperazine | 2,5-dimethylpyridin-3-yl | HCl salt | 501 |
| 96 | oxazolidinone, CH3 | 2,6-diF phenyl | N-methylpiperazine | 2,5-dimethylpyridin-3-yl | HCl salt | 431 |
| 97 | oxazolidinone, CH3 | 3-Cl, 4-yl phenyl | N-methylpiperazine | 2,5-dimethylpyridin-3-yl |  | 429 |
| 98 | oxazolidinone, CH3 | 1,4-phenylene | N-methylpiperazine | 2,3,6-trimethylpyridin-5-yl | HCl salt | 409 |

-continued
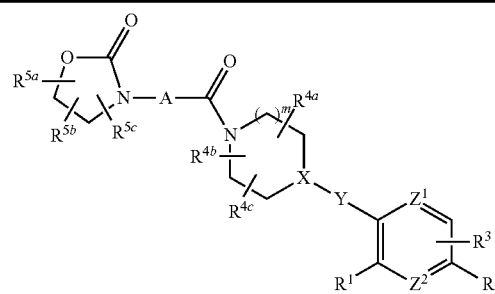
| Ex. | 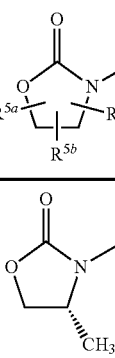 | —A—<br>(Note 1) | 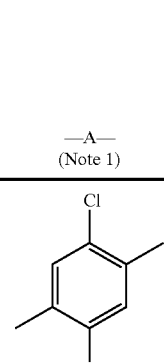<br>(Note 2) | 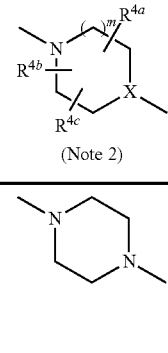 | salt | MS (ESI) m/z (M + H)+ |
|---|---|---|---|---|---|---|
| 99 | 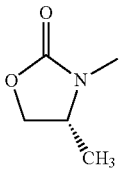 | 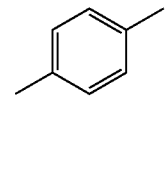 | 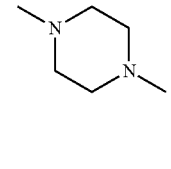 | 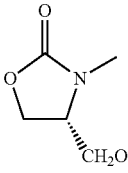 | HCl salt | 447 |
| 100 | 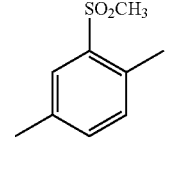 | 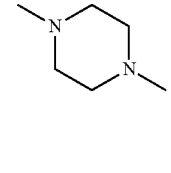 | | 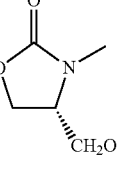 | | 396 |
| 101 | 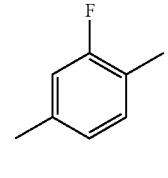 | 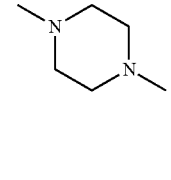 | | 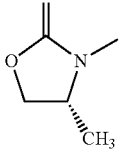 | | 489 |
| 102 | 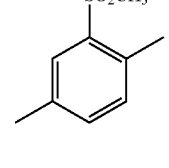 | 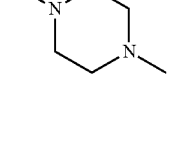 | | | | 429 |
| 103 | 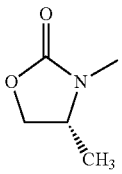 | | | | HCl salt | 487 |
| 104 | 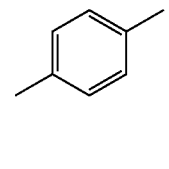 | | | 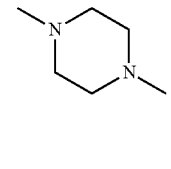 | HCl salt | 435 |

-continued

| Ex. | ![oxazolidinone with R5a R5b R5c] | —A— (Note 1) | (Note 2) | Y-Z1/Z2 aryl | salt | MS (ESI) m/z (M+H)+ |
|---|---|---|---|---|---|---|
| 105 | (5S)-5-methyl-3-methyl-oxazolidin-2-one | 1,4-phenylene | 4-methylpiperazin-1-yl | 2,5-dimethylpyridin-3-yl | HCl salt | 395 |
| 106 | (4S)-4-methyl-3-methyl-oxazolidin-2-one | 1,4-phenylene | 4-methylpiperazin-1-yl | 5-ethyl-2-methylpyridin-3-yl | HCl salt | 409 |
| 107 | (4S)-4-methyl-3-methyl-oxazolidin-2-one | 1,4-phenylene | 4-methylpiperazin-1-yl | 2-methyl-3-trifluoromethyl-5-methylpyridin-? | HCl salt | 449 |
| 108 | (4S)-4-methyl-3-methyl-oxazolidin-2-one | 2-OCH3, 4-Cl, 5-methylphenylene | 4-methylpiperazin-1-yl | 2,5-dimethylpyridin-3-yl | HCl salt | 459 |
| 109 | (4S)-4-methyl-3-methyl-oxazolidin-2-one | 6-methylpyridin-2,5-diyl | 4-methylpiperazin-1-yl | 2,5-dimethylpyridin-3-yl | 2HCl salt | 396 |
| 110 | (4S)-4-ethyl-3-methyl-oxazolidin-2-one | 2,6-difluoro-4-methylphenylene | 4-methylpiperazin-1-yl | 2,5-dimethylpyridin-3-yl |  | 445 |

-continued

| Ex. | (R5a,R5b,R5c structure) | —A— (Note 1) | (Note 2) | R1,R2,R3,Z1,Z2,Y | salt | MS (ESI) m/z (M + H)+ |
|---|---|---|---|---|---|---|
| 111 | oxazolidinone, N-Me | 2,6-difluoro-substituted phenyl | N-methylpiperazine | 3,6-dimethylpyridin-2-yl | | 417 |
| 112 | 5-(ethoxymethyl)oxazolidinone, N-Me | p-phenylene | N-methylpiperazine | 3,6-dimethylpyridin-2-yl | HCl salt | 425 |
| 113 | (4S)-4-methyloxazolidinone, N-Me | 2-methoxy-phenylene | N-methylpiperazine | 3,6-dimethylpyridin-2-yl | HCl salt | 425 |
| 114 | (4S)-4-methyloxazolidinone, N-Me | p-phenylene | N-methylpiperazine | 3-methyl-5-isopropylpyridin-2-yl | HCl salt | 423 |
| 115 | (4S)-4-methyloxazolidinone, N-Me | p-phenylene | N-methylpiperazine | 3,6-dimethylpyridin-2-yl | HCl salt | 395 |
| 116 | (4S)-4-methyloxazolidinone, N-Me | 2-(methylsulfonyl)-phenylene | N-methylpiperazine | 3-cyclopropyl-6-methylpyridin-2-yl | HCl salt | 499 |

-continued

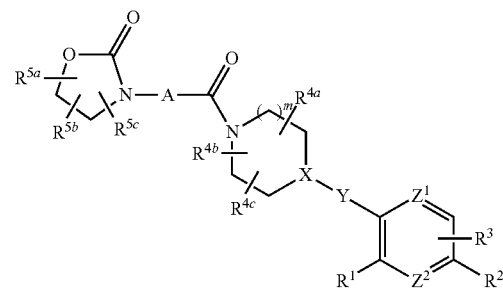

| Ex. | 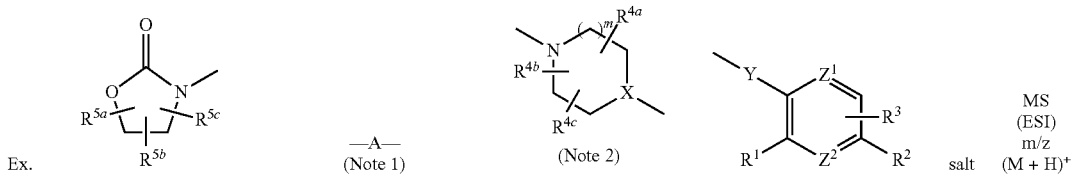 R5a R5b R5c | —A— (Note 1) | R4a R4b R4c X (Note 2) | Y Z1 Z2 R1 R2 R3 | salt | MS (ESI) m/z (M + H)+ |
|---|---|---|---|---|---|---|
| 117 | oxazolidinone N-Me, (S)-4-CH3 | 2,5-dimethyl-SO2CH3-phenyl | N-methylpiperazine | 2-methyl-3-methyl-5-cyclopropyl-pyridine | HCl salt | 499 |
| 118 | oxazolidinone N-Me, (S)-4-CH3 | 1,4-dimethylphenyl | N-methylpiperazine | 2-methyl-3-ethyl-5-methyl-pyridine | HCl salt | 409 |
| 119 | oxazolidinone N-Me, (R)-5-CH3 | 1,4-dimethylphenyl | N-methylpiperazine | 2,3-dimethyl-5-methyl-pyridine | HCl salt | 395 |
| 120 | oxazolidinone N-Me, (S)-4-i-Pr | 1,4-dimethylphenyl | N-methylpiperazine | 2-methyl-3-cyclopropyl-5-cyclopropyl-pyridine | HCl salt | 475 |
| 121 | oxazolidinone N-Me, 4,4-di-CH3 | 2,4-dimethylphenyl | N-methylpiperazine | 2,3-dimethyl-5-methyl-pyridine | HCl salt | 423 |

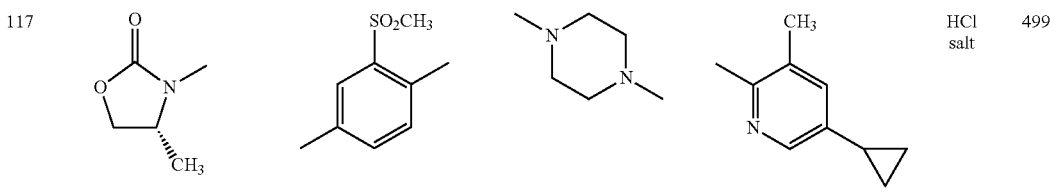
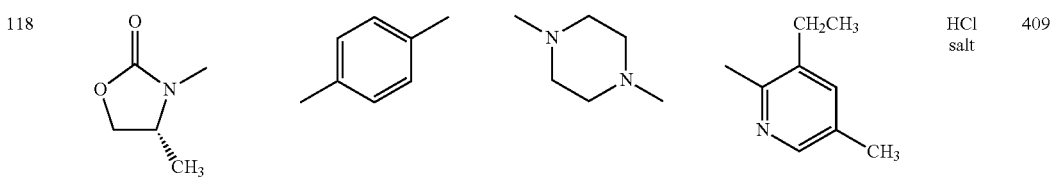
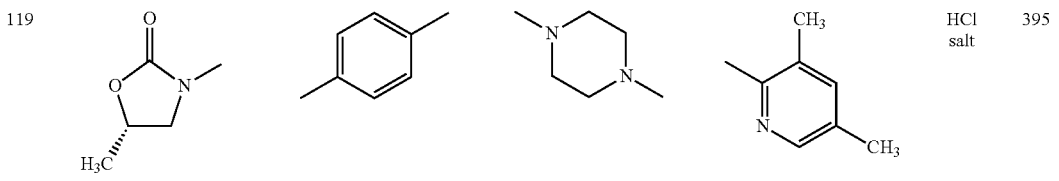
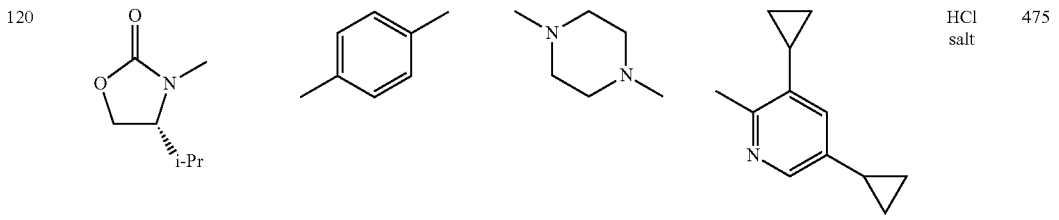
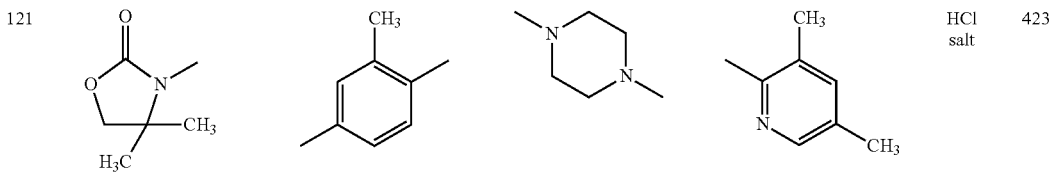

-continued
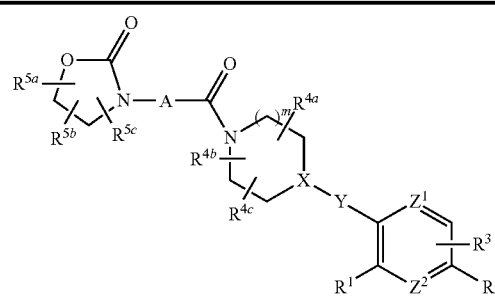
| Ex. | 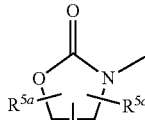 | —A— (Note 1) | 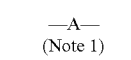 (Note 2) | 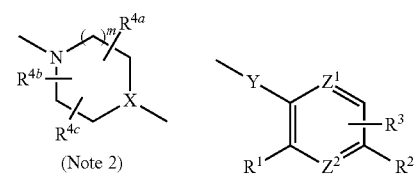 | salt | MS (ESI) m/z (M + H)+ |
|---|---|---|---|---|---|---|
| 122 | 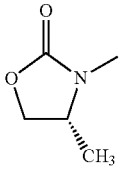 | 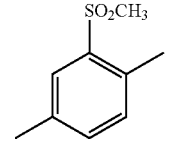 | 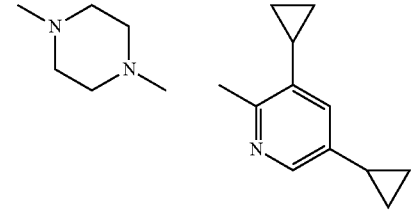 | 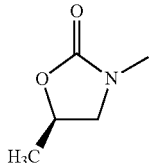 | HCl salt | 525 |
| 123 | 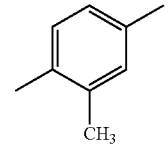 | 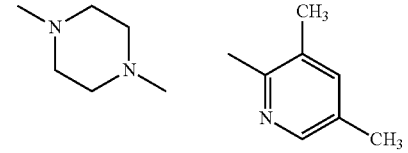 | 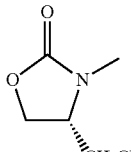 | 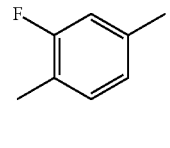 | HCl salt | 409 |
| 124 | 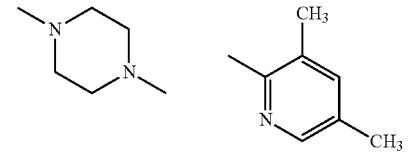 | 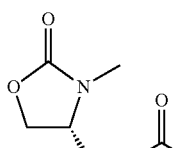 | 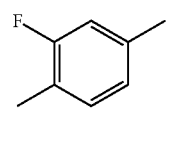 | 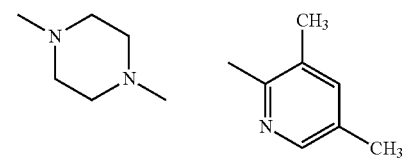 | | 427 |
| 125 | 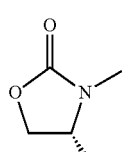 | 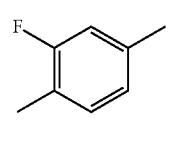 | | | | 533 |
| 126 | 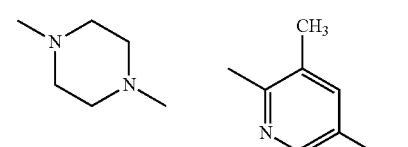 | 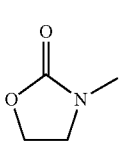 | | | | 429 |
| 127 | 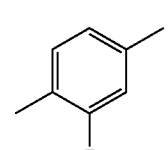 | 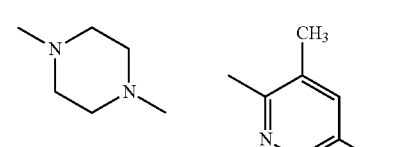 | | | | 399 |

-continued

| Ex. | R⁵ᵃ, R⁵ᵇ, R⁵ᶜ group | —A— (Note 1) | (Note 2) | R¹, R², R³, Y, Z¹, Z² group | salt | MS (ESI) m/z (M + H)⁺ |
|---|---|---|---|---|---|---|
| 128 | oxazolidinone-N-CH₃ | 2,4-dimethylphenyl | N-methylpiperazine | 2,5-dimethylpyridin-3-yl | | 395 |
| 129 | oxazolidinone-N-CH₃ | 2-NO₂-4-methylphenyl | N-methylpiperazine | 2,5-dimethylpyridin-3-yl | | 426 |
| 130 | 5,5-dimethyl-oxazolidinone-N-CH₃ | 4-methylphenyl | N-methylpiperazine | 2,5-dimethylpyridin-3-yl | | 409 |
| 131 | (4S)-4-methyl-oxazolidinone-N-CH₃ | 4-methylphenyl | N-methylpiperazine | 5-cyclopentyl-2-methylpyridin-3-yl | HCl salt | 449 |
| 132 | (4S)-4-(CH₂OCH₃)-oxazolidinone-N-CH₃ | 2-SO₂CH₃-5-methylphenyl | N-methylpiperazine | 2,5,6-trimethylpyridin-3-yl | HCl salt | 517 |
| 133 | oxazolidinone-N-CH₃ | 2-NH₂-5-methylphenyl | N-methylpiperazine | 2,5-dimethylpyridin-3-yl | | 396 |

-continued
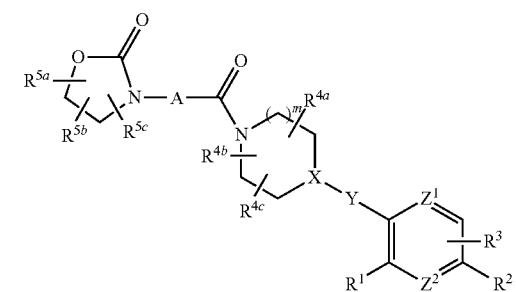
| Ex. | 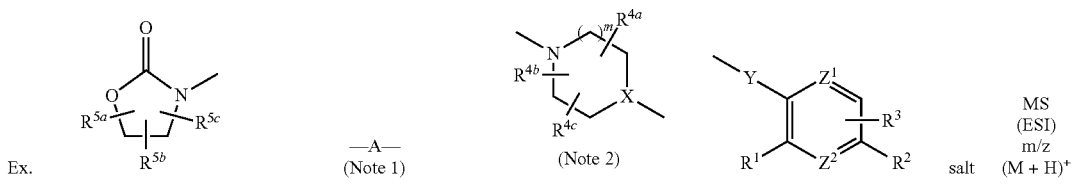 | —A— (Note 1) | (Note 2) | | salt | MS (ESI) m/z (M + H)+ |
|---|---|---|---|---|---|---|
| 134 | | | | | | 447 |
| 135 | | | | | | 438 |
| 136 | | | | | | 511 |
| 137 | | | | | | 539 |
| 138 | | | | | | 500 |
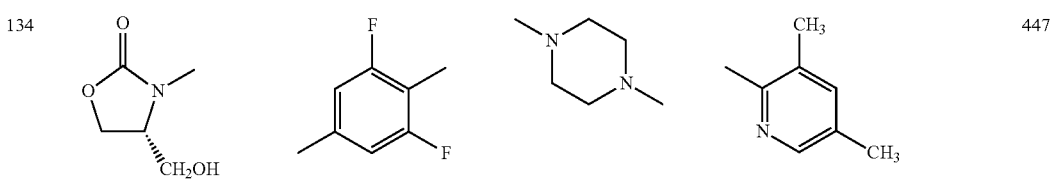
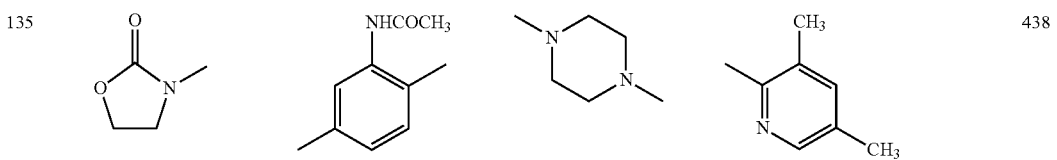
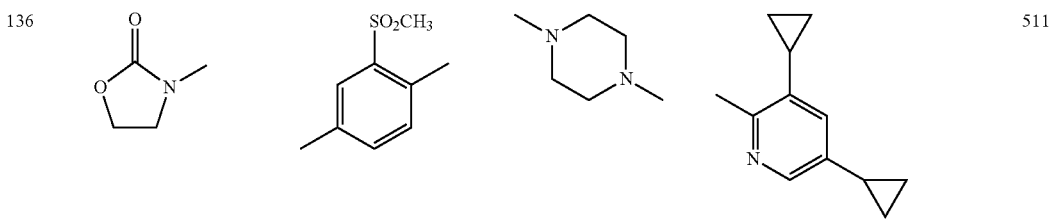
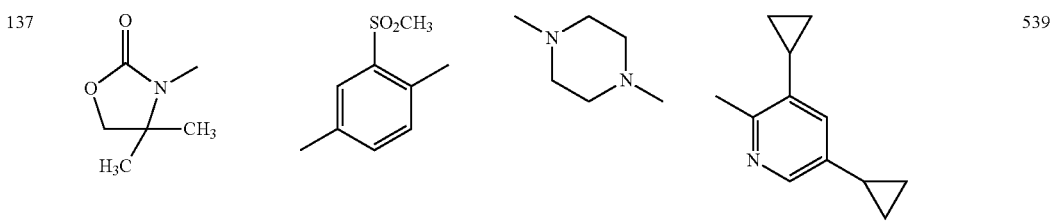
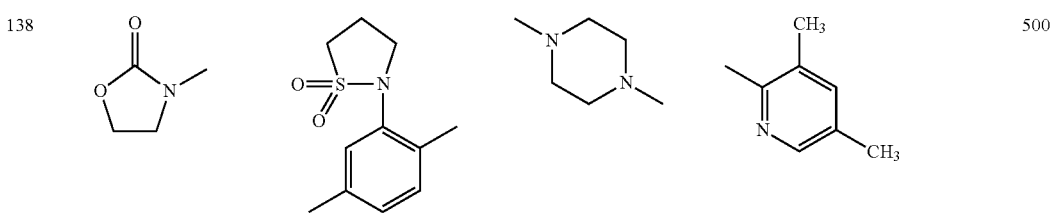

-continued

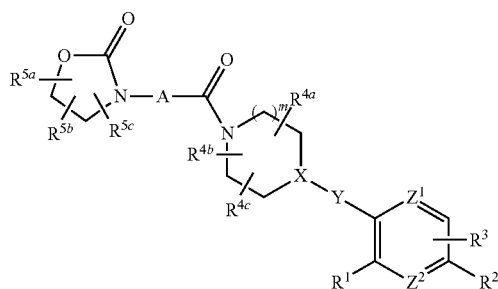

| Ex. | R5a R5b R5c | —A— (Note 1) | (Note 2) | Y...R1-R3 | salt | MS (ESI) m/z (M + H)+ |
|---|---|---|---|---|---|---|
| 139 | oxazolidinone, CH2CH3 | 2,5-dimethyl-SO2CH3-phenyl | N-methylpiperazine | 3,5-dicyclopropyl-2-methylpyridine | | 539 |
| 140 | oxazolidinone, CH3 | 2-F,5-methylphenyl | N-methylpiperazine | 2,3-dimethyl-5-cyclopropylpyridine | HCl salt | 439 |
| 141 | oxazolidinone, CH3 | 2-F,5-methylphenyl | N-methylpiperazine | 3-cyclopropyl-2-methyl-5-CF3-pyridine | HCl salt | 493 |
| 142 | oxazolidinone, CH2OCH3 | 2,5-dimethyl-SO2CH3-phenyl | N-methylpiperazine | 3,5-dicyclopropyl-2-methylpyridine | | 555 |
| 143 | oxazolidinone, CH3 | 2,5-dimethyl-SO2CH3-phenyl | N-methylpiperazine | 3,5-dicyclopropyl-2-methylpyridine | HCl salt | 525 |

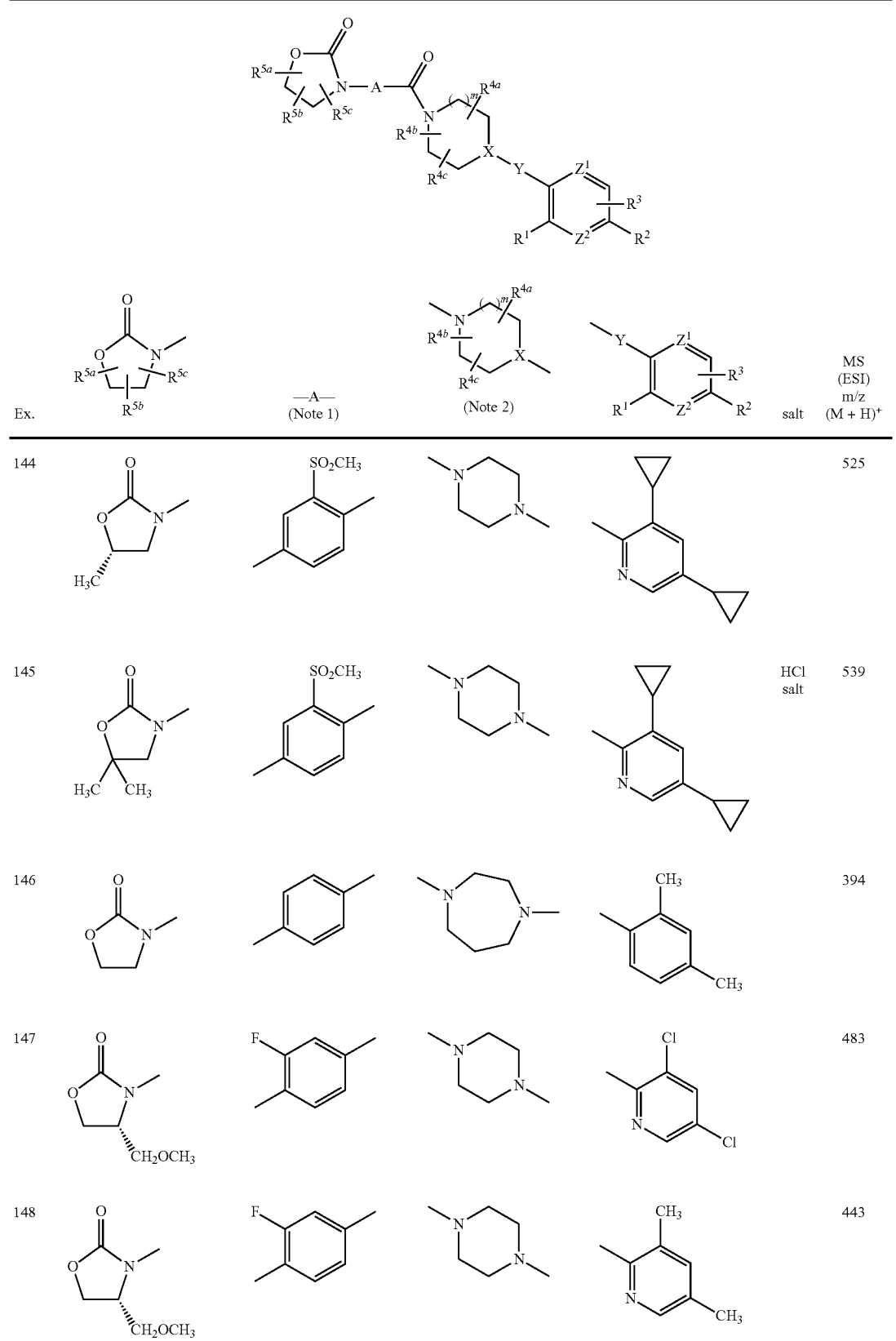

-continued

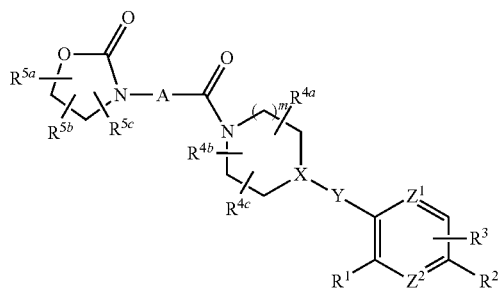

| Ex. | R5a R5b R5c | —A— (Note 1) | (Note 2) | R1 Z1 Z2 R2 R3 Y | salt | MS (ESI) m/z (M + H)+ |
|---|---|---|---|---|---|---|
| 149 | (S)-4-ethyl-3-methyl-oxazolidin-2-one | p-phenylene | 4-methylpiperazin-1-yl | 3,5-dicyclopropyl-2-methylpyridin-yl | | 461 |
| 150 | 3-methyl-oxazolidin-2-one | p-phenylene | 4-methylpiperazin-1-yl | 3,5-dicyclopropyl-2-methylpyridin-yl | | 433 |
| 151 | (R)-5-methyl-3-methyl-oxazolidin-2-one | p-phenylene | 4-methylpiperazin-1-yl | 3,5-dicyclopropyl-2-methylpyridin-yl | | 447 |
| 152 | 4,4-dimethyl-3-methyl-oxazolidin-2-one | p-phenylene | 4-methylpiperazin-1-yl | 3,5-dicyclopropyl-2-methylpyridin-yl | | 461 |
| 153 | (S)-4-ethyl-3-methyl-oxazolidin-2-one | p-phenylene | 4-methylpiperazin-1-yl | 5-cyclopropyl-2,3-dimethylpyridin-yl | | 435 |

-continued

| Ex. | R5a, R5b, R5c | —A— (Note 1) | R4a, R4b, R4c, X (Note 2) | Y, Z1, Z2, R1, R2, R3 | salt | MS (ESI) m/z (M + H)+ |
|---|---|---|---|---|---|---|
| 154 | 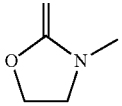 | 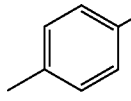 | 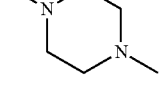 | 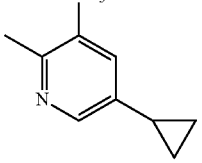 | | 407 |
| 155 | 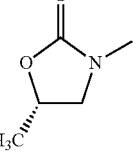 | 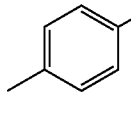 | 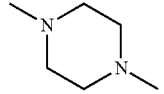 | 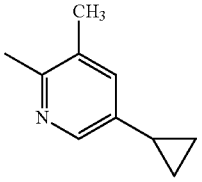 | | 421 |

(Note 1) left bond is bonded to nitrogen atom, right bond is bonded to carbon atom
(Note 2) left bond is bonded to carbon atom, right bond is bonded to Y
In the Table, t-Bu is 1,1-dimethylethyl (tert-butyl), Ph is phenyl, i-Pr is 1-methylethyl (isopropyl), n-Pr is propyl.

Example 156

Synthesis of (R)-3-{3-fluoro-4-[4-(3,5,6-trimethylpyridin-2-yl)piperazine-1-carbonyl]phenyl}-4-methyloxazolidin-2-one hydrochloride

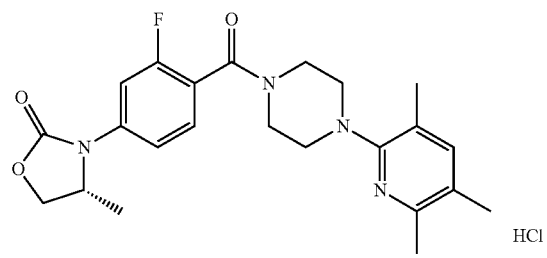 [SMILES: Cc1cc(C)c(N2CCN(C(=O)c3ccc(N4C(=O)OC[C@H]4C)cc3F)CC2)nc1C ; Cl]

By reaction and treatment in the same manner as in Example 79 and using (4-bromo-2-fluorophenyl)[4-(3,5,6-trimethylpyridin-2-yl)piperazin-1-yl]methanone (406 mg) described in Preparation Example 98 and (R)-4-methyloxazolidin-2-one (152 mg) described in Preparation Example 25, the title compound (98 mg) was obtained.

MS(ESI)m/z:427(M+H)+.

Example 157

Synthesis of (R)-3-{4-[4-(5-ethyl-3-methylpyridin-2-yl)piperazine-1-carbonyl]-3-fluorophenyl}-4-methyloxazolidin-2-one By reaction and treatment in the same manner as in Example 1 and using (4-bromo-2-fluorophenyl)[4-(5-ethyl-3-methylpyridin-2-yl)piperazin-1-yl]methanone (630 mg) described in Preparation Example 100 and (R)-4-methyloxazolidin-2-one (243 mg) described in Preparation Example 25, the title compound (385 mg) was obtained.

MS(ESI)m/z:427(M+H)+.

Example 158

Synthesis of (R)-3-{4-[4-(5-ethyl-3-methylpyridin-2-yl)piperazine-1-carbonyl]-3-methanesulfonylphenyl}-4-methyloxazolidin-2-one hydrochloride

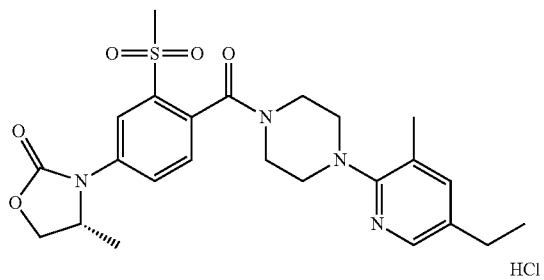 [SMILES: CCc1cnc(N2CCN(C(=O)c3ccc(N4C(=O)OC[C@H]4C)cc3S(C)(=O)=O)CC2)c(C)c1 ; Cl]

By reaction and treatment in the same manner as in Example 79 and using (4-bromo-2-methanesulfonylphenyl)[4-(5-ethyl-3-methylpyridin-2-yl)piperazin-1-yl]methanone (1.1 g) described in Preparation Example 101 and (R)-4-methyloxazolidin-2-one (354 mg) described in Preparation Example 25, the title compound (239 mg) was obtained.
MS(ESI)m/z:487(M+H)$^+$.

Example 159

Synthesis of 3-{4-[4-(3,5-dimethylpyridin-2-yl)piperazine-1-carbonyl]-3-methanesulfonylphenyl}-5,5-dimethyloxazolidin-2-one

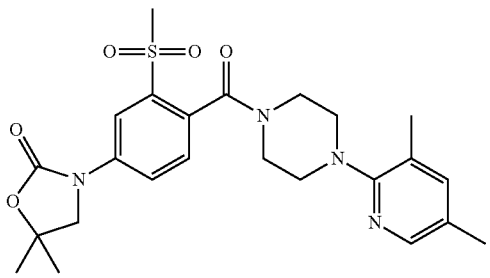 [SMILES: Cc1cnc(N2CCN(C(=O)c3ccc(N4CC(C)(C)OC4=O)cc3S(C)(=O)=O)CC2)c(C)c1]

By reaction and treatment in the same manner as in Example 1 and using (4-bromo-2-methanesulfonylphenyl)[4-(3,5-dimethylpyridin-2-yl)piperazin-1-yl]methanone (679 mg) described in Preparation Example 61 and 5,5-dimethyloxazolidin-2-one (259 mg) described in Preparation Example 43, the title compound (232 mg) was obtained.
MS(ESI)m/z:487(M+H)$^+$.

Example 160

Synthesis of (S)-3-{4-[4-(3,5-dimethylpyridin-2-yl)piperazine-1-carbonyl]-3-fluorophenyl}-5-methyloxazolidin-2-one

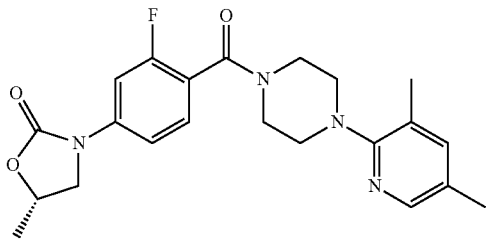 [SMILES: Cc1cnc(N2CCN(C(=O)c3ccc(N4C[C@H](C)OC4=O)cc3F)CC2)c(C)c1]

By reaction and treatment in the same manner as in Example 1 and using (4-bromo-2-fluorophenyl)[4-(3,5-dimethylpyridin-2-yl)piperazin-1-yl]methanone (498 mg) described in Preparation Example 65 and (S)-5-methyloxazolidin-2-one (197 mg) described in Preparation Example 42, the title compound (429 mg) was obtained.
MS(ESI)m/z:413(M+H)$^+$.

Example 161

Synthesis of (S)-3-{4-[4-(3,5-dimethylpyridin-2-yl)piperazine-1-carbonyl]-3,5-difluorophenyl}-5-methyloxazolidin-2-one

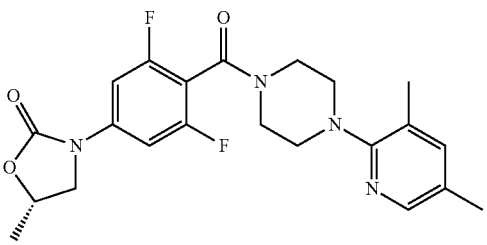 [SMILES: Cc1cnc(N2CCN(C(=O)c3c(F)cc(N4C[C@H](C)OC4=O)cc3F)CC2)c(C)c1]

By reaction and treatment in the same manner as in Example 1 and using (4-bromo-2,6-difluorophenyl)[4-(3,5-dimethylpyridin-2-yl)piperazin-1-yl]methanone (615 mg) described in Preparation Example 60 and (S)-5-methyloxazolidin-2-one (243 mg) described in Preparation Example 42, the title compound (337 mg) was obtained.
MS(ESI)m/z:431(M+H)$^+$.

Example 162

Synthesis of (R)-4-methyl-3-{4-[4-(3-methyl-5-propylpyridin-2-yl)piperazine-1-carbonyl]phenyl}oxazolidin-2-one hydrochloride

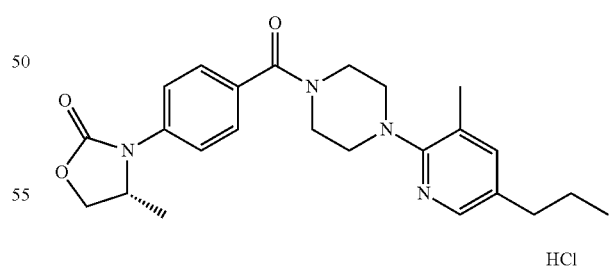

By reaction and treatment in the same manner as in Example 87 and using (R)-4-(4-methyl-2-oxooxazolidin-3-yl)benzoic acid (332 mg) described in Preparation Example 37 and 1-(3-methyl-5-propylpyridin-2-yl)piperazine (325 mg) described in Preparation Example 102, the title compound (126 mg) was obtained.
MS(ESI)m/z:423(M+H)$^+$.

Example 163

Synthesis of 3-{4-[4-(3,5-dimethylpyridin-2-yl)piperazine-1-carbonyl]phenyl}-5-ethyloxazolidin-2-one hydrochloride

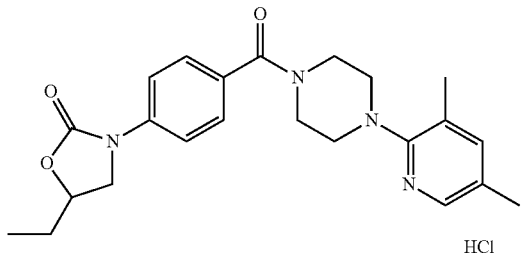 [SMILES: CCC1CN(c2ccc(C(=O)N3CCN(c4ncc(C)cc4C)CC3)cc2)C(=O)O1 ; Cl]

By reaction and treatment in the same manner as in Example 79 and using [4-(3,5-dimethylpyridin-2-yl)piperazin-1-yl](4-iodophenyl)methanone (231 mg) described in Preparation Example 77 and 5-ethyloxazolidin-2-one (115 mg) described in Preparation Example 103, the title compound (227 mg) was obtained.

MS(ESI)m/z:409(M+H)$^+$.

Example 164

Synthesis of (R)-3-{5-[4-(3,5-dimethylpyridin-2-yl)piperazine-1-carbonyl]pyridin-2-yl}-4-methyloxazolidin-2-one

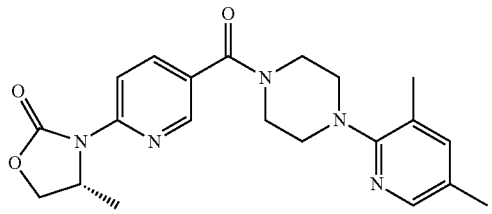 [SMILES: Cc1cnc(N2CCN(C(=O)c3ccc(N4C(=O)OC[C@H]4C)nc3)CC2)c(C)c1]

By reaction and treatment in the same manner as in Example 1 and using (6-bromopyridin-3-yl)[4-(3,5-dimethylpyridin-2-yl)piperazin-1-yl]methanone (187.6 mg) described in Preparation Example 73 and (R)-4-methyloxazolidin-2-one (50.6 mg) described in Preparation Example 25, the title compound (94.5 mg) was obtained.

MS(ESI)m/z:396(M+H)$^+$

Example 165

Synthesis of 3-{5-[4-(3,5-dimethylpyridin-2-yl)piperazine-1-carbonyl]pyridin-2-yl}-5,5-dimethyloxazolidin-2-one 2hydrochloride

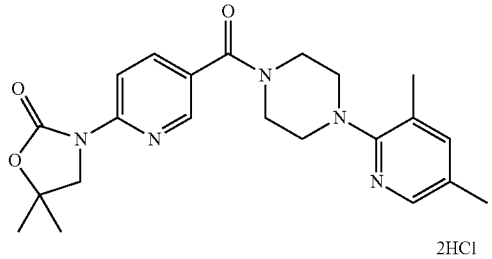 [SMILES: Cc1cnc(N2CCN(C(=O)c3ccc(N4CC(C)(C)OC4=O)nc3)CC2)c(C)c1 ; "2HCl"]

By reaction and treatment in the same manner as in Example 79 and using (6-bromopyridin-3-yl)[4-(3,5-dimethylpyridin-2-yl)piperazin-1-yl]methanone (748 mg) described in Preparation Example 73 and 5,5-dimethyloxazolidin-2-one (276 mg) described in Preparation Example 43, the title compound (336 mg) was obtained.

MS(ESI)m/z:410(M+H)$^+$.

Example 166

Synthesis of (S)-3-{5-[4-(3,5-dimethylpyridin-2-yl)piperazine-1-carbonyl]pyridin-2-yl}-5-methyloxazolidin-2-one

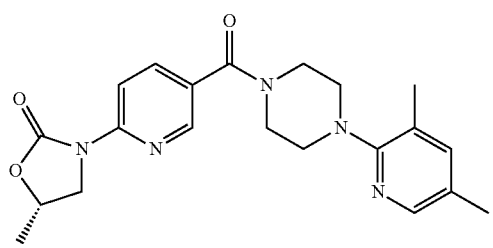 [SMILES: Cc1cnc(N2CCN(C(=O)c3ccc(N4C[C@H](C)OC4=O)nc3)CC2)c(C)c1]

By reaction and treatment in the same manner as in Example 1 and using (6-bromopyridin-3-yl)[4-(3,5-dimethylpyridin-2-yl)piperazin-1-yl]methanone (748 mg) described in Preparation Example 73 and (S)-5-methyloxazolidin-2-one (243 mg) described in Preparation Example 42, the title compound (706 mg) was obtained.

MS(ESI)m/z:396(M+H)$^+$.

Example 167

Synthesis of 3-{4-[4-(3,5-dimethylpyridin-2-yl)piperazine-1-carbonyl]-3-fluorophenyl}-5,5-dimethyloxazolidin-2-one

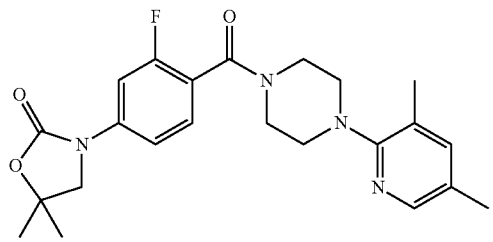 [SMILES: Cc1cnc(N2CCN(C(=O)c3ccc(N4CC(C)(C)OC4=O)cc3F)CC2)c(C)c1]

By reaction and treatment in the same manner as in Example 1 and using (4-bromo-2-fluorophenyl)[4-(3,5-dimethylpyridin-2-yl)piperazin-1-yl]methanone (574 mg) described in Preparation Example 65 and 5,5-dimethyloxazolidin-2-one (265 mg) described in Preparation Example 43, the title compound (203 mg) was obtained.

MS(ESI)m/z:427(M+H)$^+$.

Example 168

Synthesis of (R)-3-{5-[4-(3,5-dimethylpyridin-2-yl)piperazine-1-carbonyl]pyridin-2-yl}-4-ethyloxazolidin-2-one 2hydrochloride

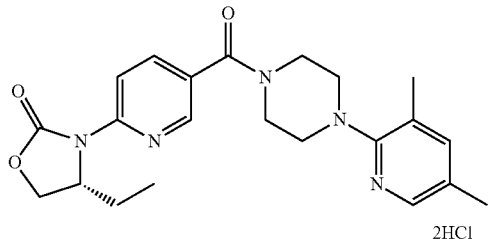 [SMILES: CC[C@@H]1COC(=O)N1c1ccc(C(=O)N2CCN(c3ncc(C)cc3C)CC2)cn1]

By reaction and treatment in the same manner as in Example 79 and using (6-bromopyridin-3-yl)[4-(3,5-dimethylpyridin-2-yl)piperazin-1-yl]methanone (748 mg) described in Preparation Example 73 and (R)-4-ethyloxazolidin-2-one (276 mg) described in Preparation Example 26, the title compound (764 mg) was obtained.
MS(ESI)m/z:410(M+H)+.

Example 169

Synthesis of (R)-3-{4-[4-(3-ethyl-5-methylpyridin-2-yl)piperazine-1-carbonyl]-3-fluorophenyl}-4-methyloxazolidin-2-one hydrochloride

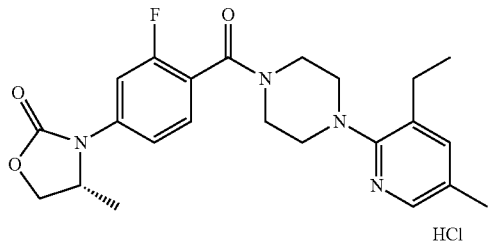 [SMILES: CCc1cc(C)cnc1N1CCN(C(=O)c2ccc(N3C(=O)OC[C@H]3C)cc2F)CC1 ; Cl]

By reaction and treatment in the same manner as in Example 79 and using (4-bromo-2-fluorophenyl)[4-(3-ethyl-5-methylpyridin-2-yl)piperazin-1-yl]methanone (551 mg) described in Preparation Example 104 and (R)-4-methyloxazolidin-2-one (212 mg) described in Preparation Example 25, the title compound (421 mg) was obtained.
MS(ESI)m/z:427(M+H)+.

Example 170

Synthesis of (R)-3-{4-[4-(3,5-dimethylpyrazin-2-yl)piperazine-1-carbonyl]-3-fluorophenyl}-4-methyloxazolidin-2-one

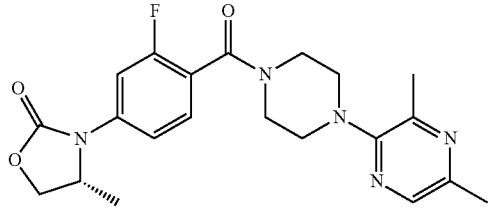 [SMILES: Cc1cnc(N2CCN(C(=O)c3ccc(N4C(=O)OC[C@H]4C)cc3F)CC2)c(C)n1]

By reaction and treatment in the same manner as in Example 1 and using (4-bromo-2-fluorophenyl)[4-(3,5-dimethylpyrazin-2-yl)piperazin-1-yl]methanone (611 mg) described in Preparation Example 105 and (R)-4-methyloxazolidin-2-one (212 mg) described in Preparation Example 25, the title compound (528 mg) was obtained.
MS(ESI)m/z:414(M+H)+.

Example 171

Synthesis of 3-{4-[4-(3-ethyl-5-methylpyridin-2-yl)piperazine-1-carbonyl]-3-fluorophenyl}-5,5-dimethyloxazolidin-2-one

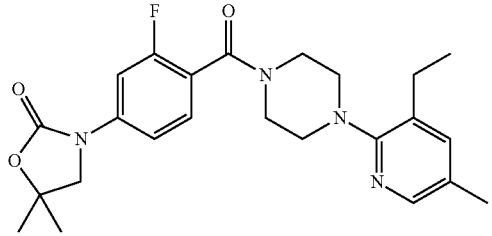 [SMILES: CCc1cc(C)cnc1N1CCN(C(=O)c2ccc(N3CC(C)(C)OC3=O)cc2F)CC1]

By reaction and treatment in the same manner as in Example 1 and using (4-bromo-2-fluorophenyl)[4-(3-ethyl-5-methylpyridin-2-yl)piperazin-1-yl]methanone (539 mg) described in Preparation Example 104 and 5,5-dimethyloxazolidin-2-one (276 mg) described in Preparation Example 43, the title compound (287 mg) was obtained.
MS(ESI)m/z:441(M+H)+.

Example 172

Synthesis of 3-{4-[4-(5-ethyl-3-methylpyridin-2-yl)piperazine-1-carbonyl]-3-fluorophenyl}oxazolidin-2-one

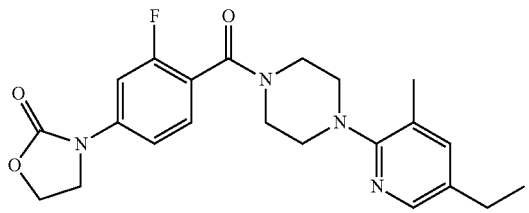 [SMILES: CCc1cnc(N2CCN(C(=O)c3ccc(N4CCOC4=O)cc3F)CC2)c(C)c1]

By reaction and treatment in the same manner as in Example 1 and using (4-bromo-2-fluorophenyl)[4-(5-ethyl-3-methylpyridin-2-yl)piperazin-1-yl]methanone (863 mg) described in Preparation Example 100 and oxazolidin-2-one (261 mg), the title compound (623 mg) was obtained.
MS(ESI)m/z:413(M+H)+.

Example 173

Synthesis of 3-{4-[4-(5-ethyl-3-methylpyridin-2-yl)piperazine-1-carbonyl]-3-fluorophenyl}-5,5-dimethyloxazolidin-2-one

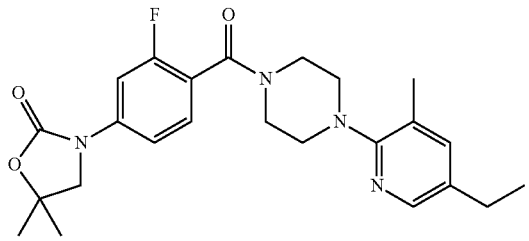 [SMILES: CCc1cnc(N2CCN(C(=O)c3ccc(N4CC(C)(C)OC4=O)cc3F)CC2)c(C)c1]

By reaction and treatment in the same manner as in Example 1 and using (4-bromo-2-fluorophenyl)[4-(5-ethyl-3-methylpyridin-2-yl)piperazin-1-yl]methanone (1 g) described in Preparation Example 100 and 5,5-dimethyloxazolidin-2-one (437 mg) described in Preparation Example 43, the title compound (307 mg) was obtained.
MS(ESI)m/z:441(M+H)+.

Example 174

Synthesis of (R)-3-{5-[4-(5-cyclopropyl-3-methylpyridin-2-yl)piperazine-1-carbonyl]pyridin-2-yl}-4-methyloxazolidin-2-one

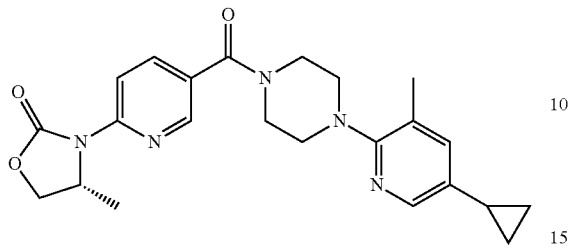

By reaction and treatment in the same manner as in Example 1 and using (6-bromopyridin-3-yl)[4-(5-cyclopropyl-3-methylpyridin-2-yl)piperazin-1-yl]methanone (525 mg) described in Preparation Example 106 and (R)-4-methyloxazolidin-2-one (212 mg) described in Preparation Example 25, the title compound (394 mg) was obtained.
MS(ESI)m/z:422(M+H)$^+$.

Example 175

Synthesis of (R)-3-{3-fluoro-4-[4-(3-fluoro-5-methylpyridin-2-yl)piperazine-1-carbonyl]phenyl}-4-methyloxazolidin-2-one hydrochloride

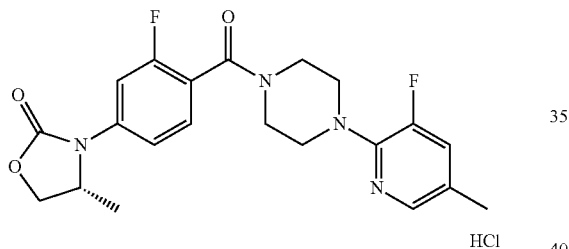

By reaction and treatment in the same manner as in Example 79 and using (4-bromo-2-fluorophenyl)[4-(3-fluoro-5-methylpyridin-2-yl)piperazin-1-yl]methanone (911 mg) described in Preparation Example 108 and (R)-4-methyloxazolidin-2-one (354 mg) described in Preparation Example 25, the title compound (639 mg) was obtained.
MS(ESI)m/z:417(M+H)$^+$.

Example 176

Synthesis of 3-{5-[4-(5-cyclopropyl-3-methylpyridin-2-yl)piperazine-1-carbonyl]pyridin-2-yl}oxazolidin-2-one

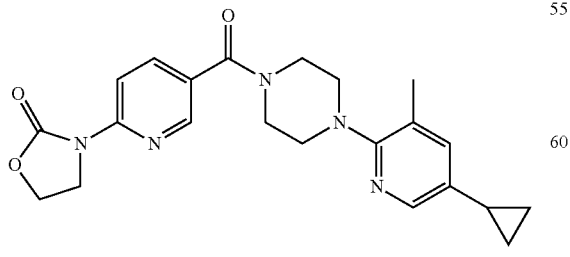

By reaction and treatment in the same manner as in Example 1 and using (6-bromopyridin-3-yl)[4-(5-cyclopropyl-3-methylpyridin-2-yl)piperazin-1-yl]methanone (525 mg) described in Preparation Example 106 and oxazolidin-2-one (183 mg), the title compound (133 mg) was obtained.
MS(ESI)m/z:408(M+H)$^+$.

Example 177

Synthesis of (R)-3-{4-[4-(3-cyclopropyl-5-methylpyridin-2-yl)piperazine-1-carbonyl]-3-fluorophenyl}-4-methyloxazolidin-2-one

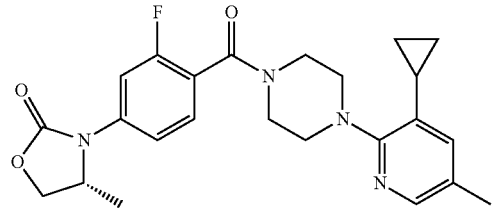 [SMILES: Cc1cnc(N2CCN(C(=O)c3ccc(N4C(=O)OC[C@H]4C)cc3F)CC2)c(C2CC2)c1]

By reaction and treatment in the same manner as in Example 1 and using (4-bromo-2-fluorophenyl)[4-(3-cyclopropyl-5-methylpyridin-2-yl)piperazin-1-yl]methanone (962 mg) described in Preparation Example 109 and (R)-4-methyloxazolidin-2-one (354 mg) described in Preparation Example 25, the title compound (990 mg) was obtained.
MS(ESI)m/z:439(M+H)$^+$.

Example 178

Synthesis of 3-{5-[4-(5-cyclopropyl-3-methylpyridin-2-yl)piperazine-1-carbonyl]pyridin-2-yl}-5,5-dimethyloxazolidin-2-one

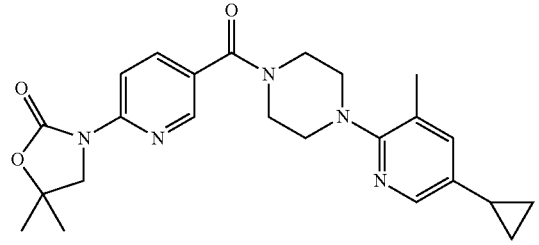 [SMILES: Cc1cc(C2CC2)cnc1N1CCN(C(=O)c2ccc(N3CC(C)(C)OC3=O)nc2)CC1]

By reaction and treatment in the same manner as in Example 1 and using (6-bromopyridin-3-yl)[4-(5-cyclopropyl-3-methylpyridin-2-yl)piperazin-1-yl]methanone (525 mg) described in Preparation Example 106 and 5,5-dimethyloxazolidin-2-one (242 mg) described in Preparation Example 43, the title compound (393 mg) was obtained.
MS(ESI)m/z:436(M+H)$^+$.

Example 179

Synthesis of (R)-3-{4-[4-(3-chloro-5-methylpyridin-2-yl)piperazine-1-carbonyl]-3-fluorophenyl}-4-methyloxazolidin-2-one

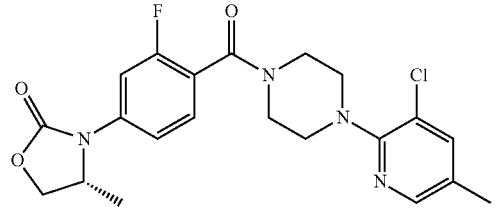

By reaction and treatment in the same manner as in Example 1 and using (4-bromo-2-fluorophenyl)[4-(3-chloro-5-methylpyridin-2-yl)piperazin-1-yl]methanone (626 mg) described in Preparation Example 110 and (R)-4-methyloxazolidin-2-one (227 mg) described in Preparation Example 25, the title compound (627 mg) was obtained.

MS(ESI)m/z:433(M+H)+.

Example 180

Synthesis of (R)-3-{5-[4-(5-cyclopropyl-3-methylpyridin-2-yl)piperazine-1-carbonyl]pyridin-2-yl}-4-ethyloxazolidin-2-one 2hydrochloride

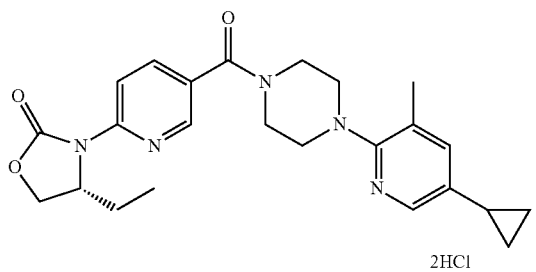 [SMILES: CC[C@@H]1COC(=O)N1c1ccc(C(=O)N2CCN(c3ncc(C4CC4)cc3C)CC2)cn1]

By reaction and treatment in the same manner as in Example 79 and using (6-bromopyridin-3-yl)[4-(5-cyclopropyl-3-methylpyridin-2-yl)piperazin-1-yl]methanone (525 mg) described in Preparation Example 106 and (R)-4-ethyloxazolidin-2-one (242 mg) described in Preparation Example 26, the title compound (482 mg) was obtained.

MS(ESI)m/z:436(M+H)+.

Example 181

Synthesis of (R)-3-{5-[4-(3-cyclopropyl-5-trifluoromethylpyridin-2-yl)piperazine-1-carbonyl]pyridin-2-yl}-4-methyloxazolidin-2-one 2hydrochloride

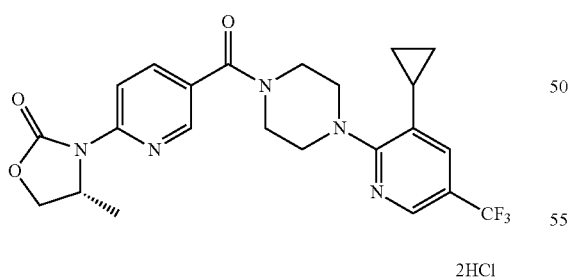

By reaction and treatment in the same manner as in Example 79 and using (6-bromopyridin-3-yl)[4-(3-cyclopropyl-5-trifluoromethylpyridin-2-yl)piperazin-1-yl]methanone (760 mg) described in Preparation Example 111 and (R)-4-methyloxazolidin-2-one (263 mg) described in Preparation Example 25, the title compound (643 mg) was obtained.

MS(ESI)m/z:476(M+H)+.

Example 182

Synthesis of (R)-3-{5-[4-(3,5-dicyclopropylpyridin-2-yl)piperazine-1-carbonyl]pyridin-2-yl}-4-methyloxazolidin-2-one 2hydrochloride

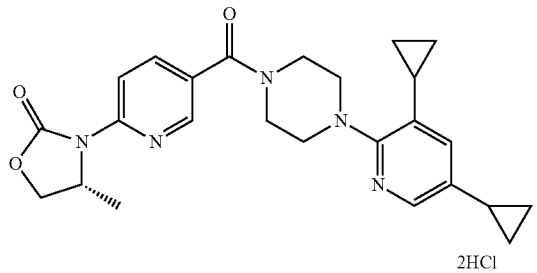 [SMILES: C[C@@H]1COC(=O)N1c1ccc(C(=O)N2CCN(c3ncc(C4CC4)cc3C3CC3)CC2)cn1]

By reaction and treatment in the same manner as in Example 79 and using (6-bromopyridin-3-yl)[4-(3,5-dicyclopropylpyridin-2-yl)piperazin-1-yl]methanone (641 mg) described in Preparation Example 112 and (R)-4-methyloxazolidin-2-one (227 mg) described in Preparation Example 25, the title compound (602 mg) was obtained.

MS(ESI)m/z:448(M+H)+.

Example 183

Synthesis of 3-{5-[4-(3,5-dicyclopropylpyridin-2-yl)piperazine-1-carbonyl]pyridin-2-yl}oxazolidin-2-one

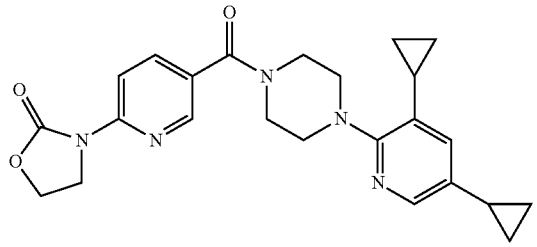 [SMILES: O=C(c1ccc(N2CCOC2=O)nc1)N1CCN(c2ncc(C3CC3)cc2C2CC2)CC1]

By reaction and treatment in the same manner as in Example 1 and using (6-bromopyridin-3-yl)[4-(3,5-dicyclopropylpyridin-2-yl)piperazin-1-yl]methanone (641 mg) described in Preparation Example 112 and oxazolidin-2-one (200 mg), the title compound (172 mg) was obtained.

MS(ESI)m/z:434(M+H)+.

Example 184

Synthesis of (R)-3-{5-[4-(3-cyclopropyl-5-trifluoromethylpyridin-2-yl)piperazine-1-carbonyl]pyridin-2-yl}-4-ethyloxazolidin-2-one 2hydrochloride

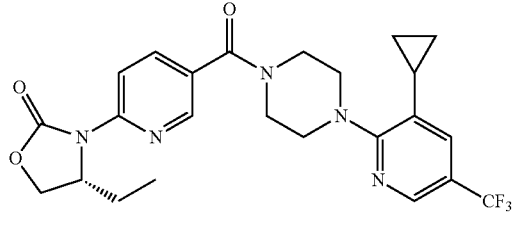

By reaction and treatment in the same manner as in Example 79 and using (6-bromopyridin-3-yl)[4-(3-cyclopropyl-5-trifluoromethylpyridin-2-yl)piperazin-1-yl]methanone (760 mg) described in Preparation Example 111 and (R)-4-ethyloxazolidin-2-one (263 mg) described in Preparation Example 26, the title compound (142 mg) was obtained.

MS(ESI)m/z:490(M+H)⁺.

Example 185

Synthesis of 3-{5-[4-(3,5-dimethylpyridin-2-yl)piperazine-1-carbonyl]-4-methylpyridin-2-yl}oxazolidin-2-one 2hydrochloride

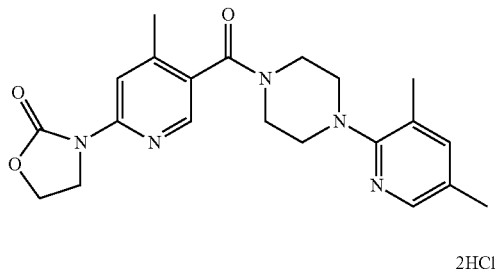 [SMILES: Cc1cnc(N2CCN(C(=O)c3cnc(N4CCOC4=O)cc3C)CC2)c(C)c1]

2HCl

To a solution of oxazolidin-2-one (174 mg) in DMF (4 mL) was added sodium hydride (80 mg) at 10° C., and the mixture was stirred for 30 min. Furthermore, [4-(5-bromo-3-methylpyridin-2-yl)piperazin-1-yl](6-fluoro-4-methylpyridin-3-yl)methanone (590 mg) described in Preparation Example 113 was added, and the mixture was stirred at 80° C. for 5 hr. After cooling, water was added to the reaction mixture, and the mixture was extracted with ethyl acetate. The organic layer was washed with saturated brine, and the solvent was evaporated. The residue was purified by column chromatography (hexane:ethyl acetate) to give 3-{5-[4-(5-bromo-3-methylpyridin-2-yl)piperazine-1-carbonyl]-4-methylpyridin-2-yl}oxazolidin-2-one (423 mg).

To a mixture of 3-{5-[4-(5-bromo-3-methylpyridin-2-yl)piperazine-1-carbonyl]-4-methylpyridin-2-yl}oxazolidin-2-one (423 mg), 1,1'-bis(diphenylphosphino)ferrocene palladium (II) dichloride dichloromethane adduct (75 mg), potassium fluoride (163 mg) and methylboronic acid (84 mg) was added tetrahydrofuran (3 mL), and the mixture was refluxed for 8 hr. After cooling, water was added to the reaction mixture, and the mixture was extracted with ethyl acetate. The organic layer was washed with saturated brine, and the solvent was evaporated. The residue was purified by column chromatography (hexane:ethyl acetate). The obtained compound was dissolved in ethyl acetate (10 mL), 4N hydrogen chloride/ethyl acetate (0.5 mL) was added, and the mixture was stirred at room temperature overnight. Ethyl acetate was added, and the precipitate was collected by filtration to give the title compound (293 mg).

MS(ESI)m/z:396(M+H)⁺.

Example 186

Synthesis of 3-{5-[4-(3,5-dimethylpyridin-2-yl)piperazine-1-carbonyl]pyridin-2-yl}-4-methyloxazolidin-2-one 2hydrochloride

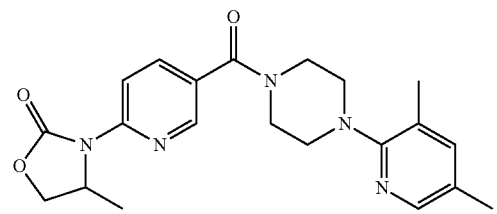

2HCl

By reaction and treatment in the same manner as in Example 79 and using (6-bromopyridin-3-yl)[4-(3,5-dimethylpyridin-2-yl)piperazin-1-yl]methanone (563 mg) described in Preparation Example 73 and 4-methyloxazolidin-2-one (227 mg) described in Preparation Example 114, the title compound (463 mg) was obtained.

MS(ESI)m/z:396(M+H)⁺.

Example 187

Synthesis of (R)-3-{5-[4-(3,5-dimethylpyridin-2-yl)piperazine-1-carbonyl]-4-methylpyridin-2-yl}-4-methyloxazolidin-2-one 2hydrochloride

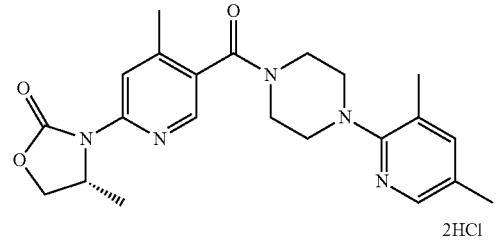 [SMILES: Cc1cnc(N2CCN(C(=O)c3cnc(N4C(=O)OC[C@H]4C)cc3C)CC2)c(C)c1]

2HCl

To a solution of (R)-4-methyloxazolidin-2-one (222 mg) described in Preparation Example 25 in DMF (4 mL) was added sodium hydride (84 mg) at 10° C., and the mixture was stirred for 30 min. Furthermore, [4-(5-bromo-3-methylpyridin-2-yl)piperazin-1-yl](6-fluoro-4-methylpyridin-3-yl)methanone (447 mg) described in Preparation Example 113 was added, and the mixture was stirred at 80° C. for 3 hr and at 100° C. for 3 hr. After cooling, water was added to the reaction mixture, and the mixture was extracted with ethyl acetate. The organic layer was washed with saturated brine, and the solvent was evaporated. The residue was purified by column chromatography (hexane:ethyl acetate) to give (R)-3-{5-[4-(5-bromo-3-methylpyridin-2-yl)piperazine-1-carbonyl]-4-methylpyridin-2-yl}-4-methyloxazolidin-2-one (260 mg).

To a mixture of (R)-3-{5-[4-(5-bromo-3-methylpyridin-2-yl)piperazine-1-carbonyl]-4-methylpyridin-2-yl}-4-methyloxazolidin-2-one (260 mg), 1,1'-bis(diphenylphosphino)ferrocene palladium (II) dichloride dichloromethane adduct (90 mg), potassium fluoride (256 mg) and methylboronic acid (132 mg) was added dioxane (4 mL), and the mixture was refluxed for 8 hr. After cooling, water was added to the reaction mixture, and the mixture was extracted with ethyl acetate. The organic layer was washed with saturated brine, and the solvent was evaporated. The residue was purified by column chromatography (hexane:ethyl acetate). The obtained compound was dissolved in ethyl acetate (10 mL), 4N hydrogen chloride/ethyl acetate (0.6 mL) was added, and the mixture was stirred at room temperature overnight. Ethyl acetate was added, and the precipitate was collected by filtration to give the title compound (213 mg).

MS(ESI)m/z:410(M+H)$^+$.

Example 188

Synthesis of 3-{4-[4-(5-cyclopropyl-3-methylpyridin-2-yl)piperazine-1-carbonyl]-3-fluorophenyl}-5,5-dimethyloxazolidin-2-one

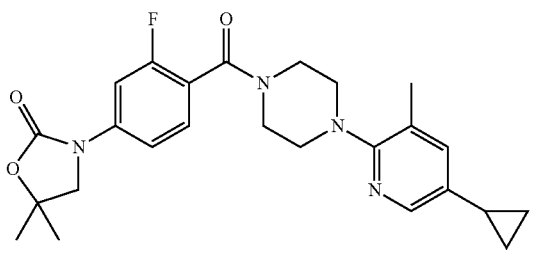 [SMILES: Cc1cc(C2CC2)cnc1N1CCN(C(=O)c2ccc(N3CC(C)(C)OC3=O)cc2F)CC1]

By reaction and treatment in the same manner as in Example 1 and using (4-bromo-2-fluorophenyl)[4-(5-cyclopropyl-3-methylpyridin-2-yl)piperazin-1-yl]methanone (480 mg) described in Preparation Example 86 and 5,5-dimethyloxazolidin-2-one (196 mg) described in Preparation Example 43, the title compound (119 mg) was obtained.

MS(ESI)m/z:453(M+H)$^+$.

Example 189

Synthesis of 3-{4-[4-(5-cyclopropyl-3-methylpyridin-2-yl)piperazine-1-carbonyl]-3-fluorophenyl}oxazolidin-2-one hydrochloride

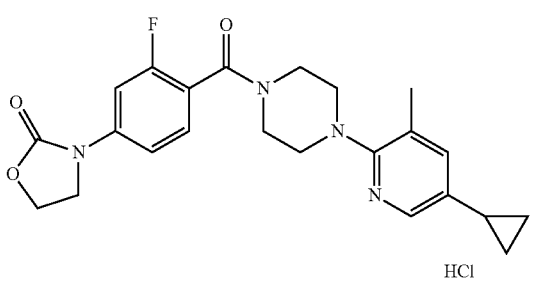 [SMILES: Cc1cc(C2CC2)cnc1N1CCN(C(=O)c2ccc(N3CCOC3=O)cc2F)CC1 ; Cl]

By reaction and treatment in the same manner as in Example 79 and using (4-bromo-2-fluorophenyl)[4-(5-cyclopropyl-3-methylpyridin-2-yl)piperazin-1-yl]methanone (618 mg) described in Preparation Example 86 and oxazolidin-2-one (196 mg), the title compound (35 mg) was obtained.

MS(ESI)m/z:425(M+H)$^+$.

Example 190

Synthesis of (R)-3-{5-[4-(5-ethyl-3-methylpyridin-2-yl)piperazine-1-carbonyl]pyridin-2-yl}-4-methyloxazolidin-2-one 2hydrochloride

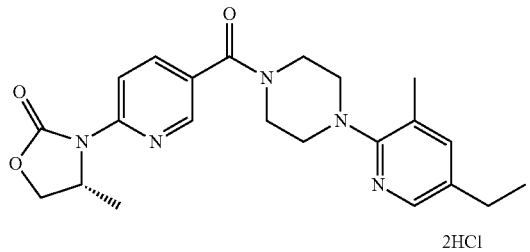 [SMILES: CCc1cnc(N2CCN(C(=O)c3ccc(N4C(=O)OC[C@H]4C)nc3)CC2)c(C)c1]

By reaction and treatment in the same manner as in Example 79 and using (6-bromopyridin-3-yl)[4-(5-ethyl-3-methylpyridin-2-yl)piperazin-1-yl]methanone (584 mg) described in Preparation Example 115 and (R)-4-methyloxazolidin-2-one (228 mg) described in Preparation Example 25, the title compound (275 mg) was obtained.

MS(ESI)m/z:410(M+H)$^+$.

Example 191

Synthesis of 3-{5-[4-(5-ethyl-3-methylpyridin-2-yl)piperazine-1-carbonyl]pyridin-2-yl}oxazolidin-2-one

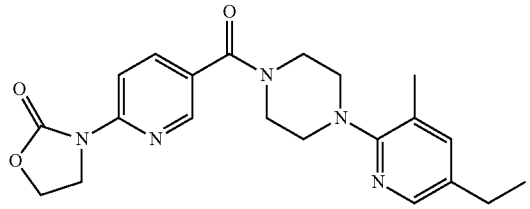 [SMILES: CCc1cnc(N2CCN(C(=O)c3ccc(N4CCOC4=O)nc3)CC2)c(C)c1]

By reaction and treatment in the same manner as in Example 1 and using (6-bromopyridin-3-yl)[4-(5-ethyl-3-methylpyridin-2-yl)piperazin-1-yl]methanone (584 mg) described in Preparation Example 115 and oxazolidin-2-one (197 mg), the title compound (392 mg) was obtained.

MS(ESI)m/z:396(M+H)$^+$.

Example 192

Synthesis of 3-{4-[4-(5-cyclopropyl-3-methylpyridin-2-yl)piperazine-1-carbonyl]-3-(1,1-dioxoisothiazolidin-2-yl)phenyl}oxazolidin-2-one

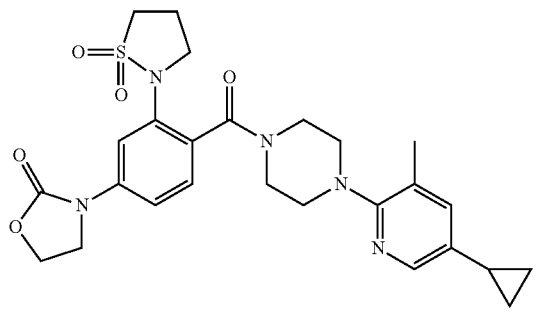 [SMILES: Cc1cc(C2CC2)cnc1N1CCN(C(=O)c2ccc(N3CCOC3=O)cc2N2CCCS2(=O)=O)CC1]

By reaction and treatment in the same manner as in Example 63 and using methyl 2-(1,1-dioxoisothiazolidin-2-yl)-4-(2-oxooxazolidin-3-yl)benzoate (170 mg) described in Preparation Example 117 and 1-(5-cyclopropyl-3-methylpyridin-2-yl)piperazine hydrochloride (127 mg) described in Preparation Example 49, the title compound (48.7 mg) was obtained.

MS(ESI)m/z:526(M+H)$^+$.

Example 193

Synthesis of 3-{4-[4-(3,5-dicyclopropylpyridin-2-yl)piperazine-1-carbonyl]-3-(1,1-dioxoisothiazolidin-2-yl)phenyl}oxazolidin-2-one

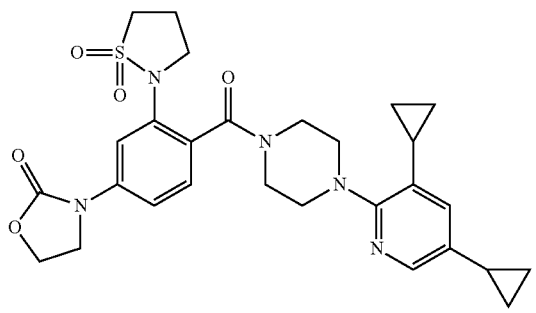 [SMILES: O=C(c1ccc(N2CCOC2=O)cc1N1CCCS1(=O)=O)N1CCN(c2ncc(C3CC3)cc2C2CC2)CC1]

By reaction and treatment in the same manner as in Example 63 and using methyl 2-(1,1-dioxoisothiazolidin-2-yl)-4-(2-oxooxazolidin-3-yl)benzoate (170 mg) described in Preparation Example 117 and 1-(3,5-dicyclopropylpyridin-2-yl)piperazine (121 mg) described in Preparation Example 62, the title compound (61 mg) was obtained.

MS(ESI)m/z:552(M+H)$^+$.

Example 194

Synthesis of 3-{3-(1,1-dioxoisothiazolidin-2-yl)-4-[4-(3,5,6-trimethylpyridin-2-yl)piperazine-1-carbonyl]phenyl}oxazolidin-2-one

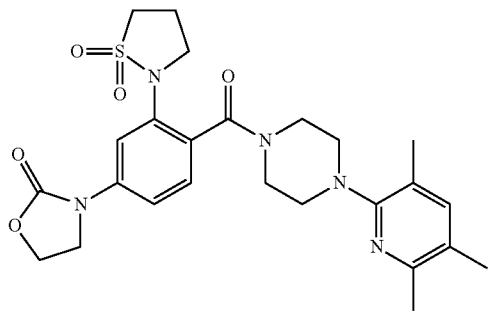 [SMILES: Cc1cc(C)c(N2CCN(C(=O)c3ccc(N4CCOC4=O)cc3N3CCCS3(=O)=O)CC2)nc1C]

By reaction and treatment in the same manner as in Example 63 and using methyl 2-(1,1-dioxoisothiazolidin-2-yl)-4-(2-oxooxazolidin-3-yl)benzoate (170 mg) described in Preparation Example 117 and 1-(3,5,6-trimethylpyridin-2-yl)piperazine (103 mg) described in Preparation Example 175, the title compound (64.2 mg) was obtained.

MS(ESI)m/z:514(M+H)$^+$.

Example 195

Synthesis of (R)-3-{4-[4-(3,5-dimethylpyridin-2-yl)piperazine-1-carbonyl]-3-(1,1-dioxoisothiazolidin-2-yl)phenyl}-4-methyloxazolidin-2-one hydrochloride

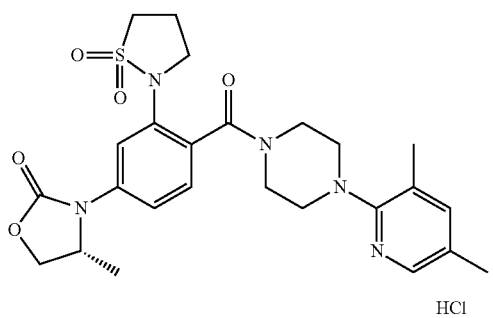 [SMILES: Cc1cnc(N2CCN(C(=O)c3ccc(N4C(=O)OC[C@H]4C)cc3N3CCCS3(=O)=O)CC2)c(C)c1 ; Cl]

By reaction and treatment in the same manner as in Example 79 and using [4-bromo-2-(1,1-dioxoisothiazolidin-2-yl)phenyl][4-(3,5-dimethylpyridin-2-yl)piperazin-1-yl]methanone (247 mg) described in Preparation Example 118 and (R)-4-methyloxazolidin-2-one (50.6 mg) described in Preparation Example 25, the title compound (214.5 mg) was obtained.

MS(ESI)m/z:514(M+H)$^+$.

Example 196

Synthesis of (R)-3-{4-[4-(3,5-dimethylpyridin-2-yl)piperazine-1-carbonyl]-3-(1,1-dioxoisothiazolidin-2-yl)phenyl}-4-ethyloxazolidin-2-one hydrochloride

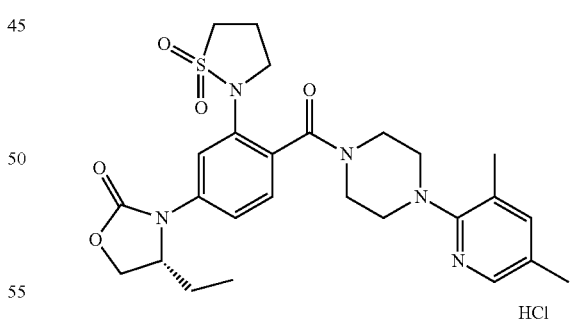

By reaction and treatment in the same manner as in Example 79 and using [4-bromo-2-(1,1-dioxoisothiazolidin-2-yl)phenyl][4-(3,5-dimethylpyridin-2-yl)piperazin-1-yl]methanone (247 mg) described in Preparation Example 118 and (R)-4-ethyloxazolidin-2-one (57.6 mg) described in Preparation Example 26, the title compound (164.2 mg) was obtained.

MS(ESI)m/z:528(M+H)$^+$.

Example 197

Synthesis of 3-{4-[4-(3,5-dimethylpyridin-2-yl)piperazine-1-carbonyl]-3-(1,1-dioxoisothiazolidin-2-yl)phenyl}-5,5-dimethyloxazolidin-2-one

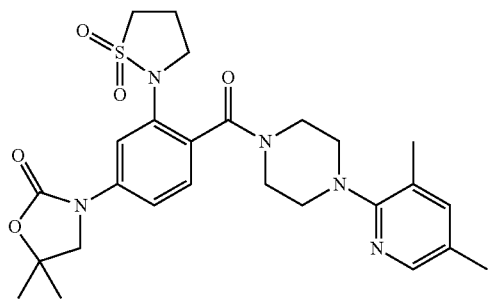 [SMILES: Cc1cnc(N2CCN(C(=O)c3ccc(N4CC(C)(C)OC4=O)cc3N3CCCS3(=O)=O)CC2)c(C)c1]

By reaction and treatment in the same manner as in Example 1 and using [4-bromo-2-(1,1-dioxoisothiazolidin-2-yl)phenyl][4-(3,5-dimethylpyridin-2-yl)piperazin-1-yl]methanone (247 mg) described in Preparation Example 118 and 5,5-dimethyloxazolidin-2-one (57.6 mg) described in Preparation Example 43, the title compound (86.6 mg) was obtained.

MS(ESI)m/z:528(M+H)$^+$.

Example 198

Synthesis of (R)-3-{4-[4-(3,5-dimethylpyridin-2-yl)piperazine-1-carbonyl]-3-(1,1-dioxoisothiazolidin-2-yl)phenyl}-4-methoxymethyloxazolidin-2-one

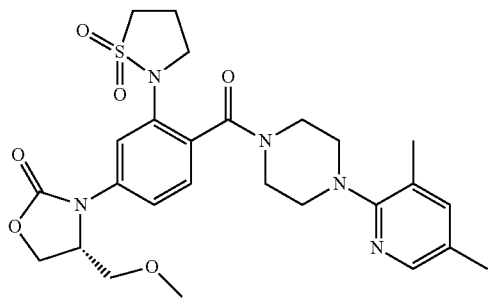 [SMILES: COC[C@@H]1COC(=O)N1c1ccc(C(=O)N2CCN(c3ncc(C)cc3C)CC2)c(N2CCCS2(=O)=O)c1]

By reaction and treatment in the same manner as in Example 1 and using [4-bromo-2-(1,1-dioxoisothiazolidin-2-yl)phenyl][4-(3,5-dimethylpyridin-2-yl)piperazin-1-yl]methanone (247 mg) described in Preparation Example 118 and (R)-4-methoxymethyloxazolidin-2-one (65.6 mg) described in Preparation Example 38, the title compound (194.2 mg) was obtained.

MS(ESI)m/z:544(M+H)$^+$.

Example 199

Synthesis of (R)-3-{4-[4-(3,5-dimethylpyridin-2-yl)piperazine-1-carbonyl]-3-(1,1-dioxoisothiazolidin-2-yl)phenyl}-4-propyloxazolidin-2-one

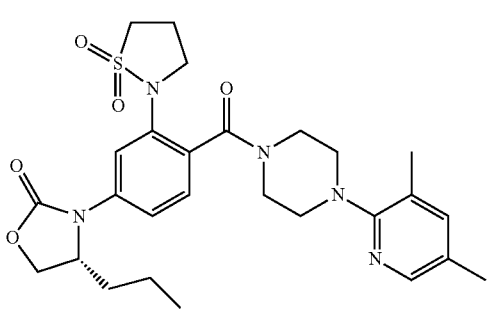 [SMILES: CCC[C@@H]1COC(=O)N1c1ccc(C(=O)N2CCN(c3ncc(C)cc3C)CC2)c(N2CCCS2(=O)=O)c1]

By reaction and treatment in the same manner as in Example 1 and using [4-bromo-2-(1,1-dioxoisothiazolidin-2-yl)phenyl][4-(3,5-dimethylpyridin-2-yl)piperazin-1-yl]methanone (247 mg) described in Preparation Example 118 and (R)-4-propyloxazolidin-2-one (64.58 mg) described in Preparation Example 29, the title compound (188.8 mg) was obtained.

MS(ESI)m/z:542(M+H)$^+$.

Example 200

Synthesis of 3-{4-[4-(3,5-dimethylpyridin-2-yl)piperazine-1-carbonyl]-3-(1,1-dioxoisothiazolidin-2-yl)phenyl}-4,4-dimethyloxazolidin-2-one

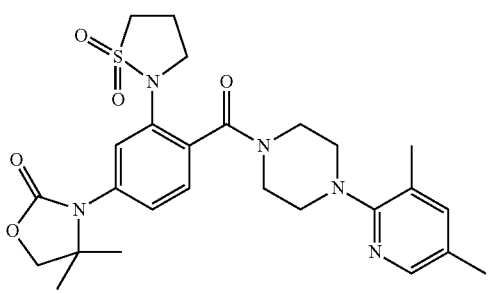 [SMILES: Cc1cnc(N2CCN(C(=O)c3ccc(N4C(=O)OCC4(C)C)cc3N3CCCS3(=O)=O)CC2)c(C)c1]

By reaction and treatment in the same manner as in Example 1 and using [4-bromo-2-(1,1-dioxoisothiazolidin-2-yl)phenyl][4-(3,5-dimethylpyridin-2-yl)piperazin-1-yl]methanone (247 mg) described in Preparation Example 118 and 4,4-dimethyloxazolidin-2-one (57.6 mg), the title compound (63.6 mg) was obtained.

MS(ESI)m/z:528(M+H)$^+$.

Example 201

Synthesis of (R)-3-{4-[4-(3,5-dimethylpyridin-2-yl)piperazine-1-carbonyl]-3-(2-oxooxazolidin-3-yl)phenyl}-4-methyloxazolidin-2-one

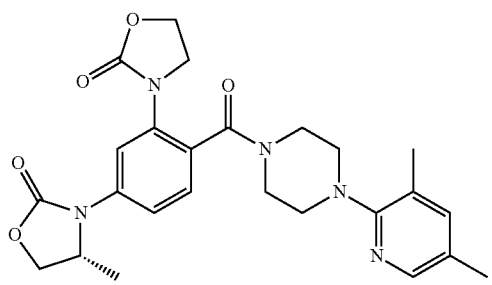 [SMILES: Cc1cnc(N2CCN(C(=O)c3ccc(N4C(=O)OC[C@H]4C)cc3N3CCOC3=O)CC2)c(C)c1]

To a mixture of 3-{5-chloro-2-[4-(3,5-dimethylpyridin-2-yl)piperazine-1-carbonyl]phenyl}oxazolidin-2-one (207 mg) described in Preparation Example 120, (R)-4-methyloxazolidin-2-one (50.6 mg) described in Preparation Example 25, cesium carbonate (228 mg), tris(dibenzylideneacetone)dipalladium (0) chloroform (51.8 mg) and 2-di-tert-butylphosphino-3,4,5,6-tetramethyl-2',4',6'-triisopropyl-1,1'-biphenyl (24 mg) was added toluene (1 mL), and the mixture was refluxed for 8 hr. After cooling, water was added to the reaction mixture, and the mixture was extracted with ethyl acetate. After evaporation of the solvent, the residue was purified by column chromatography (ethyl acetate:methanol) to give the title compound (97.5 mg).

MS(ESI)m/z:480(M+H)⁺.

Example 202

Synthesis of 3-{4-[4-(3,5-dimethylpyridin-2-yl)piperazine-1-carbonyl]-3-(2-oxooxazolidin-3-yl)phenyl}oxazolidin-2-one

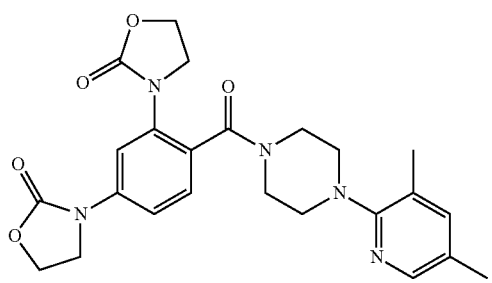 [SMILES: Cc1cnc(N2CCN(C(=O)c3ccc(N4CCOC4=O)cc3N3CCOC3=O)CC2)c(C)c1]

By reaction and treatment in the same manner as in Example 201 and using 3-{5-chloro-2-[4-(3,5-dimethylpyridin-2-yl)piperazine-1-carbonyl]phenyl}oxazolidin-2-one (207 mg) described in Preparation Example 120 and oxazolidin-2-one (43.5 mg), the title compound (40.1 mg) was obtained.

MS(ESI)m/z:466(M+H)⁺.

Example 203

Synthesis of 3-{4-[4-(3,5-dimethylpyridin-2-yl)piperazine-1-carbonyl]-3-(2-oxopyrrolidin-1-yl)phenyl}oxazolidin-2-one

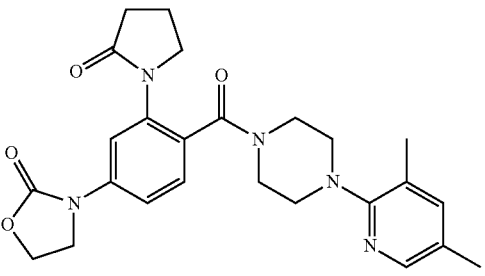 [SMILES: Cc1cnc(N2CCN(C(=O)c3ccc(N4CCOC4=O)cc3N3CCCC3=O)CC2)c(C)c1]

By reaction and treatment in the same manner as in Example 201 and using 1-{5-chloro-2-[4-(3,5-dimethylpyridin-2-yl)piperazine-1-carbonyl]phenyl}pyrrolidin-2-one (206 mg) described in Preparation Example 121 and oxazolidin-2-one (43.5 mg), the title compound (24.1 mg) was obtained.

MS(ESI)m/z:464(M+H)⁺.

Example 204

Synthesis of (R)-3-{4-[4-(3,5-dimethylpyridin-2-yl)piperazine-1-carbonyl]-3-(2-oxopyrrolidin-1-yl)phenyl}-4-methyloxazolidin-2-one hydrochloride

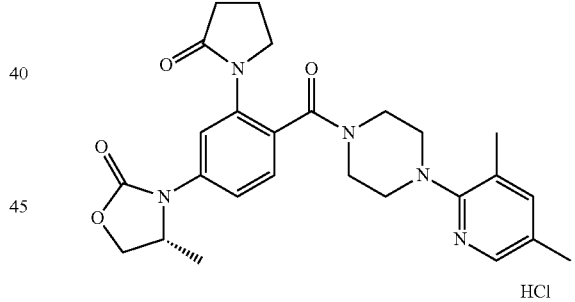

To a mixture of 1-{5-chloro-2-[4-(3,5-dimethylpyridin-2-yl)piperazine-1-carbonyl]phenyl}pyrrolidin-2-one (206 mg) described in Preparation Example 121, (R)-4-methyloxazolidin-2-one (50.6 mg) described in Preparation Example 25, cesium carbonate (228 mg), tris(dibenzylideneacetone)dipalladium (0) chloroform (51.8 mg) and 2-di-tert-butylphosphino-3,4,5,6-tetramethyl-2',4',6'-triisopropyl-1,1'-biphenyl (24 mg) was added toluene (1 mL), and the mixture was refluxed for 8 hr. After cooling, water was added to the reaction mixture, and the mixture was extracted with ethyl acetate. After evaporation of the solvent, the residue was purified by column chromatography (ethyl acetate:methanol). The obtained compound was dissolved in ethyl acetate, 4N hydrogen chloride/ethyl acetate (0.13 mL) was added, and the precipitate was collected by filtration to give the title compound (89.3 mg).

MS(ESI)m/z:478(M+H)⁺.

Example 205

Synthesis of 3-{4-[4-(3,5-dimethylpyridin-2-yl)piperazine-1-carbonyl]-3-methanesulfonylaminophenyl}oxazolidin-2-one

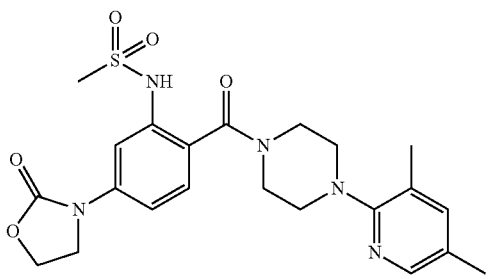 [SMILES: Cc1cnc(N2CCN(C(=O)c3ccc(N4CCOC4=O)cc3NS(C)(=O)=O)CC2)c(C)c1]

By reaction and treatment in the same manner as in Example 1 and using [N-{5-bromo-2-[4-(3,5-dimethylpyridin-2-yl)piperazine-1-carbonyl]phenyl}methanesulfonamide (321 mg) described in Preparation Example 123 and oxazolidin-2-one (59.8 mg), the title compound (57.8 mg) was obtained.

MS(ESI)m/z:474(M+H)⁺.

Example 206

Synthesis of (R)-3-{4-[4-(3,5-dimethylpyridin-2-yl)piperazine-1-carbonyl]-3-methanesulfonylaminophenyl}-4-methyloxazolidin-2-one

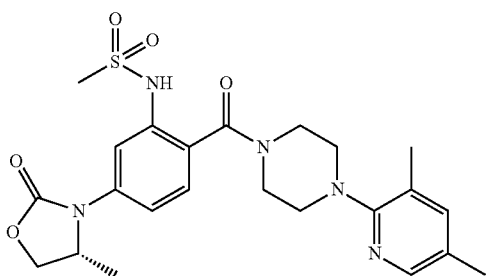

By reaction and treatment in the same manner as in Example 1 and using [N-{5-bromo-2-[4-(3,5-dimethylpyridin-2-yl)piperazine-1-carbonyl]phenyl}methanesulfonamide (234 mg) described in Preparation Example 123 and (R)-4-methyloxazolidin-2-one (50.6 mg) described in Preparation Example 25, the title compound (20.8 mg) was obtained.

MS(ESI)m/z:488(M+H)⁺.

Example 207

Synthesis of 3-{5-[4-(3,5-dimethylpyridin-2-yl)piperazine-1-carbonyl]pyridin-2-yl}-5-methyloxazolidin-2-one

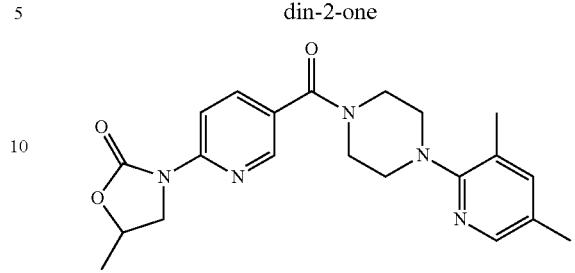

By reaction and treatment in the same manner as in Example 1 and using (6-bromopyridin-3-yl)[4-(3,5-dimethylpyridin-2-yl)piperazin-1-yl]methanone (93 mg) described in Preparation Example 73 and 5-methyloxazolidin-2-one (30 mg), the title compound (29 mg) was obtained.

MS(ESI)m/z:396(M+H)⁺.

Example 208

Synthesis of (R)-3-{4-[4-(3,5-dimethylpyridin-2-yl)piperazine-1-carbonyl]-3-(3-methyl-1,1-dioxoisothiazolidin-2-yl)phenyl}oxazolidin-2-one

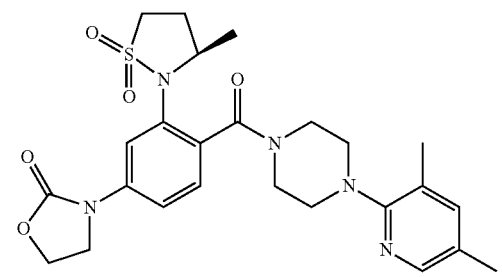 [SMILES: Cc1cnc(N2CCN(C(=O)c3ccc(N4CCOC4=O)cc3N3[C@H](C)CCS3(=O)=O)CC2)c(C)c1]

By reaction and treatment in the same manner as in Example 201 and using (R)-[4-chloro-2-(3-methyl-1,1-dioxoisothiazolidin-2-yl)phenyl][4-(3,5-dimethylpyridin-2-yl)piperazin-1-yl]methanone (95.1 mg) described in Preparation Example 125 and oxazolidin-2-one (17.9 mg), the title compound (15.9 mg) was obtained.

MS(ESI)m/z:514(M+H)⁺.

Example 209

Synthesis of 3-{3-(3-acetyl-2-oxoimidazolidin-1-yl)-4-[4-(3,5-dimethylpyridin-2-yl)piperazine-1-carbonyl]phenyl}oxazolidin-2-one

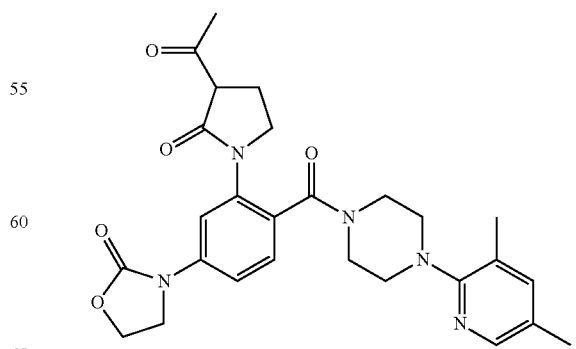

By reaction and treatment in the same manner as in Example 201 and using 1-acetyl-3-{5-chloro-2-[4-(3,5-dimethylpyridin-2-yl)piperazine-1-carbonyl]phenyl}imidazolidin-2-one (221.5 mg) described in Preparation Example 126 and oxazolidin-2-one (42.3 mg), the title compound (25.2 mg) was obtained.

MS(ESI)m/z:507(M+H)⁺.

Example 210

Synthesis of 3-{4-[4-(3,5-dimethylpyridin-2-yl)piperazine-1-carbonyl]-3-(2-oxoimidazolidin-1-yl)phenyl}oxazolidin-2-one

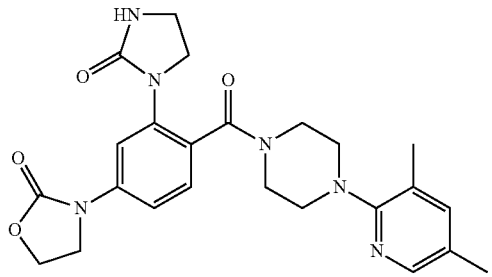 [SMILES: Cc1cnc(N2CCN(C(=O)c3ccc(N4CCOC4=O)cc3N3CCNC3=O)CC2)c(C)c1]

To 3-{3-(3-acetyl-2-oxoimidazolidin-1-yl)-4-[4-(3,5-dimethylpyridin-2-yl)piperazine-1-carbonyl]phenyl}oxazolidin-2-one (156 mg) described in Example 209 were added methanol (2 mL) and 1N aqueous sodium hydroxide solution (0.31 mL), and the mixture was stirred at 50° C. 1N hydrochloric acid (0.31 mL) and water were added, and the mixture was extracted with ethyl acetate. The solvent was evaporated, and the residue was purified by column chromatography (ethyl acetate:methanol) to give the title compound (13 mg).

MS(ESI)m/z:465(M+H)⁺.

Example 211

Synthesis of (R)-3-{3-(3-acetyl-2-oxoimidazolidin-1-yl)-4-[4-(3,5-dimethylpyridin-2-yl)piperazine-1-carbonyl]phenyl}-4-methyloxazolidin-2-one

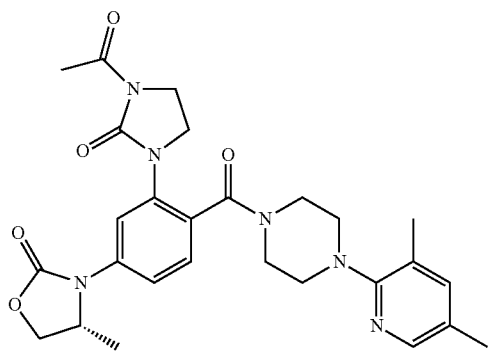 [SMILES: CC(=O)N1CCN(c2cc(N3C(=O)OC[C@H]3C)ccc2C(=O)N2CCN(c3ncc(C)cc3C)CC2)C1=O]

By reaction and treatment in the same manner as in Example 201 and using 1-acetyl-3-{5-chloro-2-[4-(3,5-dimethylpyridin-2-yl)piperazine-1-carbonyl]phenyl}imidazolidin-2-one (519 mg) described in Preparation Example 126 and (R)-4-methyloxazolidin-2-one (115 mg) described in Preparation Example 25, the title compound (69.9 mg) was obtained.

MS(ESI)m/z:521(M+H)⁺.

Example 212

Synthesis of (R)-3-{4-[4-(3,5-dimethylpyridin-2-yl)piperazine-1-carbonyl]-3-(2-oxoimidazolidin-1-yl)phenyl}-4-methyloxazolidin-2-one

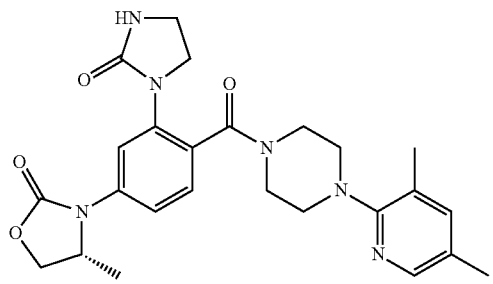

A deacetylation product simultaneously resulting from the synthesis of (R)-3-{3-(3-acetyl-2-oxoimidazolidin-1-yl)-4-[4-(3,5-dimethylpyridin-2-yl)piperazine-1-carbonyl]phenyl}-4-methyloxazolidin-2-one described in Example 211 was purified by column chromatography (ethyl acetate:methanol) to give the title compound (80.4 mg).

MS(ESI)m/z:479(M+H)⁺.

Example 213

Synthesis of (R)-3-{4-[4-(3,5-dimethylpyridin-2-yl)piperazine-1-carbonyl]-3-(3-methyl-2-oxoimidazolidin-1-yl)phenyl}-4-methyloxazolidin-2-one

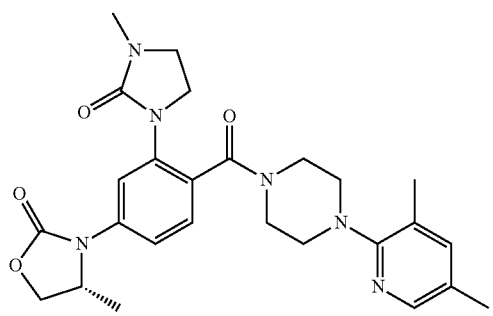 [SMILES: Cc1cnc(N2CCN(C(=O)c3ccc(N4C(=O)OC[C@H]4C)cc3N3CCN(C)C3=O)CC2)c(C)c1]

By reaction and treatment in the same manner as in Example 201 and using 1-{5-chloro-2-[4-(3,5-dimethylpyridin-2-yl)piperazine-1-carbonyl]phenyl}-3-methylimidazolidin-2-one (184 mg) described in Preparation Example 127 and (R)-4-methyloxazolidin-2-one (47.8 mg) described in Preparation Example 25, the title compound (82.6 mg) was obtained.

MS(ESI)m/z:493(M+H)⁺.

Example 214

Synthesis of 3-{4-[4-(3,5-dimethylpyridin-2-yl)piperazine-1-carbonyl]-3-(1,1-dioxo-1,2-thiazinan-2-yl)phenyl}oxazolidin-2-one

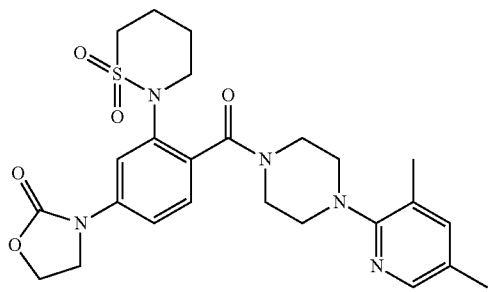 [SMILES: Cc1cnc(N2CCN(C(=O)c3ccc(N4CCOC4=O)cc3N3CCCCS3(=O)=O)CC2)c(C)c1]

By reaction and treatment in the same manner as in Example 201 and using [4-chloro-2-(1,1-dioxo-1,2-thiazinan-2-yl)phenyl][4-(3,5-dimethylpyridin-2-yl)piperazin-1-yl]methanone (161.5 mg) described in Preparation Example 128 and oxazolidin-2-one (30.4 mg), the title compound (35.4 mg) was obtained.

MS(ESI)m/z:514(M+H)[+].

Example 215

Synthesis of (R)-3-{4-[4-(3,5-dimethylpyridin-2-yl)piperazine-1-carbonyl]-3-(1,1-dioxo-1,2-thiazinan-2-yl)phenyl}-4-methyloxazolidin-2-one

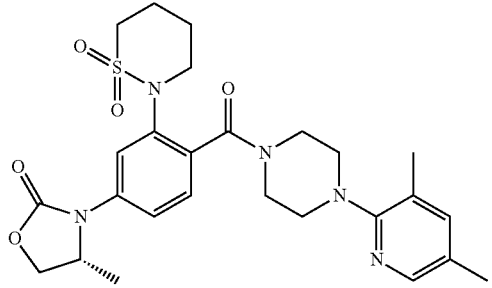 [SMILES: Cc1cnc(N2CCN(C(=O)c3ccc(N4C(=O)OC[C@H]4C)cc3N3CCCCS3(=O)=O)CC2)c(C)c1]

By reaction and treatment in the same manner as in Example 201 and using [4-chloro-2-(1,1-dioxo-1,2-thiazinan-2-yl)phenyl][4-(3,5-dimethylpyridin-2-yl)piperazin-1-yl]methanone (218 mg) described in Preparation Example 128 and (R)-4-methyloxazolidin-2-one (47.6 mg) described in Preparation Example 25, the title compound (78.5 mg) was obtained.

MS(ESI)m/z:528(M+H)[+].

Example 216

Synthesis of 3-{4-[4-(5-cyclopropyl-3-methylpyridin-2-yl)piperazine-1-carbonyl]-3-methanesulfonylaminophenyl}oxazolidin-2-one

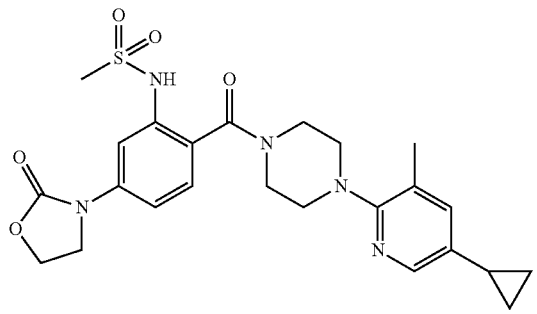 [SMILES: Cc1cc(C2CC2)cnc1N1CCN(C(=O)c2ccc(N3CCOC3=O)cc2NS(C)(=O)=O)CC1]

By reaction and treatment in the same manner as in Example 1 and using N-{5-bromo-2-[4-(5-cyclopropyl-3-methylpyridin-2-yl)piperazine-1-carbonyl]phenyl}methanesulfonamide (247 mg) described in Preparation Example 124 and oxazolidin-2-one (43.5 mg), the title compound (80.1 mg) was obtained.

MS(ESI)m/z:500(M+H)[+].

Example 217

Synthesis of (R)-3-{4-[4-(5-cyclopropyl-3-methylpyridin-2-yl)piperazine-1-carbonyl]-3-methanesulfonylaminophenyl}-4-methyloxazolidin-2-one

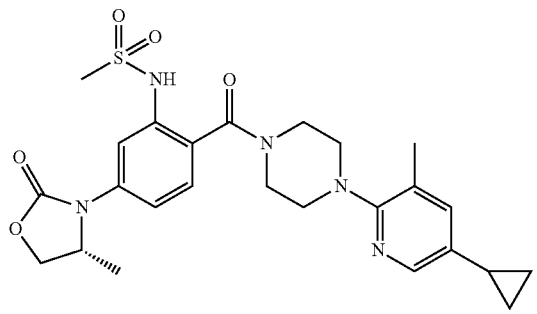 [SMILES: Cc1cc(C2CC2)cnc1N1CCN(C(=O)c2ccc(N3C(=O)OC[C@H]3C)cc2NS(C)(=O)=O)CC1]

By reaction and treatment in the same manner as in Example 1 and using N-{5-bromo-2-[4-(5-cyclopropyl-3-methylpyridin-2-yl)piperazine-1-carbonyl]phenyl}methanesulfonamide (247 mg) described in Preparation Example 124 and (R)-4-methyloxazolidin-2-one (50.6 mg) described in Preparation Example 25, the title compound (35.9 mg) was obtained.

MS(ESI)m/z:514 (M+H)[+].

Example 218

Synthesis of 3-{4-[4-(5-ethyl-3-methylpyridin-2-yl)piperazine-1-carbonyl]-3-methylphenyl}oxazolidin-2-one

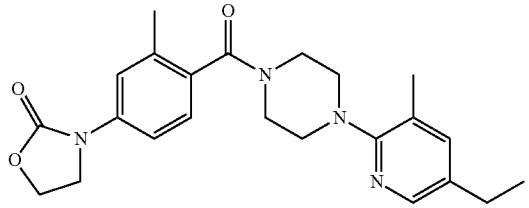 [SMILES: CCc1cnc(N2CCN(C(=O)c3ccc(N4CCOC4=O)cc3C)CC2)c(C)c1]

By reaction and treatment in the same manner as in Example 1 and using (4-bromo-2-methylphenyl)[4-(5-ethyl-3-methylpyridin-2-yl)piperazin-1-yl]methanone (350 mg) described in Preparation Example 129 and oxazolidin-2-one (114 mg), the title compound (283 mg) was obtained.
MS(ESI)m/z:409(M+H)$^+$.

Example 219

Synthesis of (R)-3-{4-[4-(5-ethyl-3-methylpyridin-2-yl)piperazine-1-carbonyl]-3-methylphenyl}-4-methyloxazolidin-2-one hydrochloride

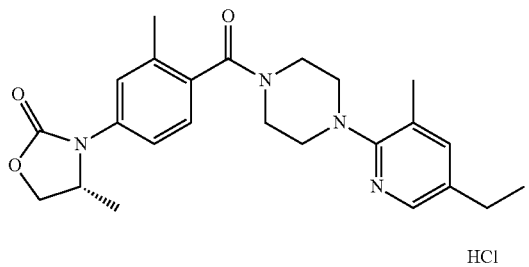 [SMILES: CCc1cnc(N2CCN(C(=O)c3ccc(N4C(=O)OC[C@H]4C)cc3C)CC2)c(C)c1 ; Cl]

By reaction and treatment in the same manner as in Example 79 and using (4-bromo-2-methylphenyl)[4-(5-ethyl-3-methylpyridin-2-yl)piperazin-1-yl]methanone (350 mg) described in Preparation Example 129 and (R)-4-methyloxazolidin-2-one (132 mg) described in Preparation Example 25, the title compound (184 mg) was obtained.
MS(ESI)m/z:423(M+H)$^+$.

Example 220

Synthesis of 3-{4-[4-(5-cyclopropyl-3-methylpyridin-2-yl)piperazine-1-carbonyl]-3-methylphenyl}oxazolidin-2-one

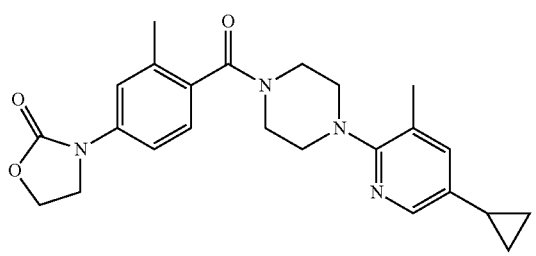 [SMILES: Cc1cc(N2CCOC2=O)ccc1C(=O)N1CCN(c2ncc(C3CC3)cc2C)CC1]

By reaction and treatment in the same manner as in Example 1 and using (4-bromo-2-methylphenyl)[4-(5-cyclopropyl-3-methylpyridin-2-yl)piperazin-1-yl]methanone (347 mg) described in Preparation Example 130 and oxazolidin-2-one (109 mg), the title compound (313 mg) was obtained.
MS(ESI)m/z:421(M+H)$^+$.

Example 221

Synthesis of (R)-3-{4-[4-(5-cyclopropyl-3-methylpyridin-2-yl)piperazine-1-carbonyl]-3-methylphenyl}-4-methyloxazolidin-2-one

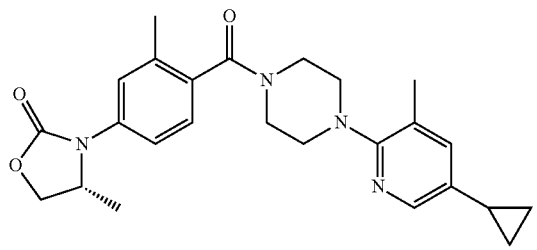 [SMILES: Cc1cc(N2C(=O)OC[C@H]2C)ccc1C(=O)N1CCN(c2ncc(C3CC3)cc2C)CC1]

By reaction and treatment in the same manner as in Example 1 and using (4-bromo-2-methylphenyl)[4-(5-cyclopropyl-3-methylpyridin-2-yl)piperazin-1-yl]methanone (347 mg) described in Preparation Example 130 and (R)-4-methyloxazolidin-2-one (127 mg) described in Preparation Example 25, the title compound (152 mg) was obtained.
MS(ESI)m/z:435(M+H)$^+$.

Example 222

Synthesis of (R)-3-{4-[4-(5-ethyl-3-methylpyridin-2-yl)piperazine-1-carbonyl]-3-methylphenyl}-4-hydroxymethyloxazolidin-2-one

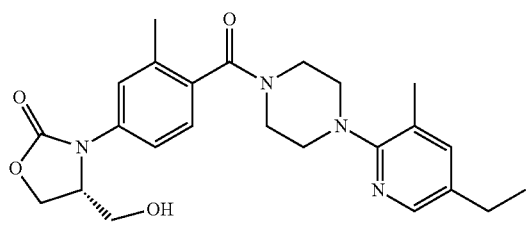 [SMILES: CCc1cnc(N2CCN(C(=O)c3ccc(N4C(=O)OC[C@H]4CO)cc3C)CC2)c(C)c1]

By reaction and treatment in the same manner as in Example 19 and using (4-bromo-2-methylphenyl)[4-(5-ethyl-3-methylpyridin-2-yl)piperazin-1-yl]methanone (350 mg) described in Preparation Example 129 and benzoic acid (R)-2-oxooxazolidin-4-ylmethyl ester (289 mg), the title compound (280 mg) was obtained.
MS(ESI)m/z:439(M+H)$^+$.

Example 223

Synthesis of (R)-3-{4-[4-(5-cyclopropyl-3-methylpyridin-2-yl)piperazine-1-carbonyl]-3-methylphenyl}-4-hydroxymethyloxazolidin-2-one

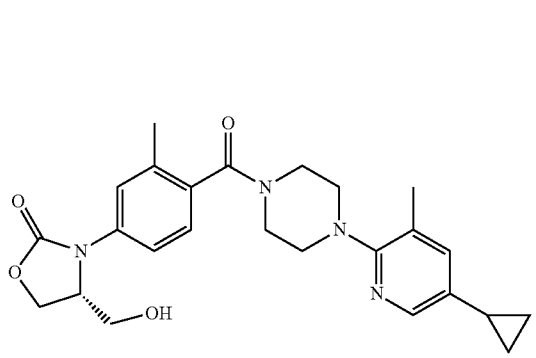 [SMILES: Cc1cc(N2C(=O)OC[C@H]2CO)ccc1C(=O)N1CCN(c2ncc(C3CC3)cc2C)CC1]

By reaction and treatment in the same manner as in Example 19 and using (4-bromo-2-methylphenyl)[4-(5-cyclopropyl-3-methylpyridin-2-yl)piperazin-1-yl]methanone (347 mg) described in Preparation Example 130 and benzoic acid (R)-2-oxooxazolidin-4-ylmethyl ester (278 mg), the title compound (270 mg) was obtained.
MS(ESI)m/z:451(M+H)$^+$.

Example 224

Synthesis of (R)-3-{4-[4-(5-ethyl-3-methylpyridin-2-yl)piperazine-1-carbonyl]-3-methylphenyl}-4-methoxymethyloxazolidin-2-one hydrochloride

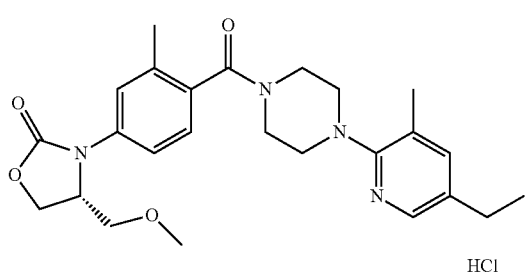 [SMILES: CCc1cnc(N2CCN(C(=O)c3ccc(N4C(=O)OC[C@H]4COC)cc3C)CC2)c(C)c1 ; Cl]

By reaction and treatment in the same manner as in Example 73 and using (R)-3-{4-[4-(5-ethyl-3-methylpyridin-2-yl)piperazine-1-carbonyl]-3-methylphenyl}-4-hydroxymethyloxazolidin-2-one (150 mg) described in Example 222 and methyl iodide (21 μL), (R)-3-{4-[4-(5-ethyl-3-methylpyridin-2-yl)piperazine-1-carbonyl]-3-methylphenyl}-4-methoxymethyloxazolidin-2-one was obtained. The obtained compound was dissolved in a mixture of ethyl acetate and methanol, 4N hydrogen chloride/ethyl acetate was added, and the solvent was evaporated. To the obtained residue was added diisopropyl ether, and the mixture was filtered to give the title compound (140 mg).
MS(ESI)m/z:453(M+H)$^+$.

Example 225

Synthesis of (R)-3-{4-[4-(5-cyclopropyl-3-methylpyridin-2-yl)piperazine-1-carbonyl]-3-methylphenyl}-4-methoxymethyloxazolidin-2-one hydrochloride

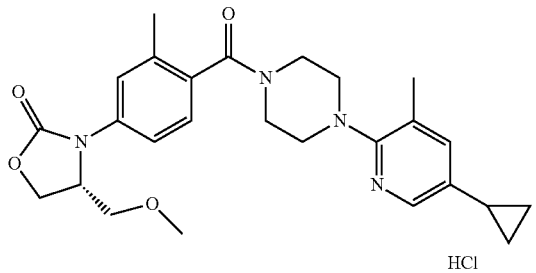 [SMILES: COC[C@@H]1COC(=O)N1c1ccc(C(=O)N2CCN(c3ncc(C4CC4)cc3C)CC2)c(C)c1 ; Cl]

By reaction and treatment in the same manner as in Example 224 and using (R)-3-{4-[4-(5-cyclopropyl-3-methylpyridin-2-yl)piperazine-1-carbonyl]-3-methylphenyl}-4-hydroxymethyloxazolidin-2-one (150 mg) described in Example 223 and methyl iodide (20 μL), the title compound (142 mg) was obtained.
MS(ESI)m/z:465(M+H)$^+$.

Example 226

Synthesis of (R)-3-{5-[4-(5-ethyl-3-methylpyridin-2-yl)piperazine-1-carbonyl]pyridin-2-yl}-4-methyloxazolidin-2-one

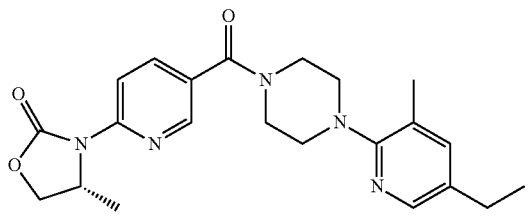 [SMILES: CCc1cnc(N2CCN(C(=O)c3ccc(N4C(=O)OC[C@H]4C)nc3)CC2)c(C)c1]

By reaction and treatment in the same manner as in Example 1 and using (6-bromopyridin-3-yl)[4-(5-ethyl-3-methylpyridin-2-yl)piperazin-1-yl]methanone (1.37 g) described in Preparation Example 115 and (R)-4-methyloxazolidin-2-one (0.53 g) described in Preparation Example 25, the title compound (892 mg) was obtained.
MS(ESI)m/z:410(M+H)$^+$.

Example 227

Synthesis of 3-{5-[4-(5-cyano-3-methylpyridin-2-yl)piperazine-1-carbonyl]pyridin-2-yl}oxazolidin-2-one

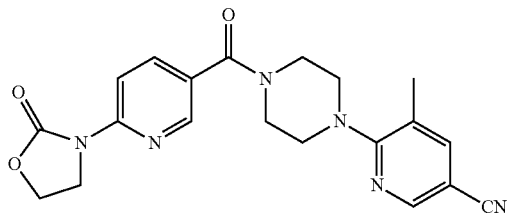 [SMILES: Cc1cc(C#N)cnc1N1CCN(C(=O)c2ccc(N3CCOC3=O)nc2)CC1]

By reaction and treatment in the same manner as in Example 1 and using 6-[4-(6-bromopyridine-3-carbonyl)piperazin-1-yl]-5-methylnicotinonitrile (200 mg) described in Preparation Example 131 and oxazolidin-2-one (68 mg), the title compound (167 mg) was obtained.
MS(ESI)m/z:393(M+H)$^+$.

Example 228

Synthesis of (R)-3-{5-[4-(5-cyano-3-methylpyridin-2-yl)piperazine-1-carbonyl]pyridin-2-yl}-4-methyloxazolidin-2-one

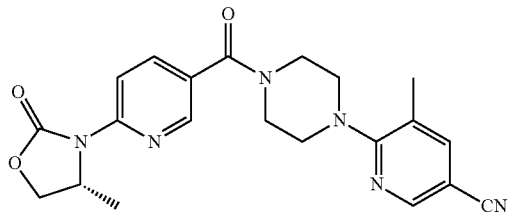 [SMILES: Cc1cc(C#N)cnc1N1CCN(C(=O)c2ccc(N3C(=O)OC[C@H]3C)nc2)CC1]

By reaction and treatment in the same manner as in Example 1 and using 6-[4-(6-bromopyridine-3-carbonyl)piperazin-1-yl]-5-methylnicotinonitrile (200 mg) described in Preparation Example 131 and (R)-4-methyloxazolidin-2-one (79 mg) described in Preparation Example 25, the title compound (170 mg) was obtained.
MS(ESI)m/z:407(M+H)$^+$.

Example 229

Synthesis of 3-{3-methyl-4-[4-(3,5,6-trimethylpyridin-2-yl)piperazine-1-carbonyl]phenyl}oxazolidin-2-one

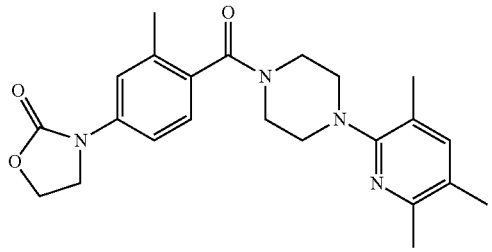 [SMILES: Cc1cc(N2CCOC2=O)ccc1C(=O)N1CCN(c2nc(C)c(C)cc2C)CC1]

By reaction and treatment in the same manner as in Example 1 and using (4-bromo-2-methylphenyl)[4-(3,5,6-trimethylpyridin-2-yl)piperazin-1-yl]methanone (172 mg) described in Preparation Example 132 and oxazolidin-2-one (56 mg), the title compound (130 mg) was obtained.
MS(ESI)m/z:409(M+H)$^+$.

Example 230

Synthesis of (R)-4-methyl-3-{3-methyl-4-[4-(3,5,6-trimethylpyridin-2-yl)piperazine-1-carbonyl]phenyl}oxazolidin-2-one

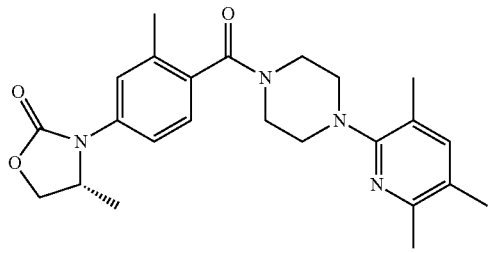 [SMILES: Cc1cc(N2C(=O)OC[C@H]2C)ccc1C(=O)N1CCN(c2nc(C)c(C)cc2C)CC1]

By reaction and treatment in the same manner as in Example 1 and using (4-bromo-2-methylphenyl)[4-(3,5,6-trimethylpyridin-2-yl)piperazin-1-yl]methanone (172 mg) described in Preparation Example 132 and (R)-4-methyloxazolidin-2-one (65 mg) described in Preparation Example 25, the title compound (104 mg) was obtained.
MS(ESI)m/z:423(M+H)$^+$.

Example 231

Synthesis of 3-{4-[4-(5-cyano-3-methylpyridin-2-yl)piperazine-1-carbonyl]-3-methylphenyl}oxazolidin-2-one

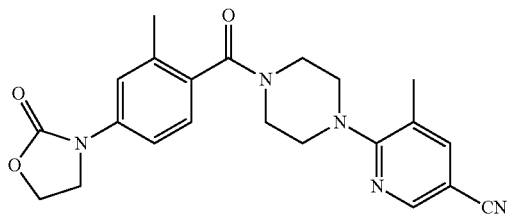 [SMILES: Cc1cc(N2CCOC2=O)ccc1C(=O)N1CCN(c2ncc(C#N)cc2C)CC1]

By reaction and treatment in the same manner as in Example 1 and using 6-[4-(4-bromo-2-methylbenzoyl)piperazin-1-yl]-5-methylnicotinonitrile (210 mg) described in Preparation Example 133 and oxazolidin-2-one (69 mg), the title compound (50 mg) was obtained.
MS(ESI)m/z:406(M+H)$^+$.

Example 232

Synthesis of (R)-3-{4-[4-(5-cyano-3-methylpyridin-2-yl)piperazine-1-carbonyl]-3-methylphenyl}-4-methyloxazolidin-2-one

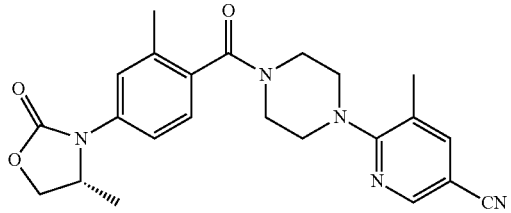 [SMILES: Cc1cc(N2C(=O)OC[C@H]2C)ccc1C(=O)N1CCN(c2ncc(C#N)cc2C)CC1]

By reaction and treatment in the same manner as in Example 1 and using 6-[4-(4-bromo-2-methylbenzoyl)piperazin-1-yl]-5-methylnicotinonitrile (210 mg) described in Preparation Example 133 and (R)-4-methyloxazolidin-2-one (80 mg) described in Preparation Example 25, the title compound (145 mg) was obtained.
MS(ESI)m/z:420(M+H)$^+$.

Example 233

Synthesis of 3-{4-[4-(5-cyano-3-methylpyridin-2-yl)piperazine-1-carbonyl]-3-fluorophenyl}oxazolidin-2-one

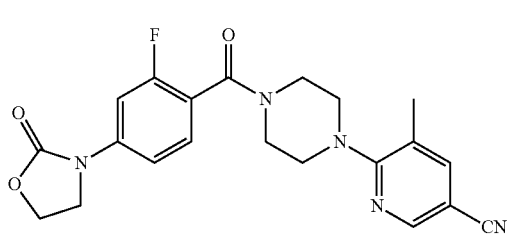 [SMILES: Cc1cc(C#N)cnc1N1CCN(C(=O)c2ccc(N3CCOC3=O)cc2F)CC1]

By reaction and treatment in the same manner as in Example 1 and using 6-[4-(4-bromo-2-fluorobenzoyl)piperazin-1-yl]-5-methylnicotinonitrile (215 mg) described in Preparation Example 134 and oxazolidin-2-one (70 mg), the title compound (178 mg) was obtained.

MS(ESI)m/z:410(M+H)+.

Example 234

Synthesis of (R)-3-{4-[4-(5-cyano-3-methylpyridin-2-yl)piperazine-1-carbonyl]-3-fluorophenyl}-4-methyloxazolidin-2-one

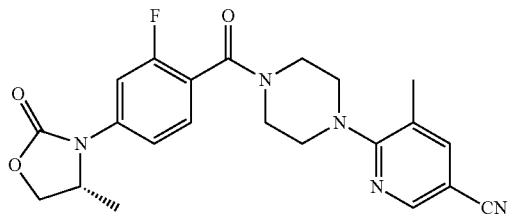 [SMILES: Cc1cc(C#N)cnc1N1CCN(C(=O)c2ccc(N3C(=O)OC[C@H]3C)cc2F)CC1]

By reaction and treatment in the same manner as in Example 1 and using 6-[4-(4-bromo-2-fluorobenzoyl)piperazin-1-yl]-5-methylnicotinonitrile (215 mg) described in Preparation Example 134 and (R)-4-methyloxazolidin-2-one (81 mg) described in Preparation Example 25, the title compound (173 mg) was obtained.

MS(ESI)m/z:424(M+H)+.

Example 235

Synthesis of 3-{5-[4-(5-cyano-3-methylpyridin-2-yl)piperazine-1-carbonyl]pyridin-2-yl}-5,5-dimethyloxazolidin-2-one

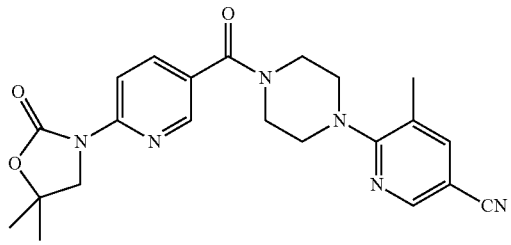 [SMILES: Cc1cc(C#N)cnc1N1CCN(C(=O)c2ccc(N3CC(C)(C)OC3=O)nc2)CC1]

By reaction and treatment in the same manner as in Example 1 and using 6-[4-(6-bromopyridine-3-carbonyl)piperazin-1-yl]-5-methylnicotinonitrile (105 mg) described in Preparation Example 131 and 5,5-dimethyloxazolidin-2-one (47 mg) described in Preparation Example 43, the title compound (59 mg) was obtained.

MS(ESI)m/z:421(M+H)+.

Example 236

Synthesis of 3-{5-[4-(2,4-dimethylphenyl)piperazine-1-carbonyl]-4-methylpyridin-2-yl}oxazolidin-2-one hydrochloride

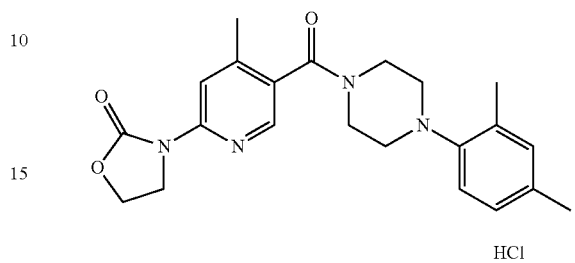

To a solution of sodium hydride (73 mg, 60% in oil) in N,N-dimethylformamide (5 mL) was added oxazolidin-2-one (159 mg) under ice-cooling, and the mixture was stirred at room temperature. Thereto was added a solution of [4-(2,4-dimethylphenyl)piperazin-1-yl](6-fluoro-4-methylpyridin-3-yl)methanone (400 mg) described in Preparation Example 135 in N,N-dimethylformamide (5 mL), and the mixture was stirred at 80° C. Water was poured into the reaction mixture, and the mixture was extracted with ethyl acetate. The organic layer was washed twice with water, washed with saturated brine, and dried over sodium sulfate. The solvent was evaporated under reduced pressure and the residue was purified by column chromatography (ethyl acetate:hexane). The obtained compound was dissolved in dichloromethane (5 mL), 1N hydrogen chloride/diethyl ether (5 mL) was added, and the precipitate was collected by filtration to give the title compound (37 mg).

MS(ESI)m/z:395(M+H)+.

Example 237

Synthesis of 3-{5-[4-(5-cyclopropyl-3-methylpyridin-2-yl)piperazine-1-carbonyl]-4-methylpyridin-2-yl}oxazolidin-2-one 2hydrochloride

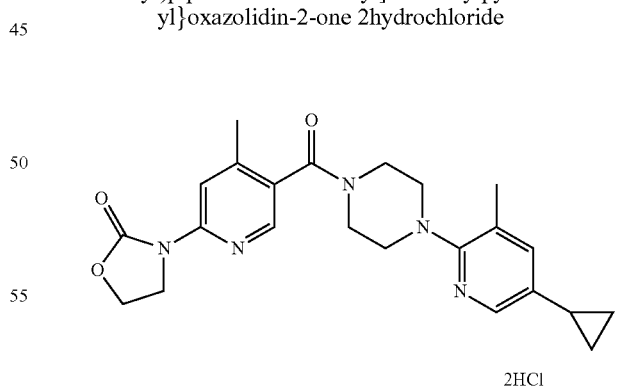

By reaction and treatment in the same manner as in Example 236 and using [4-(5-cyclopropyl-3-methylpyridin-2-yl)piperazin-1-yl](6-fluoro-4-methylpyridin-3-yl)methanone (1.14 g) described in Preparation Example 136 and oxazolidin-2-one (561 mg), the title compound (615 mg) was obtained.

MS(ESI)m/z:422(M+H)+.

Example 238

Synthesis of 3-{5-[4-(5-ethyl-3-methylpyridin-2-yl)piperazine-1-carbonyl]-4-methylpyridin-2-yl}oxazolidin-2-one 2hydrochloride

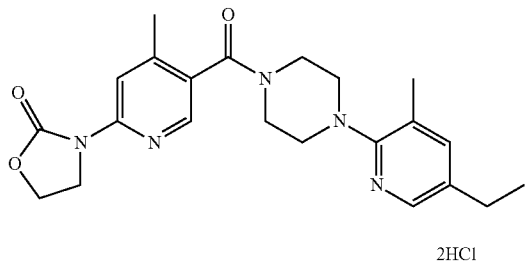 [SMILES: CCc1cnc(N2CCN(C(=O)c3cnc(N4CCOC4=O)cc3C)CC2)c(C)c1 ; "2HCl"]

By reaction and treatment in the same manner as in Example 236 and using [4-(5-ethyl-3-methylpyridin-2-yl)piperazin-1-yl](6-fluoro-4-methylpyridin-3-yl)methanone (320 mg) described in Preparation Example 137 and oxazolidin-2-one (162 mg), the title compound (250 mg) was obtained.
MS(ESI)m/z:410(M+H)$^+$.

Example 239

Synthesis of 3-{5-[4-(3,5-dimethylpyridin-2-yl)piperazine-1-carbonyl]pyridin-2-yl}oxazolidin-2-one

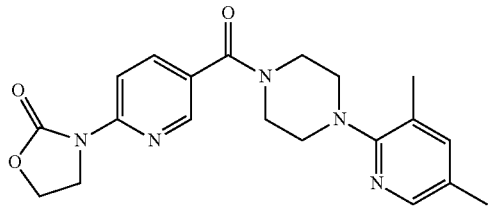 [SMILES: Cc1cnc(N2CCN(C(=O)c3ccc(N4CCOC4=O)nc3)CC2)c(C)c1]

By reaction and treatment in the same manner as in Example 63 and using 6-(2-oxooxazolidin-3-yl)nicotinic acid methyl ester (250 mg) described in Preparation Example 138 and 1-(3,5-dimethylpyridin-2-yl)piperazine (233 mg) described in Preparation Example 47, the title compound (95 mg) was obtained.
MS(ESI)m/z:382(M+H)$^+$.

Example 240

Synthesis of 3-{5-[4-(3,5-dicyclopropylpyridin-2-yl)piperazine-1-carbonyl]-4-methylpyridin-2-yl}oxazolidin-2-one

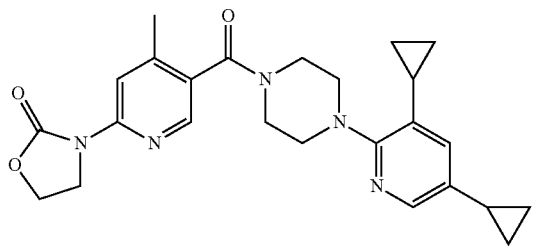

To a solution of sodium hydride (168 mg, 60% in oil) in N,N-dimethylformamide (10 mL) was added oxazolidin-2-one (367 mg) under ice-cooling, and the mixture was stirred at room temperature. Thereto was added a solution of [4-(3,5-dicyclopropylpyridin-2-yl)piperazin-1-yl](6-fluoro-4-methylpyridin-3-yl)methanone (400 mg) described in Preparation Example 139 in N,N-dimethylformamide (5 mL) and the mixture was stirred at 90° C. for 5 hr. Water was poured into the reaction mixture, and the mixture was extracted with ethyl acetate. The organic layer was washed twice with water, washed with saturated brine, and dried over sodium sulfate. The solvent was evaporated under reduced pressure and the residue was purified by column chromatography (ethyl acetate:hexane). Then, diethyl ether was added and the mixture was stirred at room temperature. The solid was collected by filtration to give the title compound (215 mg).
MS(ESI)m/z:448(M+H)$^+$.

Example 241

Synthesis of 3-{5-[4-(3,5,6-trimethylpyridin-2-yl)piperazine-1-carbonyl]pyridin-2-yl}oxazolidin-2-one

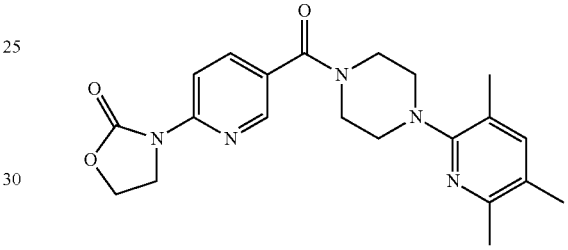

By reaction and treatment in the same manner as in Example 63 and using 6-(2-oxooxazolidin-3-yl)nicotinic acid methyl ester (250 mg) described in Preparation Example 138 and 1-(3,5,6-trimethylpyridin-2-yl)piperazine hydrochloride (328 mg) described in Preparation Example 52 after neutralization and conversion to a free form, the title compound (95 mg) was obtained.
MS(ESI)m/z:396(M+H)$^+$.

Example 242

Synthesis of 3-{5-[4-(4-cyclopropyl-2-methylphenyl)piperazine-1-carbonyl]pyridin-2-yl}oxazolidin-2-one

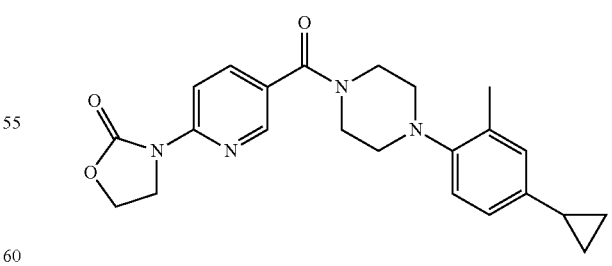

By reaction and treatment in the same manner as in Example 1 and using (6-bromopyridin-3-yl)[4-(4-cyclopropyl-2-methylphenyl)piperazin-1-yl]methanone (260 mg) described in Preparation Example 140 and oxazolidin-2-one (66 mg), the title compound (205 mg) was obtained.
MS(ESI)m/z:407(M+H)$^+$.

Example 243

Synthesis of 3-{5-[4-(2,4-dicyclopropylphenyl)piperazine-1-carbonyl]pyridin-2-yl}oxazolidin-2-one

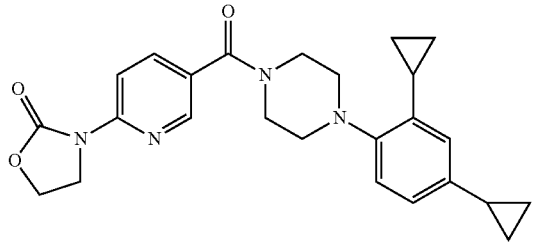

By reaction and treatment in the same manner as in Example 1 and using (6-bromopyridin-3-yl)[4-(2,4-dicyclopropylphenyl)piperazin-1-yl]methanone (500 mg) described in Preparation Example 141 and oxazolidin-2-one (148 mg), the title compound (385 mg) was obtained.
MS(ESI)m/z:433(M+H)$^+$.

Example 244

Synthesis of 3-{5-[4-(2,4-dicyclopropylphenyl)piperazine-1-carbonyl]-4-methylpyridin-2-yl}oxazolidin-2-one

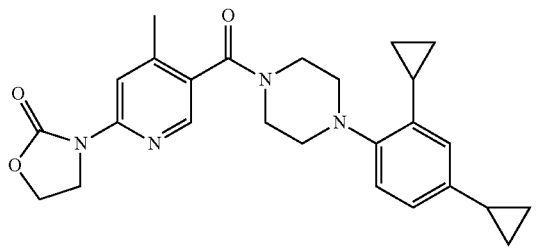 [SMILES: Cc1cc(N2CCOC2=O)ncc1C(=O)N1CCN(c2ncc(C3CC3)cc2C2CC2)CC1]

By reaction and treatment in the same manner as in Example 240 and using [4-(2,4-dicyclopropylphenyl)piperazin-1-yl](6-fluoro-4-methylpyridin-3-yl)methanone (500 mg) described in Preparation Example 142 and oxazolidin-2-one (459 mg), the title compound (190 mg) was obtained.
MS(ESI)m/z:447(M+H)$^+$.

Example 245

Synthesis of (R)-3-{5-[4-(5-cyclopropyl-3-methylpyridin-2-yl)piperazine-1-carbonyl]pyridin-2-yl}-4-hydroxymethyloxazolidin-2-one

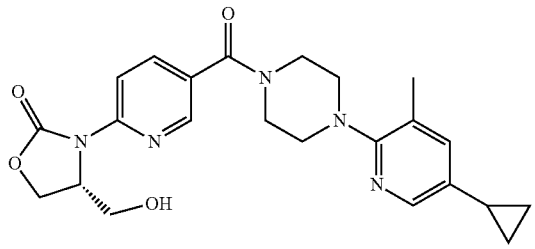 [SMILES: Cc1cc(C2CC2)cnc1N1CCN(C(=O)c2ccc(N3C(=O)OC[C@H]3CO)nc2)CC1]

By reaction and treatment in the same manner as in Example 19 and using (6-bromopyridin-3-yl)[4-(5-cyclopropyl-3-methylpyridin-2-yl)piperazin-1-yl]methanone (500 mg) described in Preparation Example 106 and benzoic acid (R)-2-oxooxazolidin-4-ylmethyl ester (426 mg), the title compound (345 mg) was obtained.
MS(ESI)m/z:438(M+H)$^+$.

Example 246

Synthesis of (R)-3-{5-[4-(3,5-dimethylpyridin-2-yl)piperazine-1-carbonyl]pyridin-2-yl}-4-hydroxymethyloxazolidin-2-one

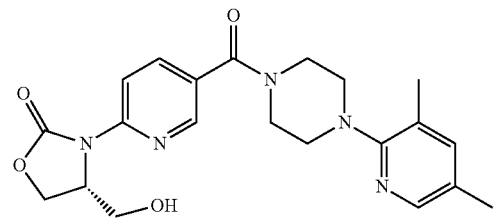 [SMILES: Cc1cnc(N2CCN(C(=O)c3ccc(N4C(=O)OC[C@H]4CO)nc3)CC2)c(C)c1]

By reaction and treatment in the same manner as in Example 19 and using (6-bromopyridin-3-yl)[4-(3,5-dimethylpyridin-2-yl)piperazin-1-yl]methanone (940 mg) described in Preparation Example 73 and benzoic acid (R)-2-oxooxazolidin-4-ylmethyl ester (814 mg), the title compound (660 mg) was obtained.
MS(ESI)m/z:412(M+H)$^+$.

Example 247

Synthesis of (R)-3-{5-[4-(5-cyclopropyl-3-methylpyridin-2-yl)piperazine-1-carbonyl]pyridin-2-yl}-4-methoxymethyloxazolidin-2-one

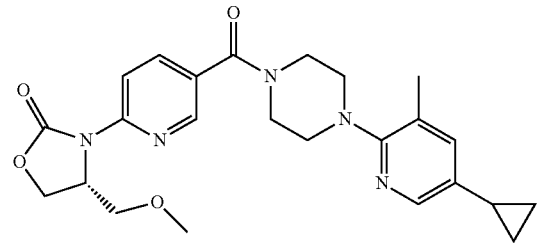 [SMILES: COC[C@@H]1COC(=O)N1c1ccc(C(=O)N2CCN(c3ncc(C4CC4)cc3C)CC2)cn1]

By reaction and treatment in the same manner as in Example 73 and using (R)-3-{5-[4-(5-cyclopropyl-3-methylpyridin-2-yl)piperazine-1-carbonyl]pyridin-2-yl}-4-hydroxymethyloxazolidin-2-one (144 mg) described in Example 245 and methyl iodide (38 μL), the title compound (85 mg) was obtained.
MS(ESI)m/z:452(M+H)$^+$.

Example 248

Synthesis of 3-{5-[4-(2,4,5-trimethylphenyl)piperazine-1-carbonyl]pyridin-2-yl}oxazolidin-2-one

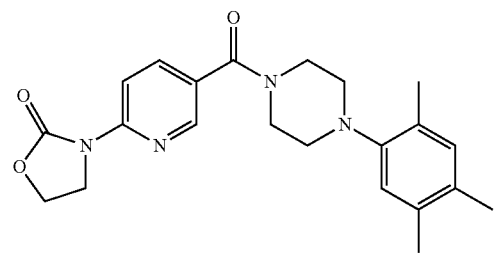 [SMILES: Cc1cc(C)c(N2CCN(C(=O)c3ccc(N4CCOC4=O)nc3)CC2)cc1C]

By reaction and treatment in the same manner as in Example 1 and using (6-bromopyridin-3-yl)[4-(2,4,5-trimethylphenyl)piperazin-1-yl]methanone (430 mg) described in Preparation Example 143 and oxazolidin-2-one (128 mg), the title compound (345 mg) was obtained.
MS(ESI)m/z:395(M+H)$^+$.

Example 249

Synthesis of 3-{5-[4-(3-cyclopropyl-5-methylpyridin-2-yl)piperazine-1-carbonyl]pyridin-2-yl}oxazolidin-2-one

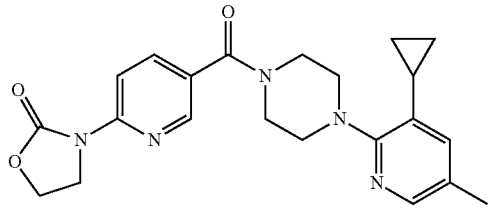 [SMILES: Cc1cnc(N2CCN(C(=O)c3ccc(N4CCOC4=O)nc3)CC2)c(C2CC2)c1]

By reaction and treatment in the same manner as in Example 1 and using (6-bromopyridin-3-yl)[4-(3-cyclopropyl-5-methylpyridin-2-yl)piperazin-1-yl]methanone (170 mg) described in Preparation Example 144 and oxazolidin-2-one (55 mg), the title compound (97 mg) was obtained.
MS(ESI)m/z:408(M+H)⁺.

Example 250

Synthesis of (R)-3-{5-[4-(3,5-dimethylpyridin-2-yl)piperazine-1-carbonyl]pyridin-2-yl}-4-methoxymethyloxazolidin-2-one

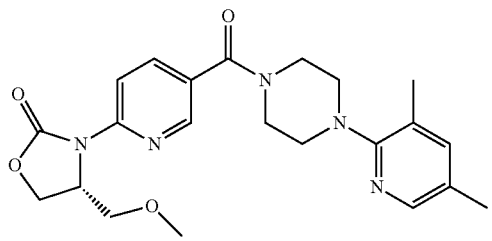 [SMILES: COC[C@@H]1COC(=O)N1c1ccc(C(=O)N2CCN(c3ncc(C)cc3C)CC2)cn1]

By reaction and treatment in the same manner as in Example 73 and using (R)-3-{5-[4-(3,5-dimethylpyridin-2-yl)piperazine-1-carbonyl]pyridin-2-yl}-4-hydroxymethyloxazolidin-2-one (340 mg) described in Example 246 and methyl iodide (62 μL), the title compound (157 mg) was obtained.
MS(ESI)m/z:426(M+H)⁺.

Example 251

Synthesis of (R)-3-{5-[4-(5-ethyl-3-methylpyridin-2-yl)piperazine-1-carbonyl]pyridin-2-yl}-4-hydroxymethyloxazolidin-2-one

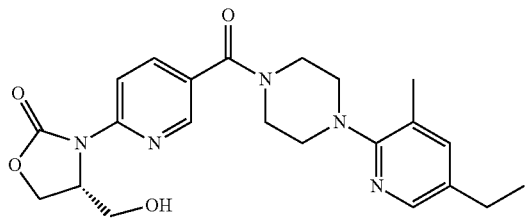 [SMILES: CCc1cnc(N2CCN(C(=O)c3ccc(N4C(=O)OC[C@H]4CO)nc3)CC2)c(C)c1]

By reaction and treatment in the same manner as in Example 19 and using (6-bromopyridin-3-yl)[4-(5-ethyl-3-methylpyridin-2-yl)piperazin-1-yl]methanone (530 mg) described in Preparation Example 145 and benzoic acid (R)-2-oxooxazolidin-4-ylmethyl ester (466 mg), the title compound (315 mg) was obtained.
MS(ESI)m/z:426(M+H)⁺.

Example 252

Synthesis of (R)-3-{5-[4-(3,5-dicyclopropylpyridin-2-yl)piperazine-1-carbonyl]pyridin-2-yl}-4-hydroxymethyloxazolidin-2-one

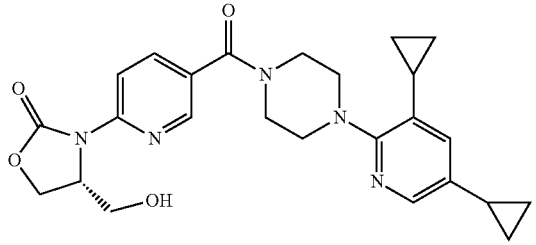 [SMILES: O=C(c1ccc(N2C(=O)OC[C@H]2CO)nc1)N1CCN(c2ncc(C3CC3)cc2C2CC2)CC1]

By reaction and treatment in the same manner as in Example 19 and using (6-bromopyridin-3-yl)[4-(3,5-dicyclopropylpyridin-2-yl)piperazin-1-yl]methanone (880 mg) described in Preparation Example 112 and benzoic acid (R)-2-oxooxazolidin-4-ylmethyl ester (650 mg), the title compound (510 mg) was obtained.
MS(ESI)m/z:464(M+H)⁺.

Example 253

Synthesis of (R)-3-{5-[4-(3,5-dicyclopropylpyridin-2-yl)piperazine-1-carbonyl]pyridin-2-yl}-4-methoxymethyloxazolidin-2-one

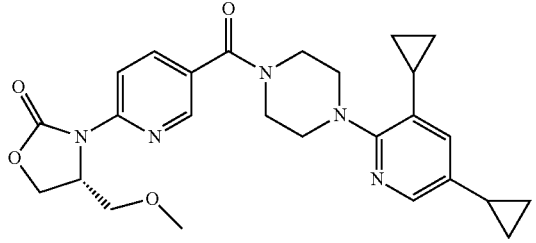 [SMILES: COC[C@@H]1COC(=O)N1c1ccc(C(=O)N2CCN(c3ncc(C4CC4)cc3C3CC3)CC2)cn1]

By reaction and treatment in the same manner as in Example 73 and using (R)-3-{5-[4-(3,5-dicyclopropylpyridin-2-yl)piperazine-1-carbonyl]pyridin-2-yl}-4-hydroxymethyloxazolidin-2-one (310 mg) described in Example 252 and methyl iodide (50 μL), the title compound (85 mg) was obtained.
MS(ESI)m/z:478(M+H)⁺.

Example 254

Synthesis of (R)-4-hydroxymethyl-3-{5-[4-(3,5,6-trimethylpyridin-2-yl)piperazine-1-carbonyl]pyridin-2-yl}oxazolidin-2-one

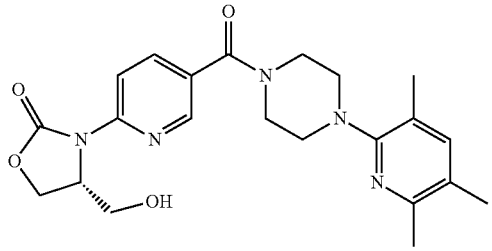 [SMILES: Cc1cc(C)c(N2CCN(C(=O)c3ccc(N4C(=O)OC[C@H]4CO)nc3)CC2)nc1C]

By reaction and treatment in the same manner as in Example 19 and using (6-bromopyridin-3-yl)[4-(3,5,6-trimethylpyridin-2-yl)piperazin-1-yl]methanone (540 mg) described in Preparation Example 146 and benzoic acid (R)-2-oxooxazolidin-4-ylmethyl ester (474 mg), the title compound (295 mg) was obtained.
MS(ESI)m/z:426(M+H)⁺.

Example 255

Synthesis of (R)-4-methoxymethyl-3-{5-[4-(3,5,6-trimethylpyridin-2-yl)piperazine-1-carbonyl]pyridin-2-yl}oxazolidin-2-one

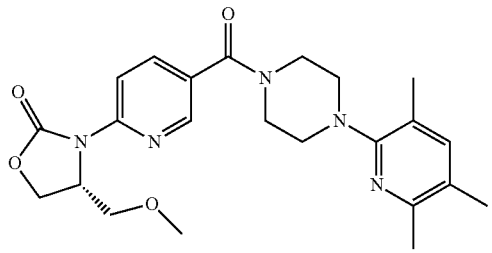 [SMILES: COC[C@@H]1COC(=O)N1c1ccc(C(=O)N2CCN(c3nc(C)c(C)cc3C)CC2)cn1]

By reaction and treatment in the same manner as in Example 73 and using (R)-4-hydroxymethyl-3-{5-[4-(3,5,6-trimethylpyridin-2-yl)piperazine-1-carbonyl]pyridin-2-yl}oxazolidin-2-one (200 mg) described in Example 254 and methyl iodide (35 μL), the title compound (158 mg) was obtained.
MS(ESI)m/z:440(M+H)+.

Example 256

Synthesis of 3-{5-[4-(5-cyclopropyl-3-methylpyridin-2-yl)piperazine-1-carbonyl]-3-methylpyridin-2-yl}-oxazolidin-2-one

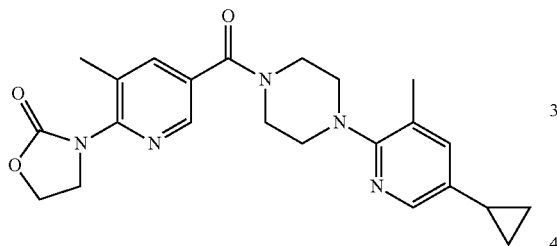

By reaction and treatment in the same manner as in Example 240 and using [4-(5-cyclopropyl-3-methylpyridin-2-yl)piperazin-1-yl](6-fluoro-5-methylpyridin-3-yl)methanone (500 mg) described in Preparation Example 147 and oxazolidin-2-one (246 mg), the title compound (201 mg) was obtained.
MS(ESI)m/z:422(M+H)+.

Example 257

Synthesis of 3-{5-[4-(3,5-dimethylpyridin-2-yl)piperazine-1-carbonyl]-3-methylpyridin-2-yl}-oxazolidin-2-one

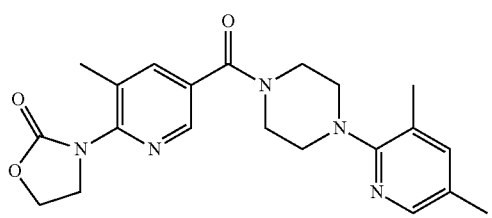

By reaction and treatment in the same manner as in Example 240 and using [4-(3,5-dimethylpyridin-2-yl)piperazin-1-yl](6-fluoro-5-methylpyridin-3-yl)methanone (529 mg) described in Preparation Example 148 and oxazolidin-2-one (281 mg), the title compound (245 mg) was obtained.
MS(ESI)m/z:396(M+H)+.

Example 258

Synthesis of (R)-3-{5-[4-(5-cyclopropyl-3-methylpyridin-2-yl)piperazine-1-carbonyl]-3-methylpyridin-2-yl}-4-methyloxazolidin-2-one 2hydrochloride

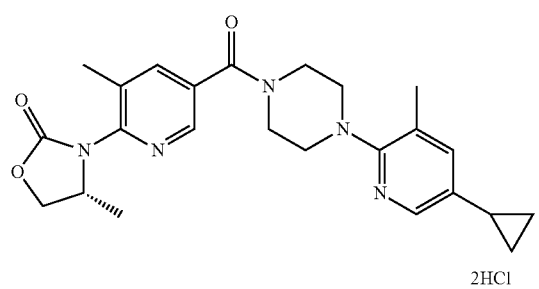 [SMILES: Cc1cc(C2CC2)cnc1N1CCN(C(=O)c2cnc(N3C(=O)OC[C@H]3C)c(C)c2)CC1]

2HCl

By reaction and treatment in the same manner as in Example 236 and using [4-(5-cyclopropyl-3-methylpyridin-2-yl)piperazin-1-yl](6-fluoro-5-methylpyridin-3-yl)methanone (529 mg) described in Preparation Example 147 and (R)-4-methyloxazolidin-2-one (376 mg) described in Preparation Example 25, the title compound (272 mg) was obtained.
MS(ESI)m/z:436(M+H)+.

Example 259

Synthesis of (R)-3-{5-[4-(5-ethyl-3-methylpyridin-2-yl)piperazine-1-carbonyl]-3-methylpyridin-2-yl}-4-methyloxazolidin-2-one

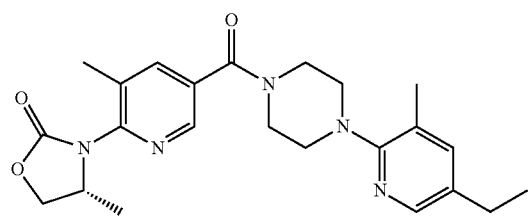 [SMILES: CCc1cnc(N2CCN(C(=O)c3cnc(N4C(=O)OC[C@H]4C)c(C)c3)CC2)c(C)c1]

By reaction and treatment in the same manner as in Example 240 and using [4-(5-ethyl-3-methylpyridin-2-yl)piperazin-1-yl](6-fluoro-5-methylpyridin-3-yl)methanone (440 mg) described in Preparation Example 149 and (R)-4-methyloxazolidin-2-one (261 mg) described in Preparation Example 25, the title compound (173 mg) was obtained.
MS(ESI)m/z:424(M+H)+.

Example 260

Synthesis of (R)-3-{5-[4-(3,5-dimethylpyridin-2-yl)piperazine-1-carbonyl]-3-methylpyridin-2-yl}-4-methyloxazolidin-2-one

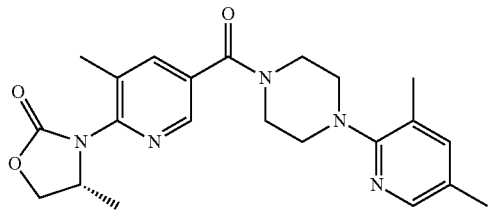 [SMILES: Cc1cnc(N2CCN(C(=O)c3cnc(N4C(=O)OC[C@H]4C)c(C)c3)CC2)c(C)c1]

By reaction and treatment in the same manner as in Example 240 and using [4-(3,5-dimethylpyridin-2-yl)piperazin-1-yl](6-fluoro-5-methylpyridin-3-yl)methanone (720 mg) described in Preparation Example 148 and (R)-4-methyloxazolidin-2-one (443 mg) described in Preparation Example 25, the title compound (161 mg) was obtained.
MS(ESI)m/z:410(M+H)+.

Example 261

Synthesis of 3-{6-[4-(3,5-dimethylpyridin-2-yl)piperazine-1-carbonyl]pyridin-3-yl}oxazolidin-2-one

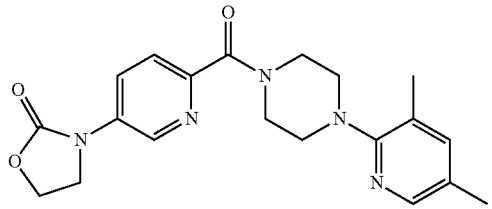 [SMILES: Cc1cnc(N2CCN(C(=O)c3ccc(N4CCOC4=O)cn3)CC2)c(C)c1]

By reaction and treatment in the same manner as in Example 1 and using (5-bromopyridin-2-yl)[4-(3,5-dimethylpyridin-2-yl)piperazin-1-yl]methanone (375 mg) described in Preparation Example 150 and oxazolidin-2-one (96 mg), the title compound (190 mg) was obtained.
MS(ESI)m/z:382(M+H)+.

Example 262

Synthesis of 3-{6-[4-(5-cyclopropyl-3-methylpyridin-2-yl)piperazine-1-carbonyl]pyridin-3-yl}oxazolidin-2-one

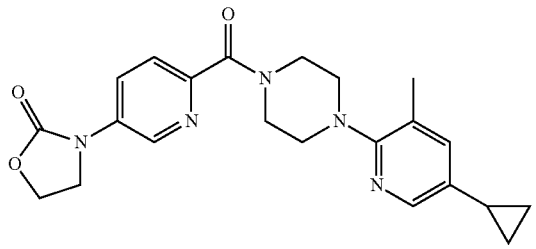 [SMILES: Cc1cc(C2CC2)cnc1N1CCN(C(=O)c2ccc(N3CCOC3=O)cn2)CC1]

By reaction and treatment in the same manner as in Example 1 and using (5-bromopyridin-2-yl)[4-(5-cyclopropyl-3-methylpyridin-2-yl)piperazin-1-yl]methanone (380 mg) described in Preparation Example 151 and oxazolidin-2-one (91 mg), the title compound (217 mg) was obtained.
MS(ESI)m/z:408(M+H)+.

Example 263

Synthesis of (R)-3-{6-[4-(5-cyclopropyl-3-methylpyridin-2-yl)piperazine-1-carbonyl]pyridin-3-yl}-4-methyloxazolidin-2-one

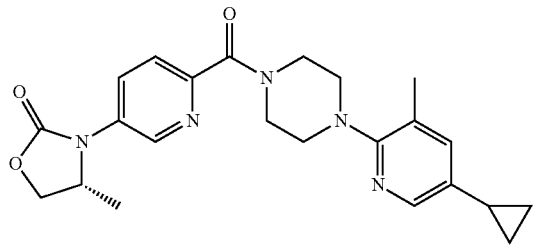 [SMILES: Cc1cc(C2CC2)cnc1N1CCN(C(=O)c2ccc(N3C(=O)OC[C@H]3C)cn2)CC1]

By reaction and treatment in the same manner as in Example 1 and using (5-bromopyridin-2-yl)[4-(5-cyclopropyl-3-methylpyridin-2-yl)piperazin-1-yl]methanone (350 mg) described in Preparation Example 151 and (R)-4-methyloxazolidin-2-one (97 mg) described in Preparation Example 25, the title compound (197 mg) was obtained.
MS(ESI)m/z:422(M+H)+.

Example 264

Synthesis of (R)-3-{6-[4-(3,5-dimethylpyridin-2-yl)piperazine-1-carbonyl]pyridin-3-yl}-4-methyloxazolidin-2-one

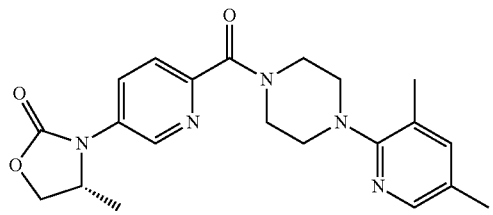 [SMILES: Cc1cnc(N2CCN(C(=O)c3ccc(N4C(=O)OC[C@H]4C)cn3)CC2)c(C)c1]

By reaction and treatment in the same manner as in Example 1 and using (5-bromopyridin-2-yl)[4-(3,5-dimethylpyridin-2-yl)piperazin-1-yl]methanone (375 mg) described in Preparation Example 150 and (R)-4-methyloxazolidin-2-one (111 mg) described in Preparation Example 25, the title compound (88 mg) was obtained.
MS(ESI)m/z:396(M+H)+.

Example 265

Synthesis of (R)-3-{5-[4-(4-cyclopropylphenoxy)piperidine-1-carbonyl]pyridin-2-yl}-4-methyloxazolidin-2-one

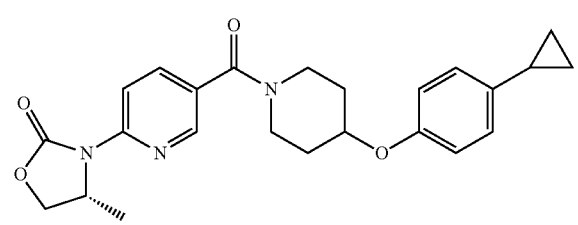 [SMILES: C[C@@H]1COC(=O)N1c1ccc(C(=O)N2CCC(Oc3ccc(C4CC4)cc3)CC2)cn1]

By reaction and treatment in the same manner as in Example 1 and using (6-bromopyridin-3-yl)[4-(4-cyclopropylphenoxy)piperidin-1-yl]methanone (401 mg) described in Preparation Example 152 and (R)-4-methyloxazolidin-2-one (111 mg) described in Preparation Example 25, the title compound (252 mg) was obtained.
MS(ESI)m/z:422(M+H)⁺.

Example 266

Synthesis of 3-{4-[4-(3,5-dicyclopropylpyridin-2-yl)piperazine-1-carbonyl]phenyl}-5,5-dimethyloxazolidin-2-one

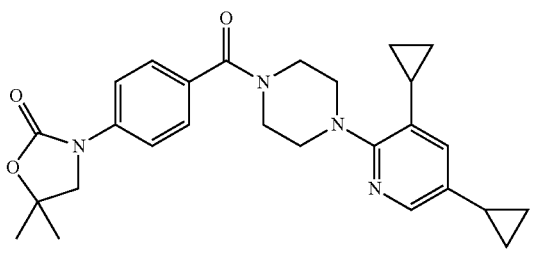 [SMILES: CC1(C)CN(c2ccc(C(=O)N3CCN(c4ncc(C5CC5)cc4C4CC4)CC3)cc2)C(=O)O1]

By reaction and treatment in the same manner as in Example 110 and using [4-(3,5-dicyclopropylpyridin-2-yl)piperazin-1-yl](4-iodophenyl)methanone (473 mg) described in Preparation Example 95 and 5,5-dimethyloxazolin-2-one (138 mg) described in Preparation Example 43, the title compound (131 mg) was obtained.
MS(ESI)m/z:461(M+H)⁺.

Example 267

Synthesis of 3-{4-[4-(5-cyclopropyl-3-methylpyridin-2-yl)piperazine-1-carbonyl]phenyl}-5,5-dimethyloxazolidin-2-one

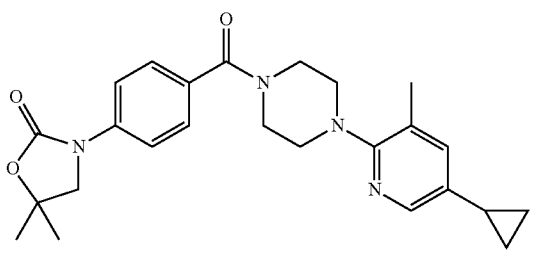 [SMILES: Cc1cc(C2CC2)cnc1N1CCN(C(=O)c2ccc(N3CC(C)(C)OC3=O)cc2)CC1]

By reaction and treatment in the same manner as in Example 110 and using [4-(5-cyclopropyl-3-methylpyridin-2-yl)piperazin-1-yl](4-iodophenyl)methanone (447 mg) described in Preparation Example 97 and 5,5-dimethyloxazolin-2-one (138 mg) described in Preparation Example 43, the title compound (123 mg) was obtained.
MS(ESI)m/z:435(M+H)⁺.

Example 268

Synthesis of (R)-3-{4-[4-(3,5-dichloropyridin-2-yl)piperazine-1-carbonyl]phenyl}-4-methoxymethyloxazolidin-2-one

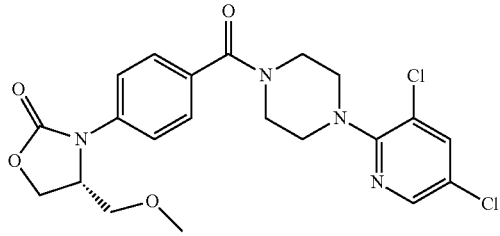 [SMILES: COC[C@@H]1COC(=O)N1c1ccc(C(=O)N2CCN(c3ncc(Cl)cc3Cl)CC2)cc1]

By reaction and treatment in the same manner as in Example 147 and using (R)-4-methoxymethyl-3-[4-(piperazine-1-carbonyl)phenyl]oxazolidin-2-one (473 mg) described in Preparation Example 165 and 2,3,5-trichloropyridine (405 mg), the title compound (455 mg) was obtained.
MS(ESI)m/z:465(M+H)⁺.

Example 269

Synthesis of (R)-3-{4-[4-(3,5-dicyclopropylpyridin-2-yl)piperazine-1-carbonyl]phenyl}-4-methoxymethyloxazolidin-2-one

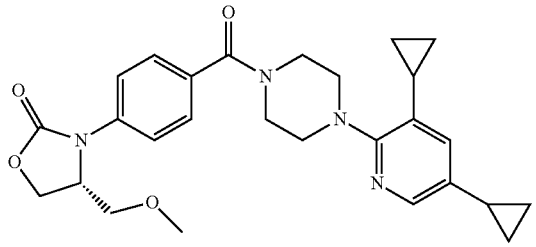 [SMILES: COC[C@@H]1COC(=O)N1c1ccc(C(=O)N2CCN(c3ncc(C4CC4)cc3C3CC3)CC2)cc1]

By reaction and treatment in the same manner as in Preparation Example 186 and using (R)-3-{4-[4-(3,5-dichloropyridin-2-yl)piperazine-1-carbonyl]phenyl}-4-methoxymethyloxazolidin-2-one (410 mg) described in Example 268 and cyclopropylboronic acid (227 mg), the title compound (215 mg) was obtained.
MS(ESI)m/z:477(M+H)⁺.

Example 270

Synthesis of 3-{4-[4-(3,5,6-trimethylpyridin-2-yl)piperazine-1-carbonyl]phenyl}oxazolidin-2-one

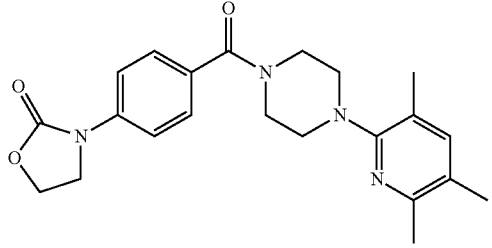 [SMILES: Cc1cc(C)c(N2CCN(C(=O)c3ccc(N4CCOC4=O)cc3)CC2)nc1C]

By reaction and treatment in the same manner as in Example 149 and using (4-iodophenyl)[4-(3,5,6-trimethylpyridin-2-yl)piperazin-1-yl]methanone (435 mg) described in Preparation Example 176 and oxazolin-2-one (104 mg), the title compound (118 mg) was obtained.
MS(ESI)m/z:395(M+H)⁺.

Example 271

Synthesis of (R)-4-ethyl-3-{4-[4-(3,5,6-trimethylpyridin-2-yl)piperazine-1-carbonyl]phenyl}oxazolidin-2-one

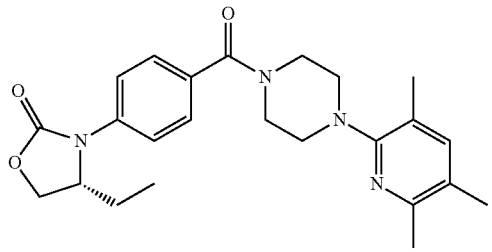 [SMILES: CC[C@@H]1COC(=O)N1c1ccc(C(=O)N2CCN(c3nc(C)c(C)cc3C)CC2)cc1]

By reaction and treatment in the same manner as in Example 149 and using (4-iodophenyl)[4-(3,5,6-trimethylpyridin-2-yl)piperazin-1-yl]methanone (435 mg) described in Preparation Example 176 and (R)-4-ethyloxazolidin-2-one (138 mg) described in Preparation Example 26, the title compound (326 mg) was obtained.
MS(ESI)m/z:423(M+H)$^+$.

Example 272

Synthesis of (S)-5-methyl-3-{4-[4-(3,5,6-trimethylpyridin-2-yl)piperazine-1-carbonyl]phenyl}oxazolidin-2-one

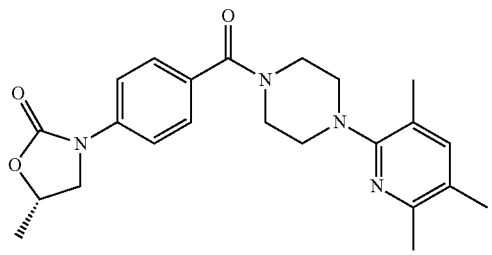 [SMILES: Cc1cc(C)c(N2CCN(C(=O)c3ccc(N4C[C@H](C)OC4=O)cc3)CC2)nc1C]

By reaction and treatment in the same manner as in Example 149 and using (4-iodophenyl)[4-(3,5,6-trimethylpyridin-2-yl)piperazin-1-yl]methanone (435 mg) described in Preparation Example 176 and (S)-5-methyloxazolidin-2-one (121 mg) described in Preparation Example 42, the title compound (308 mg) was obtained.
MS(ESI)m/z:409(M+H)$^+$.

Example 273

Synthesis of 5,5-dimethyl-3-{4-[4-(3,5,6-trimethylpyridin-2-yl)piperazine-1-carbonyl]phenyl}oxazolidin-2-one

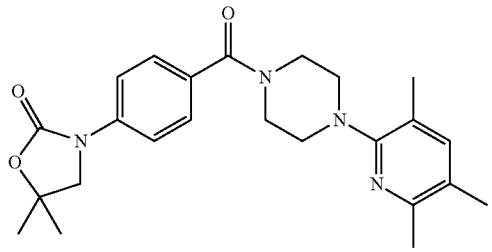 [SMILES: Cc1cc(C)c(N2CCN(C(=O)c3ccc(N4CC(C)(C)OC4=O)cc3)CC2)nc1C]

By reaction and treatment in the same manner as in Example 110 and using (4-iodophenyl)[4-(3,5,6-trimethylpyridin-2-yl)piperazin-1-yl]methanone (579 mg) described in Preparation Example 176 and 5,5-dimethyloxazolidin-2-one (153 mg) described in Preparation Example 43, the title compound (143 mg) was obtained.
MS(ESI)m/z:423(M+H)$^+$.

Example 274

Synthesis of (R)-3-{4-[4-(3,5-dichloropyridin-2-yl)piperazine-1-carbonyl]-3-fluorophenyl}-4-methoxymethyloxazolidin-2-one

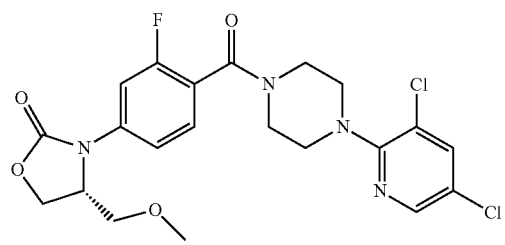 [SMILES: COC[C@@H]1COC(=O)N1c1ccc(C(=O)N2CCN(c3ncc(Cl)cc3Cl)CC2)c(F)c1]

By reaction and treatment in the same manner as in Example 147 and using (R)-3-[3-fluoro-4-(piperazine-1-carbonyl)phenyl]-4-methoxymethyloxazolidin-2-one (875 mg) described in Preparation Example 158 and 2,3,5-trichloropyridine (945 mg), the title compound (746 mg) was obtained.
MS(ESI)m/z:483(M+H)$^+$.

Example 275

Synthesis of (R)-3-{4-[4-(3,5-dicyclopropylpyridin-2-yl)piperazine-1-carbonyl]-3-fluorophenyl}-4-methoxymethyloxazolidin-2-one

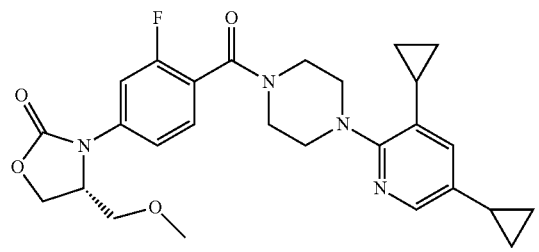 [SMILES: COC[C@@H]1COC(=O)N1c1ccc(C(=O)N2CCN(c3ncc(C4CC4)cc3C3CC3)CC2)c(F)c1]

By reaction and treatment in the same manner as in Preparation Example 186 and using (R)-3-{4-[4-(3,5-dichloropyridin-2-yl)piperazine-1-carbonyl]-3-fluorophenyl}-4-methoxymethyloxazolidin-2-one (409 mg) described in Example 274 and cyclopropylboronic acid (291 mg), the title compound (215 mg) was obtained.
MS(ESI)m/z:495(M+H)$^+$.

Example 276

Synthesis of (R)-3-{4-[4-(3,5-dimethylpyridin-2-yl)piperazine-1-carbonyl]-3-fluorophenyl}-4-methoxymethyloxazolidin-2-one

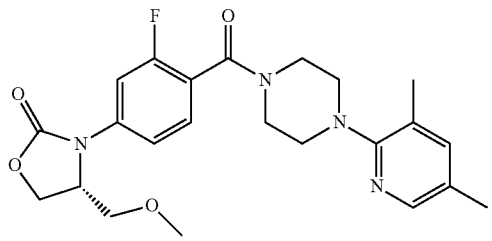 [SMILES: COC[C@@H]1COC(=O)N1c1ccc(C(=O)N2CCN(c3ncc(C)cc3C)CC2)c(F)c1]

By reaction and treatment in the same manner as in Preparation Example 182 and using (R)-3-{4-[4-(3,5-dichloropyridin-2-yl)piperazine-1-carbonyl]-3-fluorophenyl}-4-methoxymethyloxazolidin-2-one (300 mg) described in Example 274 and methylboronic acid (148 mg), the title compound (226 mg) was obtained.
MS(ESI)m/z:443(M+H)+.

Example 277

Synthesis of (R)-4-methoxymethyl-3-{4-[4-(3,5,6-trichloropyridin-2-yl)piperazine-1-carbonyl]phenyl}oxazolidin-2-one

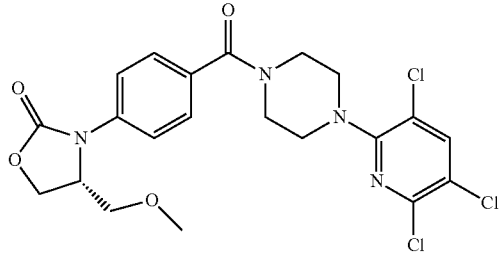 [SMILES: COC[C@@H]1COC(=O)N1c1ccc(C(=O)N2CCN(c3nc(Cl)c(Cl)cc3Cl)CC2)cc1]

By reaction and treatment in the same manner as in Example 147 and using (R)-4-methoxymethyl-3-[4-(piperazine-1-carbonyl)phenyl]oxazolidin-2-one (972 mg) described in Preparation Example 165 and 2,3,5,6-tetrachloropyridine (990 mg), the title compound (1.25 g) was obtained.
MS(ESI)m/z:499(M+H)+.

Example 278

Synthesis of (R)-4-methoxymethyl-3-{4-[4-(3,5,6-trimethylpyridin-2-yl)piperazine-1-carbonyl]phenyl}-oxazolidin-2-one

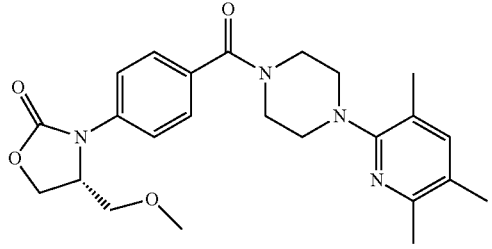 [SMILES: COC[C@@H]1COC(=O)N1c1ccc(C(=O)N2CCN(c3nc(C)c(C)cc3C)CC2)cc1]

By reaction and treatment in the same manner as in Preparation Example 182 and using (R)-4-methoxymethyl-3-{4-[4-(3,5,6-trichloropyridin-2-yl)piperazine-1-carbonyl]phenyl}oxazolidin-2-one (600 mg) described in Example 277 and methylboronic acid (431 mg), the title compound (459 mg) was obtained.
MS(ESI)m/z:439(M+H)+.

Example 279

Synthesis of (R)-4-benzoyloxymethyl-3-{4-[4-(3,5-dicyclopropylpyridin-2-yl)piperazine-1-carbonyl]phenyl}oxazolidin-2-one

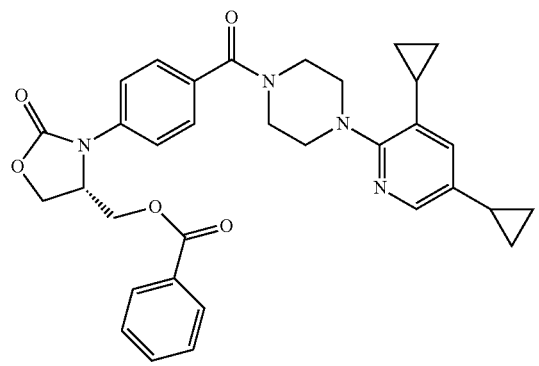 [SMILES: O=C(OC[C@@H]1COC(=O)N1c1ccc(C(=O)N2CCN(c3ncc(C4CC4)cc3C3CC3)CC2)cc1)c1ccccc1]

By reaction and treatment in the same manner as in Example 149 and using [4-(3,5-dicyclopropylpyridin-2-yl)piperazin-1-yl](4-iodophenyl)methanone (1.42 g) described in Preparation Example 95 and benzoic acid (R)-2-oxooxazolidin-4-ylmethyl ester (664 mg), the title compound (1.53 g) was obtained.
MS(ESI)m/z:567(M+H)+.

Example 280

Synthesis of (R)-3-{4-[4-(3,5-dicyclopropylpyridin-2-yl)piperazine-1-carbonyl]phenyl}-4-hydroxymethyloxazolidin-2-one

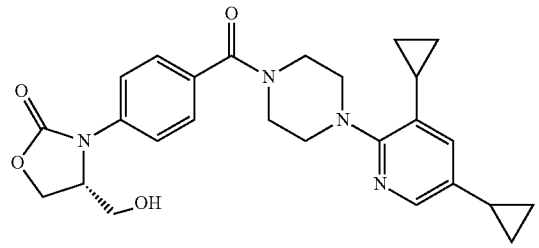

By reaction and treatment in the same manner as in Preparation Example 92 and using (R)-4-benzoyloxymethyl-3-{4-[4-(3,5-dicyclopropylpyridin-2-yl)piperazine-1-carbonyl]phenyl}oxazolidin-2-one (1.48 g) described in Example 279, the title compound (1.05 g) was obtained.
MS(ESI)m/z:463(M+H)+.

Example 281

Synthesis of (R)-3-{3-fluoro-4-[4-(3,5,6-trichloropyridin-2-yl)piperazine-1-carbonyl]phenyl}-4-methoxymethyloxazolidin-2-one

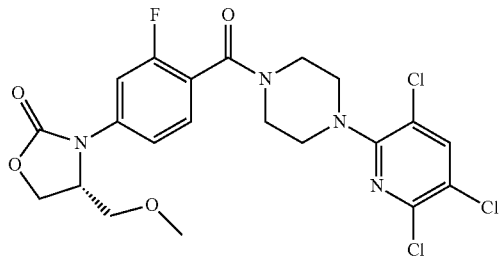 [SMILES: COC[C@@H]1COC(=O)N1c1ccc(C(=O)N2CCN(c3nc(Cl)c(Cl)cc3Cl)CC2)c(F)c1]

By reaction and treatment in the same manner as in Example 147 and using (R)-3-[3-fluoro-4-(piperazine-1-carbonyl)phenyl]-4-methoxymethyloxazolidin-2-one (405 mg) described in Preparation Example 158 and 2,3,5,6-tetrachloropyridine (390 mg), the title compound (452 mg) was obtained.
MS(ESI)m/z:519(M+H)$^+$.

Example 282

Synthesis of (R)-3-{3-fluoro-4-[4-(3,5,6-trimethylpyridin-2-yl)piperazine-1-carbonyl]-phenyl}-4-methoxymethyloxazolidin-2-one

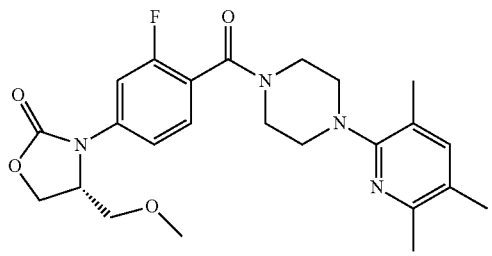 [SMILES: COC[C@@H]1COC(=O)N1c1ccc(C(=O)N2CCN(c3nc(C)c(C)cc3C)CC2)c(F)c1]

By reaction and treatment in the same manner as in Preparation Example 182 and using (R)-3-{3-fluoro-4-[4-(3,5,6-trichloropyridin-2-yl)piperazine-1-carbonyl]phenyl}-4-methoxymethyloxazolidin-2-one (454 mg) described in Example 281 and methylboronic acid (315 mg), the title compound (339 mg) was obtained.
MS(ESI)m/z:457(M+H)$^+$.

Example 283

Synthesis of (R)-4-ethoxymethyl-3-{4-[4-(3,5,6-trichloropyridin-2-yl)piperazine-1-carbonyl]phenyl}oxazolidin-2-one

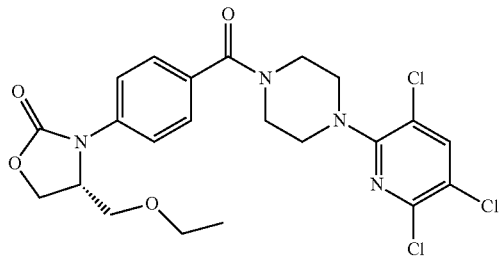 [SMILES: CCOC[C@@H]1COC(=O)N1c1ccc(C(=O)N2CCN(c3nc(Cl)c(Cl)cc3Cl)CC2)cc1]

By reaction and treatment in the same manner as in Example 147 and using (R)-4-ethoxymethyl-3-[4-(piperazine-1-carbonyl)phenyl]oxazolidin-2-one (500 mg) described in Preparation Example 167 and 2,3,5,6-tetrachloropyridine (488 mg), the title compound (651 mg) was obtained.
MS(ESI)m/z:513(M+H)$^+$.

Example 284

Synthesis of (R)-3-{4-[4-(3,5-dichloropyridin-2-yl)piperazine-1-carbonyl]phenyl}-4-ethoxymethyloxazolidin-2-one

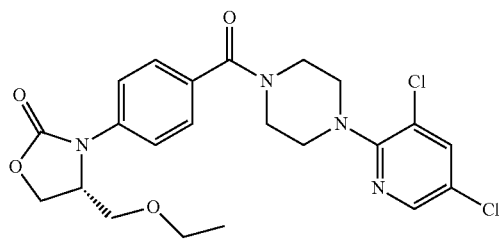 [SMILES: CCOC[C@@H]1COC(=O)N1c1ccc(C(=O)N2CCN(c3ncc(Cl)cc3Cl)CC2)cc1]

By reaction and treatment in the same manner as in Example 147 and using (R)-4-ethoxymethyl-3-[4-(piperazine-1-carbonyl)phenyl]oxazolidin-2-one (1.39 g) described in Preparation Example 167 and 2,3,5-trichloropyridine (1.53 g), the title compound (1.19 g) was obtained.
MS(ESI)m/z:479(M+H)$^+$.

Example 285

Synthesis of (R)-4-ethoxymethyl-3-{4-[4-(3,5,6-trimethylpyridin-2-yl)piperazine-1-carbonyl]phenyl}oxazolidin-2-one

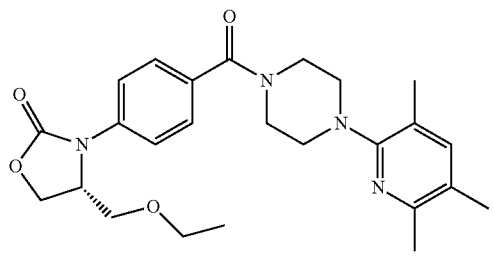 [SMILES: CCOC[C@@H]1COC(=O)N1c1ccc(C(=O)N2CCN(c3nc(C)c(C)cc3C)CC2)cc1]

By reaction and treatment in the same manner as in Preparation Example 182 and using (R)-4-ethoxymethyl-3-{4-[4-(3,5,6-trichloropyridin-2-yl)piperazine-1-carbonyl]phenyl}oxazolidin-2-one (565 mg) described in Example 283 and methylboronic acid (395 mg), the title compound (429 mg) was obtained.
MS(ESI)m/z:453(M+H)$^+$.

Example 286

Synthesis of (R)-4-ethoxymethyl-3-{3-fluoro-4-[4-(3,5,6-trichloropyridin-2-yl)piperazine-1-carbonyl]phenyl}oxazolidin-2-one

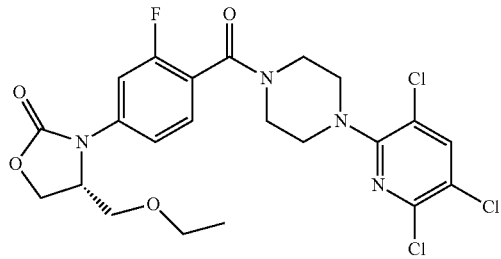 [SMILES: CCOC[C@@H]1COC(=O)N1c1ccc(C(=O)N2CCN(c3nc(Cl)c(Cl)cc3Cl)CC2)c(F)c1]

By reaction and treatment in the same manner as in Example 147 and using (R)-4-ethoxymethyl-3-[3-fluoro-4-(piperazine-1-carbonyl)phenyl]oxazolidin-2-one (387 mg)

Example 287

Synthesis of (R)-4-ethoxymethyl-3-{3-fluoro-4-[4-(3,5,6-trimethylpyridin-2-yl)piperazine-1-carbonyl]phenyl}oxazolidin-2-one

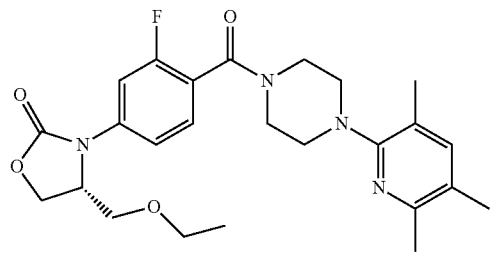 [SMILES: CCOC[C@@H]1COC(=O)N1c1ccc(C(=O)N2CCN(c3nc(C)c(C)cc3C)CC2)c(F)c1]

By reaction and treatment in the same manner as in Preparation Example 182 and using (R)-4-ethoxymethyl-3-{3-fluoro-4-[4-(3,5,6-trichloropyridin-2-yl)piperazine-1-carbonyl]phenyl}oxazolidin-2-one (425 mg) described in Example 286 and methylboronic acid (287 mg), the title compound (310 mg) was obtained.
MS(ESI)m/z:471(M+H)$^+$.

Example 288

Synthesis of (R)-3-{4-[4-(3,5-dimethylpyridin-2-yl)piperazine-1-carbonyl]phenyl}-4-ethoxymethyloxazolidin-2-one

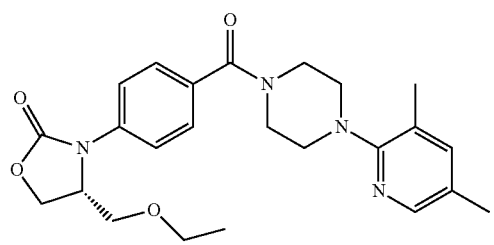 [SMILES: CCOC[C@@H]1COC(=O)N1c1ccc(C(=O)N2CCN(c3ncc(C)cc3C)CC2)cc1]

By reaction and treatment in the same manner as in Preparation Example 182 and using (R)-3-{4-[4-(3,5-dichloropyridin-2-yl)piperazine-1-carbonyl]phenyl}-4-ethoxymethyloxazolidin-2-one (431 mg) described in Example 284 and methylboronic acid (323 mg), the title compound (365 mg) was obtained.
MS (ESI)m/z:439(M+H)$^+$.

Example 289

Synthesis of (R)-3-{4-[4-(3,5-dicyclopropylpyridin-2-yl)piperazine-1-carbonyl]phenyl}-4-ethoxymethyloxazolidin-2-one

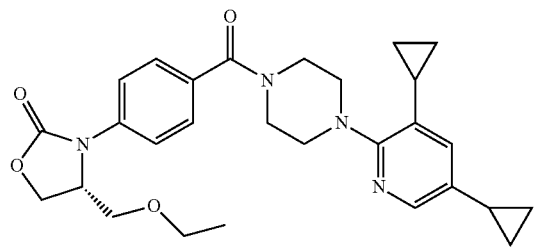

By reaction and treatment in the same manner as in Preparation Example 186 and using (R)-3-{4-[4-(3,5-dichloropyridin-2-yl)piperazine-1-carbonyl]phenyl}-4-ethoxymethyloxazolidin-2-one (678 mg) described in Example 284 and cyclopropylboronic acid (486 mg), the title compound (389 mg) was obtained.
MS(ESI)m/z:491(M+H)$^+$.

Example 290

Synthesis of (R)-3-{4-[4-(3,5-dichloropyridin-2-yl)piperazine-1-carbonyl]-3-fluorophenyl}-4-ethoxymethyloxazolidin-2-one

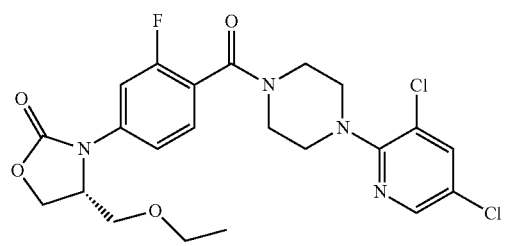 [SMILES: CCOC[C@@H]1COC(=O)N1c1ccc(C(=O)N2CCN(c3ncc(Cl)cc3Cl)CC2)c(F)c1]

By reaction and treatment in the same manner as in Example 147 and using (R)-4-ethoxymethyl-3-[3-fluoro-4-(piperazine-1-carbonyl)phenyl]oxazolidin-2-one (1.23 g) described in Preparation Example 160 and 2,3,5-trichloropyridine (1.28 g), the title compound (1.16 g) was obtained.
MS(ESI)m/z:497(M+H)$^+$.

Example 291

Synthesis of (R)-3-{4-[4-(3,5-dimethylpyridin-2-yl)piperazine-1-carbonyl]-3-fluorophenyl}-4-ethoxymethyloxazolidin-2-one

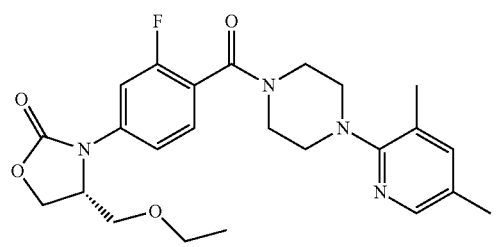 [SMILES: CCOC[C@@H]1COC(=O)N1c1ccc(C(=O)N2CCN(c3ncc(C)cc3C)CC2)c(F)c1]

By reaction and treatment in the same manner as in Preparation Example 182 and using (R)-3-{4-[4-(3,5-dichloropyridin-2-yl)piperazine-1-carbonyl]-3-fluorophenyl}-4-ethoxymethyloxazolidin-2-one (423 mg) described in Example 290 and methylboronic acid (204 mg), the title compound (340 mg) was obtained.
MS(ESI)m/z:457(M+H)$^+$.

Example 292

Synthesis of (R)-3-{4-[4-(3,5-dicyclopropylpyridin-2-yl)piperazine-1-carbonyl]-3-fluorophenyl}-4-ethoxymethyloxazolidin-2-one

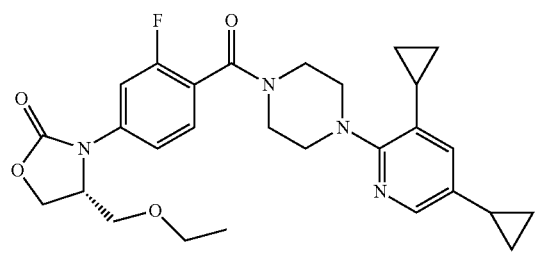 [SMILES: CCOC[C@@H]1COC(=O)N1c1ccc(C(=O)N2CCN(c3ncc(C4CC4)cc3C3CC3)CC2)c(F)c1]

By reaction and treatment in the same manner as in Preparation Example 186 and using (R)-3-{4-[4-(3,5-dichloropyridin-2-yl)piperazine-1-carbonyl]-3-fluorophenyl}-4-ethoxymethyloxazolidin-2-one (647 mg) described in Example 290 and cyclopropylboronic acid (447 mg), the title compound (364 mg) was obtained.

MS(ESI)m/z:509(M+H)⁺.

Example 293

Synthesis of (R)-4-benzoyloxymethyl-3-{4-[4-(3,5,6-trimethylpyridin-2-yl)piperazine-1-carbonyl]phenyl}oxazolidin-2-one

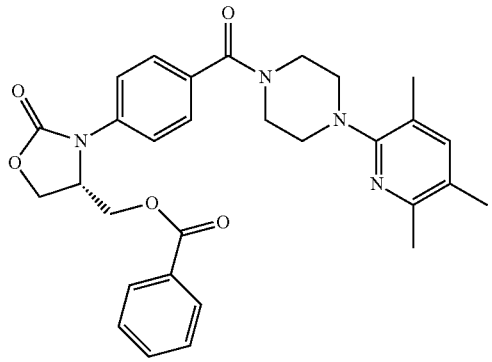 [SMILES: Cc1cc(C)c(N2CCN(C(=O)c3ccc(N4C(=O)OC[C@H]4COC(=O)c4ccccc4)cc3)CC2)nc1C]

By reaction and treatment in the same manner as in Preparation Example 91 and using (4-iodophenyl)[4-(3,5,6-trimethylpyridin-2-yl)piperazin-1-yl]methanone (2.18 g) described in Preparation Example 176 and benzoic acid (R)-2-oxooxazolidin-4-ylmethyl ester (1.11 g), the title compound (2.56 g) was obtained.

MS (ESI) m/z:529(M+H)⁺.

Example 294

Synthesis of (R)-4-hydroxymethyl-3-{4-[4-(3,5,6-trimethylpyridin-2-yl)piperazine-1-carbonyl]phenyl}-oxazolidin-2-one

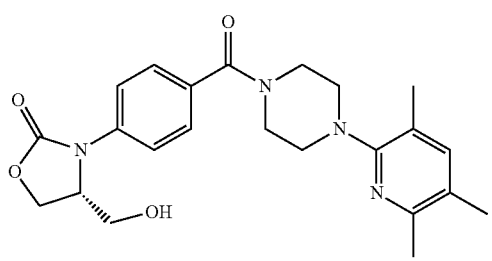 [SMILES: Cc1cc(C)c(N2CCN(C(=O)c3ccc(N4C(=O)OC[C@H]4CO)cc3)CC2)nc1C]

By reaction and treatment in the same manner as in Preparation Example 92 and using (R)-4-benzoyloxymethyl-3-{4-[4-(3,5,6-trimethylpyridin-2-yl)piperazine-1-carbonyl]phenyl}oxazolidin-2-one (2.52 g) described in Example 293, the title compound (1.80 g) was obtained.

MS (ESI) m/z:425(M+H)⁺.

Example 295

Synthesis of (R)-4-(2-methoxyethoxymethyl)-3-{4-[4-(3,5,6-trimethylpyridin-2-yl)piperazine-1-carbonyl]phenyl}oxazolidin-2-one

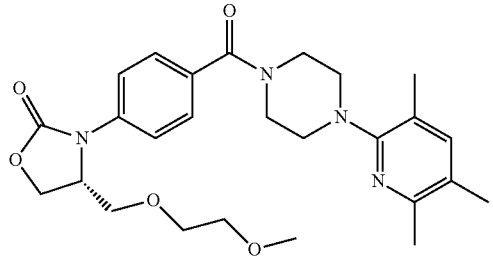 [SMILES: COCCOC[C@@H]1COC(=O)N1c1ccc(C(=O)N2CCN(c3nc(C)c(C)cc3C)CC2)cc1]

By reaction and treatment in the same manner as in Preparation Example 93 and using (R)-4-hydroxymethyl-3-{4-[4-(3,5,6-trimethylpyridin-2-yl)piperazine-1-carbonyl]phenyl}-oxazolidin-2-one (424 mg) described in Example 294 and 1-bromo-2-methoxyethane (167 mg), the title compound (179 mg) was obtained.

MS (ESI) m/z:483(M+H)⁺.

Example 296

Synthesis of (R)-3-{4-[4-(3,5-dichloropyridin-2-yl)piperazine-1-carbonyl]-3-methanesulfonylphenyl}-4-methoxymethyloxazolidin-2-one

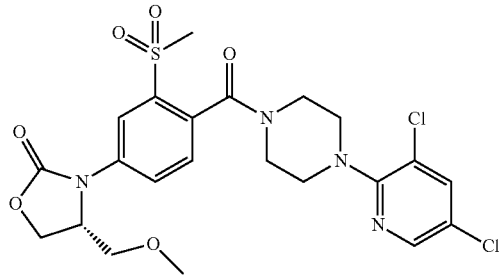 [SMILES: COC[C@@H]1COC(=O)N1c1ccc(C(=O)N2CCN(c3ncc(Cl)cc3Cl)CC2)c(S(C)(=O)=O)c1]

By reaction and treatment in the same manner as in Example 147 and using (R)-3-[3-methanesulfonyl-4-(piperazine-1-carbonyl)phenyl]-4-methoxymethyloxazolidin-2-one (1.19 g) described in Preparation Example 172 and 2,3,5-trichloropyridine (1.09 g), the title compound (740 mg) was obtained.

MS (ESI) m/z:543(M+H)⁺.

Example 297

Synthesis of (R)-3-{4-[4-(3,5-dimethylpyridin-2-yl)piperazine-1-carbonyl]-3-methanesulfonylphenyl}-4-methoxymethyloxazolidin-2-one

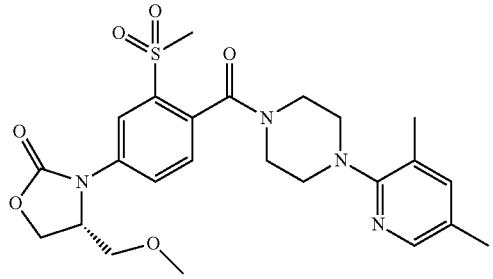 [SMILES: COC[C@@H]1COC(=O)N1c1ccc(C(=O)N2CCN(c3ncc(C)cc3C)CC2)c(S(C)(=O)=O)c1]

By reaction and treatment in the same manner as in Preparation Example 182 and using (R)-3-{4-[4-(3,5-dichloropyridin-2-yl)piperazine-1-carbonyl]-3-methanesulfonylphenyl}-4-methoxymethyloxazolidin-2-one (446 mg) described in Example 296 and methylboronic acid (197 mg), the title compound (322 mg) was obtained.

MS (ESI) m/z:503(M+H)⁺.

Example 298

Synthesis of (R)-4-benzoyloxymethyl-3-{4-[4-(5-cyclopropyl-3-methylpyridin-2-yl)piperazine-1-carbonyl]phenyl}oxazolidin-2-one

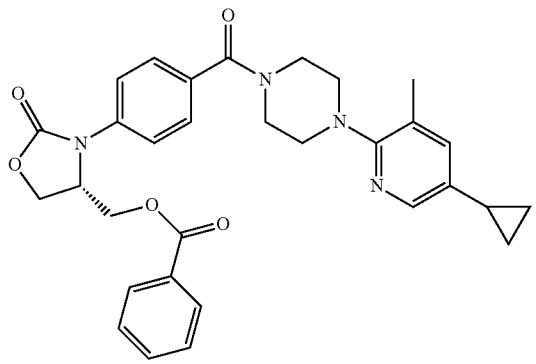 [SMILES: Cc1cc(C2CC2)cnc1N1CCN(C(=O)c2ccc(N3C(=O)OC[C@H]3COC(=O)c3ccccc3)cc2)CC1]

By reaction and treatment in the same manner as in Preparation Example 91 and using [4-(5-cyclopropyl-3-methylpyridin-2-yl)piperazin-1-yl](4-iodophenyl)methanone (2.08 g) described in Preparation Example 97 and benzoic acid (R)-2-oxooxazolidin-4-ylmethyl ester (1.06 g), the title compound (2.29 g) was obtained.

MS (ESI) m/z:541(M+H)⁺.

Example 299

Synthesis of (R)-3-{4-[4-(5-cyclopropyl-3-methylpyridin-2-yl)piperazine-1-carbonyl]phenyl}-4-hydroxymethyloxazolidin-2-one

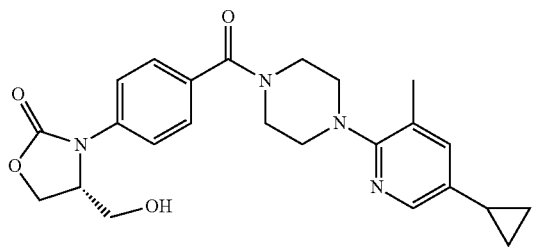

By reaction and treatment in the same manner as in Preparation Example 92 and using (R)-4-benzoyloxymethyl-3-{4-[4-(5-cyclopropyl-3-methylpyridin-2-yl)piperazine-1-carbonyl]phenyl}oxazolidin-2-one (2.28 g) described in Example 298, the title compound (1.64 g) was obtained.

MS (ESI) m/z:437(M+H)⁺.

Example 300

Synthesis of (R)-3-{4-[4-(5-cyclopropyl-3-methylpyridin-2-yl)piperazine-1-carbonyl]phenyl}-4-(2-methoxyethoxymethyl)oxazolidin-2-one

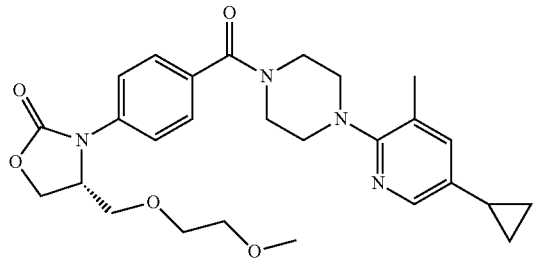 [SMILES: COCCOC[C@@H]1COC(=O)N1c1ccc(C(=O)N2CCN(c3ncc(C4CC4)cc3C)CC2)cc1]

By reaction and treatment in the same manner as in Preparation Example 93 and using (R)-3-{4-[4-(5-cyclopropyl-3-methylpyridin-2-yl)piperazine-1-carbonyl]phenyl}-4-hydroxymethyloxazolidin-2-one (655 mg) described in Example 299 and 1-bromo-2-methoxyethane (250 mg), the title compound (323 mg) was obtained.

MS (ESI) m/z:495(M+H)⁺.

Example 301

Synthesis of (R)-3-{4-[4-(3,5-dicyclopropylpyridin-2-yl)piperazine-1-carbonyl]phenyl}-4-(2-methoxyethoxymethyl)oxazolidin-2-one

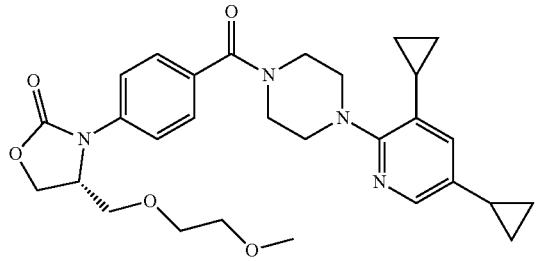 [SMILES: COCCOC[C@@H]1COC(=O)N1c1ccc(C(=O)N2CCN(c3ncc(C4CC4)cc3C3CC3)CC2)cc1]

By reaction and treatment in the same manner as in Preparation Example 93 and using (R)-3-{4-[4-(3,5-dicyclopropylpyridin-2-yl)piperazine-1-carbonyl]phenyl}-4-hydroxymethyloxazolidin-2-one (694 mg) described in Example 280 and 1-bromo-2-methoxyethane (250 mg), the title compound (318 mg) was obtained.

MS (ESI) m/z:521(M+H)⁺.

Example 302

Synthesis of (R)-3-{4-[4-(5-cyclopropyl-3-methylpyridin-2-yl)piperazine-1-carbonyl]phenyl}-4-methoxymethyloxazolidin-2-one

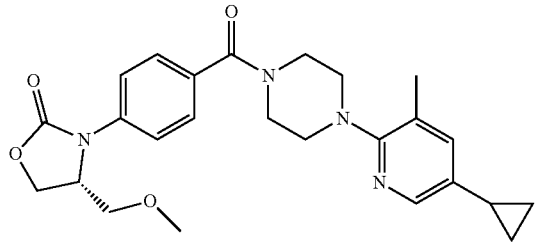 [SMILES: COC[C@@H]1COC(=O)N1c1ccc(C(=O)N2CCN(c3ncc(C4CC4)cc3C)CC2)cc1]

By reaction and treatment in the same manner as in Preparation Example 93 and using (R)-3-{4-[4-(5-cyclopropyl-3-methylpyridin-2-yl)piperazine-1-carbonyl]phenyl}-4-hydroxymethyloxazolidin-2-one (655 mg) described in Example 299 and methyl iodide (255 mg), the title compound (583 mg) was obtained.
MS (ESI) m/z:451(M+H)⁺.

Example 303

Synthesis of 3-{4-[4-(5-ethyl-3-methylpyridin-2-yl) piperazine-1-carbonyl]phenyl}oxazolidin-2-one

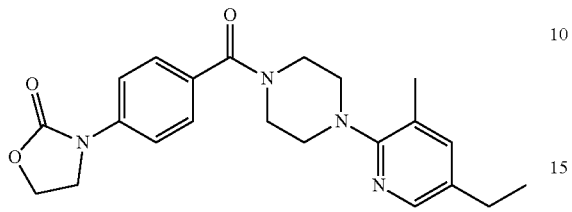

By reaction and treatment in the same manner as in Example 149 and using [4-(5-ethyl-3-methylpyridin-2-yl) piperazin-1-yl](4-iodophenyl)methanone (435 mg) described in Preparation Example 177 and oxazolin-2-one (104 mg), the title compound (347 mg) was obtained.
MS (ESI) m/z:395(M+H)⁺.

Example 304

Synthesis of (S)-3-{4-[4-(5-ethyl-3-methylpyridin-2-yl)piperazine-1-carbonyl]phenyl}-5-methyloxazolidin-2-one

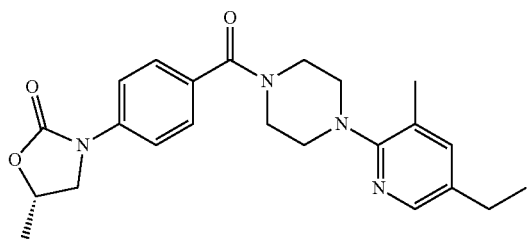 [SMILES: CCc1cnc(N2CCN(C(=O)c3ccc(N4C[C@H](C)OC4=O)cc3)CC2)c(C)c1]

By reaction and treatment in the same manner as in Example 149 and using [4-(5-ethyl-3-methylpyridin-2-yl) piperazin-1-yl](4-iodophenyl)methanone (435 mg) described in Preparation Example 177 and (S)-5-methyloxazolidin-2-one (121 mg) described in Preparation Example 42, the title compound (330 mg) was obtained.
MS (ESI) m/z:409(M+H)⁺.

Example 305

Synthesis of 3-{4-[4-(5-ethyl-3-methylpyridin-2-yl) piperazine-1-carbonyl]phenyl}-5,5-dimethyloxazolidin-2-one

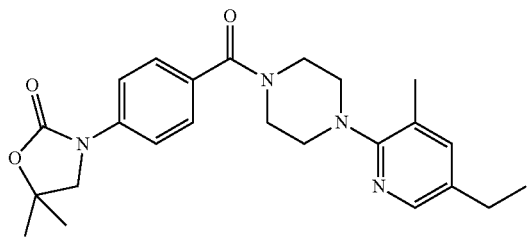 [SMILES: CCc1cnc(N2CCN(C(=O)c3ccc(N4CC(C)(C)OC4=O)cc3)CC2)c(C)c1]

By reaction and treatment in the same manner as in Example 110 and using [4-(5-ethyl-3-methylpyridin-2-yl) piperazin-1-yl](4-iodophenyl)methanone (871 mg) described in Preparation Example 177 and 5,5-dimethyloxazolin-2-one (276 mg) described in Preparation Example 43, the title compound (433 mg) was obtained.
MS (ESI) m/z:423(M+H)⁺.

Example 306

Synthesis of (R)-4-benzoyloxymethyl-3-{4-[4-(5-ethyl-3-methylpyridin-2-yl)piperazine-1-carbonyl] phenyl}oxazolidin-2-one

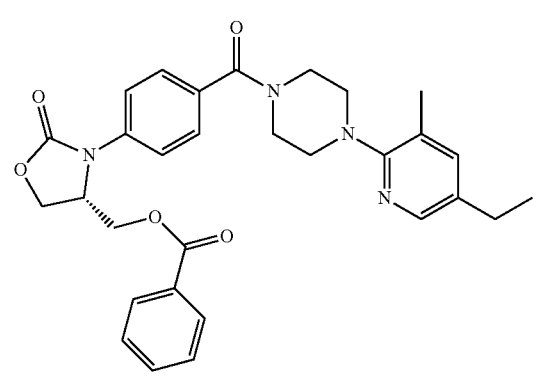 [SMILES: CCc1cnc(N2CCN(C(=O)c3ccc(N4C(=O)OC[C@H]4COC(=O)c4ccccc4)cc3)CC2)c(C)c1]

By reaction and treatment in the same manner as in Preparation Example 91 and using [4-(5-ethyl-3-methylpyridin-2-yl)piperazin-1-yl](4-iodophenyl)methanone (2.18 g) described in Preparation Example 177 and benzoic acid (R)-2-oxooxazolidin-4-ylmethyl ester (1.11 g), the title compound (2.53 g) was obtained.
MS (ESI) m/z:529(M+H)⁺.

Example 307

Synthesis of (R)-3-{4-[4-(5-ethyl-3-methylpyridin-2-yl)piperazine-1-carbonyl]phenyl}-4-hydroxymethyloxazolidin-2-one

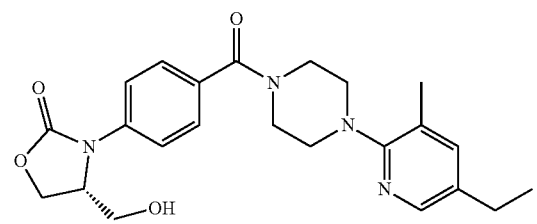 [SMILES: CCc1cnc(N2CCN(C(=O)c3ccc(N4C(=O)OC[C@H]4CO)cc3)CC2)c(C)c1]

By reaction and treatment in the same manner as in Preparation Example 92 and using (R)-4-benzoyloxymethyl-3-{4-[4-(5-ethyl-3-methylpyridin-2-yl)piperazine-1-carbonyl] phenyl}oxazolidin-2-one (2.51 g) described in Example 306, the title compound (1.85 g) was obtained.
MS (ESI) m/z:425(M+H)⁺.

Example 308

Synthesis of (R)-3-{4-[4-(5-ethyl-3-methylpyridin-2-yl)piperazine-1-carbonyl]phenyl}-4-methoxymethyloxazolidin-2-one

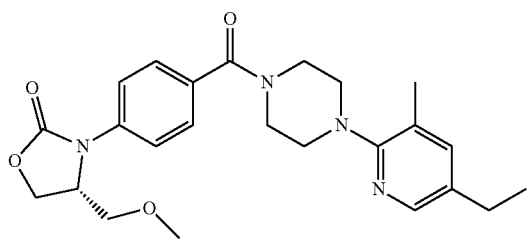 [SMILES: CCc1cnc(N2CCN(C(=O)c3ccc(N4C(=O)OC[C@H]4COC)cc3)CC2)c(C)c1]

By reaction and treatment in the same manner as in Preparation Example 93 and using (R)-3-{4-[4-(5-ethyl-3-methylpyridin-2-yl)piperazine-1-carbonyl]phenyl}-4-hydroxymethyloxazolidin-2-one (637 mg) described in Example 307 and methyl iodide (255 mg), the title compound (582 mg) was obtained.

MS (ESI) m/z:439(M+H)⁺.

Example 309

Synthesis of (S)-3-{4-[4-(3,5-dimethylpyridin-2-yl)piperazine-1-carbonyl]-3-(1,1-dioxoisothiazolidin-2-yl)phenyl}-5-methyloxazolidin-2-one

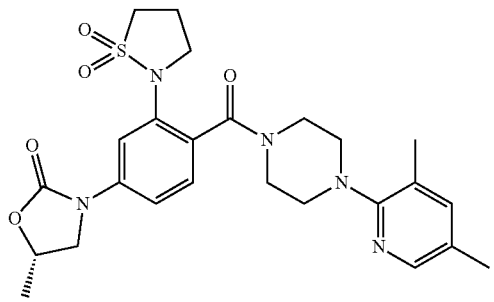 [SMILES: Cc1cnc(N2CCN(C(=O)c3ccc(N4C[C@H](C)OC4=O)cc3N3CCCS3(=O)=O)CC2)c(C)c1]

By reaction and treatment in the same manner as in Example 110 and using [4-bromo-2-(1,1-dioxoisothiazolidin-2-yl)phenyl][4-(3,5-dimethylpyridin-2-yl)piperazin-1-yl]methanone (493 mg) described in Preparation Example 118 and (S)-5-methyloxazolidin-2-one (121 mg) described in Preparation Example 42, the title compound (323 mg) was obtained.

MS (ESI) m/z:514(M+H)⁺.

Example 310

Synthesis of (R)-4-benzoyloxymethyl-3-{4-[4-(3,5-dimethylpyridin-2-yl)piperazine-1-carbonyl]-3-(1,1-dioxoisothiazolidin-2-yl)phenyl}oxazolidin-2-one

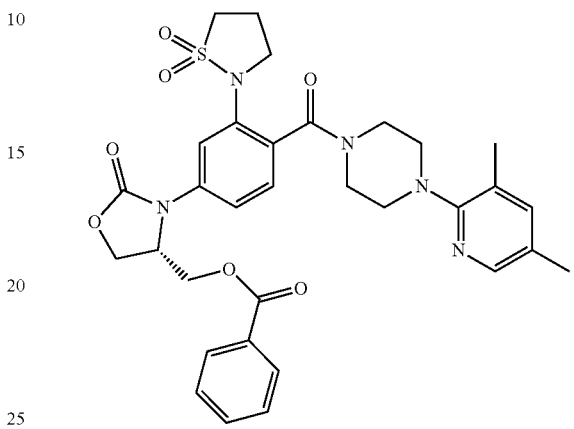

By reaction and treatment in the same manner as in Preparation Example 91 and using [4-bromo-2-(1,1-dioxoisothiazolidin-2-yl)phenyl][4-(3,5-dimethylpyridin-2-yl)piperazin-1-yl]methanone (986 mg) described in Preparation Example 118 and benzoic acid (R)-2-oxooxazolidin-4-ylmethyl ester (487 mg), the title compound (838 mg) was obtained.

MS (ESI) m/z:634(M+H)⁺.

Example 311

Synthesis of (R)-3-{4-[4-(3,5-dimethylpyridin-2-yl)piperazine-1-carbonyl]-3-(1,1-dioxoisothiazolidin-2-yl)phenyl}-4-hydroxymethyloxazolidin-2-one

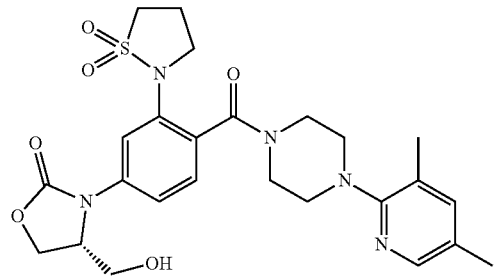 [SMILES: Cc1cnc(N2CCN(C(=O)c3ccc(N4C(=O)OC[C@H]4CO)cc3N3CCCS3(=O)=O)CC2)c(C)c1]

By reaction and treatment in the same manner as in Preparation Example 92 and using (R)-4-benzoyloxymethyl-3-{4-[4-(3,5-dimethylpyridin-2-yl)piperazine-1-carbonyl]-3-(1,1-dioxoisothiazolidin-2-yl)phenyl}oxazolidin-2-one (830 mg) described in Example 310, the title compound (342 mg) was obtained.

MS (ESI) m/z:530(M+H)⁺.

Example 312

Synthesis of (S)-3-{4-[4-(5-cyclopropyl-3-methylpyridin-2-yl)piperazine-1-carbonyl]-3-(1,1-dioxoisothiazolidin-2-yl)phenyl}-5-methyloxazolidin-2-one

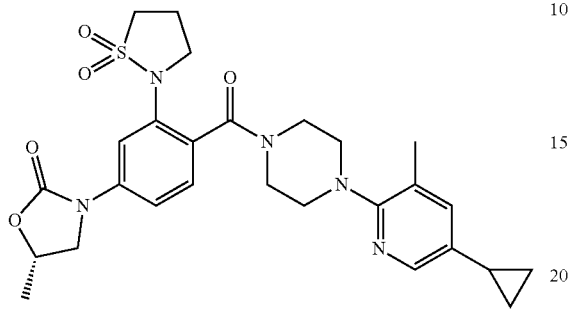

By reaction and treatment in the same manner as in Example 149 and using [4-bromo-2-(1,1-dioxoisothiazolidin-2-yl)phenyl][4-(5-cyclopropyl-3-methylpyridin-2-yl)piperazin-1-yl]methanone (519 mg) described in Preparation Example 179 and (S)-5-methyloxazolidin-2-one (121 mg) described in Preparation Example 42, the title compound (457 mg) was obtained.

MS (ESI) m/z:540(M+H)$^+$.

Example 313

Synthesis of 3-{4-[4-(5-cyclopropyl-3-methylpyridin-2-yl)piperazine-1-carbonyl]-3-(1,1-dioxoisothiazolidin-2-yl)phenyl}-5,5-dimethyloxazolidin-2-one

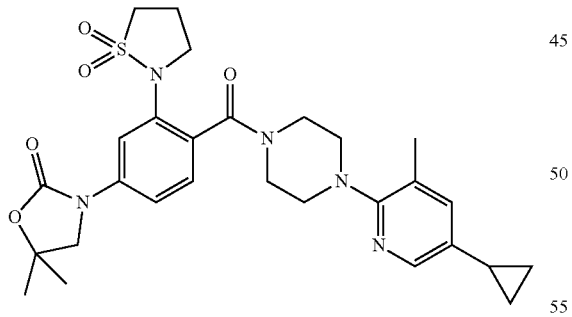

By reaction and treatment in the same manner as in Example 110 and using [4-bromo-2-(1,1-dioxoisothiazolidin-2-yl)phenyl][4-(5-cyclopropyl-3-methylpyridin-2-yl)piperazin-1-yl]methanone (779 mg) described in Preparation Example 179 and 5,5-dimethyloxazolin-2-one (207 mg) described in Preparation Example 43, the title compound (420 mg) was obtained.

MS (ESI) m/z:554(M+H)$^+$.

Example 314

Synthesis of (R)-3-{4-[4-(5-cyclopropyl-3-methylpyridin-2-yl)piperazine-1-carbonyl]-3-(1,1-dioxoisothiazolidin-2-yl)phenyl}-4-ethyloxazolidin-2-one

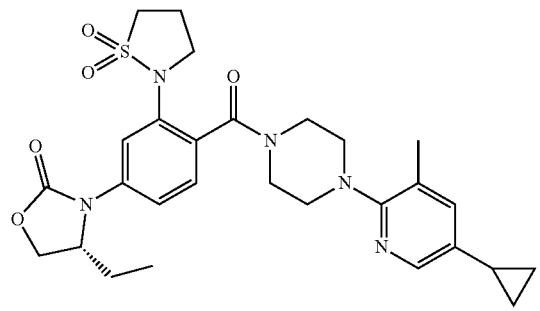 [SMILES: CC[C@@H]1COC(=O)N1c1ccc(C(=O)N2CCN(c3ncc(C4CC4)cc3C)CC2)c(N2CCCS2(=O)=O)c1]

By reaction and treatment in the same manner as in Example 149 and using [4-bromo-2-(1,1-dioxoisothiazolidin-2-yl)phenyl][4-(5-cyclopropyl-3-methylpyridin-2-yl)piperazin-1-yl]methanone (519 mg) described in Preparation Example 179 and (R)-4-ethyloxazolidin-2-one (138 mg) described in Preparation Example 26, the title compound (474 mg) was obtained.

MS (ESI) m/z:554(M+H)$^+$.

Example 315

Synthesis of (R)-3-{4-[4-(5-cyclopropyl-3-methylpyridin-2-yl)piperazine-1-carbonyl]-3-(1,1-dioxoisothiazolidin-2-yl)phenyl}-4-methyloxazolidin-2-one

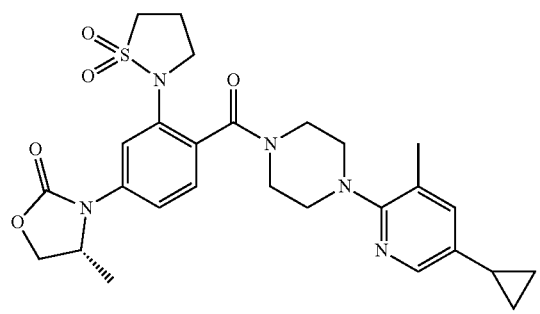 [SMILES: Cc1cc(C2CC2)cnc1N1CCN(C(=O)c2ccc(N3C(=O)OC[C@H]3C)cc2N2CCCS2(=O)=O)CC1]

By reaction and treatment in the same manner as in Example 149 and using [4-bromo-2-(1,1-dioxoisothiazolidin-2-yl)phenyl][4-(5-cyclopropyl-3-methylpyridin-2-yl)piperazin-1-yl]methanone (519 mg) described in Preparation Example 179 and (R)-4-methyloxazolidin-2-one (121 mg) described in Preparation Example 25, the title compound (455 mg) was obtained.

MS (ESI) m/z:540(M+H)$^+$.

Example 316

Synthesis of (R)-4-benzoyloxymethyl-3-{4-[4-(5-cyclopropyl-3-methylpyridin-2-yl)piperazine-1-carbonyl]-3-(1,1-dioxoisothiazolidin-2-yl)phenyl}oxazolidin-2-one

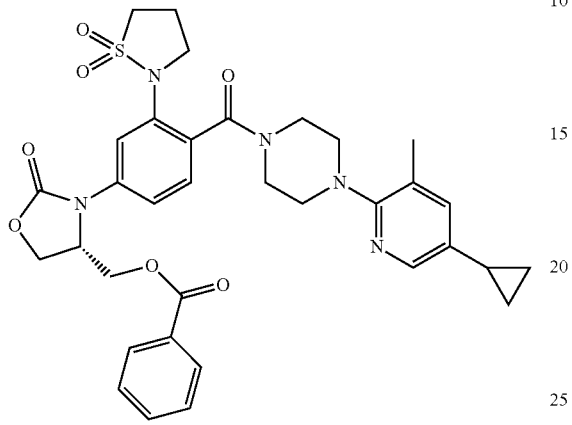

By reaction and treatment in the same manner as in Preparation Example 91 and using [4-bromo-2-(1,1-dioxoisothiazolidin-2-yl)phenyl][4-(5-cyclopropyl-3-methylpyridin-2-yl)piperazin-1-yl]methanone (3.12 g) described in Preparation Example 179 and benzoic acid (R)-2-oxooxazolidin-4-ylmethyl ester (1.33 g), the title compound (3.47 g) was obtained.

MS (ESI) m/z:660(M+H)$^+$.

Example 317

Synthesis of (R)-3-{4-[4-(5-cyclopropyl-3-methylpyridin-2-yl)piperazine-1-carbonyl]-3-(1,1-dioxoisothiazolidin-2-yl)phenyl}-4-hydroxymethyloxazolidin-2-one

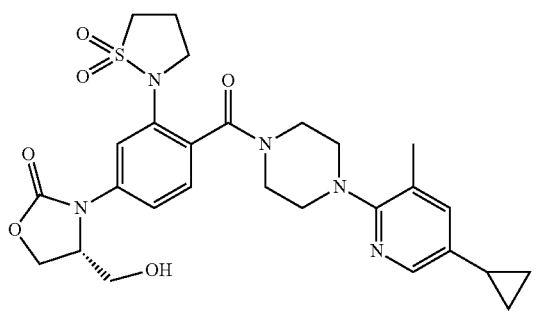 [SMILES: Cc1cc(C2CC2)cnc1N1CCN(C(=O)c2ccc(N3C(=O)OC[C@H]3CO)cc2N2CCCS2(=O)=O)CC1]

By reaction and treatment in the same manner as in Preparation Example 92 and using (R)-4-benzoyloxymethyl-3-{4-[4-(5-cyclopropyl-3-methylpyridin-2-yl)piperazine-1-carbonyl]-3-(1,1-dioxoisothiazolidin-2-yl)phenyl}oxazolidin-2-one (3.46 g) described in Example 316, the title compound (1.58 g) was obtained.

MS (ESI) m/z:556(M+H)$^+$.

Example 318

Synthesis of (R)-3-{4-[4-(5-cyclopropyl-3-methylpyridin-2-yl)piperazine-1-carbonyl]-3-(1,1-dioxoisothiazolidin-2-yl)phenyl}-4-methoxymethyloxazolidin-2-one

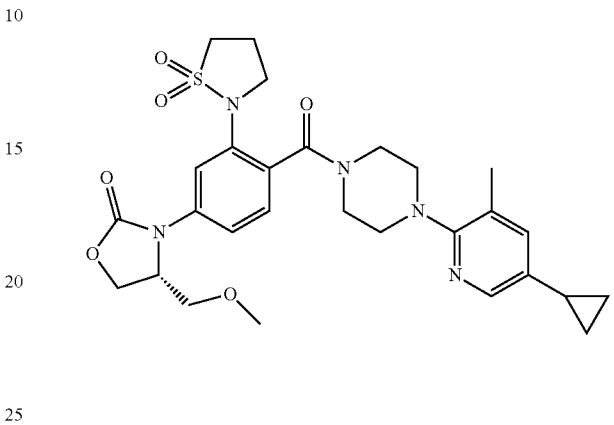

By reaction and treatment in the same manner as in Preparation Example 93 and using (R)-3-{4-[4-(5-cyclopropyl-3-methylpyridin-2-yl)piperazine-1-carbonyl]-3-(1,1-dioxoisothiazolidin-2-yl)phenyl}-4-hydroxymethyloxazolidin-2-one (778 mg) described in Example 317 and methyl iodide (238 mg), the title compound (586 mg) was obtained.

MS (ESI) m/z:570(M+H)$^+$.

Example 319

Synthesis of 3-{4-[4-(5-cyclopropyl-3-methylpyridin-2-yl)piperazine-1-carbonyl]-3-(1,1-dioxoisothiazolidin-2-yl)phenyl}-4,4-dimethyloxazolidin-2-one

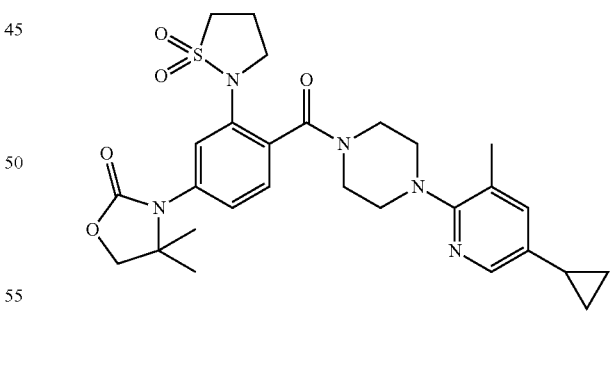

By reaction and treatment in the same manner as in Example 110 and using [4-bromo-2-(1,1-dioxoisothiazolidin-2-yl)phenyl][4-(5-cyclopropyl-3-methylpyridin-2-yl)piperazin-1-yl]methanone (779 mg) described in Preparation Example 179 and 4,4-dimethyloxazolin-2-one (207 mg), the title compound (533 mg) was obtained.

MS (ESI) m/z:554(M+H)$^+$.

Example 320

Synthesis of (R)-3-{3-(1,1-dioxoisothiazolidin-2-yl)-4-[4-(5-ethyl-3-methylpyridin-2-yl)piperazine-1-carbonyl]phenyl}-4-methyloxazolidin-2-one

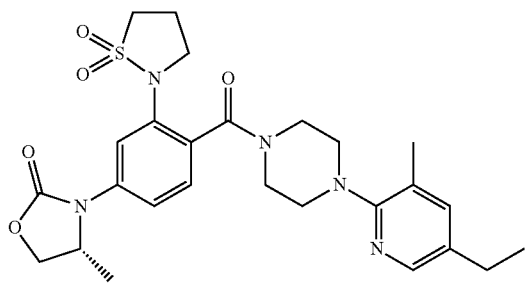 [SMILES: CCc1cnc(N2CCN(C(=O)c3ccc(N4C(=O)OC[C@H]4C)cc3N3CCCS3(=O)=O)CC2)c(C)c1]

By reaction and treatment in the same manner as in Example 149 and using [4-bromo-2-(1,1-dioxoisothiazolidin-2-yl)phenyl][4-(5-ethyl-3-methylpyridin-2-yl)piperazin-1-yl]methanone (507 mg) described in Preparation Example 180 and (R)-4-methyloxazolidin-2-one (121 mg) described in Preparation Example 25, the title compound (474 mg) was obtained.

MS (ESI) m/z:528(M+H)$^+$.

Example 321

Synthesis of 3-{3-(1,1-dioxoisothiazolidin-2-yl)-4-[4-(5-ethyl-3-methylpyridin-2-yl)piperazine-1-carbonyl]phenyl}oxazolidin-2-one

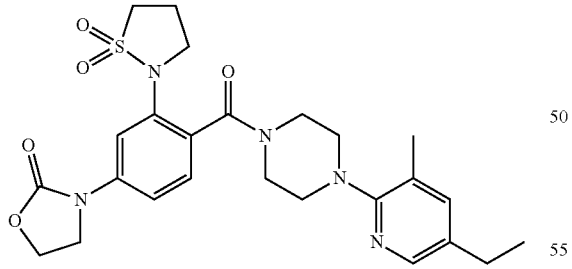

By reaction and treatment in the same manner as in Example 149 and using [4-bromo-2-(1,1-dioxoisothiazolidin-2-yl)phenyl][4-(5-ethyl-3-methylpyridin-2-yl)piperazin-1-yl]methanone (507 mg) described in Preparation Example 180 and oxazolin-2-one (104 mg), the title compound (419 mg) was obtained.

MS (ESI) m/z:514(M+H)$^+$.

Example 322

Synthesis of (S)-3-{3-(1,1-dioxoisothiazolidin-2-yl)-4-[4-(5-ethyl-3-methylpyridin-2-yl)piperazine-1-carbonyl]phenyl}-5-methyloxazolidin-2-one

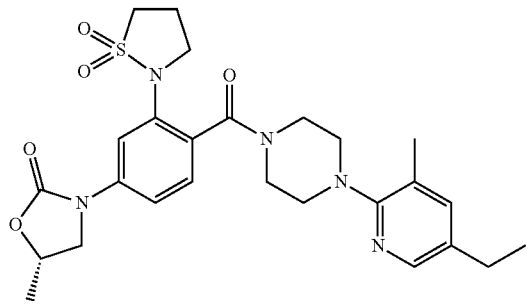 [SMILES: CCc1cnc(N2CCN(C(=O)c3ccc(N4C[C@H](C)OC4=O)cc3N3CCCS3(=O)=O)CC2)c(C)c1]

By reaction and treatment in the same manner as in Example 149 and using [4-bromo-2-(1,1-dioxoisothiazolidin-2-yl)phenyl][4-(5-ethyl-3-methylpyridin-2-yl)piperazin-1-yl]methanone (507 mg) described in Preparation Example 180 and (S)-5-methyloxazolidin-2-one (121 mg) described in Preparation Example 42, the title compound (437 mg) was obtained.

MS (ESI) m/z:528(M+H)$^+$.

Example 323

Synthesis of 3-{3-(1,1-dioxoisothiazolidin-2-yl)-4-[4-(5-ethyl-3-methylpyridin-2-yl)piperazine-1-carbonyl]phenyl}-5,5-dimethyloxazolidin-2-one

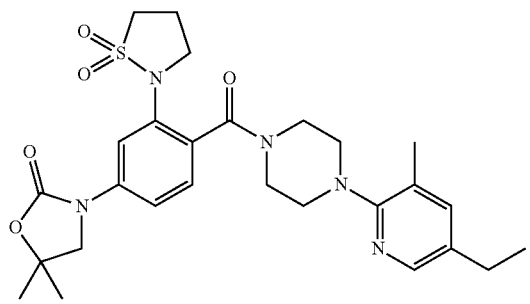 [SMILES: CCc1cnc(N2CCN(C(=O)c3ccc(N4CC(C)(C)OC4=O)cc3N3CCCS3(=O)=O)CC2)c(C)c1]

By reaction and treatment in the same manner as in Example 110 and using [4-bromo-2-(1,1-dioxoisothiazolidin-2-yl)phenyl][4-(5-ethyl-3-methylpyridin-2-yl)piperazin-1-yl]methanone (761 mg) described in Preparation Example 180 and 5,5-dimethyloxazolin-2-one (207 mg) described in Preparation Example 43, the title compound (392 mg) was obtained.

MS (ESI) m/z:542(M+H)$^+$.

Example 324

Synthesis of (R)-3-{3-(1,1-dioxoisothiazolidin-2-yl)-4-[4-(5-ethyl-3-methylpyridin-2-yl)piperazine-1-carbonyl]phenyl}-4-ethyloxazolidin-2-one

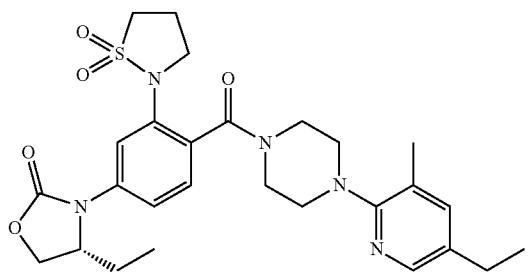 [SMILES: CCc1cnc(N2CCN(C(=O)c3ccc(N4C(=O)OC[C@H]4CC)cc3N3CCCS3(=O)=O)CC2)c(C)c1]

By reaction and treatment in the same manner as in Example 149 and using [4-bromo-2-(1,1-dioxoisothiazolidin-2-yl)phenyl][4-(5-ethyl-3-methylpyridin-2-yl)piperazin-1-yl]methanone (507 mg) described in Preparation Example 180 and (R)-4-ethyloxazolidin-2-one (138 mg) described in Preparation Example 26, the title compound (459 mg) was obtained.

MS (ESI) m/z:542(M+H)$^+$.

Example 325

Synthesis of 3-{3-(1,1-dioxoisothiazolidin-2-yl)-4-[4-(5-ethyl-3-methylpyridin-2-yl)piperazine-1-carbonyl]phenyl}-4,4-dimethyloxazolidin-2-one

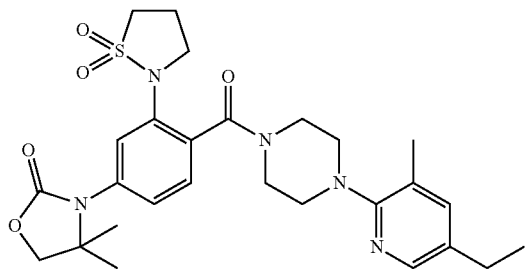 [SMILES: CCc1cnc(N2CCN(C(=O)c3ccc(N4C(=O)OCC4(C)C)cc3N3CCCS3(=O)=O)CC2)c(C)c1]

By reaction and treatment in the same manner as in Example 110 and using [4-bromo-2-(1,1-dioxoisothiazolidin-2-yl)phenyl][4-(5-ethyl-3-methylpyridin-2-yl)piperazin-1-yl]methanone (761 mg) described in Preparation Example 180 and 4,4-dimethyloxazolin-2-one (207 mg), the title compound (553 mg) was obtained.

MS (ESI) m/z:542(M+H)$^+$.

Example 326

Synthesis of (R)-4-benzoyloxymethyl-3-{3-(1,1-dioxoisothiazolidin-2-yl)-4-[4-(5-ethyl-3-methylpyridin-2-yl)piperazine-1-carbonyl]phenyl}oxazolidin-2-one

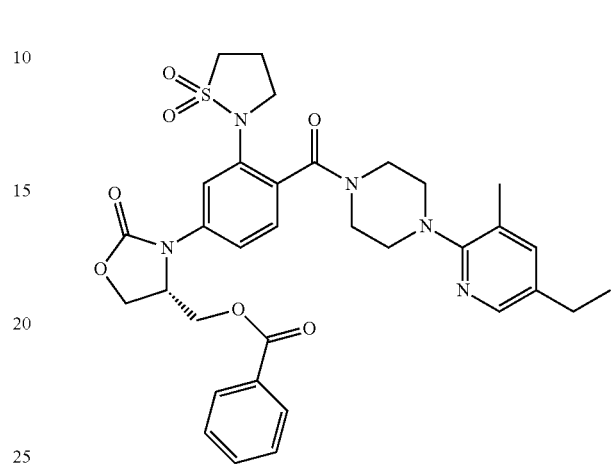

By reaction and treatment in the same manner as in Preparation Example 91 and using [4-bromo-2-(1,1-dioxoisothiazolidin-2-yl)phenyl][4-(5-ethyl-3-methylpyridin-2-yl)piperazin-1-yl]methanone (3.04 g) described in Preparation Example 180 and benzoic acid (R)-2-oxooxazolidin-4-ylmethyl ester (1.33 g), the title compound (3.52 g) was obtained.

MS (ESI) m/z:648(M+H)$^+$.

Example 327

Synthesis of (R)-3-{3-(1,1-dioxoisothiazolidin-2-yl)-4-[4-(5-ethyl-3-methylpyridin-2-yl)piperazine-1-carbonyl]phenyl}-4-hydroxymethyloxazolidin-2-one

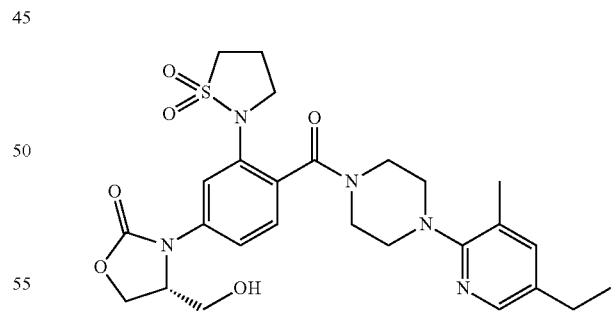

By reaction and treatment in the same manner as in Preparation Example 92 and using (R)-4-benzoyloxymethyl-3-{3-(1,1-dioxoisothiazolidin-2-yl)-4-[4-(5-ethyl-3-methylpyridin-2-yl)piperazine-1-carbonyl]phenyl}oxazolidin-2-one (3.44 g) described in Example 326, the title compound (2.04 g) was obtained.

MS (ESI) m/z:544(M+H)$^+$.

Example 328

Synthesis of (R)-3-{3-(1,1-dioxoisothiazolidin-2-yl)-4-[4-(5-ethyl-3-methylpyridin-2-yl)piperazine-1-carbonyl]phenyl}-4-methoxymethyloxazolidin-2-one

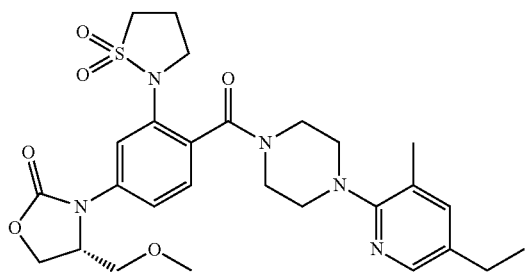 [SMILES: CCc1cnc(N2CCN(C(=O)c3ccc(N4C(=O)OC[C@H]4COC)cc3N3CCCS3(=O)=O)CC2)c(C)c1]

By reaction and treatment in the same manner as in Preparation Example 93 and using (R)-3-{3-(1,1-dioxoisothiazolidin-2-yl)-4-[4-(5-ethyl-3-methylpyridin-2-yl)piperazine-1-carbonyl]phenyl}-4-hydroxymethyloxazolidin-2-one (761 mg) described in Example 327 and methyl iodide (238 mg), the title compound (572 mg) was obtained.

MS (ESI) m/z:558(M+H)$^+$.

Example 329

Synthesis of (R)-3-{4-[4-(2,4-dimethylphenyl)piperazine-1-carbonyl]-3-(1,1-dioxoisothiazolidin-2-yl)phenyl}-4-methyloxazolidin-2-one

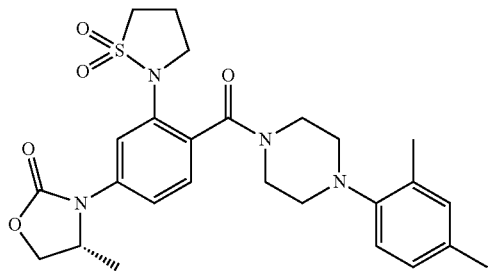 [SMILES: Cc1ccc(N2CCN(C(=O)c3ccc(N4C(=O)OC[C@H]4C)cc3N3CCCS3(=O)=O)CC2)c(C)c1]

By reaction and treatment in the same manner as in Example 149 and using [4-bromo-2-(1,1-dioxoisothiazolidin-2-yl)phenyl][4-(2,4-dimethylphenyl)piperazin-1-yl]methanone (492 mg) described in Preparation Example 181 and (R)-4-methyloxazolidin-2-one (121 mg) described in Preparation Example 25, the title compound (448 mg) was obtained.

MS (ESI) m/z:513(M+H)$^+$.

Example 330

Synthesis of 3-{4-[4-(2,4-dimethylphenyl)piperazine-1-carbonyl]-3-(1,1-dioxoisothiazolidin-2-yl)phenyl}oxazolidin-2-one

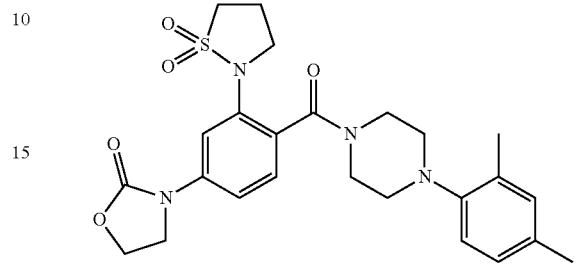

By reaction and treatment in the same manner as in Example 149 and using [4-bromo-2-(1,1-dioxoisothiazolidin-2-yl)phenyl][4-(2,4-dimethylphenyl)piperazin-1-yl]methanone (492 mg) described in Preparation Example 181 and oxazolin-2-one (104 mg), the title compound (443 mg) was obtained.

MS (ESI) m/z:499(M+H)$^+$.

Example 331

Synthesis of (R)-4-benzoyloxymethyl-3-{4-[4-(2,4-dimethylphenyl)piperazine-1-carbonyl]-3-(1,1-dioxoisothiazolidin-2-yl)phenyl}oxazolidin-2-one

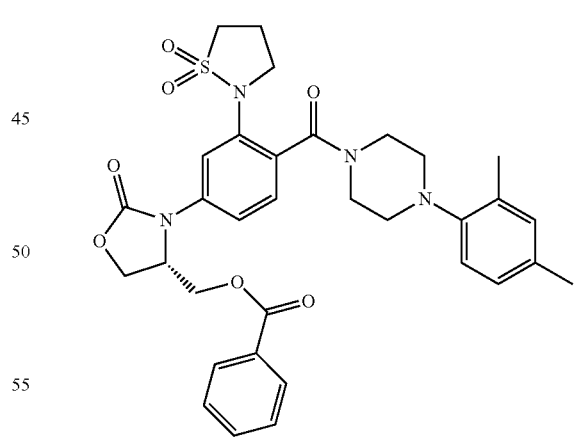

By reaction and treatment in the same manner as in Preparation Example 91 and using [4-bromo-2-(1,1-dioxoisothiazolidin-2-yl)phenyl][4-(2,4-dimethylphenyl)piperazin-1-yl]methanone (1.72 g) described in Preparation Example 181 and benzoic acid (R)-2-oxooxazolidin-4-ylmethyl ester (852 mg), the title compound (2.12 g) was obtained.

MS (ESI) m/z:633(M+H)$^+$.

Example 332

Synthesis of (R)-3-{4-[4-(2,4-dimethylphenyl)piperazine-1-carbonyl]-3-(1,1-dioxoisothiazolidin-2-yl)phenyl}-4-hydroxymethyloxazolidin-2-one

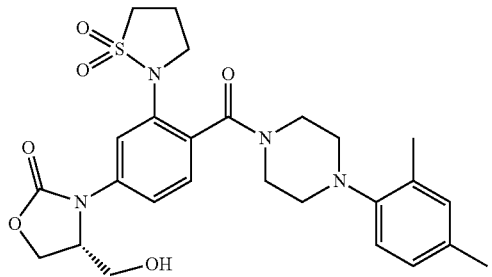 [SMILES: Cc1ccc(N2CCN(C(=O)c3ccc(N4C(=O)OC[C@H]4CO)cc3N3CCCS3(=O)=O)CC2)c(C)c1]

By reaction and treatment in the same manner as in Preparation Example 92 and using (R)-4-benzoyloxymethyl-3-{4-[4-(2,4-dimethylphenyl)piperazine-1-carbonyl]-3-(1,1-dioxoisothiazolidin-2-yl)phenyl}oxazolidin-2-one (2.11 g) described in Example 331, the title compound (1.26 g) was obtained.
MS (ESI) m/z:529(M+H)$^+$.

Example 333

Synthesis of (R)-3-{4-[4-(2,4-dimethylphenyl)piperazine-1-carbonyl]-3-(1,1-dioxoisothiazolidin-2-yl)phenyl}-4-methoxymethyloxazolidin-2-one

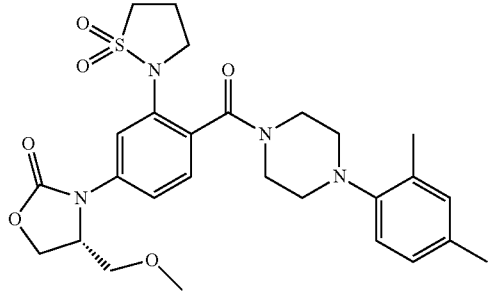 [SMILES: COC[C@@H]1COC(=O)N1c1ccc(C(=O)N2CCN(c3ccc(C)cc3C)CC2)c(N2CCCS2(=O)=O)c1]

By reaction and treatment in the same manner as in Preparation Example 93 and using (R)-3-{4-[4-(2,4-dimethylphenyl)piperazine-1-carbonyl]-3-(1,1-dioxoisothiazolidin-2-yl)phenyl}-4-hydroxymethyloxazolidin-2-one (687 mg) described in Example 332 and methyl iodide (221 mg), the title compound (488 mg) was obtained.
MS (ESI) m/z:543(M+H)$^+$.

Example 334

Synthesis of (R)-3-{3-fluoro-4-[4-(5-methylpyridin-2-yl)piperazine-1-carbonyl]phenyl}-4-methyloxazolidin-2-one

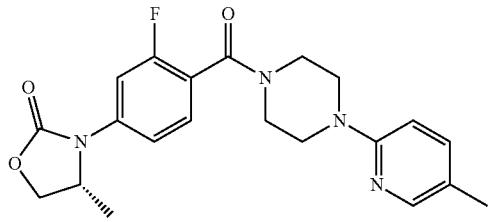 [SMILES: Cc1ccc(N2CCN(C(=O)c3ccc(N4C(=O)OC[C@H]4C)cc3F)CC2)nc1]

By reaction and treatment in the same manner as in Example 110 and using (4-bromo-2-fluorophenyl)[4-(5-methylpyridin-2-yl)piperazin-1-yl]methanone (378 mg) described in Preparation Example 184 and (R)-4-methyloxazolidin-2-one (171 mg) described in Preparation Example 25, the title compound (377 mg) was obtained.
MS (ESI) m/z:399(M+H)$^+$.

Example 335

Synthesis of 3-{3-fluoro-4-[4-(5-methylpyridin-2-yl)piperazine-1-carbonyl]phenyl}oxazolidin-2-one

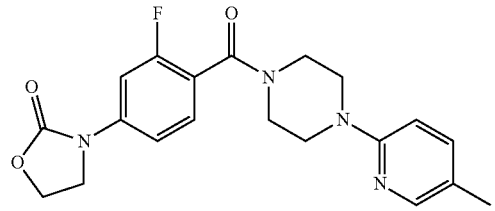 [SMILES: Cc1ccc(N2CCN(C(=O)c3ccc(N4CCOC4=O)cc3F)CC2)nc1]

By reaction and treatment in the same manner as in Example 110 and using (4-bromo-2-fluorophenyl)[4-(5-methylpyridin-2-yl)piperazin-1-yl]methanone (378 mg) described in Preparation Example 184 and oxazolin-2-one (104 mg), the title compound (264 mg) was obtained.
MS (ESI) m/z:385(M+H)$^+$.

Example 336

Synthesis of 3-{3-fluoro-4-[4-(5-methylpyridin-2-yl)piperazine-1-carbonyl]phenyl}-5,5-dimethyloxazolidin-2-one

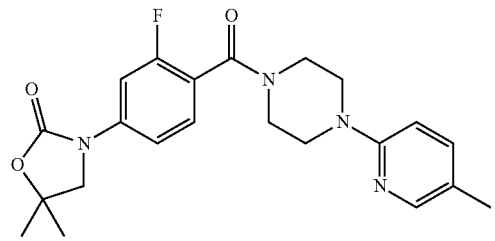 [SMILES: Cc1ccc(N2CCN(C(=O)c3ccc(N4CC(C)(C)OC4=O)cc3F)CC2)nc1]

By reaction and treatment in the same manner as in Example 110 and using (4-bromo-2-fluorophenyl)[4-(5-methylpyridin-2-yl)piperazin-1-yl]methanone (567 mg) described in Preparation Example 184 and 5,5-dimethyloxazolin-2-one (207 mg) described in Preparation Example 43, the title compound (335 mg) was obtained.
MS (ESI) m/z:413(M+H)$^+$.

Example 337

Synthesis of 3-{3,5-difluoro-4-[4-(5-methylpyridin-2-yl)piperazine-1-carbonyl]phenyl}oxazolidin-2-one

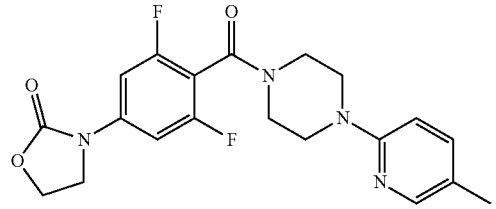 [SMILES: Cc1ccc(N2CCN(C(=O)c3c(F)cc(N4CCOC4=O)cc3F)CC2)nc1]

By reaction and treatment in the same manner as in Example 110 and using (4-bromo-2,6-difluorophenyl)[4-(5-methylpyridin-2-yl)piperazin-1-yl]methanone (396 mg) described in Preparation Example 185 and oxazolin-2-one (104 mg), the title compound (256 mg) was obtained.

MS (ESI) m/z:403(M+H)$^+$.

Example 338

Synthesis of (R)-3-{3,5-difluoro-4-[4-(5-methylpyridin-2-yl)piperazine-1-carbonyl]phenyl}-4-methyloxazolidin-2-one

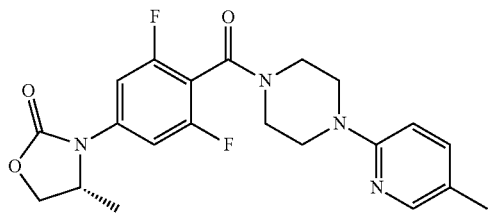 [SMILES: Cc1ccc(N2CCN(C(=O)c3c(F)cc(N4C(=O)OC[C@H]4C)cc3F)CC2)nc1]

By reaction and treatment in the same manner as in Example 110 and using (4-bromo-2,6-difluorophenyl)[4-(5-methylpyridin-2-yl)piperazin-1-yl]methanone (393 mg) described in Preparation Example 185 and (R)-4-methyloxazolidin-2-one (132 mg) described in Preparation Example 25, the title compound (277 mg) was obtained.

MS (ESI) m/z:417(M+H)$^+$.

Example 339

Synthesis of 3-{3,5-difluoro-4-[4-(5-methylpyridin-2-yl)piperazine-1-carbonyl]phenyl}-5,5-dimethyloxazolidin-2-one

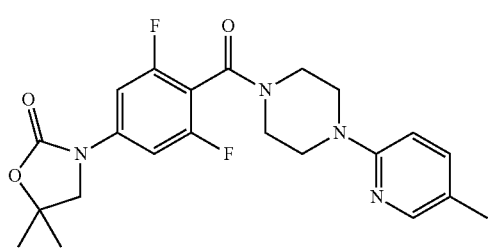 [SMILES: Cc1ccc(N2CCN(C(=O)c3c(F)cc(N4CC(C)(C)OC4=O)cc3F)CC2)nc1]

By reaction and treatment in the same manner as in Example 110 and using (4-bromo-2,6-difluorophenyl)[4-(5-methylpyridin-2-yl)piperazin-1-yl]methanone (594 mg) described in Preparation Example 185 and 5,5-dimethyloxazolin-2-one (207 mg) described in Preparation Example 43, the title compound (308 mg) was obtained.

MS (ESI) m/z:431(M+H)$^+$.

Example 340

Synthesis of 3-{4-[4-(5-cyclopropylpyridin-2-yl)piperazine-1-carbonyl]-3-fluorophenyl}oxazolidin-2-one

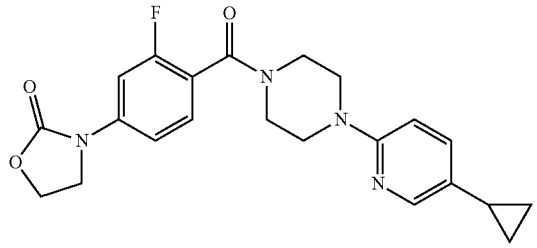 [SMILES: O=C(c1ccc(N2CCOC2=O)cc1F)N1CCN(c2ccc(C3CC3)cn2)CC1]

By reaction and treatment in the same manner as in Example 110 and using (4-bromo-2-fluorophenyl)[4-(5-cyclopropylpyridin-2-yl)piperazin-1-yl]methanone (404 mg) described in Preparation Example 188 and oxazolin-2-one (104 mg), the title compound (305 mg) was obtained.

MS (ESI) m/z:411(M+H)$^+$.

Example 341

Synthesis of (R)-3-{4-[4-(5-cyclopropylpyridin-2-yl)piperazine-1-carbonyl]-3-fluorophenyl}-4-methyloxazolidin-2-one

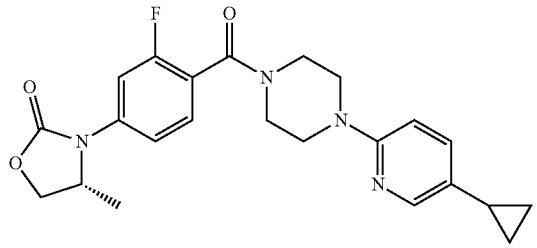 [SMILES: C[C@@H]1COC(=O)N1c1ccc(C(=O)N2CCN(c3ccc(C4CC4)cn3)CC2)c(F)c1]

By reaction and treatment in the same manner as in Example 110 and using (4-bromo-2-fluorophenyl)[4-(5-cyclopropylpyridin-2-yl)piperazin-1-yl]methanone (404 mg) described in Preparation Example 188 and (R)-4-methyloxazolidin-2-one (121 mg) described in Preparation Example 25, the title compound (379 mg) was obtained.

MS (ESI) m/z:425(M+H)$^+$.

Example 342

Synthesis of 3-{4-[4-(5-cyclopropylpyridin-2-yl)piperazine-1-carbonyl]-3-fluorophenyl}-5,5-dimethyloxazolidin-2-one

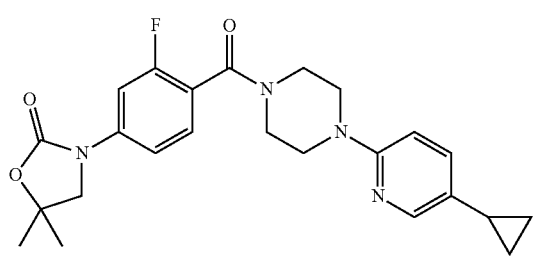 [SMILES: CC1(C)CN(c2ccc(C(=O)N3CCN(c4ccc(C5CC5)cn4)CC3)c(F)c2)C(=O)O1]

By reaction and treatment in the same manner as in Example 110 and using (4-bromo-2-fluorophenyl)[4-(5-cyclopropylpyridin-2-yl)piperazin-1-yl]methanone (606 mg)

described in Preparation Example 188 and 5,5-dimethyloxazolin-2-one (207 mg) described in Preparation Example 43, the title compound (284 mg) was obtained.
MS (ESI) m/z:439(M+H)⁺.

Example 343

Synthesis of 3-{4-[4-(5-cyclopropylpyridin-2-yl)piperazine-1-carbonyl]-3,5-difluorophenyl}oxazolidin-2-one

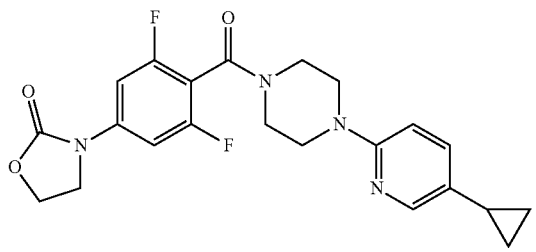 [SMILES: O=C(c1c(F)cc(N2CCOC2=O)cc1F)N1CCN(c2ccc(C3CC3)cn2)CC1]

By reaction and treatment in the same manner as in Example 110 and using (4-bromo-2,6-difluorophenyl)[4-(5-cyclopropylpyridin-2-yl)piperazin-1-yl]methanone (422 mg) described in Preparation Example 189 and oxazolin-2-one (104 mg), the title compound (292 mg) was obtained.
MS (ESI) m/z:429(M+H)⁺.

Example 344

Synthesis of (R)-3-{4-[4-(5-cyclopropylpyridin-2-yl)piperazine-1-carbonyl]-3,5-difluorophenyl}-4-methyloxazolidin-2-one

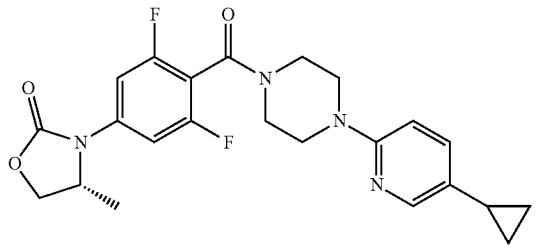 [SMILES: C[C@@H]1COC(=O)N1c1cc(F)c(C(=O)N2CCN(c3ccc(C4CC4)cn3)CC2)c(F)c1]

By reaction and treatment in the same manner as in Example 110 and using (4-bromo-2,6-difluorophenyl)[4-(5-cyclopropylpyridin-2-yl)piperazin-1-yl]methanone (422 mg) described in Preparation Example 189 and (R)-4-methyloxazolidin-2-one (134 mg) described in Preparation Example 25, the title compound (257 mg) was obtained.
MS (ESI) m/z:443(M+H)⁺.

Example 345

Synthesis of 3-{3-cyano-4-[4-(3,5-dimethylpyridin-2-yl)piperazine-1-carbonyl]phenyl}oxazolidin-2-one

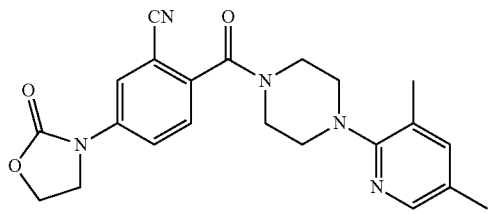 [SMILES: Cc1cnc(N2CCN(C(=O)c3ccc(N4CCOC4=O)cc3C#N)CC2)c(C)c1]

By reaction and treatment in the same manner as in Example 110 and using 5-bromo-2-[4-(3,5-dimethylpyridin-2-yl)piperazine-1-carbonyl]benzonitrile (399 mg) described in Preparation Example 193 and oxazolin-2-one (104 mg), the title compound (327 mg) was obtained.
MS (ESI) m/z:406(M+H)⁺.

Example 346

Synthesis of (R)-3-{3-cyano-4-[4-(3,5-dimethylpyridin-2-yl)piperazine-1-carbonyl]phenyl}-4-methyloxazolidin-2-one

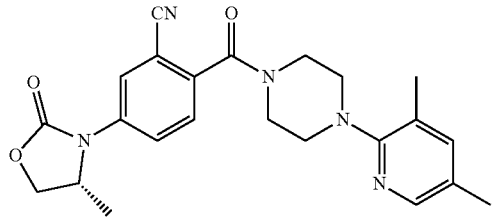 [SMILES: Cc1cnc(N2CCN(C(=O)c3ccc(N4C(=O)OC[C@H]4C)cc3C#N)CC2)c(C)c1]

By reaction and treatment in the same manner as in Example 149 and using 5-bromo-2-[4-(3,5-dimethylpyridin-2-yl)piperazine-1-carbonyl]benzonitrile (399 mg) described in Preparation Example 193 and (R)-4-methyloxazolidin-2-one (121 mg) described in Preparation Example 25, the title compound (326 mg) was obtained.
MS (ESI) m/z:420(M+H)⁺.

Example 347

Synthesis of 3-{3-cyano-4-[4-(3,5-dimethylpyridin-2-yl)piperazine-1-carbonyl]phenyl}-4,4-dimethyloxazolidin-2-one

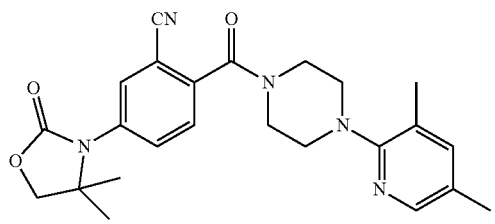 [SMILES: Cc1cnc(N2CCN(C(=O)c3ccc(N4C(=O)OCC4(C)C)cc3C#N)CC2)c(C)c1]

By reaction and treatment in the same manner as in Example 110 and using 5-bromo-2-[4-(3,5-dimethylpyridin-2-yl)piperazine-1-carbonyl]benzonitrile (559 mg) described in Preparation Example 193 and 4,4-dimethyloxazolin-2-one (193 mg), the title compound (267 mg) was obtained.
MS (ESI) m/z:434(M+H)⁺.

Example 348

Synthesis of (R)-4-benzoyloxymethyl-3-{3-cyano-4-[4-(3,5-dimethylpyridin-2-yl)piperazine-1-carbonyl]phenyl}oxazolidin-2-one

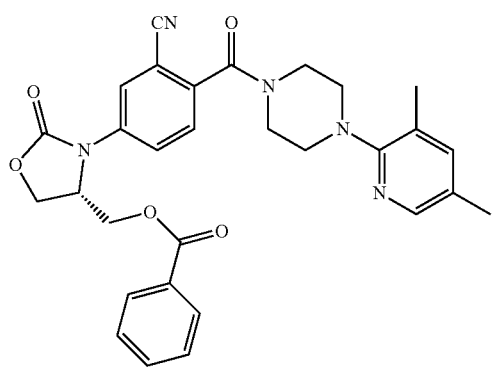 [SMILES: Cc1cnc(N2CCN(C(=O)c3ccc(N4C(=O)OC[C@H]4COC(=O)c4ccccc4)cc3C#N)CC2)c(C)c1]

By reaction and treatment in the same manner as in Preparation Example 91 and using 5-bromo-2-[4-(3,5-dimethylpyridin-2-yl)piperazine-1-carbonyl]benzonitrile (1.68 g) described in Preparation Example 193 and benzoic acid (R)-2-oxooxazolidin-4-ylmethyl ester (1.02 g), the title compound (1.56 g) was obtained.

MS (ESI) m/z:540(M+H)$^+$.

Example 349

Synthesis of (R)-3-{3-cyano-4-[4-(3,5-dimethylpyridin-2-yl)piperazine-1-carbonyl]phenyl}-4-hydroxymethyloxazolidin-2-one

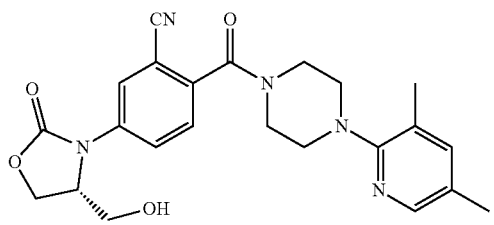 [SMILES: Cc1cnc(N2CCN(C(=O)c3ccc(N4C(=O)OC[C@H]4CO)cc3C#N)CC2)c(C)c1]

By reaction and treatment in the same manner as in Preparation Example 92 and using (R)-4-benzoyloxymethyl-3-{3-cyano-4-[4-(3,5-dimethylpyridin-2-yl)piperazine-1-carbonyl]phenyl}oxazolidin-2-one (1.54 g) described in Example 348, the title compound (921 mg) was obtained.

MS (ESI) m/z:436(M+H)$^+$.

Example 350

Synthesis of (R)-3-{3-cyano-4-[4-(3,5-dimethylpyridin-2-yl)piperazine-1-carbonyl]phenyl}-4-methoxymethyloxazolidin-2-one

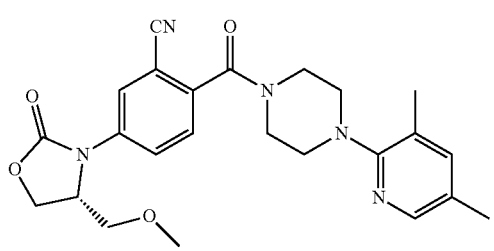 [SMILES: COC[C@@H]1COC(=O)N1c1ccc(C(=O)N2CCN(c3ncc(C)cc3C)CC2)c(C#N)c1]

By reaction and treatment in the same manner as in Preparation Example 93 and using (R)-3-{3-cyano-4-[4-(3,5-dimethylpyridin-2-yl)piperazine-1-carbonyl]phenyl}-4-hydroxymethyloxazolidin-2-one (566 mg) described in Example 349 and methyl iodide (221 mg), the title compound (371 mg) was obtained.

MS (ESI) m/z:450(M+H)$^+$.

Example 351

Synthesis of (S)-3-{3-cyano-4-[4-(3,5-dimethylpyridin-2-yl)piperazine-1-carbonyl]phenyl}-5-methyloxazolidin-2-one

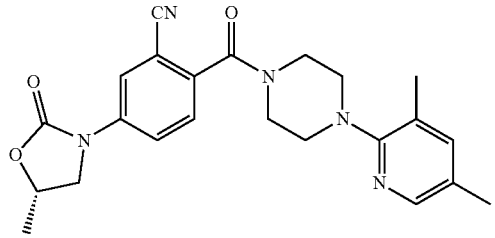 [SMILES: Cc1cnc(N2CCN(C(=O)c3ccc(N4C[C@H](C)OC4=O)cc3C#N)CC2)c(C)c1]

By reaction and treatment in the same manner as in Example 110 and using 5-bromo-2-[4-(3,5-dimethylpyridin-2-yl)piperazine-1-carbonyl]benzonitrile (399 mg) described in Preparation Example 193 and (S)-4-methyloxazolidin-2-one (121 mg) described in Preparation Example 42, the title compound (282 mg) was obtained.

MS (ESI) m/z:420(M+H)$^+$.

Example 352

Synthesis of (R)-3-{3-cyano-4-[4-(5-cyclopropyl-3-methylpyridin-2-yl)piperazine-1-carbonyl]phenyl}-4-methyloxazolidin-2-one

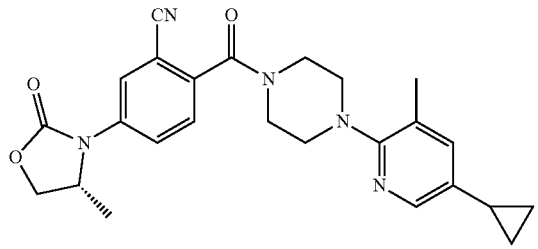 [SMILES: Cc1cc(C2CC2)cnc1N1CCN(C(=O)c2ccc(N3C(=O)OC[C@H]3C)cc2C#N)CC1]

By reaction and treatment in the same manner as in Example 110 and using 5-bromo-2-[4-(5-cyclopropyl-3-methylpyridin-2-yl)piperazine-1-carbonyl]benzonitrile (425 mg) described in Preparation Example 194 and (R)-4-methyloxazolidin-2-one. (121 mg) described in Preparation Example 25, the title compound (363 mg) was obtained.

MS (ESI) m/z:446(M+H)$^+$.

Example 353

Synthesis of (S)-3-{3-cyano-4-[4-(5-cyclopropyl-3-methylpyridin-2-yl)piperazine-1-carbonyl]phenyl}-5-methyloxazolidin-2-one

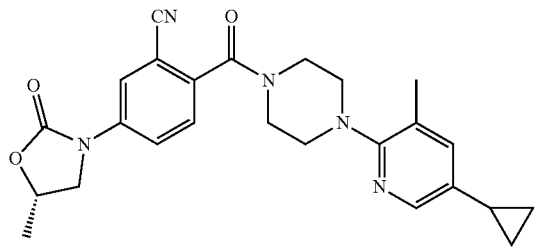 [SMILES: Cc1cc(C2CC2)cnc1N1CCN(C(=O)c2ccc(N3C[C@H](C)OC3=O)cc2C#N)CC1]

By reaction and treatment in the same manner as in Example 149 and using 5-bromo-2-[4-(5-cyclopropyl-3-methylpyridin-2-yl)piperazine-1-carbonyl]benzonitrile (425 mg) described in Preparation Example 194 and (S)-4-methyloxazolidin-2-one (121 mg) described in Preparation Example 42, the title compound (283 mg) was obtained.
MS (ESI) m/z:446(M+H)+.

Example 354

Synthesis of 3-{3-cyano-4-[4-(5-cyclopropyl-3-methylpyridin-2-yl)piperazine-1-carbonyl]phenyl}oxazolidin-2-one

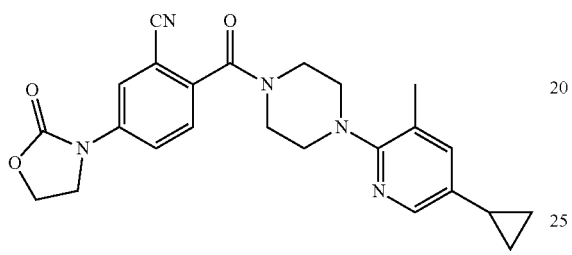

By reaction and treatment in the same manner as in Example 110 and using 5-bromo-2-[4-(5-cyclopropyl-3-methylpyridin-2-yl)piperazine-1-carbonyl]benzonitrile (425 mg) described in Preparation Example 194 and oxazolin-2-one (104 mg), the title compound (352 mg) was obtained.
MS (ESI) m/z:432(M+H)+.

Example 355

Synthesis of 3-{3-cyano-4-[4-(5-cyclopropyl-3-methylpyridin-2-yl)piperazine-1-carbonyl]phenyl}-4,4-dimethyloxazolidin-2-one

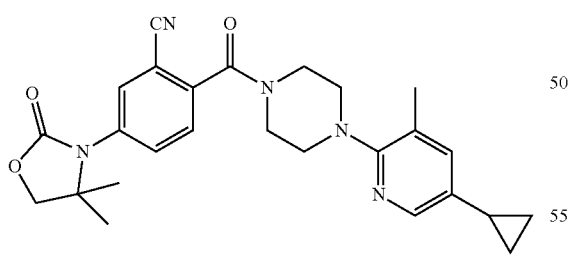

By reaction and treatment in the same manner as in Example 110 and using 5-bromo-2-[4-(5-cyclopropyl-3-methylpyridin-2-yl)piperazine-1-carbonyl]benzonitrile (425 mg) described in Preparation Example 194 and 4,4-dimethyloxazolin-2-one (138 mg), the title compound (227 mg) was obtained.
MS (ESI) m/z:460(M+H)+.

Example 356

Synthesis of (R)-4-benzoyloxymethyl-3-{3-cyano-4-[4-(5-cyclopropyl-3-methylpyridin-2-yl)piperazine-1-carbonyl]phenyl}oxazolidin-2-one

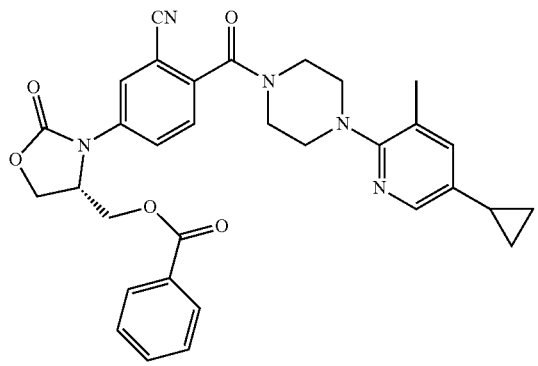 [SMILES: Cc1cc(C2CC2)cnc1N1CCN(C(=O)c2ccc(N3C(=O)OC[C@H]3COC(=O)c3ccccc3)cc2C#N)CC1]

By reaction and treatment in the same manner as in Preparation Example 91 and using 5-bromo-2-[4-(5-cyclopropyl-3-methylpyridin-2-yl)piperazine-1-carbonyl]benzonitrile (1.58 g) described in Preparation Example 194 and benzoic acid (R)-2-oxooxazolidin-4-ylmethyl ester (906 mg), the title compound (1.56 g) was obtained.
MS (ESI) m/z:566(M+H)+.

Example 357

Synthesis of (R)-3-{3-cyano-4-[4-(5-cyclopropyl-3-methylpyridin-2-yl)piperazine-1-carbonyl]phenyl}-4-hydroxymethyloxazolidin-2-one

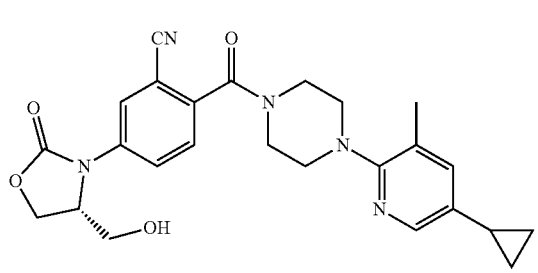 [SMILES: Cc1cc(C2CC2)cnc1N1CCN(C(=O)c2ccc(N3C(=O)OC[C@H]3CO)cc2C#N)CC1]

By reaction and treatment in the same manner as in Preparation Example 92 and using (R)-4-benzoyloxymethyl-3-{3-cyano-4-[4-(5-cyclopropyl-3-methylpyridin-2-yl)piperazine-1-carbonyl]phenyl}oxazolidin-2-one (1.57 g) described in Example 356, the title compound (1.06 g) was obtained.
MS (ESI) m/z:462(M+H)+.

Example 358

Synthesis of (R)-3-{3-cyano-4-[4-(5-cyclopropyl-3-methylpyridin-2-yl)piperazine-1-carbonyl]phenyl}-4-methoxymethyloxazolidin-2-one

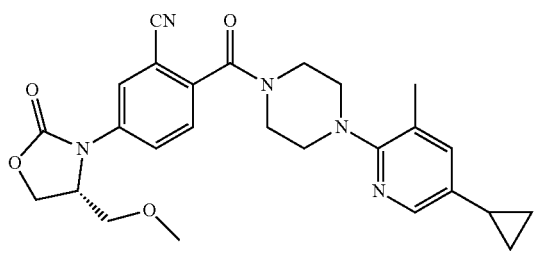 [SMILES: COC[C@@H]1COC(=O)N1c1ccc(C(=O)N2CCN(c3ncc(C4CC4)cc3C)CC2)c(C#N)c1]

By reaction and treatment in the same manner as in Preparation Example 93 and using (R)-3-{3-cyano-4-[4-(5-cyclopropyl-3-methylpyridin-2-yl)piperazine-1-carbonyl]phenyl}-4-hydroxymethyloxazolidin-2-one (600 mg) described in Example 357 and methyl iodide (221 mg), the title compound (339 mg) was obtained.
MS (ESI) m/z:476(M+H)⁺.

Example 359

Synthesis of 3-{3-(3-acetyl-2-oxoimidazolidin-1-yl)-4-[4-(5-cyclopropyl-3-methylpyridin-2-yl)piperazine-1-carbonyl]phenyl}oxazolidin-2-one

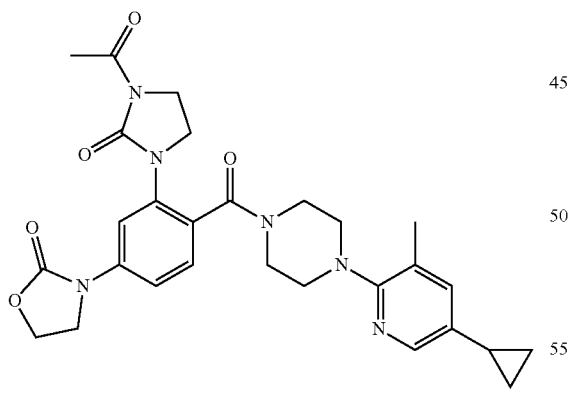

By reaction and treatment in the same manner as in Example 201 and using 1-acetyl-3-{5-chloro-2-[4-(5-cyclopropyl-3-methylpyridin-2-yl)piperazine-1-carbonyl]phenyl}imidazolidin-2-one (342 mg) described in Preparation Example 196 and oxazolidin-2-one (61.8 mg), the title compound (13.6 mg) was obtained.
MS (ESI) m/z:533(M+H)⁺.

Example 360

Synthesis of 3-{4-[4-(5-cyclopropyl-3-methylpyridin-2-yl)piperazine-1-carbonyl]-3-(2-oxoimidazolidin-1-yl)phenyl}oxazolidin-2-one

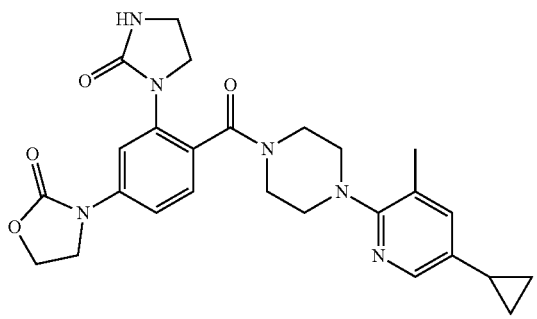 [SMILES: Cc1cc(C2CC2)cnc1N1CCN(C(=O)c2ccc(N3CCOC3=O)cc2N2CCNC2=O)CC1]

A deacetylation product simultaneously resulting from the synthesis of 3-{3-(3-acetyl-2-oxoimidazolidin-1-yl)-4-[4-(5-cyclopropyl-3-methylpyridin-2-yl)piperazine-1-carbonyl]phenyl}oxazolidin-2-one described in Example 359 was purified by column chromatography (ethyl acetate:methanol) to give the title compound (25.4 mg).
MS (ESI) m/z:491(M+H)⁺.

Example 361

Synthesis of (R)-3-{3-(3-acetyl-2-oxoimidazolidin-1-yl)-4-[4-(5-cyclopropyl-3-methylpyridin-2-yl)piperazine-1-carbonyl]phenyl}-4-methyloxazolidin-2-one

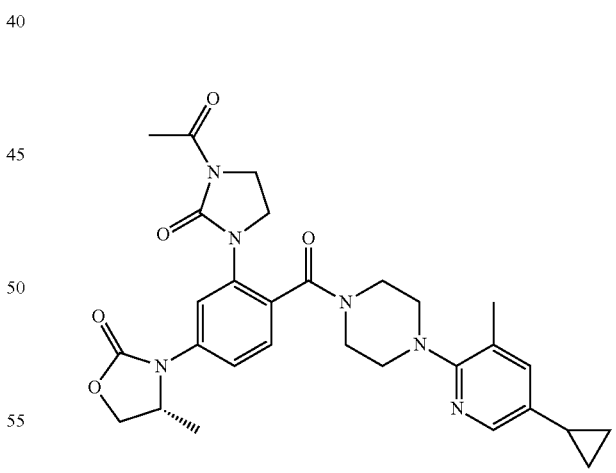

By reaction and treatment in the same manner as in Example 201 and using 1-acetyl-3-{5-chloro-2-[4-(5-cyclopropyl-3-methylpyridin-2-yl)piperazine-1-carbonyl]phenyl}imidazolidin-2-one (344 mg) described in Preparation Example 196 and (R)-4-methyloxazolidin-2-one (61.8 mg) described in Preparation Example 25, the title compound (51.3 mg) was obtained.
MS (ESI) m/z:547(M+H)⁺.

Example 362

Synthesis of (R)-3-{4-[4-(5-cyclopropyl-3-methylpyridin-2-yl)piperazine-1-carbonyl]-3-(2-oxoimidazolidin-1-yl)phenyl}-4-methyloxazolidin-2-one

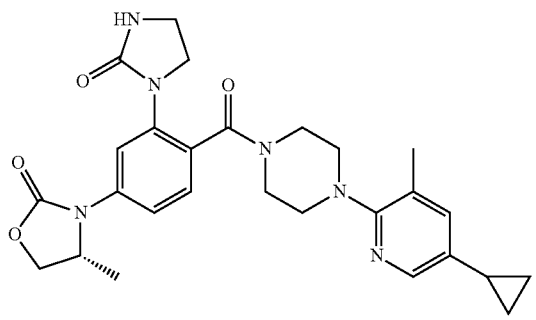 [SMILES: Cc1cc(C2CC2)cnc1N1CCN(C(=O)c2ccc(N3C(=O)OC[C@H]3C)cc2N2CCNC2=O)CC1]

A deacetylation product simultaneously resulting from the synthesis of (R)-3-{3-(3-acetyl-2-oxoimidazolidin-1-yl)-4-[4-(5-cyclopropyl-3-methylpyridin-2-yl)piperazine-1-carbonyl]phenyl}-4-methyloxazolidin-2-one described in Example 361 was purified by column chromatography (ethyl acetate:methanol) to give the title compound (43.3 mg).

MS (ESI) m/z:504(M+H)$^+$.

Example 363

Synthesis of (S)-4-benzyl-3-{4-[4-(2,4-dimethylphenyl)piperazine-1-carbonyl]phenyl}oxazolidin-2-one

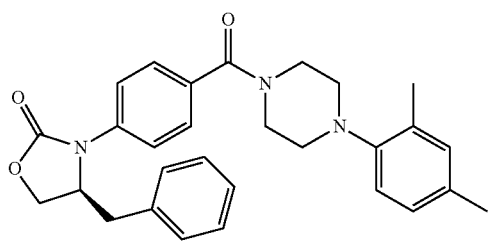 [SMILES: Cc1ccc(N2CCN(C(=O)c3ccc(N4C(=O)OC[C@@H]4Cc4ccccc4)cc3)CC2)c(C)c1]

By reaction and treatment in the same manner as in Example 34 and using methyl (S)-4-(4-benzyl-2-oxooxazolidin-3-yl)benzoate (142 mg) described in Preparation Example 197 and 1-(2,4-dimethylphenyl)piperazine (87 mg), the title compound (101.8 mg) was obtained.

MS (ESI) m/z:470(M+H)$^+$.

Example 364

Synthesis of (R)-4-methyl-3-{4-[4-(3-methyl-5-phenylpyridin-2-yl)piperazine-1-carbonyl]phenyl}oxazolidin-2-one hydrochloride

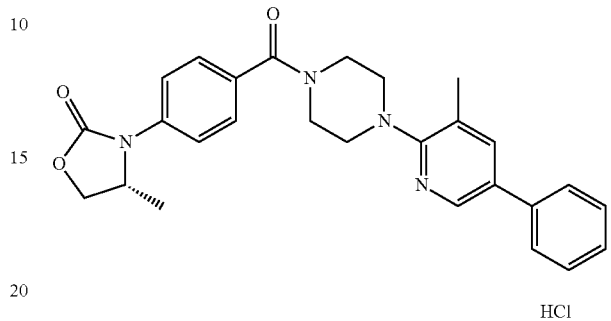

By reaction and treatment in the same manner as in Preparation Example 67 and using (R)-4-(4-methyl-2-oxooxazolidin-3-yl)benzoic acid (1.3 g) described in Preparation Example 37 and 1-(5-bromo-3-methylpyridin-2-yl)piperazine (1.5 g), (R)-3-{4-[4-(5-bromo-3-methylpyridin-2-yl)piperazine-1-carbonyl]phenyl}-4-methyloxazolidin-2-one (2.6 g) was obtained.

By reaction and treatment in the same manner as in Preparation Example 186 and using the obtained (R)-3-{4-[4-(5-bromo-3-methylpyridin-2-yl)piperazine-1-carbonyl]phenyl}-4-methyloxazolidin-2-one (535 mg) and phenylboronic acid (183 mg), (R)-4-methyl-3-{4-[4-(3-methyl-5-phenylpyridin-2-yl)piperazine-1-carbonyl]phenyl}oxazolidin-2-one was obtained. The obtained compound was dissolved in ethyl acetate (10 mL), 4N hydrogen chloride/ethyl acetate (0.3 mL) was added, and the precipitate was collected by filtration to give the title compound (475 mg).

MS (ESI) m/z:457(M+H)$^+$.

Example 365

Synthesis of 3-{4-[4-(2,6-dimethylpyridin-3-yl)piperazine-1-carbonyl]phenyl}oxazolidin-2-one

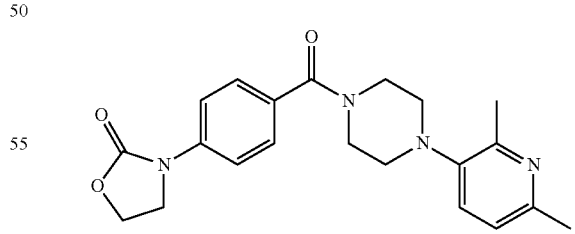

By reaction and treatment in the same manner as in Example 34 and using ethyl 4-(2-oxooxazolidin-3-yl)benzoate (353 mg) described in Preparation Example 12 and 1-(2,6-dimethylpyridin-3-yl)piperazine (287 mg) described in Preparation Example 153, the title compound (90.2 mg) was obtained.

MS (ESI) m/z:381(M+H)$^+$.

Example 366

Synthesis of 3-{4-[4-(2,4-dimethylphenyl)-3-oxopiperazine-1-carbonyl]-3-methanesulfonylphenyl}oxazolidin-2-one

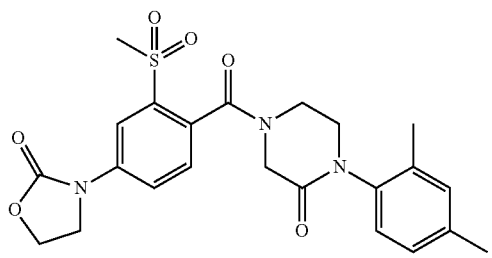 [SMILES: Cc1ccc(N2CCN(C(=O)c3ccc(N4CCOC4=O)cc3S(C)(=O)=O)CC2=O)c(C)c1]

To a mixture of 3-oxopiperazine-1-carboxylic acid tert-butyl ester (5 g), 1-bromo-2,4-dimethylbenzene (3.4 mL), potassium carbonate (10.6 g) and copper (I) iodide (952 mg) were added toluene (25 mL) and N,N'-dimethylethylenediamine (1.1 mL), and the mixture was refluxed for 8 hr. After cooling, water was added to the reaction mixture, and the mixture was extracted with chloroform. The organic layer was washed with saturated brine, and the solvent was evaporated. The residue was purified by column chromatography (chloroform:methanol) to give 4-(2,4-dimethylphenyl)-3-oxopiperazine-1-carboxylic acid tert-butyl ester. The obtained 4-(2,4-dimethylphenyl)-3-oxopiperazine-1-carboxylic acid tert-butyl ester was dissolved in chloroform (10 mL), 4N hydrogen chloride/ethyl acetate (10 mL) was added, and the mixture was stirred at room temperature for 3 hr. The precipitate was collected by filtration to give 1-(2,4-dimethylphenyl)piperazin-2-one hydrochloride (3 g).

To a mixture of 1-(2,4-dimethylphenyl)piperazin-2-one hydrochloride (1.2 g), 4-bromo-2-methanesulfonylbenzoic acid (1.4 g) and 4-(4,6-dimethoxy[1.3.5]triazin-2-yl)-4-methylmorpholinium chloride hydrate (DMT-MM) (2.1 g) were added chloroform (7.5 mL), methanol (7.5 mL) and N-methylmorpholine (550 μL), and the mixture was stirred at room temperature overnight. After evaporation of the solvent, the residue was purified by column chromatography (chloroform) to give 4-(4-bromo-2-methanesulfonylbenzoyl)-1-(2,4-dimethylphenyl)piperazin-2-one (2.24 g).

To a mixture of 4-(4-bromo-2-methanesulfonylbenzoyl)-1-(2,4-dimethylphenyl)piperazin-2-one (931 mg), oxazolidin-2-one (209 mg), potassium carbonate (849 mg) and copper (I) iodide (76 mg) were added toluene (2 mL) and N,N'-dimethylethylenediamine (90 μL), and the mixture was refluxed for 8 hr. After cooling, water was added to the reaction mixture, and the mixture was extracted with chloroform. The organic layer was washed with saturated brine, and the solvent was evaporated. The residue was purified by column chromatography (chloroform:methanol) and recrystallized from a mixed solution of hexane and ethyl acetate to give the title compound (603 mg).

MS (ESI) m/z:472(M+H)$^+$.

Example 367

Synthesis of 3-{4-[(R)-4-(2,4-dimethylphenyl)-3-methylpiperazine-1-carbonyl]-3-methanesulfonylphenyl}oxazolidin-2-one

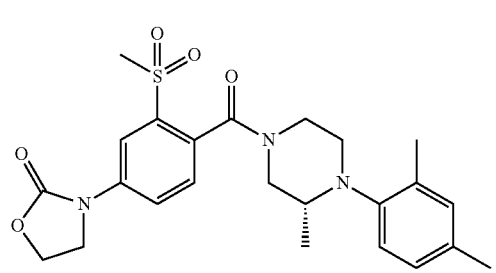 [SMILES: Cc1ccc(N2CCN(C(=O)c3ccc(N4CCOC4=O)cc3S(C)(=O)=O)C[C@H]2C)c(C)c1]

To a mixture of 1-bromo-2,4-dimethylbenzene (3.8 mL), (R)-4-N-Boc-2-methylpiperazine (5.0 g), palladium (II) acetate (281 mg), 2-(dicyclohexylphosphino)-2',4',6'-tri-isopropyl-1,1'-biphenyl (1.19 g) and sodium tert-butoxide (3.4 g) was added toluene (50 mL), and the mixture was refluxed for 3 hr. After cooling, the mixture was extracted with ethyl acetate. The organic layer was washed with saturated brine, and the solvent was evaporated. The residue was purified by column chromatography (chloroform) to give (R)-4-(2,4-dimethylphenyl)-3-methylpiperazine-1-carboxylic acid tert-butyl ester. The compound was dissolved in chloroform (8.0 mL), 4N hydrogen chloride/ethyl acetate (8.0 mL) was added, and the mixture was stirred at room temperature overnight. The reaction mixture was alkalified, and extracted with chloroform. The organic layer was evaporated to give (R)-1-(2,4-dimethylphenyl)-2-methylpiperazine (1.2 g).

By reaction and treatment in the same manner as in Preparation Example 67 and using (R)-1-(2,4-dimethylphenyl)-2-methylpiperazine (1.2 g) and 4-bromo-2-methanesulfonylbenzoic acid (1.7 g), (4-bromo-2-methanesulfonylphenyl)[(R)-4-(2,4-dimethylphenyl)-3-methylpiperazin-1-yl]methanone (2.0 g) was obtained.

By reaction and treatment in the same manner as in Example 1 and using (4-bromo-2-methanesulfonylphenyl)[(R)-4-(2,4-dimethylphenyl)-3-methylpiperazin-1-yl]methanone (814 mg) and oxazolidin-2-one (168 mg), the title compound (327 mg) was obtained.

MS (ESI) m/z:472(M+H)$^+$.

Example 368

3-{4-[4-(2-chloro-5-fluoro-4-methylphenyl)piperazine-1-carbonyl]-3-methanesulfonylphenyl}oxazolidin-2-one described in Preparation Example 14

Example 369 benzoic acid (R)-3-{4-[4-(4-chlorobenzoyl)piperidine-1-carbonyl]-3-methanesulfonylphenyl}-2-oxooxazolidin-4-ylmethyl ester described in Preparation Example 24

Example 370

(R)-3-{4-[4-(4-chlorobenzoyl)piperidine-1-carbonyl]phenyl}-4-isopropyloxazolidin-2-one described in Preparation Example 27

Example 371

3-{4-[4-(4-chlorobenzoyl)piperidine-1-carbonyl]-3-methanesulfonylphenyl}oxazolidin-2-one described in Preparation Example 31

Example 372

3-{5-[4-(4-chlorobenzoyl)piperidine-1-carbonyl]pyridin-2-yl}oxazolidin-2-one described in Preparation Example 32

Example 373

(R)-3-{5-[4-(4-chlorobenzoyl)piperidine-1-carbonyl]pyridin-2-yl}-4-methyloxazolidin-2-one described in Preparation Example 33

Example 374

(R)-3-{5-[4-(4-chlorobenzoyl)piperidine-1-carbonyl]pyridin-2-yl}-4-ethyloxazolidin-2-one described in Preparation Example 34

Example 375

(R)-3-{6-[4-(4-chlorobenzoyl)piperidine-1-carbonyl]pyridin-3-yl}-4-methyloxazolidin-2-one described in Preparation Example 36

Example 376

Synthesis of 3-{3-(3-acetyl-2-oxoimidazolidin-1-yl)-4-[4-(5-cyclopropyl-3-methylpyridin-2-yl)piperazine-1-carbonyl]phenyl}-5,5-dimethyloxazolidin-2-one

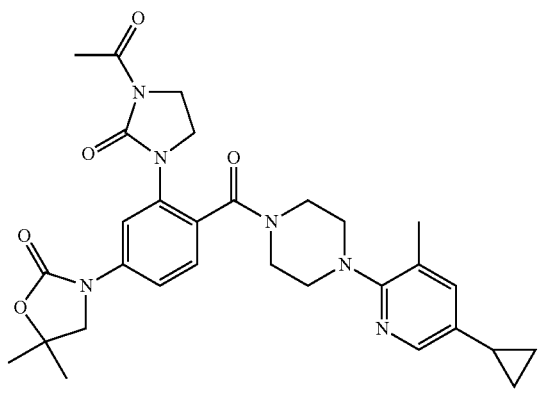 [SMILES: CC(=O)N1CCN(c2cc(N3CC(C)(C)OC3=O)ccc2C(=O)N2CCN(c3ncc(C4CC4)cc3C)CC2)C1=O]

By reaction and treatment in the same manner as in Example 201 and using 1-acetyl-3-{5-chloro-2-[4-(5-cyclopropyl-3-methylpyridin-2-yl)piperazine-1-carbonyl]phenyl}imidazolidin-2-one (336 mg) described in Preparation Example 196 and 5,5-dimethyloxazolin-2-one (80.3 mg) described in Preparation Example 43, the title compound (91.3 mg) was obtained.

MS(ESI)m/z:561(M+H)⁺.

Example 377

Synthesis of 3-{4-[4-(5-cyclopropyl-3-methylpyridin-2-yl)piperazine-1-carbonyl]-3-(2-oxoimidazolidin-1-yl)phenyl}-5,5-dimethyloxazolidin-2-one

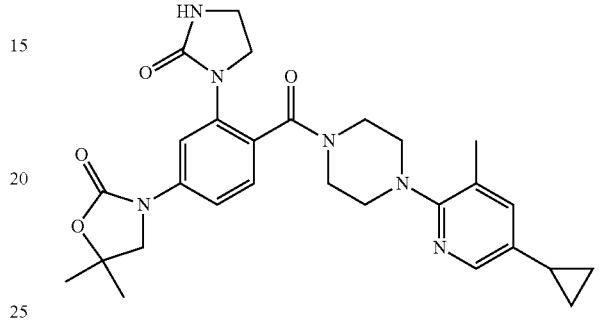

A deacetylation product simultaneously resulting from the synthesis of 3-{3-(3-acetyl-2-oxoimidazolidin-1-yl)-4-[4-(5-cyclopropyl-3-methylpyridin-2-yl)piperazine-1-carbonyl]phenyl}-5,5-dimethyloxazolidin-2-one described in Example 376 was purified by column chromatography (ethyl acetate:methanol) to give the title compound (22.7 mg).

MS(ESI)m/z:519(M+H)⁺.

Example 378

Synthesis of 3-{3-(3-acetyl-2-oxoimidazolidin-1-yl)-4-[4-(3,5-dimethylpyridin-2-yl)piperazine-1-carbonyl]phenyl}-5,5-dimethyloxazolidin-2-one

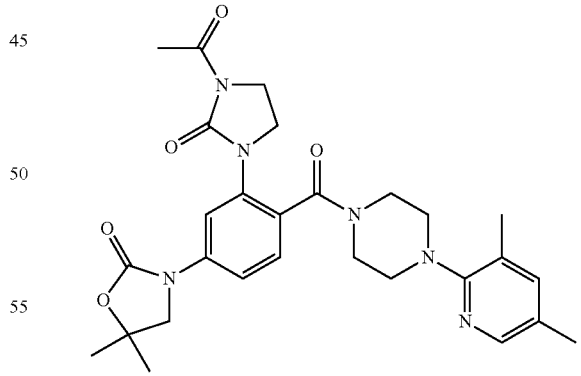

By reaction and treatment in the same manner as in Example 201 and using 1-acetyl-3-{5-chloro-2-[4-(3,5-dimethylpyridin-2-yl)piperazine-1-carbonyl]phenyl}imidazolidin-2-one (653 mg) described in Preparation Example 126 and 5,5-dimethyloxazolin-2-one (165 mg) described in Preparation Example 43, the title compound (86.5 mg) was obtained.

MS(ESI)m/z:535(M+H)⁺.

Example 379

Synthesis of 3-{4-[4-(3,5-dimethylpyridin-2-yl)piperazine-1-carbonyl]-3-(2-oxoimidazolidin-1-yl)phenyl}-5,5-dimethyloxazolidin-2-one

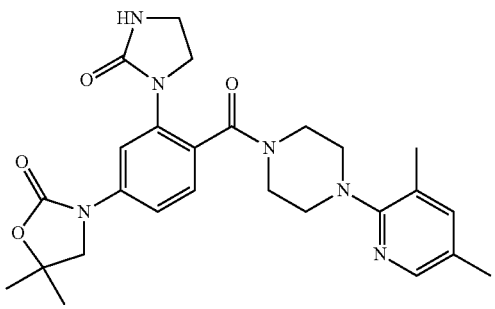

A deacetylation product simultaneously resulting from the synthesis of 3-{3-(3-acetyl-2-oxoimidazolidin-1-yl)-4-[4-(3,5-dimethylpyridin-2-yl)piperazine-1-carbonyl]phenyl}-5,5-dimethyloxazolidin-2-one described in Example 378 was purified by column chromatography (ethyl acetate:methanol) to give the title compound (38.6 mg).
MS(ESI)m/z:493(M+H)$^+$.

Experimental Example 1

Action of Human TNFα Stimulated THP-1 Cell on proMMP-9 Production

THP-1 cell (human monocytic leukemia cell line) was adjusted to 1×10$^7$ cells/mL in a culture medium (10% fetal bovine serum/RPMI1640 medium), and dispensed to a 96 well multiplate. This was equilibrated under the conditions of 37° C./5% $CO_2$, and a culture medium containing human TNFα (final concentration 10 ng/mL) and a test compound was added thereto. After incubation under the conditions of 37° C./5% $CO_2$ for 24 hr, the culture medium was centrifugated and the culture supernatant was collected, which was subjected to the following measurement.
Quantification of proMMP-9 in Culture Supernatant The proMMP-9 concentration of the collected culture supernatant was quantified using a commercially available measurement reagent (manufactured by GE Healthcare, MMP-9, Human, Biotrak ELISA System).
Calculation of proMMP-9 Suppression Rate The proMMP-9 suppression rate of the test compound was calculated from the following formula:

% suppression=100−((Test−Min)/(Max−Min)×100)

wherein Max is proMMP-9 concentration of culture supernatant induced by stimulation with human TNFα, without addition of a test compound (added with solvent alone)
Min is proMMP-9 concentration of culture supernatant without addition of a test compound (added with solvent alone) and without stimulation with human TNFα, and
Test is proMMP-9 concentration of culture supernatant induced by stimulation with human TNFα when a test compound is added.

Furthermore, the concentration of the test compound necessary for suppressing proMMP-9 production by human TNFα stimulated THP-1 cell by 50% ($IC_{50}$ value) was calculated from 3 points of proMMP-9 suppression rate at test compound concentrations of 10, 100 and 1,000 nmol/L.

Experimental Example 2

Action of THP-1 Cell on Hemostatic Type proMMP-2 Production

THP-1 cell (human monocytic leukemia cell line) was adjusted to 1×10$^7$ cells/mL in a culture medium (10% fetal bovine serum/RPMI1640 medium), and dispensed to a 96 well multiplate. This was equilibrated under the conditions of 37° C./5% $CO_2$, and a culture medium containing a test compound was added thereto. After incubation under the conditions of 37° C./5% $CO_2$ for 24 hr, the culture medium was centrifugated and the culture supernatant was collected, which was subjected to the following measurement.
Quantification of proMMP-2 in Culture Supernatant The proMMP-2 concentration of the collected culture supernatant was quantified using a commercially available measurement reagent (manufactured by GE Healthcare, MMP-2, Human, Biotrak ELISA System).
Calculation of proMMP-2 Suppression Rate The proMMP-2 suppression rate of the test compound was calculated from the following formula:

% suppress=100−((Test/Cont)×100).

wherein Cont is proMMP-2 concentration of culture supernatant without addition of a test compound (added with solvent alone) and Test is proMMP-2 concentration of culture supernatant with addition of a test compound.

The results of the Example compounds of the present invention in Experimental Examples 1 and 2 are shown below.

TABLE 1

| Example compounds | Experimental Example 1 proMMP-9 production suppression ($IC_{50}$, nM) | Experimental Example 2 proMMP-2 production suppression (% suppression, 10 μM) |
|---|---|---|
| 1 | 44 | 17.4 |
| 6 | 59 | 12.6 |
| 8 | 48 | 11.6 |
| 11 | 40 | 12.4 |
| 19 | 11 | 22.5 |

Experimental Example 3

Suppressive Action on Hindpaw Edema of Rat Adjuvant Induced Arthritis Model

Anesthetized rats (LEW, male, 6-week-old) were immunized with M. Butyricum (5 mg/mL) at a dose of 0.1 mL/body by subcutaneous administration from the tail root. On day 15, the hindpaw volume was measured (rat hindpaw edema volume measuring apparatus, Plethysmometer, manufactured by: Unicom (Yachiyo. Chiba, Japan) standard: TK-101 Series No.: 101 gH1), and the rats were allocated such that each test group had a uniform hindpaw volume. The test compound was orally administered once a day from immediately after allocation on day 15 to day 20 at doses of 3 and 30 mg/kg, and the hindpaw volume was measured again on day 21. The amount of hindpaw edema was the difference in the amount between hindpaw volume on day 15 and that on day 21.

The results of the Example compound of the present invention in Experimental Example 3 are shown below.

TABLE 2

| test group | dose | hindpaw edema volume |
|---|---|---|
| normal group without treatment | | 0.02 ± 0.05 |
| pathology group | | 0.69 ± 0.10 |
| Example compound 8 | 3 mg/kg | 0.27 ± 0.17 |
| Example compound 8 | 30 mg/kg | 0.20 ± 0.18 |

Experimental Example 4

Suppressive Action on Articular Joints Injury of Rat Monoiodoacetic Acid-Induced Osteoarthritis Model Monoiodoacetic acid solution (0.3 mg/25 µL) was injected into the right hindpaw knee joint cavity of anesthetized rats (LEW, male, 7-week-old). A test compound was orally administered once a day from immediately after monoiodoacetic acid injection to day 6 at a dose of 10 mg/kg. On day 7, right hindpaw knee joint was taken from euthanized rats, and fixed with 10% neutral formalin solution. A pathology specimen of knee joint was prepared, stained with Hematoxylin Eosin and Safranine O, and the state of joint cartilage injury was scored under microscopic observation. For articular joint injury scores, changes in each pathological finding in medial condyle of femur and medial condyle of tibia (cartilage surface tuberosity, erosion/ulcer/fibrillation, chondrocyte disorganization/disappearance/hypertrophy, reduction of Safranine staining) were divided into mild, moderate and severe according to the method of Kobayashi et al. (Kobayashi K et al. J. Vet. Med. Sci. 65, 1195 1199 2003), and indicated in the scores of 1, 2 and 3 and totaled. Furthermore, an average of the score of medial condyle of femur and that of medial condyle of tibia was determined and used as an articular joint injury score.

The results of the Example compounds of the present invention in Experimental Example 4 are shown below.

TABLE 3

| compound administered | dose | articular joint injury score of disease group (administered with solvent) | articular joint injury score of compound administration group |
|---|---|---|---|
| Example compound 8 | 3 mg/kg | 6.0 ± 0.8 | 4.4 ± 0.5 |
| Example compound 42 | 10 mg/kg | 6.2 ± 0.2 | 3.8 ± 0.7 |
| Example compound 81 | 10 mg/kg | 6.8 ± 0.6 | 4.4 ± 0.4 |
| Example compound 109 | 3 mg/kg | 6.3 ± 0.5 | 4.1 ± 0.4 |

Experimental Example 5

Suppressive Action on Large Intestine Weight Increase of Rat Dinitrobenzene-Induced Colitis Model A dinitrobenzene solution (30 mg/0.1 mL) was injected into the large intestine of anesthetized rats (Wistar, male, 6-week-old). A test compound was orally administered once a day from the previous day of the dinitrobenzene injection to day 7 at a dose of 30 mg/kg. On day 8, the large intestine was isolated from euthanized rats, and the wet weight thereof was measured. The large intestine weight was amended to the weight per 100 g body weight of the rats on day 8.

The results of the Example compound of the present invention in Experimental Example 5 are shown below.

TABLE 4

| test group | dose | large intestine weight (g/100 g body weight) |
|---|---|---|
| normal group without treatment | | 0.215 ± 0.011 |
| pathology group | | 0.633 ± 0.041 |
| Example compound 8 | 30 mg/kg | 0.457 ± 0.031 |

MMP-9 is produced as a precursor proMMP-9 by the stimulated cells, extracellularly activated and expresses the physiological activity as MMP-9. That is, evaluation of the suppression of proMMP-9 produced by the cell means evaluation of the suppression of production of MMP-9. The same applies to MMP-2, and evaluation of the suppression of proMMP-2 produced by the cell means evaluation of the suppression of production of MMP-2.

As is clear from Table 1, the compound of the present invention has a selective MMP-9 production suppressive action, and is useful as a highly safe prophylactic drug or therapeutic drug for autoimmune diseases, inflammatory bowel diseases (ulcerative colitis, Crohn's disease) or osteoarthritis, which shows suppressed expression of side effects caused by the suppression of MMP-2 production.

INDUSTRIAL APPLICABILITY

According to the present invention, a compound having a selective MMP-9 production suppressive action, and a medicament containing same as an active ingredient can be provided.

This application is based on patent application No. 2008-276147 filed in Japan, the contents of which are encompassed in full herein.

The invention claimed is:
1. A compound of formula (I)

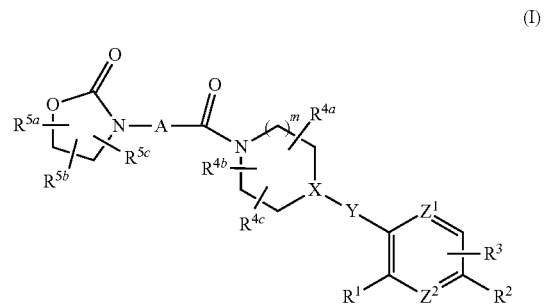

(I)

wherein
A is a group represented by the following formula

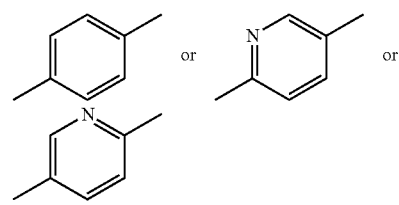

wherein phenylene and pyridinyl optionally have one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6, and cyclic aminosulfonyl, the right bond is bonded to carbonyl, and the left bond is bonded to a nitrogen atom, $R^1$ and $R^2$ are the same or different and each is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), alkoxycarbonyl having a total carbon number of 2-7 and optionally having substituent(s), carbamoyl, acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6 or cyclic aminosulfonyl, and $R^1$ and $R^2$ do not simultaneously show a hydrogen atom, $R^3$ is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), alkoxycarbonyl having a total carbon number of 2-7 and optionally having substituent(s), carboxy, carbamoyl, acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6 or cyclic aminosulfonyl, $R^{4a}$, $R^{4b}$ and $R^{4c}$ are each independently a hydrogen atom, alkyl having a carbon number of 1-6 and optionally having substituent(s), oxo or alkoxy having a carbon number of 1-6 and optionally having substituent(s), $R^{5a}$, $R^{5b}$ and $R^{5c}$ are the same or different and each is a hydrogen atom, alkyl having a carbon number of 1-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxycarbonyl having a total carbon number of 2-7 and optionally having substituent(s) or oxo, X is a carbon atom (substituted with H or any of $R^{4a}$, $R^{4b}$ and $R^{4c}$, but the carbon atom is not substituted by oxo) or a nitrogen atom (when Y is a single bond, the nitrogen atom may be oxidized to form N-oxide), Y is a single bond, carbonyl or an oxygen atom, $Z^1$ and $Z^2$ are each independently a carbon atom (substituted with H or $R^3$) or a nitrogen atom, and m is 1 or 2, or a pharmacologically acceptable salt thereof.

2. The compound of claim 1 wherein A is a group represented by the following formula

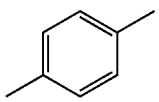

wherein phenylene optionally has one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6 and cyclic aminosulfonyl, the right bond is bonded to carbonyl, and the left bond is bonded to a nitrogen atom, or a pharmacologically acceptable salt thereof.

3. The compound of claim 1 wherein A is a group represented by the following formula

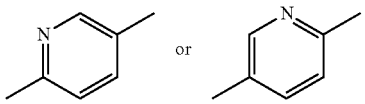

wherein pyridinyl optionally has one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), aryl having a carbon number of 6-10 and optionally having substituent(s), heteroaryl containing 1 to 6 nitrogen atom(s), oxygen atom(s) and sulfur atom(s), having a ring-constituting atom number of 5-10 and optionally having substituent(s), alkoxy having a carbon number of 1-6 and optionally having substituent(s), acyl having a total carbon number of 2-7 and optionally having substituent(s), acyloxy having a total carbon number of 2-7 and optionally having substituent(s), a halogen atom, hydroxyl group, nitro, cyano, mercapto, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylaminocarbonyl having a total carbon number of 2-7, cycloalkylaminocarbonyl having a total carbon number of 4-7, cyclic aminocarbonyl, alkylsulfonylamino having a carbon number of 1-6, cycloalkylsulfonylamino having a carbon number of 3-6, alkylaminosulfonyl having a carbon number of 1-6, cycloalkylaminosulfonyl having a carbon number of 3-6 and cyclic aminosulfonyl, the right bond is bonded to carbonyl, and the left bond is bonded to a nitrogen atom, or a pharmacologically acceptable salt thereof.

4. The compound of claim 1, wherein phenylene and pyridinyl for A optionally have one or the same or different 2 or 3 substituents selected from alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, hydroxyl group, nitro, cyano, alkylthio having a carbon number of 1-6 and optionally having substituent(s), alkylsulfinyl having a carbon number of 1-6 and optionally having substituent(s), alkylsulfonyl having a carbon number of 1-6 and optionally having substituent(s), amino, alkylamino having a carbon number of 1-6 and optionally having substituent(s), dialkylamino having a total carbon number of 2-12 and optionally having substituent(s), cyclic amino optionally having substituent(s), acylamino having a total carbon number of 2-7, alkylsulfonylamino having a carbon number of 1-6 and cycloalkylsulfonylamino having a carbon number of 3-6, or a pharmacologically acceptable salt thereof.

5. The compound of claim 1, wherein X is a carbon atom substituted with H or any of $R^{4a}$, $R^{4b}$ and $R^{4c}$, but the carbon atom is not substituted by oxo), or a pharmacologically acceptable salt thereof.

6. The compound of claim 1, wherein
$R^1$ and $R^2$ are the same or different and each is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, cyano, alkylthio having a carbon number of 1-6 and optionally having substituent(s), alkylsulfinyl having a carbon number of 1-6 and optionally having substituent(s) or alkylsulfonyl having a carbon number of 1-6 and optionally having substituent(s), wherein $R^1$ and $R^2$ are not simultaneously hydrogen atoms,
$R^3$ is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, cyano, alkylthio having a carbon number of 1-6 and optionally having substituent(s), alkylsulfinyl having a carbon number of 1-6 and optionally having substituent(s) or alkylsulfonyl having a carbon number of 1-6 and optionally having substituent(s), $R^{4a}$, $R^{4b}$ and $R^{4c}$ are each independently a hydrogen atom or alkyl having a carbon number of 1-6 and optionally having substituent(s), $R^{5a}$, $R^{5b}$ and $R^{5c}$ are the same or different hydrogen atom, alkyl having a carbon number of 1-6 and optionally having substituent(s) or aryl having a carbon number of 6-10 and optionally having substituent(s), X is a carbon atom substituted with H or any of $R^{4a}$, $R^{4b}$ and $R^{4c}$, but the carbon atom is not substituted by oxo), Y is carbonyl or an oxygen atom, $Z^1$ and $Z^2$ are each a carbon atom substituted with H or $R^3$, and m is 1, or a pharmacologically acceptable salt thereof.

7. The compound of claim 1, wherein X is a nitrogen atom (nitrogen atom may be oxidized to form N-oxide), or a pharmacologically acceptable salt thereof.

8. The compound of claim 1, wherein
$R^1$ and $R^2$ are the same or different and each is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, cyano, alkylthio having a carbon number of 1-6 and optionally having substituent(s), alkylsulfinyl having a carbon number of 1-6 and optionally having substituent(s) or alkylsulfonyl having a carbon number of 1-6 and optionally having substituent(s), wherein $R^1$ and $R^2$ are not simultaneously hydrogen atoms, $R^3$ is a hydrogen atom, alkyl having a carbon number of 1-6 and optionally having substituent(s), alkenyl having a carbon number of 2-6 and optionally having substituent(s), alkynyl having a carbon number of 2-6 and optionally having substituent(s), cycloalkyl having a carbon number of 3-6 and optionally having substituent(s), alkoxy having a carbon number of 1-6 and optionally having substituent(s), a halogen atom, cyano, alkylthio having a carbon number of 1-6 and optionally having substituent(s), alkylsulfinyl having a carbon number of 1-6 and optionally having substituent(s) or alkylsulfonyl having a carbon number of 1-6 and optionally having substituent(s), $R^{4a}$, $R^{4b}$ and $R^{4c}$ are each independently a hydrogen atom, alkyl having a carbon number of 1-6 and optionally having substituent(s) or oxo, $R^{5a}$, $R^{5b}$ and $R^{5c}$ are the same or different hydrogen atom, alkyl having a carbon number of 1-6 and optionally having substituent(s) or aryl having a carbon number of 6-10 and optionally having substituent(s), X is a nitrogen atom (nitrogen atom may be oxidized to form N-oxide), Y is a single bond, $Z^1$ and $Z^2$ are each independently a carbon atom substituted with H or $R^3$ or a nitrogen atom, and m is 1 or 2, or a pharmacologically acceptable salt thereof.

9. The compound of claim 1, wherein
$R^1$ and $R^2$ are the same or different and each is alkyl having a carbon number of 1-6 and optionally having substituent(s), cycloalkyl having a carbon number of 3-6 and optionally having substituent(s), alkoxy having a carbon number of 1-6 and optionally having substituent(s), a halogen atom or cyano, $R^3$ is a hydrogen atom, alkyl having a carbon number of 1-6 and optionally having substituent(s), cycloalkyl having a carbon number of 3-6 and optionally having substituent(s), alkoxy having a carbon number of 1-6 and optionally having substituent(s), a halogen atom or cyano, $R^{4a}$, $R^{4b}$ and $R^{4c}$ are each independently a hydrogen atom or alkyl having a carbon number of 1-6 and optionally having substituent(s), $R^{5a}$, $R^{5b}$ and $R^{5c}$ are the same or different and each is a hydrogen atom, alkyl having a carbon number of 1-6 and optionally having substituent(s) or aryl having a carbon number of 6-10 and optionally having substituent(s), X is a nitrogen atom (nitrogen atom may be oxidized to form N-oxide), Y is a single bond, $Z^1$ and $Z^2$ are each independently a carbon atom substituted with H or $R^3$ or a nitrogen atom, and m is 1 or 2, or a pharmacologically acceptable salt thereof.

10. A pharmaceutical composition comprising (a) the compound of claim 1, or a pharmacologically acceptable salt thereof, and (b) a pharmaceutically acceptable additive.

11. A method for suppressing MMP-9 production in a patient, comprising administering an effective amount of the compound of claim 1, or a pharmacologically acceptable salt thereof, to a patient, thereby suppressing MMP-9 production in the patient.

12. A method of treating rheumatoid arthritis, multiple sclerosis or systemic lupus erythematosus in a patient, comprising administering an effective amount of the compound of claim 1, or a pharmacologically acceptable salt thereof, to a patient in need thereof, thereby treating rheumatoid arthritis, multiple sclerosis or systemic lupus erythematosus in the patient.

13. A method of treating Crohn's disease or ulcerative colitis in a patient, comprising administering an effective amount of the compound of claim 1, or a pharmacologically acceptable salt thereof, to a patient in need thereof, thereby treating Crohn's disease or ulcerative colitis in the patient.

14. A method of treating osteoarthritis in a patient, comprising administering an effective amount of the compound of claim 1, or a pharmacologically acceptable salt thereof, to a patient in need thereof, thereby treating osteoarthritis in the patient.

* * * * *